United States Patent
Black et al.

(10) Patent No.: US 10,696,686 B2
(45) Date of Patent: Jun. 30, 2020

(54) HERBICIDALLY ACTIVE (ALKYNYL-PHENYL)-SUBSTITUTED CYCLIC DIONE COMPOUNDS AND DERIVATIVES THEREOF

(71) Applicant: Syngenta Limited, Guildford (GB)

(72) Inventors: Janice Black, Bracknell Berkshire (GB); James Nicholas Scutt, Bracknell Berkshire (GB); Louisa Whalley, Bracknell Berkshire (GB); Nigel James Willets, Bracknell Berkshire (GB)

(73) Assignee: Syngenta Limited, Guildford, Surrey (GB)

( * ) Notice: Subject to any disclaimer, the term of this patent is extended or adjusted under 35 U.S.C. 154(b) by 858 days.

(21) Appl. No.: 14/894,698

(22) PCT Filed: May 29, 2014

(86) PCT No.: PCT/EP2014/061206
§ 371 (c)(1),
(2) Date: Nov. 30, 2015

(87) PCT Pub. No.: WO2014/191534
PCT Pub. Date: Dec. 4, 2014

(65) Prior Publication Data
US 2016/0207934 A1    Jul. 21, 2016

(30) Foreign Application Priority Data

May 30, 2013   (GB) .................................. 1309679.7
Dec. 23, 2013  (GB) .................................. 1322855.6

(51) Int. Cl.
*C07D 493/08*   (2006.01)
*A01N 43/16*    (2006.01)
(Continued)

(52) U.S. Cl.
CPC ........... *C07D 493/08* (2013.01); *A01N 35/06* (2013.01); *A01N 37/02* (2013.01); *A01N 37/10* (2013.01); *A01N 43/16* (2013.01); *A01N 43/18* (2013.01); *A01N 43/40* (2013.01); *A01N 43/90* (2013.01); *A01N 47/06* (2013.01); *C07C 49/517* (2013.01); *C07C 49/577* (2013.01); *C07C 49/753* (2013.01); *C07C 69/24* (2013.01); *C07C 69/78* (2013.01); *C07C 69/96* (2013.01); *C07C 323/22* (2013.01); *C07C 381/14* (2013.01); *C07D 307/42* (2013.01); *C07D 309/32* (2013.01); *C07D 311/96* (2013.01);
(Continued)

(58) Field of Classification Search
None
See application file for complete search history.

(56) References Cited

U.S. PATENT DOCUMENTS

2005/0054535 A1   3/2005  Fischer et al.

FOREIGN PATENT DOCUMENTS

PG   2011073060 A2   6/2011
WO   2007068427 A2   6/2007
(Continued)

OTHER PUBLICATIONS

International Search Report of International Application PCT/EP2014/061206, dated Aug. 25, 2015.

*Primary Examiner* — Hasan S Ahmed
*Assistant Examiner* — Frank Choi
(74) *Attorney, Agent, or Firm* — Baker & Hostetler LLP; Toni-Junell Herbert

(57) ABSTRACT

The present invention relates to a compound of formula (I): wherein: X is methyl or chlorine; $R^1$ is fluorine or bromine; $R^2$ is ethynyl, $C_1$-$C_3$alkoxy, $C_1$-$C_3$haloalkoxy, or $C_1$-$C_3$alkoxy-$C_1$-$C_3$alkoxy-; and Q is a pyran-3,5-dione-4-yl, a thiopyran-3,5-dione-4-yl, a piperidine-3,5-dione-4-yl, a cyclopentane-1,3-dione-2-yl, a cyclohexane-1,3, 5-trione-2-yl, a cyclohexane-1,3-dione-2-yl, or a cycloheptane-1,3-dione-2-yl, or a derivative thereof (e.g. a fused such as fused bicyclic derivative, and/or a spirocyclic derivative), or an enol ketone tautomer derivative thereof, wherein Q is further defined herein; and wherein the compound of formula (I) is optionally present as an agrochemically acceptable salt thereof. Preferably, X is methyl; and/or $R^1$ is fluorine; and/or $R^2$ is —O—$R^{2.4}$, wherein $R^{2.4}$ is methyl, ethyl, trifluoromethyl, difluoromethyl, trifluoroethyl, or —$CH_2CH_2OCH_3$. These compounds are suitable for use as herbicides. The invention therefore also relates to a method of controlling weeds, especially grassy monocotyledonous weeds, in crops of useful plants, comprising applying a compound of formula (I), or a herbicidal composition comprising such a compound, to the weeds and/or to the plants and/or to the locus thereof.

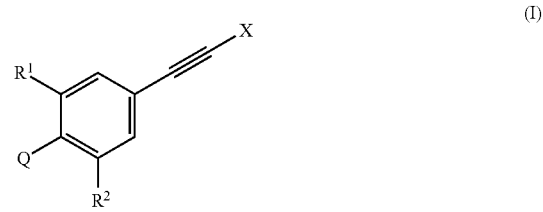

22 Claims, No Drawings

(51) Int. Cl.
    *C07D 309/32*     (2006.01)
    *C07D 311/96*     (2006.01)
    *C07C 49/753*     (2006.01)
    *A01N 43/18*     (2006.01)
    *C07C 323/22*     (2006.01)
    *A01N 43/40*     (2006.01)
    *C07D 307/42*     (2006.01)
    *A01N 35/06*     (2006.01)
    *A01N 37/02*     (2006.01)
    *A01N 37/10*     (2006.01)
    *A01N 47/06*     (2006.01)
    *C07C 49/577*     (2006.01)
    *C07C 69/24*     (2006.01)
    *C07C 69/78*     (2006.01)
    *C07C 69/96*     (2006.01)
    *C07C 381/14*     (2006.01)
    *A01N 43/90*     (2006.01)
    *C07C 49/517*     (2006.01)

(52) U.S. Cl.
    CPC ...... *C07C 2601/08* (2017.05); *C07C 2601/10* (2017.05); *C07C 2601/14* (2017.05); *C07C 2602/44* (2017.05)

(56) References Cited

FOREIGN PATENT DOCUMENTS

| | | |
|---|---|---|
| WO | 2008110307 A1 | 9/2008 |
| WO | 2009019015 A1 | 2/2009 |
| WO | 2010000773 A1 | 1/2010 |
| WO | 2010081689 A2 | 7/2010 |
| WO | 2013079672 A1 | 6/2013 |
| WO | 2013079708 A1 | 6/2013 |

HERBICIDALLY ACTIVE (ALKYNYL-PHENYL)-SUBSTITUTED CYCLIC DIONE COMPOUNDS AND DERIVATIVES THEREOF

RELATED APPLICATION INFORMATION

This application is a 371 of International Application No. PCT/EP2014/061206, filed May 29, 2014, which claims priority to 1309679.7 filed May 30, 2013, and to 1322855.6 filed Dec. 23, 2013, the contents of which are incorporated herein by reference herein.

The present invention relates to herbicidally active (alkynyl-phenyl)-substituted cyclic dione compounds, in particular pyrandione, thiopyrandione, piperidinedione, cyclopentanedione, cyclohexanedione, cyclohexanetrione or cycloheptanedione compounds, and derivatives thereof (e.g. enol ketone tautomer derivatives thereof and/or fused and/or bicyclic derivatives thereof as appropriate), to processes for their preparation, to herbicidal compositions comprising those compounds, and to their use in controlling weeds such as grassy monocotyledonous weeds, especially in crops of useful plants, or in inhibiting undesired plant growth.

WO 01/17972 A2 (Syngenta Participations AG) discloses (4-methyl-phenyl)-substituted (such as 4-methyl-2,6-diethyl-phenyl-substituted) carbocycles or heterocycles, in particular carbocyclic or heterocyclic diones, suitable for use as herbicides.

WO 03/013249 A1 (Bayer AG) and its equivalent US 2005/0054535 A1 disclose selective herbicidal compositions comprising (a) a (substituted-phenyl)-substituted cyclic ketoenol and (b) a compound which improves crop plant compatibility, in particular cloquintocet-mexyl or mefenpyr-diethyl. In WO 03/013249 A1 and US 2005/0054535 A1, the cyclic ketoenol (whose tautomer is a cyclic dione) can in particular be a 3-(substituted-phenyl)-pyrrolidine-2,4-dione, a 3-(substituted-phenyl)-tetrahydrofuran-2,4-dione, a 3-(substituted-phenyl)-pyran-2,4-dione derivative, a 2-(substituted-phenyl)-cyclopentane-1,3-dione, or a 2-(substituted-phenyl)-cyclohexane-1,3-dione, et al., or a derivative (e.g. ester or carbonate derivative) of these cyclic ketoenols/cyclic diones.

WO 2007/068427 A2 (Bayer CropScience AG) and its equivalent US 2009/0227563 A1 disclose a composition comprising (a) a (substituted-phenyl)-substituted cyclic ketoenol as a herbicide, and (b) an ammonium and/or phosphonium salt to boost activity. In WO 2007/068427 A2 and US 2009/0227563 A1, the cyclic ketoenol (whose tautomer is a cyclic dione) can in particular be a 3-(substituted-phenyl)-pyrrolidine-2,4-dione, a 3-(substituted-phenyl)-tetrahydrofuran-2,4-dione, a 3-(substituted-phenyl)-pyran-2,4-dione derivative, a 2-(substituted-phenyl)-cyclopentane-1,3-dione, or a 2-(substituted-phenyl)-cyclohexane-1,3-dione, a 4-(substituted-phenyl)-pyrazolidine-3,5-dione, et al., or a derivative (e.g. ester or carbonate derivative) of these cyclic ketoenols/cyclic diones.

WO 2008/071405 A1 and WO 2009/074314 A1 (both Syngenta Limited and Syngenta Participations AG) each disclose herbicidally active pyran-3,5-diones, thiopyran-3,5-diones and cyclohexane-1,3,5-triones, each substituted at the 4-position of the cyclic dione or trione by an aryl-substituted-phenyl or by a heteroaryl-substituted-phenyl.

WO 2010/081755 A1 and WO 2010/089211 A1 (both Syngenta Limited) each disclose herbicidally active pyran-3,5-diones, thiopyran-3,5-diones, cyclohexanediones, cycloheptanediones and cyclohexanetriones, each substituted by an aryloxy-substituted-phenyl or by a heteroaryloxy-substituted-phenyl.

WO 2008/110308 A1 (Syngenta Participations AG) discloses 2-(substituted-phenyl)-cyclohexane-1,3-dione compounds and derivatives, containing a $R^8$—X—$(CR^6R^7)_n$— substituent (wherein X is O, S, S(O) or S(O)$_2$), which can e.g. be a heteroatom-X-containing-spirocyle, at the 5-position of the cyclohexane-1,3-dione, and having herbicidal properties. WO 2010/081689 A2 (Bayer CropScience AG) discloses the use of 2-(substituted-phenyl)-5-[$R^8$—X—$(CR^6R^7)_n$-]-cyclohexane-1,3-dione compounds or derivatives (i.e. compounds substantially as disclosed in WO 2008/110308) as insecticides and/or acaricides and/or fungicides.

WO 2008/110307 A1 (Syngenta Participations AG) discloses 2-(substituted-phenyl)-5-(carbon-linked-heterocyclyl)-cyclohexane-1,3-dione compounds and derivatives, and their use as herbicides. WO 2010/081687 A1 (Bayer CropScience AG) discloses the use of 2-(substituted-phenyl)-5-(carbon-linked-heterocyclyl)-cyclohexane-1,3-dione compounds or derivatives (i.e. compounds substantially as disclosed in WO 2008/110307) as insecticides and/or acaricides and/or fungicides.

WO 2010/046194 A1 (Syngenta Limited) discloses 2-(substituted-phenyl)-cyclohexane-1,3-dione compounds and derivatives, containing a Q-$CR^6R^7$— substituent at the 5-position of the cyclohexane-1,3-dione (wherein Q is a saturated or mono-unsaturated heterocycle), and having herbicidal properties.

WO 2008/145336 A1 and A8 (Syngenta Limited) disclose herbicidally active phenyl-substituted bicyclic (carbon-bridged, e.g. alkanediyl-bridged) 1,3-dione compounds, such as 3-(substituted-phenyl)-bicyclo[3.2.1]octane-2,4-diones.

Cyclopentane-1,3-dione compounds substituted at the 2-position by substituted-phenyl and having herbicidal activity are described, for example, in WO 2010/000773 A1, WO 2010/069834 A1, WO 2010/089210 A1, WO 2010/102848 A1 and WO 2011/007146 A1 (all Syngenta Limited et al.); and in e.g. WO 01/74770 (Bayer AG). For example, WO 2010/000773 A1 (Syngenta Limited) discloses 5-(heterocyclylalkyl)-3-hydroxy-2-phenylcyclopent-2-en-1-one compounds and certain derivatives thereof as herbicides. WO 2011/073060 A2 (Syngenta Participations AG) discloses a method of combating and controlling insects, acarines, nematodes or moluscs comprising applying a WO 2010/000773 compound. Also, for example, WO 2010/069834 A1 (Syngenta Limited) discloses cyclopentane-1,3-diones having both heteroarylmethyl- and 2-(substituted-phenyl)-substituents on the cyclopentane ring, and derivatives thereof containing latentiating groups; these compounds are disclosed as having herbicidal properties. Fused bicyclic and oxygen-bridged cyclopentanedione derivatives, specifically 10-oxatricyclo-[5.2.1.0$^{2,6}$]decane-3,5-diones and derivatives, which are substituted by substituted-phenyl and which have herbicidal activity, are disclosed in WO 2009/019005 A2 and WO 2009/019015 A1 (both Syngenta Limited). Phenyl-substituted fused bicyclooctane-1,3-dione derivatives, and their use as pesticides and/or herbicides, are disclosed in WO 2010/040460 A2 (Bayer Cropscience AG).

Copending PCT application PCT/EP2012/074118, filed on 30 Nov. 2012 and published on 6 Jun. 2013 as WO 2013/079672 A1 (Syngenta Limited and Syngenta Participations AG) discloses that certain substituted spiroheterocyclic pyrrolidine dione compounds, having an alkynyl-phenyl-headgroup, have herbicidal properties.

Copending PCT application PCT/EP2012/074172, filed on 30 Nov. 2012 and published on 6 Jun. 2013 as WO 2013/079708 A1 (Syngenta Limited and Syngenta Participations AG) discloses cyclopentane-1,3-dione compounds and derivatives (e.g. fused and/or spirocyclic bicyclic derivatives) thereof, which are substituted at the 2-position of the cyclopentane-1,3-dione by a phenyl which itself is substituted at the 4-position by (specifically) either prop-1-ynyl or chloroethynyl and at the 2-position by (specifically) either methyl or chlorine, and derivatives of the enol ketone tautomer of such cyclopentanediones, which have herbicidal activity and/or plant-growth-inhibiting properties, especially in the control of grassy monocotyledonous weeds and/or when used post-emergence.

Certain cyclic 1,3-dione compounds (wherein one carbonyl ring-carbon is defined as being the 1-position of the cycle/ring) and derivatives (e.g. fused such as fused bicyclic derivatives, and/or spirocyclic derivatives) thereof, which are substituted at the 2-position of the cyclic 1,3-dione by a phenyl which itself is substituted at the 4-position by (specifically) either prop-1-ynyl or chloroethynyl and at the 2-position by (specifically) either fluorine or bromine, and derivatives of the enol ketone tautomer of such cyclic 1,3-diones, which have herbicidal activity and/or plant-growth-inhibiting properties, especially in the control of grassy monocotyledonous weeds and/or when used post-emergence, have now been found, which are encompassed by the present invention.

The present invention is based on the finding that cyclic diones of the general formula (I)

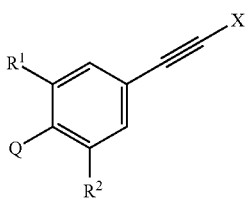

(I)

wherein:
X is methyl or chlorine (preferably methyl);
$R^1$ is fluorine or bromine (preferably fluorine);
$R^2$ is ethynyl, $C_1$-$C_3$alkoxy-, $C_1$-$C_3$haloalkoxy-, or $C_1$-$C_3$alkoxy-$C_1$-$C_3$alkoxy- (preferably —O—$R^{2A}$, wherein $R^{2A}$ is methyl, ethyl, trifluoromethyl, difluoromethyl, trifluoroethyl, or —CH$_2$CH$_2$OCH$_3$; more preferably —O—$R^{2A}$, wherein $R^{2A}$ is methyl, ethyl, trifluoromethyl or difluoromethyl); and
Q is a pyran-3,5-dione-4-yl, a thiopyran-3,5-dione-4-yl, a piperidine-3,5-dione-4-yl, a cyclopentane-1,3-dione-2-yl, a cyclohexane-1,3,5-trione-2-yl, a cyclohexane-1,3-dione-2-yl, or a cycloheptane-1,3-dione-2-yl, or a derivative thereof (e.g. a fused such as fused bicyclic derivative, and/or a spirocyclic derivative, and/or an enol ketone tautomer derivative thereof), wherein Q is as further defined herein, are novel;
and that the exemplified compounds A8, A9, A10 and A16 (and also A14 for SETFA and ZEAMX weeds) within this formula (I) and disclosed herein appear to be potent post-emergent herbicides when used against grassy (in particular warm climate grassy) monocotyledonous weeds, when applied at about 250 g/ha post-emergence (e.g. as shown in Biological Examples 1 and 2 hereinafter).

Also, the results in Biological Example 1A hereinafter appear to show that Compound A14, within the present formula (I), having a 2-fluoro-6-methoxy-4-(prop-1-ynyl)-phenyl moiety attached to the 2-position of a oxygen-containing-spirocyclic cyclohexane-1,3-dione, is a more potent herbicide against the grassy monocotyledonous weeds ALOMY (*Alopecurus myosuroides*) and ZEAMX (*Zea mays*, corn, e.g. volunteer corn), and perhaps also SETFA (*Setaria faberi*), than compound B2 which has a 2-fluoro-6-methoxy-4-ethynyl-phenyl moiety attached to the 2-position of the same oxygen-containing-spirocyclic cyclohexane-1,3-dione, when applied post-emergence at 250 g/ha under the conditions stated in Biological Example 1A.

Also, the exemplified Compound A8 within the present formula (I), e.g. when applied at 30 g/ha post-emergence appear to exhibit a low or reasonably low phytotoxicity against certain docotyledonous crops, in particular soybean and/or sugarbeet (e.g. see Biological Example 2 hereinafter); see also Biological Example 3 for the low phytotoxicity of Compound A8 on soybean. Finally, Compound A8 within the present formula (I) appear to exhibit a medium or reasonably low phytotoxicity against wheat relative to their (generally higher) herbicidal activity (phytotoxicity) against warm-climate grassy monocotyledonous weeds, e.g. when applied post-emergence (e.g. see Biological Example 2 hereinafter).

Thus, in a first aspect of the invention, there is provided a compound of formula (I):

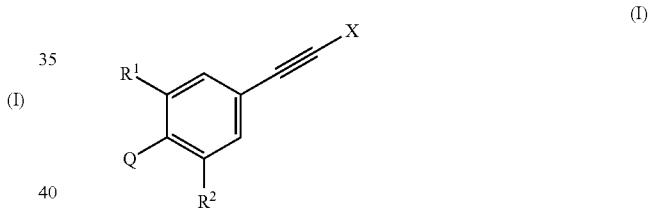

(I)

wherein:
X is methyl or chlorine;
$R^1$ is fluorine or bromine;
$R^2$ is ethynyl, $C_1$-$C_3$alkoxy-, $C_1$-$C_3$haloalkoxy- (in particular $C_1$-$C_3$fluoroalkoxy-), or $C_1$-$C_3$alkoxy-$C_1$-$C_3$alkoxy-;
and Q is a group of either formula Q1 or Q2:

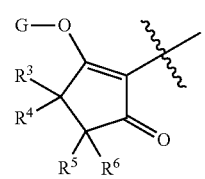

(Q1)

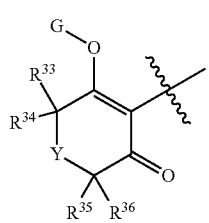

(Q2)

wherein in Q1:

$R^3$, $R^4$ and $R^5$, independently of each other, are hydrogen, $C_1$-$C_5$alkyl (e.g. $C_1$-$C_4$alkyl, e.g. $C_1$-$C_2$alkyl), $C_2$-$C_4$ alkenyl (e.g. $C_2$-$C_3$alkenyl-$CH_2$—, e.g. ethenyl-$CH_2$—), $C_2$-$C_4$alkynyl (e.g. $C_2$-$C_3$alkynyl-$CH_2$—, e.g. ethynyl-$CH_2$—), $C_1$-$C_2$fluoroalkyl or $C_1$-$C_3$alkoxy$C_1$-$C_3$alkyl; and $R^6$ is hydrogen; $C_1$-$C_5$alkyl (in particular $C_1$-$C_4$alkyl, e.g. $C_1$-$C_2$alkyl); $C_2$-$C_4$ alkenyl (in particular $C_2$-$C_3$alkenyl-$CH_2$—, e.g. ethenyl-$CH_2$—); $C_2$-$C_4$alkynyl (preferably $C_2$-$C_3$alkynyl-$CH_2$—, more preferably ethynyl-$CH_2$—); $R^{6AA}$C≡C—$CH_2$—; $C_1$-$C_2$fluoroalkyl; $C_1$-$C_3$alkoxy$C_1$-$C_3$alkyl; $C_1$-$C_3$alkylthio$C_1$-$C_3$alkyl; $C_1$-$C_3$alkylsulfinyl$C_1$-$C_3$alkyl; $C_1$-$C_3$alkylsulfonyl$C_1$-$C_3$alkyl; $C_3$-$C_4$cycloalkyl (in particular cyclopropyl); or an unsubstituted 4, 5 or 6 (in particular 4 or 5) membered monocyclic heterocyclyl having one ring heteroatom independently selected from oxygen, sulfur and nitrogen, and attached at a ring carbon atom within the heterocyclyl (preferably tetrahydrofuranyl such as tetrahydrofuran-3-yl, or tetrahydropyranyl such as tetrahydropyran-4-yl);

or $R^6$ is T-$(CH_2)_m$—$CH(R^7)$—, wherein m is 0 or 1 (preferably m is 0), and either $R^7$ is hydrogen or $R^7$ and $R^5$ together are a bond, and T is an optionally substituted heterocyclyl as defined below;

or $R^6$ is Het-$CH(R^8)$—, wherein either $R^8$ is hydrogen or $R^8$ and $R^5$ together are a bond, and Het is an optionally substituted heteroaryl as defined below;

or $R^6$ is $C_3$-$C_6$cycloalkyl$C_1$-$C_2$alkyl- (in particular $C_3$-$C_6$cycloalkylmethyl-); or is $C_4$-$C_6$cycloalkyl$C_1$-$C_2$alkyl- (in particular $C_4$-$C_6$cycloalkylmethyl-) substituted, at a cycloalkyl ring-carbon atom which is not the ring-carbon atom attached to the —$C_1$-$C_2$alkyl- moiety and which is not bonded directly to the ring-carbon atom attached to the —$C_1$-$C_2$alkyl- moiety, by one or two ring substituents which independently are: =N—O—$R^{10}$, oxo (=O), $C_1$-$C_4$alkoxy, $C_1$-$C_2$haloalkoxy, 2-($C_1$-$C_3$alkoxy)-ethoxy, $C_3$-$C_5$cycloalkyloxy, ($C_3$-$C_5$cycloalkyl)methoxy, $C_2$-$C_3$alkenyl-$CH_2$-oxy, $C_1$-$C_3$alkyl or $C_1$-$C_2$fluoroalkyl; or benzyloxy in which the phenyl ring is optionally substituted by one or two substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, S(O)$R^{6E}$, S(O)$_2R^{6E}$, —S(O)$_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro;

or $R^6$ is benzyl optionally substituted on its phenyl ring by one or two substituents which independently are: $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, S(O)$R^{6E}$, S(O)$_2R^{6E}$, —S(O)$_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro, or $R^3$ and $R^4$ taken together are —$(CH_2)_{n1}$— or —$(CH_2)_{n2}$—$X^1$—$(CH_2)_{n3}$— and $R^5$ and $R^6$ are as defined herein (e.g. hereinabove), or $R^5$ and $R^6$ taken together are —$(CH_2)_{n1}$— or —$(CH_2)_{n2}$—$X^1$—$(CH_2)_{n3}$— and $R^3$ and $R^4$ are as defined herein (e.g. hereinabove);

or $R^4$ and $R^6$ taken together are —C($R^{11}$)($R^{12}$)—C($R^{13}$)($R^{14}$)—C($R^{15}$)($R^{16}$)—C($R^{17}$)($R^{18}$)—, —C($R^{11}$)($R^{12}$)—C($R^{13}$)=C($R^{15}$)—C($R^{17}$)($R^{18}$)— or —CH($R^{19}$)—C($R^{20}$)($R^{21}$)—CH($R^{22}$)—;

T is a 4 to 7 membered monocyclic or an 8 to 11 membered fused bicyclic heterocyclyl, having one or two ring heteroatoms independently selected from oxygen, sulfur and nitrogen; and wherein the heterocyclyl T is optionally substituted by 1 or 2 ring-carbon substituents independently being $C_1$-$C_3$alkyl (preferably $C_1$-$C_2$alkyl), $C_1$-$C_2$fluoroalkyl (preferably $C_1$fluoroalkyl), —$SC_1$-$C_3$alkyl, —S(O)$C_1$-$C_3$ alkyl, —S(O)$_2C_1$-$C_3$alkyl, or oxo (=O), and/or is optionally substituted by one $C_1$-$C_4$alkyl, $C_1$-$C_2$fluoroalkyl, $C_1$-$C_4$alkoxy, $C_1$-$C_2$fluoroalkoxy; or a $R^9$—C(O)— or a $C_1$-$C_2$alkyl-S(O)$_2$— substituent on a ring nitrogen if present, and/or is optionally substituted by one or two oxo (=O) substituents on a ring sulfur if present; and wherein Het is a heteroaryl, attached at a ring-carbon, which is optionally substituted by 1, 2 or 3 (preferably 1 or 2, more preferably 1) ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, S(O)$R^{6E}$, S(O)$_2R^{6E}$, —S(O)$_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

wherein:

$R^{6AA}$ is $C_1$fluoroalkyl (preferably trifluoromethyl), fluorine, chlorine or bromine;

$R^{6B}$, $R^{6C}$ and $R^{6CC}$ independently are hydrogen, methyl, $C_1$fluoroalkyl (preferably trifluoromethyl), fluorine or chlorine; provided that $R^{6B}$, $R^{6C}$ and $R^{6CC}$ in total contain no more than one carbon atom, and $R^{6B}$, $R^{6C}$ and $R^{6CC}$ in total comprise no more than one chlorine; and $R^{6BB}$, $R^{6C1}$ and $R^{6C2}$ independently are hydrogen, methyl, $C_1$fluoroalkyl (preferably trifluoromethyl), fluorine or chlorine; provided that $R^{6BB}$, $R^{6C1}$ and $R^{6C2}$ in total contain no more than one carbon atom, and $R^{6BB}$, $R^{6C1}$ and $R^{6C2}$ in total comprise no more than one chlorine; and provided that —C($R^{6BB}$)=C($R^{6C1}$)($R^{6C2}$) is not $C_2$-$C_3$alkenyl; and $R^{6D}$ and $R^{6E}$ independently are $C_1$-$C_3$alkyl (preferably $C_1$-$C_2$alkyl such as methyl), $C_1$fluoroalkyl (preferably trifluoromethyl), or —N($R^{6H}$)($R^{6J}$);

$R^{6F}$ is —C(O)—$C_1$-$C_2$alkyl (preferably —C(O)—methyl), —C(O)—$C_1$fluoroalkyl (preferably —C(O)— trifluoromethyl), —S(O)$_2$—$C_1$-$C_2$alkyl (preferably —S(O)$_2$-methyl), —S(O)$_2$—$C_1$fluoroalkyl (preferably —S(O)$_2$-trifluoromethyl), $C_1$-$C_2$alkyl (preferably methyl), or $C_1$fluoroalkyl (preferably trifluoromethyl);

$R^{6G}$ and $R^{6J}$ independently are hydrogen, methyl or $C_1$fluoroalkyl (preferably trifluoromethyl); and $R^{6H}$ is hydrogen, $C_1$-$C_2$alkyl (preferably methyl), or $C_1$fluoroalkyl (preferably trifluoromethyl);

and wherein $R^9$ is $C_1$-$C_4$alkyl (e.g. methyl, ethyl, n-propyl, isopropyl or n-butyl), $C_2$-$C_4$alkenyl attached at a carbon atom partaking in the C=C double bond (e.g. $Me_2C$=CH—), $C_1$-$C_2$fluoroalkyl (e.g. $CF_3$ or $CHF_2CF_2$—), $C_1$-$C_2$alkoxymethyl- (e.g. methoxymethyl-), $C_1$-$C_3$alkoxy (e.g. methoxy), cyclopropyl, furanyl (e.g. furan-2-yl or furan-3-yl), morpholin-4-yl, isoxazol-3-yl, 5-methyl-isoxazol-3-yl, pyrazol-5-yl, 3-methylpyrazol-5-yl, 1-methylpyrazol-5-yl, 1,3-dimethylpyrazol-5-yl; or phenyl or phenyl substituted by 1 or 2 substituents independently being methyl, ethyl, $C_1$fluoroalkyl, methoxy, $C_1$fluoroalkoxy, fluorine, chlorine, $SC_1$-$C_3$alkyl (preferably SMe), $S(O)C_1$-$C_3$alkyl (preferably S(O)Me) or $S(O)_2C_1$-$C_3$alkyl (preferably $S(O)_2$Me);

wherein $R^{10}$ is hydrogen, $C_1$-$C_4$alkyl (e.g. methyl), $C_1$-$C_2$fluoroalkyl, 2-($C_1$-$C_3$alkoxy)-ethyl, $C_3$-$C_5$cycloalkyl or ($C_3$-$C_5$cycloalkyl)methyl;

wherein $X^1$ is O, S, S(O), $S(O)_2$, NH, $N(C_1$-$C_3$alkyl), $N(C_1$-$C_3$alkoxy), $C(H)(C_1$-$C_2$alkyl), $C(C_1$-$C_2$alkyl)$_2$, $C(H)(C_1$-$C_3$alkoxy) or $C(Me)(C_1$-$C_2$alkoxy); and n1 is 2, 3, 4 or 5 (e.g. 3, 4 or 5); and n2 and n3 are independently 1, 2 or 3 provided that n2+n3 is 2, 3 or 4;

wherein: $R^{11}$ and $R^{18}$ are both hydrogen, or $R^{11}$ and $R^{18}$ are taken together and form an —O— or —$C_1$-$C_2$alkylene-bridge; and $R^{12}$ and $R^{17}$ are independently hydrogen, $C_1$-$C_3$alkyl or $C_1$-$C_2$alkoxy$C_1$-$C_2$alkyl; $R^{13}$, $R^{14}$ and $R^{15}$ are independently hydrogen, $C_1$-$C_3$alkyl or $C_1$-$C_2$alkoxy$C_1$-$C_2$alkyl, provided that one, two or all of $R^{13}$, $R^{14}$ and $R^{15}$ are hydrogen; and $R^{16}$ is hydrogen; $C_1$-$C_3$alkyl; $C_1$-$C_2$alkoxy$C_1$-$C_2$alkyl; phenyl optionally substituted by 1, 2 or 3 (in particular 1 or 2) of, independently, being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, $S(O)R^{6E}$, $S(O)_2R^{6E}$, —$S(O)_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro; or a 5-membered or 6-membered heteroaryl, attached at a ring-carbon and optionally substituted by 1, 2 or 3 (in particular 1 or 2) ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, $S(O)R^{6E}$, $S(O)_2R^{6E}$, —$S(O)_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro;

and wherein:

$R^{19}$ and $R^{22}$ are independently hydrogen, $C_1$-$C_3$alkyl or $C_1$-$C_2$alkoxy$C_1$-$C_2$alkyl; and $R^{20}$ and $R^{21}$ are independently hydrogen, $C_1$-$C_3$alkyl or $C_1$-$C_2$alkoxy$C_1$-$C_2$alkyl;

or $R^{20}$ and $R^{21}$ taken together are oxo (=O), =N—O—$R^{10}$, or =$CH_2$;

or $R^{20}$ and $R^{21}$, together with the carbon atom to which they are attached, form a 5, 6 or 7 (in particular 5 or 6) membered saturated heterocyclyl, wherein the heterocyclyl has two ring heteroatoms independently being oxygen or sulfur and which are not directly bonded to each other, and wherein the heterocyclyl is optionally substituted by 1, 2 or 3 (e.g. 1 or 2) ring-carbon substituents independently being $C_1$-$C_2$alkyl (e.g. methyl);

and wherein in Q2:

$R^{33}$, $R^{34}$, $R^{35}$ and $R^{36}$, independently of each other, are hydrogen, $C_1$-$C_5$alkyl (in particular $C_1$-$C_4$alkyl, e.g. $C_1$-$C_2$alkyl), $C_2$-$C_4$ alkenyl (in particular $C_2$-$C_3$alkenyl-$CH_2$—, e.g. ethenyl-$CH_2$—), $C_2$-$C_4$ alkynyl (in particular $C_2$-$C_3$alkynyl-$CH_2$—, e.g. ethynyl-$CH_2$—), $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl; $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, said heterocyclyl being attached at a ring carbon atom within the heterocyclyl (in particular tetrahydrofuranyl such as tetrahydrofuran-3-yl, or tetrahydropyranyl such as tetrahydropyran-4-yl);

provided that no more than one (in particular none) of $R^{33}$, $R^{34}$, $R^{35}$ and $R^{36}$ is alkenyl, alkynyl, alkoxyalkyl, alkylthioalkyl, alkylsulfinylalkyl, alkylsulfonylalkyl, cycloalkyl or heterocyclyl;

or $R^{33}$ and $R^{34}$ taken together are —($CH_2$)$_{n31}$— or —($CH_2$)$_{n32}$—$X^{31}$—($CH_2$)$_{n33}$— and $R^{35}$ and $R^{36}$ are as defined herein (e.g. hereinabove), or $R^{35}$ and $R^{36}$ taken together are —($CH_2$)$_{n31}$— or —($CH_2$)$_{n32}$—$X^{31}$—($CH_2$)$_{n33}$— and $R^{33}$ and $R^{34}$ are as defined herein (e.g. hereinabove);

wherein $X^{31}$ is O, S, S(O), $S(O)_2$, NH, $N(C_1$-$C_2$alkyl), $N(C_1$-$C_2$alkoxy), $C(H)(C_1$-$C_2$alkyl), $C(C_1$-$C_2$alkyl)$_2$ or $C(H)(C_1$-$C_2$alkoxy);

n31 is 2, 3, 4 or 5 (in particular 4 or 5); and n32 and n33 are independently 1, 2 or 3 provided that n32+n33 is 2, 3 or 4 (in particular 3 or 4);

or $R^{34}$ and $R^{35}$ taken together are —C($R^{37c}$)=C($R^{37d}$)—;

wherein $R^{37c}$ and $R^{37d}$ independently are hydrogen or $C_1$-$C_2$alkyl; and Y is O, S, S(O), $S(O)_2$, $N(C_1$-$C_2$alkyl), $N(C_1$-$C_2$alkoxy), C(O), $CR^{38}R^{39}$ or —$CR^{310}R^{311}CR^{312}R^{313}$—; and $R^{38}$ and $R^{39}$ are, independently of each other: hydrogen, $C_1$-$C_6$alkyl (in particular $C_1$-$C_4$alkyl, e.g. $C_1$-$C_2$alkyl), $C_2$-$C_4$alkenyl (in particular $C_2$-$C_3$alkenyl-$CH_2$—, e.g. ethenyl-$CH_2$—), $C_2$-$C_4$alkynyl (in particular $C_2$-$C_3$alkynyl-$CH_2$—, e.g. ethynyl-$CH_2$—), $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl; $C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl, and in which one ring $CH_2$ moiety of a $C_4$-$C_6$cycloalkyl is optionally (e.g. preferably) replaced by an oxygen or sulfur atom or by a S(O), $S(O)_2$, NH, $N(C_1$-$C_3$alkyl), $N(C_1$-$C_2$fluoroalkyl), $N[C(O)C_1$-$C_3$alkyl], $N[C(O)C_1$-$C_2$fluoroalkyl] or $N(C_1$-$C_2$alkoxy) moiety; $C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl); $C_5$-$C_6$cycloalkenyl or $C_5$-$C_6$cycloalkenyl substituted by one or two $C_1$-$C_3$alkyl (in particular methyl) substituents; $C_3$-$C_6$cycloalkyl$C_1$-$C_2$alkyl- (in particular $C_3$-$C_6$cycloalkylmethyl-) or $C_3$-$C_6$cycloalkyl$C_1$-$C_2$alkyl- (in particular $C_3$-$C_6$cycloalkylmethyl-) substituted by one or two ring substituents which independently are $C_1$-$C_3$alkyl or $C_1$-$C_2$fluoroalkyl, and in which one ring $CH_2$ moiety of a $C_4$-$C_6$cycloalkyl$C_1$-$C_2$alkyl- (in particular $C_4$-$C_6$cycloalkylmethyl-) is optionally (e.g. preferably) replaced by an oxygen or sulfur atom or by a S(O), $S(O)_2$, NH, $N(C_1$-$C_2$alkyl), $N(C_1$-$C_2$fluoroalkyl), $N[C(O)C_1$-$C_3$alkyl], $N[C(O)C_1$-$C_2$fluoroalkyl] or $N(C_1$-$C_2$alkoxy) moiety; $C_3$-$C_6$cycloalkyl$C_1$-$C_2$alkyl- (in particular $C_3$-$C_6$cycloalkylmethyl-) substituted by one ring substituent being $C_1$-$C_3$alkoxy (in particular $C_1$-$C_2$alkoxy) and optionally further substituted by one ring substituent being $C_1$-$C_2$alkyl (in particular methyl); or HetA or HetA-$CH_2$—;

wherein HetA is a heteroaryl, attached at a ring-carbon, which is optionally substituted by 1, 2 or 3 (in particular 1 or 2, e.g. 1) ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, $S(O)R^{6E}$, —$S(O)_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

provided that no more than one of $R^{38}$ and $R^{39}$ is an optionally substituted cycloalkyl; an optionally substituted cycloalkyl in which one ring $CH_2$ moiety has been replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl; an optionally substituted cycloalkyl-alkyl-; an optionally substituted cycloalkyl-alkyl- in which one ring $CH_2$ moiety has been replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; or HetA or HetA-$CH_2$—;

or $R^{38}$ is hydrogen or $C_1$-$C_2$alkyl (in particular H or Me), and $R^{39}$ is $C_1$-$C_2$alkoxy (in particular methoxy);

or $R^{38}$ and $R^{39}$ taken together are —(CH$_2$)$_{n37}$— or —(CH$_2$)$_{n38}$—X$^{32}$—(CH$_2$)$_{n39}$—;

wherein X$^{32}$ is O, S, S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl], N($C_1$-$C_2$alkoxy), C(H)($C_1$-$C_3$alkyl), C($C_1$-$C_2$alkyl)$_2$ or C(H)($C_1$-$C_3$alkoxy);

n37 is 2, 3, 4, 5 or 6 (in particular 4 or 5); and n38 and n39 are independently 0, 1, 2 or 3 provided that n38+n39 is 2, 3, 4 or 5 (in particular 3 or 4); and $R^{310}$, $R^{311}$, $R^{312}$ and $R^{313}$ are independently of each other hydrogen or $C_1$-$C_4$alkyl (in particular $C_1$-$C_2$alkyl) provided that no more than one of $R^{310}$, $R^{311}$, $R^{312}$ and $R^{313}$ is $C_3$-$C_4$alkyl;

and wherein:

$R^{6AA}$, $R^{6BB}$, $R^{6C1}$, $R^{6C2}$, $R^{6E}$, $R^{6F}$, $R^{6G}$, $R^{6H}$ and $R^{6J}$ are as defined hereinabove for when Q is Q1; and and wherein in Q1 or Q2:

G is hydrogen; an agriculturally acceptable metal, or an agriculturally acceptable sulfonium or ammonium group; or G is —C(X$^a$)—R$^a$, —C(X$^b$)—X$^c$—R$^b$, —C(X$^d$)—N(R$^c$)—R$^d$, —SO$_2$—R$^e$, —P(X$^e$)(R$^f$)—R$^g$, —CH$_2$—X$^f$—R$^h$; or phenyl-CH$_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-CH$_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—CH$_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—CH$_2$—, $C_1$-$C_6$alkoxy-C(O)—CH=CH—, $C_2$-$C_7$alken-1-yl-CH$_2$—, $C_2$-$C_7$alken-1-yl-CH($C_1$-$C_2$alkyl)-, $C_2$-$C_4$fluoroalken-1-yl-CH$_2$—, $C_2$-$C_7$alkyn-1-yl-CH$_2$—, or $C_2$-$C_7$alkyn-1-yl-CH($C_1$-$C_2$alkyl)-;

wherein X$^a$, X$^b$, X$^c$, X$^d$, X$^e$ and X$^f$ are independently of each other oxygen or sulfur (in particular oxygen); and wherein R$^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro;

R$^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and R$^c$ and R$^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, form an unsubstituted 4, 5, 6 or 7 (e.g. 5 or 6) membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

and wherein "heteroaryl" means an aromatic ring system containing at least one ring heteroatom and consisting either of a single ring or of two fused rings;

and wherein the compound of formula (I) is optionally present (e.g. where chemically possible) as an agrochemically acceptable salt thereof.

In the substituent definitions of the compounds of the formula I, each alkyl moiety either alone or as part of a larger group (such as alkoxy, alkylthio, alkoxycarbonyl, alkylcarbonyl, alkylaminocarbonyl, or dialkylaminocarbonyl, et al.) can be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups can e.g. be $C_1$-$C_6$alkyl groups (except where already defined more narrowly), but are preferably $C_1$-$C_4$alkyl or $C_1$-$C_3$alkyl groups (except where already defined more narrowly), and, more preferably, are $C_1$-$C_2$alkyl groups such as methyl.

Alkenyl and alkynyl moieties can be in the form of straight or branched chains, and the alkenyl moieties, where appropriate, can be of either the (E)- or (Z)-configuration. The alkenyl or alkynyl are typically $C_2$-$C_3$alkenyl or $C_2$-$C_3$alkynyl such as vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Halogen is fluorine, chlorine, bromine or iodine. Preferred halogens are fluorine, chlorine or bromine.

Fluoroalkyl groups are alkyl groups which are substituted with one or more (e.g. 1, 2, 3, 4 or 5; in particular 1, 2 or 3; e.g. 1 or 2) fluorine atoms. Fluoroalkyl is typically $C_1$-$C_3$fluoroalkyl or $C_1$-$C_2$fluoroalkyl (preferably $C_1$fluoroalkyl), such as $CF_3$, $CHF_2$, $CH_2F$, $CH_3CHF$—, $CF_3CH_2$—, $CHF_2CH_2$—, $CH_2FCH_2$—, $CHF_2CF_2$— or $(CH_3)_2CF$—. Fluoroalkoxy is typically $C_1$-$C_3$fluoroalkoxy or $C_1$-$C_2$fluoroalkoxy (preferably $C_1$fluoroalkoxy), such as $CF_3O$, $CHF_2O$, $CH_2FO$, $CH_3CHFO$—, $CF_3CH_2O$—, $CHF_2CH_2O$— or $CH_2FCH_2O$—.

In the context of the present specification the term "aryl" means phenyl or naphthyl. A preferred aryl group is phenyl.

The term "heteroaryl" as used herein means an aromatic ring system containing at least one ring heteroatom and consisting either of a single ring or of two fused rings. Preferably, single heteroaryl rings will contain 1, 2 or 3 ring heteroatoms and/or bicyclic heteroaryl systems will contain 1, 2, 3 or 4 ring heteroatoms, each of which will preferably be selected from nitrogen, oxygen and sulfur. Typically, a "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; optionally present, where chemically possible, as an agrochemically acceptable salt thereof.

The term "heterocyclyl" as used herein, except where explicitly stated otherwise, means a 4, 5, 6 or 7 (in particular 5, 6 or 7) membered monocyclic organic ring or a 8, 9, 10 or 11 (in particular 8, 9 or 10) membered fused bicyclic organic ring system, which is fully saturated, and which has one or two (preferably one) ring heteroatoms independently selected from oxygen, sulfur and nitrogen. Where the heterocyclyl has two ring heteroatoms, preferably, the two ring heteroatoms are separated by at least two ring carbon atoms. Preferably, the heterocyclyl is attached at a ring carbon atom within the heterocyclyl. In particular, the heterocyclyl can be tetrahydrofuranyl, tetrahydropyranyl, tetrahydrothiophenyl, 1,4-dioxanyl, 1,4-dithianyl, morpholinyl, thiomorpholinyl, pyrrolidinyl, piperidinyl or piperazinyl; more particularly tetrahydrofuranyl (e.g. tetrahydrofuran-2-yl or particularly tetrahydrofuran-3-yl), tetrahydropyranyl (e.g. tetrahydropyran-2-yl, tetrahydropyran-3-yl or particularly tetrahydropyran-4-yl), morpholinyl, pyrrolidinyl (e.g. pyrrolidin-2-yl or particularly pyrrolidin-3-yl), piperidinyl (e.g. piperidin-2-yl, piperidin-3-yl or particularly piperidin-4-yl) or piperazinyl. In a particular embodiment, the heterocyclyl, when optionally substituted, is optionally substituted by 1 or 2 (e.g. 1) ring-carbon substituents independently being $C_1$-$C_3$alkyl (e.g. $C_1$-$C_2$alkyl), $C_1$-$C_2$fluoroalkyl or oxo (=O), and/or is optionally substituted by one $C_1$-$C_3$alkyl (e.g. $C_1$-$C_2$alkyl), $C_1$-$C_2$fluoroalkyl or $C_1$-$C_3$alkoxy (e.g. $C_1$-$C_2$alkyl or $C_1$-$C_2$fluoroalkyl) substituent on a ring nitrogen if present, and/or is optionally substituted by one or two oxo (=O) substituents on a ring sulfur if present.

Preferably, a cycloalkyl is cyclopropyl, cyclobutyl, cyclopentyl or cyclohexyl. (Cycloalkyl)alkyl is preferably (cycloalkyl)methyl such as ($C_3$-$C_6$cycloalkyl)methyl in particular cyclopropylmethyl. Preferably, cycloalkenyl is cyclopentenyl or cyclohexenyl.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula $[N(R_a R_b R_c R_d)]OH$, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_e R_f R_g]OH$, wherein $R_e$, $R_f$ and $R_g$ are each independently of the others $C_1$-$C_4$alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups (i.e. leaving or removeable groups) within G (for example, without limitation, the latentiating groups where G is —C($X^a$)—$R^a$ or —C($X^b$)—$X^c$—$R^b$, et al.) are generally selected to allow their removal, typically by one or a combination of biochemical, chemical or physical processes, to afford the corresponding compound of formula (I) where G is H, before, during or following (preferably during or following) application of the compound of formula (I) to the treated area (e.g. field) or to plants. Examples of these processes include enzymatic cleavage or other in/on-plant cleavage (e.g. cleavage of ester, carbonate and/or thiocarbonate moieties), chemical hydrolysis, and/or photoloysis. Some compounds bearing such groups G occasionally offer certain advantages or different technical properties, such as improved and/or more consistent and/or different penetration of the cuticula of the plants treated, increased and/or different tolerance (non-phytotoxicity) on certain crops, improved and/or different compatibility or stability in formulated mixtures containing other herbicides, herbicide safeners, plant growth regulators, fungicides or insecticides, or reduced and/or different leaching properties in soils.

The preferred, suitable and/or particular values of the substituents in or other features of the compound of formula (I), in particular G, X, Y, $R^1$, $R^2$, $R^{2A}$, $R^{6AA}$, $R^{6BB}$, $R^{6C1}$, $R^{6C2}$, $R^{6D}$, $R^{6E}$, $R^{6F}$, $R^{6G}$, $R^{6H}$, $R^{6J}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{33}$, $R^{34}$, $R^{35}$, $R^{36}$, $R^{37}$, $R^{37c}$, $R^{37d}$, $R^{38}$, $R^{39}$, $R^{310}$, $R^{311}$, $R^{312}$, $R^{313}$, $R^a$, $R^b$, $R^c$, $R^d$, $R^e$, $R^f$, $R^g$, $R^h$, $X^a$, $X^b$, $X^c$, $X^d$, $X^e$, $X^f$, Q, T, V, Het, HetA, $X^1$, $X^{31}$, $X^{32}$, n1, n2, n3, n31, n32, n33, n37, n38, and/or n39, are set out below (and/or generally herein), and can be either taken alone or taken together with one or more of any other preferred, suitable and/or particular features in any combination(s) thereof. In this paragraph, "preferred" is intended to encompass more preferred, even or still or yet more preferred, particularly or highly preferred, most preferred and all similar terms. For the avoidance of doubt, preferred, suitable and/or particular features can be combined together with preferred, suitable and/or particular features with different levels of ranking (e.g. with different levels of preference).

In one particular embodiment of the invention, X is chlorine. However, in the present invention, most preferably, X is methyl.

In the present invention, most preferably, $R^1$ is fluorine. In a further preferable embodiment of the invention, $R^1$ is bromine.

Therefore, most preferably, X is methyl, and $R^1$ is fluorine, for all aspects and/or embodiments of the invention. In an alternative, also highly preferable, embodiment of the invention (which e.g. can apply to all aspects and/or embodiments of the invention), X is methyl, and $R^1$ is bromine.

As described above, $R^2$ is ethynyl, $C_1$-$C_3$alkoxy-, $C_1$-$C_3$haloalkoxy- (in particular $C_1$-$C_3$fluoroalkoxy-), or $C_1$-$C_3$alkoxy-$C_1$-$C_3$alkoxy-.

In one embodiment, $R^2$ is ethynyl.

Preferably, $R^2$ is —O—$R^{2A}$, wherein $R^{2A}$ is $C_1$-$C_3$alkyl, $C_1$-$C_3$haloalkyl (in particular $C_1$-$C_3$fluoroalkyl), or $C_1$-$C_3$alkoxy-$C_1$-$C_3$alkyl-. Where $R^{2A}$ is $C_1$-$C_3$alkyl, $R^{2A}$ being methyl or ethyl is preferred. Where $R^{2A}$ is $C_1$-$C_3$haloalkyl, $R^{2A}$ being $C_1$-$C_3$fluoroalkyl is preferred (more preferably $C_1$-$C_2$fluoroalkyl, even more preferably $C_1$fluoroalkyl). Where $R^{2A}$ is $C_1$-$C_3$haloalkyl or $C_1$-$C_3$fluoroalkyl, more specifically, $R^{2A}$ being trifluoromethyl, difluoromethyl, or trifluoroethyl (e.g. 2,2,2-trifluoroethyl) is especially preferred, most particularly trifluoromethyl or difluoromethyl. Where $R^{2A}$ is $C_1$-$C_3$alkoxy-$C_1$-$C_3$alkyl-, —$CH_2CH_2OCH_3$ (i.e. 2-methoxyethyl-) is preferred. In these preferred embodiments, preferably $R^1$ is fluorine and/or X is methyl.

Therefore, more preferably, in all aspects and/or embodiments of the invention, $R^2$ is $-O-R^{2A}$, wherein $R^{2A}$ is methyl, ethyl, $C_1$-$C_2$fluoroalkyl (in particular trifluoromethyl, difluoromethyl, or trifluoroethyl such as 2,2,2-trifluoroethyl), or $-CH_2CH_2OCH_3$ (i.e. 2-methoxyethyl-). In this more preferred embodiment, preferably $R^1$ is fluorine and/or X is methyl.

Even more preferably, in all aspects and/or embodiments of the invention, $R^2$ is $-O-R^{2A}$, wherein $R^{2A}$ is methyl, ethyl or $C_1$fluoroalkyl, in particular methyl, ethyl, trifluoromethyl or difluoromethyl. In these even more preferred embodiments, preferably $R^1$ is fluorine and/or X is methyl.

Most preferably, in all aspects and/or embodiments of the invention, $R^2$ is $-O-R^{2A}$, wherein $R^{2A}$ is methyl. In this most preferred embodiment, preferably $R^1$ is fluorine and/or X is methyl.

Therefore, most preferably, in all aspects and/or embodiments of the invention, X is methyl, $R^1$ is fluorine, and $R^2$ is $-O-R^{2A}$ wherein $R^{2A}$ is methyl.

Preferably, e.g. in all aspects and/or embodiments of the invention, G is hydrogen; an agriculturally acceptable metal (e.g. an agriculturally acceptable alkali metal or alkaline earth metal, e.g. lithium, sodium, potassium, magnesium or calcium), or an agriculturally acceptable sulfonium or ammonium group; or G is $-C(X^a)-R^a$, $-C(X^b)-X^c-R^b$, $-SO_2-R^e$, or $-CH_2-X^f-R^h$; wherein $X^a$, $X^b$, $X^c$, $X^f$, $R^a$, $R^b$, $R^e$ and $R^h$ are as defined herein.

More preferably, e.g. in all aspects and/or embodiments of the invention, G is hydrogen; an agriculturally acceptable metal (e.g. an agriculturally acceptable alkali metal or alkaline earth metal, e.g. lithium, sodium, potassium, magnesium or calcium), or an agriculturally acceptable sulfonium or ammonium group; or G is $-C(X^a)-R^a$ or $-C(X^b)-X^c-R^b$, wherein $X^a$, $R^a$, $X^b$, $X^c$ and $R^b$ are as defined herein.

In a particular embodiment, G is a group $-C(X^a)-R^a$ or $-C(X^b)-X^c-R^b$, wherein $X^a$, $R^a$, $X^b$, $X^c$ and $R^b$ are as defined herein.

Preferably, e.g. in all aspects and/or embodiments of the invention, $X^a$, $X^b$, $X^c$, $X^d$, $X^e$ and/or $X^f$ are oxygen; and/or $X^c$ is sulfur.

More preferably, $X^a$, $X^b$, $X^d$, $X^e$ and $X^f$ are oxygen; and $X^c$ is oxygen or sulfur. Even more preferably, $X^a$, $X^b$, $X^c$, $X^d$, $X^e$ and $X^f$ are oxygen.

Preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl. Alternatively, preferably, $R^a$ is $C_3$-$C_7$cycloalkyl$C_1$alkyl; or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro; or heteroaryl or heteroaryl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), or cyano (in which the heteroaryl preferably consists of a single ring).

More preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, $C_1$-$C_4$alkoxy$C_1$-$C_4$alkyl, $C_3$-$C_7$cycloalkyl$C_1$alkyl; or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro.

Preferably, $R^b$ is $C_1$-$C_{10}$alkyl (e.g. $C_1$-$C_6$alkyl), $C_2$-$C_5$alkenyl-$CH_2-$ (e.g. $C_2$-$C_3$alkenyl-$CH_2-$), $C_2$-$C_4$alkenyl-$CH(Me)$- (e.g. $C_2$-$C_3$alkenyl-$CH(Me)$-), $C_2$-$C_5$alkynyl-$CH_2-$ (e.g. $C_2$-$C_3$alkynyl-$CH_2-$), $C_2$-$C_4$alkynyl-$CH(Me)$- (e.g. $C_2$-$C_3$alkynyl-$CH(Me)$-), $C_3$-$C_6$cycloalkyl or $C_1$-$C_4$alkoxy$C_1$-$C_4$alkyl. Alternatively, preferably, $R^b$ is $C_3$-$C_7$cycloalkyl$C_1$alkyl; or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro; or heteroaryl or heteroaryl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), or cyano (in which the heteroaryl preferably consists of a single ring).

More preferably, $R^b$ is $C_1$-$C_{10}$alkyl (e.g. $C_1$-$C_6$alkyl), $C_2$-$C_5$alkenyl-$CH_2-$ (e.g. $C_2$-$C_3$alkenyl-$CH_2-$), $C_2$-$C_4$alkenyl-$CH(Me)$- (e.g. $C_2$-$C_3$alkenyl-$CH(Me)$-), $C_2$-$C_5$alkynyl-$CH_2-$ (e.g. $C_2$-$C_3$alkynyl-$CH_2-$), $C_2$-$C_4$alkynyl-$CH(Me)$- (e.g. $C_2$-$C_3$alkynyl-$CH(Me)$-), $C_3$-$C_6$cycloalkyl, $C_1$-$C_4$alkoxy$C_1$-$C_4$alkyl, $C_3$-$C_7$cycloalkyl$C_1$alkyl; or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro.

Preferably, $R^e$ is $C_1$-$C_{10}$alkyl (e.g. $C_1$-$C_6$alkyl or $C_1$-$C_4$alkyl), $C_1$-$C_{10}$fluoroalkyl (e.g. $C_1$-$C_3$fluoroalkyl); or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro.

Preferably, $R^h$ is $C_1$-$C_{10}$alkyl (e.g. $C_1$-$C_6$alkyl or $C_1$-$C_4$alkyl), $C_1$-$C_{10}$fluoroalkyl (e.g. $C_1$-$C_3$fluoroalkyl) or $C_1$-$C_6$alkyl-$C(O)-$ (e.g. $C_1$-$C_4$alkyl-$C(O)-$). In particular, $R^e$ is $C_1$-$C_{10}$alkyl (e.g. $C_1$-$C_6$alkyl or $C_1$-$C_4$alkyl).

When G is $-C(X^a)-R^a$ or $-C(X^b)-X^c-R^b$, then preferably $X^a$ and $X^b$ are oxygen, and $X^c$ is oxygen or sulfur, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl; and $R^b$ is $C_1$-$C_{10}$alkyl (e.g. $C_1$-$C_6$alkyl), $C_2$-$C_5$alkenyl-$CH_2-$ (e.g. $C_2$-$C_3$alkenyl-$CH_2-$), $C_2$-$C_4$alkenyl-$CH(Me)$- (e.g. $C_2$-$C_3$alkenyl-$CH(Me)$-), $C_2$-$C_5$alkynyl-$CH_2-$ (e.g. $C_2$-$C_3$alkynyl-$CH_2-$), $C_2$-$C_4$alkynyl-$CH(Me)$- (e.g. $C_2$-$C_3$alkynyl-$CH(Me)$-), $C_3$-$C_6$cycloalkyl or $C_1$-$C_4$alkoxy$C_1$-$C_4$alkyl.

In a further particular embodiment, G is hydrogen, or an agriculturally acceptable alkali metal or alkaline earth metal (e.g. lithium, sodium, potassium, magnesium or calcium), or an agriculturally acceptable sulfonium or ammonium group. More preferably, G is hydrogen, or an agriculturally acceptable alkali metal or alkaline earth metal (e.g. lithium, sodium, potassium, magnesium or calcium). Most preferably G is hydrogen.

Particularly preferably, in all aspects and/or embodiments of the invention,

Q is a group of formula Q1, or

Q is a group of formula Q2 and Y is O.

Most preferably, in all aspects and/or embodiments of the invention, Q is a group of formula Q1.

Where Q is a group of formula Q1 as defined herein e.g. hereinabove, a compound of formula (I) has the general structure (I-1):

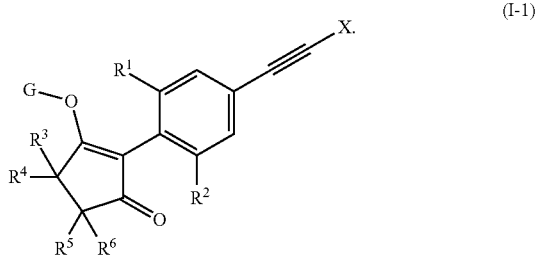

(I-1)

Preferably, $R^3$, $R^4$ and/or $R^5$, independently of each other, are hydrogen, $C_1$-$C_4$alkyl (e.g. $C_1$-$C_2$alkyl), $C_2$-$C_3$alkenyl-$CH_2$— (e.g. ethenyl-$CH_2$—), $C_2$-$C_3$alkynyl-$CH_2$— (e.g. ethynyl-$CH_2$—), $C_1$-$C_2$fluoroalkyl (e.g. $C_1$fluoroalkyl) or $C_1$-$C_2$alkoxy$C_1$-$C_2$alkyl;

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$— or —$(CH_2)_{n2}$—$X^1$—$(CH_2)_{n3}$— and $R^3$ and $R^4$ are as defined herein;

or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$=$C(R^{15})$—$C(R^{17})(R^{18})$—,
or —$CH(R^{19})$—$C(R^{20})(R^{21})$—$CH(R^{22})$— (preferably —$C(R^{11})(R^{12})$—$C(R^{13})(R^{14})$—$C(R^{15})(R^{16})$—$C(R^{17})(R^{18})$— or —$C(R^{11})(R^{12})$—$C(R^{13})$=$C(R^{15})$—$C(R^{17})(R^{18})$—).

More preferably, $R^3$, $R^4$ and/or $R^5$, independently of each other, are hydrogen or $C_1$-$C_2$alkyl (in particular hydrogen);

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$— or —$(CH_2)_{n2}$—$X^1$—$(CH_2)_{n3}$— and $R^3$ and $R^4$ are as defined herein;

or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$=$C(R^{15})$—$C(R^{17})(R^{18})$—,
or —$CH(R^{19})$—$C(R^{20})(R^{21})$—$CH(R^{22})$— (preferably —$C(R^{11})(R^{12})$—$C(R^{13})(R^{14})$—$C(R^{15})(R^{16})$—$C(R^{17})(R^{18})$— or —$C(R^{11})(R^{12})$—$C(R^{13})$=$C(R^{15})$—$C(R^{17})(R^{18})$—).

Still more preferably, $R^3$, $R^4$ and $R^5$ are hydrogen;

or $R^3$ and $R^5$ are hydrogen, and $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$=$C(R^{15})$—$C(R^{17})(R^{18})$—, or —$CH(R^{19})$—$C(R^{20})(R^{21})$—$CH(R^{22})$—.

Yet more preferably, $R^3$, $R^4$ and $R^5$ are hydrogen; or $R^3$ and $R^5$ are hydrogen, and $R^4$ and $R^6$ taken together are —$C(R^{11})(R^{12})$—$C(R^{13})(R^{14})$—$C(R^{15})(R^{16})$—$C(R^{17})(R^{18})$— or —$C(R^{11})(R^{12})$—$C(R^{13})$=$C(R^{15})$—$C(R^{17})(R^{18})$—.

Most preferably, $R^3$, $R^4$ and $R^5$ are hydrogen.

Preferably, when $R^6$ is benzyl optionally substituted on its phenyl ring by one or two substituents, these substituents are independently: cyano, —C≡C—$R^{6A}$, —$C(R^{6B})$=$C(R^{6C})(R^{6CC})$, —C(O)—$R^{6D}$, —$S(O)_2$—$R^{6E}$, $C_1$-$C_3$alkoxy (preferably $C_1$-$C_2$alkoxy such as methoxy), $C_1$-$C_2$fluoroalkoxy (preferably $C_1$fluoroalkoxy), halogen (preferably fluorine or chlorine), methyl or $C_1$fluoroalkyl, wherein $R^{6A}$ is hydrogen, methyl, ethyl, $C_1$fluoroalkyl (preferably trifluoromethyl), fluorine, chlorine or bromine and $R^{6B}$, $R^{6C}$, $R^{6CC}$, $R^{6D}$, and $R^{6E}$ are as defined herein.

When $R^6$ is optionally substituted benzyl, then, more preferably still, $R^6$ is benzyl substituted on its phenyl ring by a first substituent being:
cyano, —C≡C—$R^{6A}$, —$C(R^{6B})$=$C(R^{6C})(R^{6CC})$ or —C(O)—$R^{6D}$; and optionally substituted on its phenyl ring by a second independent substituent being:
cyano, —C≡C—$R^{6A}$, —$C(R^{6B})$=$C(R^{6C})(R^{6CC})$, —C(O)—$R^{6D}$, —$S(O)_2$—$R^{6E}$, $C_1$-$C_2$alkoxy (preferably methoxy), $C_1$-$C_2$fluoroalkoxy (preferably $C_1$fluoroalkoxy), halogen (preferably fluorine or chlorine), or methyl; in which $R^{6D}$ and $R^{6E}$ independently are methyl or trifluoromethyl.

When $R^6$ is optionally substituted benzyl, then, even more preferably, $R^6$ is benzyl substituted on its phenyl ring by a first substituent being: cyano or —C≡C—$R^{6A}$; and optionally substituted on its phenyl ring by a second independent substituent being:
cyano, —C≡C—$R^{6A}$, —$C(R^{6B})$=$C(R^{6C})(R^{6CC})$, —C(O)—$R^{6D}$, —$S(O)_2$—$R^{6E}$, methoxy, $C_1$fluoroalkoxy, fluorine, chlorine, or methyl; in which $R^{6D}$ and $R^{6E}$ independently are methyl or trifluoromethyl.

When $R^6$ is optionally substituted benzyl, then, still more preferably, $R^6$ is benzyl substituted on its phenyl ring by one substituent being cyano or —C≡C—$R^{6A}$.

Preferably, $R^6$ is: hydrogen; $C_1$-$C_4$alkyl (e.g. $C_1$-$C_2$alkyl); $C_2$-$C_3$alkenyl-$CH_2$— (e.g. ethenyl-$CH_2$—); $C_2$-$C_3$alkynyl-$CH_2$— (preferably ethynyl-$CH_2$—, which is alternatively named propargyl); $C_1$-$C_2$fluoroalkyl (e.g. $C_1$fluoroalkyl); $C_1$-$C_2$alkoxy$C_1$-$C_2$alkyl; $C_1$-$C_2$alkylthio$C_1$-$C_2$alkyl; $C_1$-$C_2$alkylsulfinyl$C_1$-$C_2$alkyl; $C_1$-$C_2$alkylsulfonyl$C_1$-$C_2$alkyl; cyclopropyl; or tetrahydrofuranyl (such as tetrahydrofuran-3-yl), or tetrahydropyranyl (such as tetrahydropyran-4-yl);

or $R^6$ is T-CH($R^7$)— (in particular, $R^7$ can be hydrogen);
or $R^6$ is Het-CH($R^8$)— (in particular, $R^8$ can be hydrogen);
or $R^6$ is $C_3$-$C_6$cycloalkylmethyl- (e.g. cyclohexylmethyl-); or is $C_4$-$C_6$cycloalkylmethyl- (e.g. cyclohexylmethyl-) substituted, at a cycloalkyl ring-carbon atom which is not the ring-carbon atom attached to the —$C_1$-$C_2$alkyl- moiety and which is not bonded directly to the ring-carbon atom attached to the —$C_1$-$C_2$alkyl- moiety, by one ring substituent being =N—O—$R^{10}$, oxo (=O), $C_1$-$C_3$alkoxy, $C_1$haloalkoxy, cyclopropyloxy, (cyclopropyl)methoxy or vinyl-$CH_2$-oxy, and optionally by a second ring substituent being $C_1$-$C_2$alkyl (e.g. methyl);

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$— or —$(CH_2)_{n2}$—$X^1$—$(CH_2)_{n3}$— and $R^3$ and $R^4$ are as defined herein;

or $R^4$ and $R^6$ taken together
are —$C(R^{11})(R^{12})$—$C(R^{13})(R^{14})$—$C(R^{15})(R^{16})$—$C(R^{17})(R^{18})$—, —$C(R^{11})(R^{12})$—$C(R^{13})$=$C(R^{15})$—$C(R^{17})(R^{18})$—, or —$CH(R^{19})$—$C(R^{20})(R^{21})$—$CH(R^{22})$—.

More preferably, $R^6$ is: hydrogen; $C_1$-$C_4$alkyl (in particular $C_1$-$C_2$alkyl); $C_2$-$C_3$alkynyl-$CH_2$— (preferably ethynyl-$CH_2$—, which is alternatively named propargyl); or $C_1$-$C_2$alkoxy$C_1$-$C_2$alkyl (in particular methoxymethyl);

or $R^6$ is T-CH($R^7$)— (in particular, $R^7$ can be hydrogen);
or $R^6$ is Het-CH($R^8$)— (in particular, $R^8$ can be hydrogen);
or $R^6$ is cyclohexylmethyl- substituted, at the 4-position of the cyclohexyl ring (calculated with respect to the ring-carbon atom attached to the -methyl- moiety), either by one ring substituent being =N—O—R$^{10}$; or by a first ring substituent being oxo (=O), C$_1$-C$_3$alkoxy, C$_1$haloalkoxy, cyclopropyloxy, (cyclopropyl)methoxy or vinyl-CH$_2$-oxy, and optionally by a second ring substituent being C$_1$-C$_2$alkyl (in particular methyl);

or R$^3$ and R$^4$ taken together are —(CH$_2$)$_{n1}$— or —(CH$_2$)$_{n2}$—X$^1$—(CH$_2$)$_{n3}$— and R$^5$ and R$^6$ are as defined herein, or R$^5$ and R$^6$ taken together are —(CH$_2$)$_{n1}$— or —(CH$_2$)$_{n2}$—X$^1$—(CH$_2$)$_{n3}$— and R$^3$ and R$^4$ are as defined herein;

or R$^4$ and R$^6$ taken together are —C(R$^{11}$)(R$^{12}$)—C(R$^{13}$)(R$^{14}$)—C(R$^{15}$)(R$^{16}$)—C(R$^{17}$)(R$^{18}$)—, —C(R$^{11}$)(R$^{12}$)—C(R$^{13}$)=C(R$^{15}$)—C(R$^{17}$)(R$^{18}$)—, or —CH(R$^{19}$)—C(R$^{20}$)(R$^{21}$)—CH(R$^{22}$)—.

Still more preferably, R$^6$ is: hydrogen; C$_1$-C$_4$alkyl (in particular C$_1$-C$_2$alkyl); C$_2$-C$_3$alkynyl-CH$_2$— (preferably ethynyl-CH$_2$—, which is alternatively named propargyl); or C$_1$-C$_2$alkoxyC$_1$-C$_2$alkyl (in particular methoxymethyl);

or R$^6$ is T-CH(R$^7$)— (in particular, R$^7$ can be hydrogen);

or R$^6$ is Het-CH(R$^8$)— (in particular, R$^8$ can be hydrogen);

or R$^4$ and R$^6$ taken together are —C(R$^{11}$)(R$^{12}$)—C(R$^{13}$)(R$^{14}$)—C(R$^{15}$)(R$^{16}$)—C(R$^{17}$)(R$^{18}$)—, —C(R$^{11}$)(R$^{12}$)—C(R$^{13}$)=C(R$^{15}$)—C(R$^{17}$)(R$^{18}$)—, or —CH(R$^{19}$)—C(R$^{20}$)(R$^{21}$)—CH(R$^{22}$)—.

Still more preferably, R$^6$ is hydrogen, C$_1$-C$_4$alkyl (in particular C$_1$-C$_2$alkyl), or C$_2$-C$_3$alkynyl-CH$_2$— (preferably ethynyl-CH$_2$—, which is alternatively named propargyl);

or R$^4$ and R$^6$ taken together are —C(R$^{11}$)(R$^{12}$)—C(R$^{13}$)(R$^{14}$)—C(R$^{15}$)(R$^{16}$)—C(R$^{17}$)(R$^{18}$)—, or —C(R$^{11}$)(R$^{12}$)—C(R$^{13}$)=C(R$^{15}$)—C(R$^{17}$)(R$^{18}$)—.

Still more preferably, R$^6$ is hydrogen, C$_1$-C$_4$alkyl, or C$_2$-C$_3$alkynyl-CH$_2$—.

Still more preferably, R$^6$ is hydrogen, C$_1$-C$_2$alkyl, or C$_2$-C$_3$alkynyl-CH$_2$—.

Yet more preferably, R$^6$ is hydrogen, or ethynyl-CH$_2$—, and most preferably R$^6$ is ethynyl-CH$_2$—, which is alternatively named propargyl).

Preferably, T is a 4 to 7 (e.g. 4, 5 or 6, preferably 5 or 6) membered monocyclic heterocyclyl, having one or two (preferably one) ring heteroatoms independently selected from oxygen, sulfur and nitrogen; and wherein the heterocyclyl T is optionally substituted by 1 or 2 ring-carbon substituents independently being C$_1$-C$_3$alkyl (in particular C$_1$-C$_2$alkyl), C$_1$-C$_2$fluoroalkyl (in particular C$_1$fluoroalkyl) or oxo (=O), and/or is optionally substituted by one C$_1$-C$_4$alkyl (in particular C$_1$-C$_3$alkyl or C$_1$-C$_2$alkyl), C$_1$-C$_2$fluoroalkyl (in particular C$_1$fluoroalkyl), C$_1$-C$_4$alkoxy (in particular C$_1$-C$_3$alkoxy or C$_1$-C$_2$alkoxy), C$_1$-C$_2$fluoroalkoxy (in particular C$_1$fluoroalkoxy), R$^9$—C(O)— or C$_1$-C$_2$alkyl-S(O)$_2$— substituent on a ring nitrogen if present, and/or is optionally substituted by one or two oxo (=O) substituents on a ring sulfur if present.

More preferably, T is a 4 to 7 (e.g. 4, 5 or 6, preferably 5 or 6) membered monocyclic heterocyclyl, having one or two (preferably one) ring heteroatoms independently selected from oxygen, sulfur and nitrogen; and wherein the heterocyclyl T is optionally substituted by one C$_1$-C$_4$alkyl (in particular C$_1$-C$_3$alkyl or C$_1$-C$_2$alkyl), C$_1$-C$_2$fluoroalkyl (in particular C$_1$fluoroalkyl), C$_1$-C$_4$alkoxy (in particular C$_1$-C$_3$alkoxy or C$_1$-C$_2$alkoxy), C$_1$-C$_2$fluoroalkoxy (in particular C$_1$fluoroalkoxy), R$^9$—C(O)— or C$_1$-C$_2$alkyl-S(O)$_2$— substituent on a ring nitrogen if present, and/or is optionally substituted by one or two oxo (=O) substituents on a ring sulfur if present.

Still more preferably, T is a 4 to 7 (e.g. 4, 5 or 6, preferably 5 or 6) membered monocyclic heterocyclyl, having one ring heteroatom independently selected from oxygen, sulfur and nitrogen; and wherein the heterocyclyl T is optionally substituted by one R$^9$—C(O)— or C$_1$-C$_2$alkyl-S(O)$_2$— (preferably R$^9$—C(O)—) substituent on a ring nitrogen if present, and/or is optionally substituted by one or two oxo (=O) substituents on a ring sulfur if present.

Most preferably, T is a 4, 5 or 6 (preferably 5 or 6) membered monocyclic heterocyclyl, having one ring heteroatom independently selected from oxygen and nitrogen; and wherein the heterocyclyl T is optionally substituted by one R$^9$—C(O)— or C$_1$-C$_2$alkyl-S(O)$_2$— (preferably R$^9$—C(O)—) substituent on a ring nitrogen if present.

It is particularly preferred that T is attached at a ring carbon atom to the —(CH$_2$)$_m$—CH(R$^7$)— or —CH(R$^7$)— moiety.

It is particularly preferred that, in T, the one or two (e.g. one) ring heteroatoms are not directly bonded to the ring atom (e.g. ring carbon atom) which is the position of attachment to the —(CH$_2$)$_m$—CH(R$^7$)— or —CH(R$^7$)— moiety.

In T, preferably, when there are two ring heteroatoms, then they are separated by one or (preferably) two carbon atoms (i.e. they are not directly bonded to each other).

Preferably, R$^9$ is C$_1$-C$_4$alkyl (in particular methyl, ethyl, n-propyl, isopropyl or n-butyl, preferably methyl, ethyl, n-propyl or isopropyl), C$_1$-C$_2$fluoroalkyl (e.g. CF$_3$ or CHF$_2$CF$_2$—), C$_1$-C$_2$alkoxymethyl- (e.g. methoxymethyl-), or cyclopropyl.

More preferably, R$^9$ is C$_1$-C$_3$alkyl (preferably methyl or ethyl), C$_1$-C$_2$fluoroalkyl (e.g. CF$_3$ or CHF$_2$CF$_2$—), methoxymethyl-, or cyclopropyl.

Most preferably, R$^9$ is methyl, ethyl, C$_1$-C$_2$fluoroalkyl (e.g. CF$_3$ or CHF$_2$CF$_2$—) or methoxymethyl-; in particular methyl.

Preferably, T is one of the following sub-formulae T$_1$, T$_2$, T$_3$, T$_4$, T$_5$, T$_6$, T$_7$, T$_{33}$, T$_{34}$, T$_{37}$, T$_{38}$, T$_{41}$, T$_{42}$, T$_{43}$, T$_{44}$, T$_{47}$, T$_{87}$, T$_{89}$, T$_{90}$ or T$_{107}$:

(T$_1$)

(T$_2$)

(T$_3$)

(T$_4$)

(T$_5$)

(T$_6$)

-continued

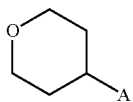 (T7)

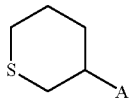 (T8)

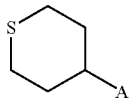 (T9)

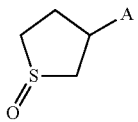 (T10)

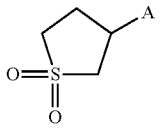 (T38)

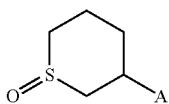 (T41)

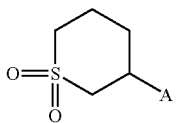 (T42)

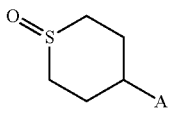 (T43)

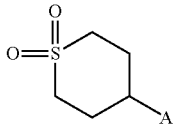 (T44)

 (T47)

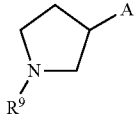 (T87)

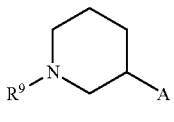 (T89)

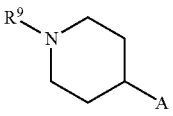 (T90)

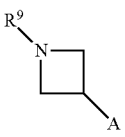 (T107)

wherein: A is the position of attachment to the —(CH$_2$)$_m$—CH(R$^7$)— or —CH(R$^7$)— moiety; and R$^9$ is as defined herein.

More preferably, T is one of the sub-formulae T$_1$, T$_2$, T$_4$, T$_6$, T$_7$, T$_{33}$, T$_{34}$, T$_{41}$, T$_{42}$, T$_{43}$, T$_{44}$, T$_{87}$, T$_{89}$ or T$_{90}$. Even more preferably, T is one of the sub-formulae T$_2$, T$_6$, T$_7$, T$_{33}$, T$_{34}$, T$_{41}$, T$_{42}$, T$_{43}$, T$_{44}$, T$_{87}$, T$_{89}$ or T$_{90}$. Yet more preferably, T is one of the sub-formulae T$_2$, T$_7$, T$_{87}$ or T$_{90}$. Further more preferably, T is one of the sub-formulae T$_2$, T$_7$ or T$_{90}$. Most preferably, T is sub-formula T$_7$.

Preferably, R$^8$ is hydrogen.

Preferably, Het is a heteroaryl, attached at a ring-carbon, which is optionally substituted by 1, 2 or 3 (preferably 1 or 2, more preferably 1) ring-carbon substituents independently being C$_1$-C$_3$alkyl (preferably C$_1$-C$_2$alkyl), C$_1$-C$_2$fluoroalkyl (preferably C$_1$fluoroalkyl), C$_1$-C$_3$alkyl-C(O)— (preferably C$_1$alkyl-C(O)— which is methyl-C(O)—), C$_1$-C$_2$fluoroalkyl-C(O)— (preferably C$_1$fluoroalkyl-C(O)—), hydroxy (including any oxo tautomer), C$_2$-C$_3$alkenyl (preferably ethenyl or prop-1-enyl), C$_2$-C$_3$alkynyl (preferably ethynyl or prop-1-ynyl), C$_1$-C$_3$alkoxy (preferably C$_1$-C$_2$alkoxy, such as C$_1$-C$_2$alkoxy which is methoxy), C$_1$-C$_2$fluoroalkoxy (preferably C$_1$fluoroalkoxy), halogen (preferably fluorine or chlorine), cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one C$_1$-C$_3$alkyl, C$_1$-C$_2$fluoroalkyl, C$_1$-C$_3$alkyl-C(O)—, C$_1$-C$_2$fluoroalkyl-C(O)— or C$_1$-C$_2$alkyl-S(O)$_2$— substituent.

More preferably, Het is a heteroaryl (in particular monocyclic heteroaryl), attached at a ring-carbon, which is optionally substituted by 1, 2 or 3 (in particular 1 or 2, e.g. 1) ring-carbon substituents independently being C$_1$-C$_2$alkyl, C$_1$fluoroalkyl, C$_1$-C$_2$alkyl-C(O)—, C$_1$fluoroalkyl-C(O)—, —SC$_1$-C$_2$alkyl, hydroxy (including any oxo tautomer), ethynyl, prop-1-ynyl, C$_1$-C$_2$alkoxy, C$_1$-C$_2$fluoroalkoxy, fluorine, chlorine, bromine, cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one C$_1$-C$_3$alkyl, C$_1$-C$_2$fluoroalkyl, C$_1$-C$_3$alkyl-C(O)—, C$_1$-C$_2$fluoroalkyl-C(O)— or C$_1$-C$_2$alkyl-S(O)$_2$— substituent.

Even more preferably, Het is a heteroaryl (in particular monocyclic heteroaryl), attached at a ring-carbon, which is optionally substituted by 1 or 2 (in particular 1) ring-carbon substituents independently being C$_1$-C$_2$alkyl (in particular methyl), C1-C2alkoxy (in particular methoxy), C$_1$fluoroalkyl (in particular CF$_3$), C$_1$-C$_2$fluoroalkoxy, C$_1$-C$_2$alkyl-C(O)— (in particular Me-C(O)—), $C_1$fluoroalkyl-C(O)—, ethynyl, prop-1-ynyl, $C_1$-$C_2$fluoroalkoxy, fluorine, chlorine or cyano; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_2$alkyl (e.g. methyl), $C_1$fluoroalkyl, methyl-C(O)— or $C_1$fluoroalkyl-C(O)— substituent.

Still more preferably, Het is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular $CF_3$), fluorine or cyano; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one methyl substituent.

Preferably, Het is an optionally substituted monocyclic heteroaryl, attached at a ring-carbon. Such as monocyclic heteroaryl can be 5-membered or 6-membered monocyclic heteroaryl.

More preferably, Het is an optionally substituted monocyclic heteroaryl, attached at a ring-carbon, which is: pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), tetrazol-5-yl, oxazolyl, thiazolyl, isoxazolyl, isothiazolyl or oxadiazolyl; optionally present (e.g. where chemically possible) as an agrochemically acceptable salt thereof (such as an agrochemically acceptable acid addition salt thereof).

Even more preferably, Het is an optionally substituted monocyclic heteroaryl, attached at a ring-carbon, which is: pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), or tetrazol-5-yl; optionally present (e.g. where chemically possible) as an agrochemically acceptable salt thereof (such as an agrochemically acceptable acid addition salt thereof).

Still more preferably, Het is an optionally substituted monocyclic heteroaryl, attached at a ring-carbon, which is: pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), or pyridazinyl (preferably pyridazin-3-yl); optionally present (e.g. where chemically possible) as an agrochemically acceptable salt thereof (such as an agrochemically acceptable acid addition salt thereof).

Yet more preferably, Het is an optionally substituted monocyclic heteroaryl, attached at a ring-carbon, which is: pyridin-3-yl, pyridin-2-yl, or pyrazolyl (preferably pyrazol-5-yl or pyrazol-4-yl, or most preferably pyrazol-3-yl); optionally present (e.g. where chemically possible) as an agrochemically acceptable salt thereof (such as an agrochemically acceptable acid addition salt thereof).

Most preferably, Het is an optionally substituted monocyclic heteroaryl, attached at a ring-carbon, which is: pyridin-2-yl or pyrazol-3-yl; optionally present (e.g. where chemically possible) as an agrochemically acceptable salt thereof (such as an agrochemically acceptable acid addition salt thereof).

It is particularly preferred that, in Het, any ring-carbon atom, which is directly bonded to the ring atom (ring-carbon atom) which is the point of attachment to the —CH($R^8$)— moiety, is unsubstituted. Therefore, for example, preferably, when Het is an optionally substituted pyridin-2-yl (optionally present as an agrochemically acceptable salt thereof), then the ring-carbon atom at the 3-position of the ring (calculated with respect to the pyridine ring nitrogen atom) is unsubstituted.

It is particularly preferred that, Het is an optionally substituted 6-membered monocyclic heteroaryl, attached at a ring-carbon, and which, if substituted, is substituted by a substituent (e.g. as defined herein) at a ring-carbon which is at the 4-position with respect to (i.e. is diametrically opposite to) the heteroaryl ring-carbon which is the point of attachment to the —CH($R^8$)— moiety. Therefore, for example, more preferably, when Het is an optionally substituted pyridin-2-yl (optionally present as an agrochemically acceptable salt thereof), then the ring-carbon atom at the 5-position of the ring (calculated with respect to the pyridine ring nitrogen atom) is substituted by a substituent (e.g. as defined herein); even more preferably in this embodiment, the ring-carbon atom at the 3-position of the ring (calculated with respect to the pyridine ring nitrogen atom) is unsubstituted.

Alternatively or additionally, in a particular embodiment, Het is an optionally substituted 6-membered monocyclic heteroaryl, attached at a ring-carbon, and which, if substituted, is substituted by a substituent (e.g. as defined herein) at a ring-carbon which is at a or the 3-position with respect to the heteroaryl ring-carbon which is the point of attachment to the —CH($R^8$)— moiety. For example, more particularly, when Het is an optionally substituted pyridin-2-yl (optionally present as an agrochemically acceptable salt thereof), then the ring-carbon atom at the 6-position of the ring (calculated with respect to the pyridine ring nitrogen atom) is substituted by a substituent (e.g. as defined herein); even more particularly in this embodiment, the ring-carbon atom at the 3-position of the ring (calculated with respect to the pyridine ring nitrogen atom) is unsubstituted.

Preferably, $R^{10}$ is hydrogen, $C_1$-$C_2$alkyl (e.g. methyl) or $C_1$fluoroalkyl.

Preferably, $X^1$ is O, NH, N($C_1$-$C_3$alkyl) (e.g. NMe), N($C_1$-$C_3$alkoxy) (e.g. N(OMe)), C(H)($C_1$-$C_3$alkoxy) (e.g. C(H)(OMe)), or C(Me)($C_1$-$C_2$alkoxy) (e.g. C(Me)(OMe)). More preferably, $X^1$ is O or C(H)($C_1$-$C_3$alkoxy), such as O or C(H)(OMe).

Preferably, n1 is 3, 4 or 5, more preferably 4 or 5.

Preferably, n2 and n3 are independently 1, 2 or 3 (in particular 1 or 2) provided that n2+n3 is 3 or 4. More preferably, n2 and n3 are both 2.

Preferably, $R^{11}$ and $R^{18}$ are both hydrogen, or $R^{11}$ and $R^{18}$ are taken together and form an —O— or —$C_1$-$C_2$alkylene-bridge (more preferably, $R^{11}$ and $R^{18}$ are taken together and form an —O— or —$C_1$-$C_2$alkylene- bridge); and $R^{12}$ and $R^{17}$ are independently hydrogen, $C_1$-$C_3$alkyl (in particular methyl) or $C_1$-$C_2$alkoxy$C_1$-$C_2$alkyl (in particular methoxymethyl); $R^{13}$, $R^{14}$ and $R^{15}$ are independently hydrogen or $C_1$-$C_3$alkyl (in particular methyl), provided that two or all (preferably all) of $R^{13}$, $R^{14}$ and $R^{15}$ are hydrogen; and $R^{16}$ is hydrogen; $C_1$-$C_3$alkyl (in particular methyl); or $C_1$-$C_2$alkoxy$C_1$-$C_2$alkyl (in particular methoxymethyl).

Preferably, $R^{12}$ and $R^{17}$ are independently hydrogen, methyl or methoxymethyl.

Preferably, $R^{13}$, $R^{14}$ and $R^{15}$ are hydrogen.

Preferably, $R^{16}$ is hydrogen.

More preferably, $R^{11}$ and $R^{18}$ are both hydrogen, or $R^{11}$ and $R^{18}$ are taken together and form an —O— or —$C_1$-$C_2$alkylene- bridge (even more preferably, $R^{11}$ and $R^{18}$ are taken together and form an —O— or —$C_1$-$C_2$alkylene- bridge); and $R^{12}$ and $R^{17}$ are independently hydrogen, methyl or methoxymethyl; and $R^{13}$, $R^{14}$, $R^{15}$ and $R^{16}$ are hydrogen.

Still more preferably, when $R^4$ and $R^6$ taken together are —C($R^{11}$)($R^{12}$)—C($R^{13}$)($R^{14}$)—C($R^{15}$)($R^{16}$)—C($R^{17}$)($R^{18}$)—, —C($R^{11}$)($R^{12}$)—C($R^{13}$)=C($R^{15}$)—C($R^{17}$)($R^{18}$)—, or —CH($R^{19}$)—C($R^{20}$)($R^{21}$)—CH($R^{22}$)—, then $R^4$ and $R^6$ taken together are:

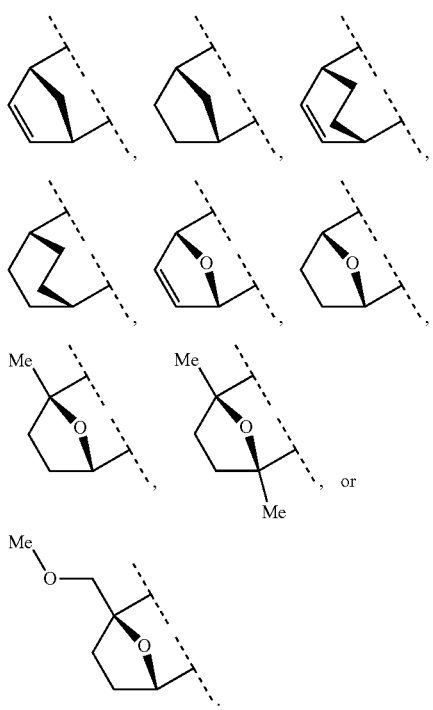

Preferably, when $R^4$ and $R^6$ taken together are —C($R^{11}$)($R^{12}$)—C($R^{13}$)($R^{14}$)—C($R^{15}$)($R^{16}$)—C($R^{17}$)($R^{18}$)—, —C($R^{11}$)($R^{12}$)—C($R^{13}$)=C($R^{15}$)—C($R^{17}$)($R^{18}$)—, or —CH($R^{19}$)—C($R^{20}$)($R^{21}$)—CH($R^{22}$)—, then the compound of formula (I) is a compound of formula (IA) or (IB):

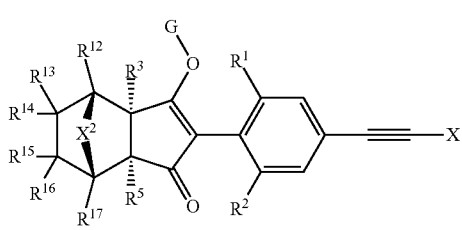

(IA)

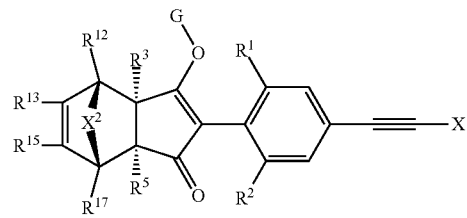

(IB)

wherein G, X, $R^1$, $R^2$, $R^3$, $R^5$, $R^{12}$, $R^{13}$, $R^{14}$, $R^{15}$, $R^{16}$ and $R^{17}$ are as defined hereinbefore, and wherein $X^2$ is —O— or —$C_1$-$C_2$alkyl-.

Preferably, $X^2$ is —O—.

Preferably, $R^{19}$ and/or $R^{22}$ are hydrogen.

Preferably, $R^{20}$ and $R^{21}$ taken together are oxo (=O), =N—O—$R^{10}$, or =$CH_2$; or $R^{20}$ and $R^{21}$, together with the carbon atom to which they are attached, form a 5, 6 or 7 (in particular 5 or 6) membered saturated heterocyclyl, wherein the heterocyclyl has two ring heteroatoms independently being oxygen or sulfur and which are not directly bonded to each other, and wherein the heterocyclyl is optionally substituted by 1, 2 or 3 (in particular 1 or 2) ring-carbon substituents independently being $C_1$-$C_2$alkyl (e.g. methyl).

In a preferable embodiment of the invention ( ) e.g. wherein Q is Q1), the compound of formula (I) is a compound described in any of Tables 1 to 46, as described and/or illustrated herein, optionally present (e.g. where chemically possible) as an agrochemically acceptable salt thereof.

In a more preferable embodiment of the invention, the compound of formula (I) is any one of the compounds A8, A9 A10, A11, A12, A13, A14, A16, or P1, as described and/or illustrated herein, optionally present (e.g. where chemically possible) as an agrochemically acceptable salt (e.g. agrochemically acceptable metal, sulfonium or ammonium salt) thereof.

In an even more preferable embodiment of the invention, the compound of formula (I) is any one of the compounds A8, A9, A10, A14 or A16, as described and/or illustrated herein, optionally present (e.g. where chemically possible) as an agrochemically acceptable salt (e.g. agrochemically acceptable metal, sulfonium or ammonium salt) thereof.

In all embodiments or aspects of the invention, wherein Q is of formula Q1, it is strongly preferred that the compound of formula (I) is a compound of formula (IC):

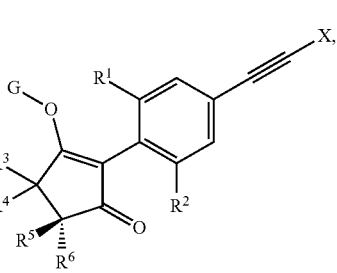

(IC)

wherein X, $R^1$, $R^2$, $R^3$, $R^4$, $R^5$, $R^6$ and G are as defined herein, and wherein 40% or more (in particular 45% or more) by molarity of the compound of formula (IC) has the indicated stereochemistry at the ring-carbon atom bonded to $R^5$ and $R^6$. For example, this broadest definition of formula (IC) includes compounds which are substantially racemic at the ring-carbon atom bonded to $R^5$ and $R^6$, and also includes compounds enriched with isomer(s) having the stereochemistry indicated at the ring-carbon atom bonded to $R^5$ and $R^6$.

More preferably, more than 50% (still more preferably more than 70% or more than 80%, most preferably more than 90% or more than 95%) by molarity of the compound of formula (IC) has the indicated stereochemistry at the ring-carbon atom bonded to $R^5$ and $R^6$. This more preferred definition of formula (IC) includes compounds enriched with isomer(s) having the stereochemistry indicated at the ring-carbon atom bonded to $R^5$ and $R^6$.

Depending on the nature of the substituents G, $R^1$, $R^2$, $R^3$, $R^4$, $R^5$ and $R^6$, compounds of formula (I-1) may exist in different isomeric forms. When G is hydrogen, for example, compounds of formula (I) may exist in different tautomeric forms, all of which are encompassed by the present invention:

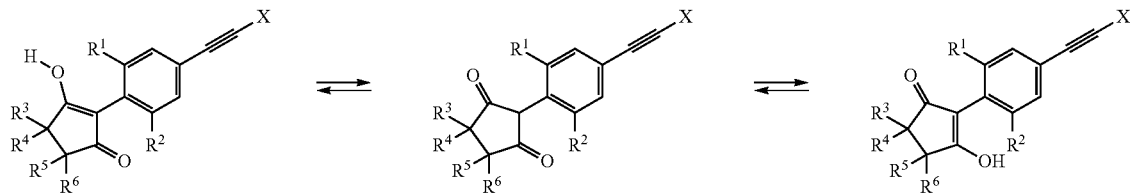

Also, when substituents contain double bonds, cis- and trans-isomers can exist. This invention covers all such isomers and tautomers and mixtures thereof in all proportions. These isomers, too, are within the scope of the claimed compounds of the formula I.

Where Q is a group of formula Q2 as defined above, a compound of formula (I) has the general structure (1-2):

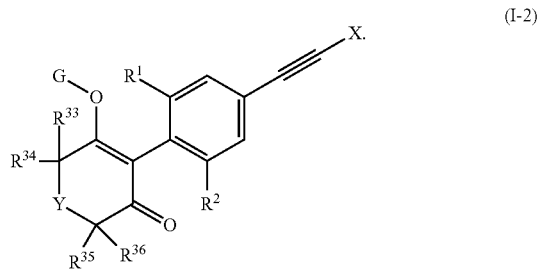

(I-2)

Preferably, e.g. in all aspects and/or embodiments of the invention when Q is Q2, $R^{33}$, $R^{34}$, $R^{35}$ and/or $R^{36}$, independently of each other, are hydrogen, $C_1$-$C_4$alkyl (e.g. $C_1$-$C_2$alkyl), $C_2$-$C_4$ alkynyl (in particular $C_2$-$C_3$alkynyl-$CH_2$—, e.g. ethynyl-$CH_2$—), $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl; $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, said heterocyclyl being attached at a ring carbon atom within the heterocyclyl (in particular tetrahydrofuranyl such as tetrahydrofuran-3-yl, or tetrahydropyranyl such as tetrahydropyran-4-yl); provided that no more than one (in particular none) of $R^{33}$, $R^{34}$, $R^{35}$ and $R^{36}$ is alkenyl, alkynyl, alkoxyalkyl, alkylthioalkyl, alkylsulfinylalkyl, alkylsulfonylalkyl, cycloalkyl or heterocyclyl;

or $R^{33}$ and $R^{34}$ taken together are —$(CH_2)_{n31}$— or —$(CH_2)_{n32}$—$X^1$—$(CH_2)_{n33}$— and $R^{35}$ and $R^{36}$ are as defined herein (e.g. hereinabove), or $R^{35}$ and $R^{36}$ taken together are —$(CH_2)_{n31}$— or —$(CH_2)_{n32}$—$X^1$—$(CH_2)_{n33}$— and $R^{33}$ and $R^{34}$ are as defined herein (e.g. hereinabove); wherein $X^1$ is O, S, S(O), S(O)$_2$, NH, N($C_1$-$C_2$alkyl), N($C_1$-$C_2$alkoxy), C(H)($C_1$-$C_2$alkyl), C($C_1$-$C_2$alkyl)$_2$ or C(H)($C_1$-$C_2$alkoxy); n31 is 4 or 5; and n32 and n33 are independently 1, 2 or 3 provided that n32+n33 is 3 or 4.

More preferably, e.g. in all aspects and/or embodiments of the invention when Q is Q2, $R^{33}$, $R^{34}$, $R^{35}$ and/or $R^{36}$, independently of each other, are hydrogen, $C_1$-$C_4$alkyl (in particular $C_1$-$C_2$alkyl), $C_2$-$C_4$alkynyl (in particular $C_2$-$C_3$alkynyl-$CH_2$—, e.g. ethynyl-$CH_2$—), $C_1$-$C_3$alkoxy$C_1$-$C_3$alkyl (in particular $C_1$-$C_2$alkoxy$C_1$-$C_2$alkyl), $C_1$-$C_3$alkylthio$C_1$-$C_3$alkyl (in particular $C_1$-$C_2$alkylthio$C_1$-$C_2$alkyl), $C_1$-$C_3$alkylsulfinyl$C_1$-$C_3$alkyl (in particular $C_1$-$C_2$alkylsulfinyl$C_1$-$C_2$alkyl), $C_1$-$C_3$alkylsulfonyl$C_1$-$C_3$alkyl (in particular $C_1$-$C_2$alkylsulfonyl$C_1$-$C_2$alkyl); $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, said heterocyclyl being attached at a ring carbon atom within the heterocyclyl (in particular tetrahydrofuranyl such as tetrahydrofuran-3-yl, or tetrahydropyranyl such as tetrahydropyran-4-yl); provided that no more than one (in particular none) of $R^{33}$, $R^{34}$, $R^{35}$ and $R^{36}$ is alkenyl, alkynyl, alkoxyalkyl, alkylthioalkyl, alkylsulfinylalkyl, alkylsulfonylalkyl, cycloalkyl or heterocyclyl.

Still more preferably, $R^{33}$, $R^{34}$, $R^{35}$ and/or $R^{36}$, independently of each other, are hydrogen, $C_1$-$C_3$alkyl (in particular $C_1$-$C_2$alkyl such as methyl) or $C_1$-$C_3$alkoxy$C_1$-$C_3$alkyl (in particular $C_1$-$C_2$alkoxy$C_1$-$C_2$alkyl); provided that no more than one (in particular none) of $R^{33}$, $R^{34}$, $R^{35}$ and $R^{36}$ is alkoxyalkyl.

Even more preferably, $R^{33}$, $R^{34}$, $R^{35}$ and/or $R^{36}$, independently of each other, are hydrogen or $C_1$-$C_2$alkyl (preferably hydrogen or methyl).

Most preferably (especially when Y is $CR^{38}R^{39}$ or —$CR^{310}R^{311}CR^{312}R^{313}$—), $R^{33}$, $R^{34}$, $R^{35}$ and $R^{36}$ are hydrogen.

Preferably, e.g. in all aspects and/or embodiments of the invention when Q is Q2, at least one (more preferably 2, 3 or 4, still more preferably 3 or 4, most preferably all four) of $R^{33}$, $R^{34}$, $R^{35}$ and $R^{36}$, independently of each other, are hydrogen or $C_1$-$C_4$alkyl (e.g. H or $C_1$-$C_3$alkyl, or H or $C_1$-$C_2$alkyl); and/or $R^{34}$ and $R^{35}$ are taken together as described herein.

Preferably, e.g. in all aspects and/or embodiments of the invention when Q is Q2, Y is O, S, S(O), S(O)$_2$, C(O), $CR^{38}R^{39}$ or —$CR^{310}R^{311}CR^{312}R^{313}$—. More preferably, Y is O, C(O), $CR^{38}R^{39}$ or —$CR^{310}R^{311}CR^{312}R^{313}$—.

Even more preferably, e.g. in all aspects and/or embodiments of the invention when Q is Q2, Y is O or $CR^{38}R^{39}$, in particular Y is O or $CH_2$.

In one preferable embodiment, Y is $CR^{38}R^{39}$, in particular Y is $CH_2$.

However, most preferably, e.g. in all aspects and/or embodiments of the invention when Q is Q2, Y is O.

Preferably, e.g. in all aspects and/or embodiments of the invention, in $R^{38}$ and $R^{39}$, one or both of $R^{38}$ and $R^{39}$ is or are hydrogen; or $R^{38}$ and $R^{39}$ taken together are —$(CH_2)_{n37}$— or preferably —$(CH_2)_{n38}$—$X^{32}$—$(CH_2)_{n39}$—. In this embodiment, preferably Y is $CR^{38}R^{39}$ and/or preferably $X^{32}$ is O.

In one particular embodiment when Q is Q2, $R^{38}$ and $R^{39}$ are taken together and are —$(CH_2)_{n37}$— or —$(CH_2)_{n38}$—$X^{32}$—$(CH_2)_{n39}$—. In this embodiment, preferably Y is $CR^{38}R^{39}$ and/or preferably $X^{32}$ is O.

Preferably, e.g. in all aspects and/or embodiments of the invention when Q is Q2, $X^{32}$ is O, S, S(O), $S(O)_2$, C(H)($C_1$-$C_3$alkyl), $C(C_1$-$C_2$alkyl$)_2$ or C(H)($C_1$-$C_3$alkoxy). Most preferably, $X^{32}$ is O.

Preferably, n37 is 2, 3, 4 or 5, more preferably 4 or 5.

Preferably, n38 and n39 are independently 1, 2 or 3 provided that n38+n39 is 2, 3 or 4. Preferably, n38+n39 is 3 or 4. Most preferably, n38 is 2 and n39 is 2 (in which case, preferably, $X^{32}$ is O).

Preferably, e.g. in all aspects and/or embodiments of the invention when Q is Q2, $R^{38}$ and $R^{39}$ are, independently of each other:

hydrogen, $C_1$-$C_4$alkyl (in particular $C_1$-$C_2$alkyl), $C_2$-$C_3$alkenyl-$CH_2$— (in particular ethenyl-$CH_2$—), $C_2$-$C_3$alkynyl-$CH_2$— (in particular ethynyl-$CH_2$—), $C_1$-$C_2$fluoroalkyl (in particular $C_1$fluoroalkyl), $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl, and in which one ring $CH_2$ moiety of a $C_4$-$C_6$cycloalkyl is optionally (e.g. preferably) replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);

$C_3$-$C_6$cycloalkyl$C_1$-$C_2$alkyl- (in particular $C_3$-$C_6$cycloalkylmethyl-) or $C_3$-$C_6$cycloalkyl$C_1$-$C_2$alkyl- (in particular $C_3$-$C_6$cycloalkylmethyl-) substituted by one or two ring substituents which independently are $C_1$-$C_3$alkyl or $C_1$-$C_2$fluoroalkyl, and in which one ring $CH_2$ moiety of a $C_4$-$C_6$cycloalkyl$C_1$-$C_2$alkyl- (in particular $C_4$-$C_6$cycloalkylmethyl-) is optionally (e.g. preferably) replaced by an oxygen or sulfur atom or by a S(O), $S(O)_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl$C_1$-$C_2$alkyl- (in particular $C_3$-$C_6$cycloalkylmethyl-) substituted by one ring substituent being $C_1$-$C_3$alkoxy (in particular $C_1$-$C_2$alkoxy) and optionally further substituted by one ring substituent being $C_1$-$C_2$alkyl (in particular methyl); or HetA or HetA-$CH_2$—, wherein HetA is a heteroaryl, attached at a ring-carbon, which is optionally substituted by 1, 2 or 3 (in particular 1 or 2, e.g. 1) ring-carbon substituents independently being $C_1$-$C_3$alkyl (e.g. $C_1$-$C_2$alkyl), $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl (e.g. ethenyl or prop-1-enyl), $C_2$-$C_3$alkynyl (e.g. ethynyl or prop-1-ynyl), $C_1$-$C_3$alkoxy (e.g. $C_1$-$C_2$alkoxy), $C_1$-$C_2$fluoroalkoxy, halogen (e.g. fluorine or chlorine), cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-$S(O)_2$— substituent;

provided that no more than one of $R^{38}$ and $R^{39}$ is an optionally substituted cycloalkyl; an optionally substituted cycloalkyl in which one ring $CH_2$ moiety has been replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl; an optionally substituted cycloalkyl-alkyl-; an optionally substituted cycloalkyl-alkyl- in which one ring $CH_2$ moiety has been replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; or HetA or HetA-$CH_2$—;

or $R^{38}$ is hydrogen or $C_1$-$C_2$alkyl (in particular H or Me), and $R^{39}$ is $C_1$-$C_2$alkoxy (in particular methoxy);

or $R^{38}$ and $R^{39}$ taken together are —$(CH_2)_{n37}$— or —$(CH_2)_{n38}$—$X^{32}$—$(CH_2)_{n39}$—.

In the above preferred embodiment, preferably Y is $CR^{38}R^{39}$ and/or preferably $X^{32}$ is O.

More preferably, e.g. in all aspects and/or embodiments of the invention when Q is Q2: $R^{38}$ is hydrogen or $C_1$-$C_2$alkyl (preferably H or Me, more preferably hydrogen); and $R^{39}$ is:

$C_1$-$C_2$alkoxy (in particular methoxy);

$C_2$-$C_3$alkynyl-$CH_2$— (in particular ethynyl-$CH_2$—);

$C_1$-$C_3$alkoxy$C_1$-$C_3$alkyl;

$C_1$-$C_3$alkylthio$C_1$-$C_3$alkyl (preferably $C_1$-$C_2$alkylthio-$CH_2CH_2$— or more preferably $C_1$-$C_2$alkylthio-CH(Me)$CH_2$—);

$C_1$-$C_3$alkylsulfinyl$C_1$-$C_3$alkyl;

$C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl, and in which one ring $CH_2$ moiety of a $C_4$-$C_6$cycloalkyl is optionally (e.g. preferably) replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or more preferably is replaced by an oxygen or sulfur atom or by a S(O), $S(O)_2$, NH, N($C_1$-$C_3$alkyl) or N($C_1$-$C_2$alkoxy) moiety; or still more preferably is replaced by an oxygen or sulfur atom);

$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);

$C_3$-$C_6$cycloalkylmethyl- or $C_3$-$C_6$cycloalkylmethyl- substituted by one or two ring substituents which independently are $C_1$-$C_3$alkyl (in particular $C_1$-$C_2$alkyl) or $C_1$-$C_2$fluoroalkyl, and in which one ring $CH_2$ moiety of a $C_4$-$C_6$cycloalkylmethyl- is optionally (e.g. preferably) replaced by an oxygen or sulfur atom or by a S(O), $S(O)_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or more preferably is replaced by an oxygen or sulfur atom or by a N[C(O)$C_1$-$C_3$alkyl] or N[C(O)$C_1$-$C_2$fluoroalkyl] moiety);

$C_3$-$C_6$cycloalkylmethyl- substituted by one ring substituent being $C_1$-$C_3$alkoxy (in particular $C_1$-$C_2$alkoxy) and optionally further substituted by one ring substituent being $C_1$-$C_2$alkyl (in particular methyl); or HetA or HetA-$CH_2$—, wherein Het A is a heteroaryl, attached at a ring-carbon, which is optionally substituted by 1, 2 or 3 (in particular 1 or 2, e.g. 1) ring-carbon substituents independently being $C_1$-$C_3$alkyl (in particular $C_1$-$C_2$alkyl), $C_1$-$C_2$fluoroalkyl (in particular $C_1$fluoroalkyl), $C_1$-$C_3$alkyl-C(O)—, $C_1$-$C_2$fluoroalkyl-C(O)—, hydroxy (including any oxo tautomer), $C_2$-$C_3$alkenyl (in particular ethenyl or prop-1-enyl), $C_2$-$C_3$alkynyl (in particular ethynyl or prop-1-ynyl), $C_1$-$C_3$alkoxy (in particular $C_1$-$C_2$alkoxy), $C_1$-$C_2$fluoroalkoxy (in particular $C_1$fluoroalkoxy), halogen (in particular fluorine or chlorine), cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

or $R^{38}$ and $R^{39}$ taken together are —$(CH_2)_{n37}$— or —$(CH_2)_{n38}$—$X^{32}$—$(CH_2)_{n39}$—.

In the above preferred embodiment, preferably Y is $CR^{38}R^{39}$ and/or preferably $X^{32}$ is O.

Even more preferably, e.g. in all aspects and/or embodiments of the invention when Q is Q2:
$R^{38}$ is hydrogen or $C_1$-$C_2$alkyl (preferably H or Me, more preferably hydrogen); and
$R^{39}$ is:
$C_1$-$C_3$alkylthio$C_1$-$C_3$alkyl (preferably $C_1$-$C_2$alkylthio-$CH_2CH_2$— or more preferably $C_1$-$C_2$alkylthio-CH(Me)$CH_2$—);
$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl, and in which one ring $CH_2$ moiety of a $C_4$-$C_6$cycloalkyl is replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or preferably is replaced by an oxygen or sulfur atom or by a S(O), S(O)$_2$, NH, N($C_1$-$C_3$alkyl) or N($C_1$-$C_2$alkoxy) moiety; or more preferably is replaced by an oxygen or sulfur atom);

$C_3$-$C_6$cycloalkylmethyl- or $C_3$-$C_6$cycloalkylmethyl- substituted by one or two ring substituents which independently are $C_1$-$C_3$alkyl (in particular $C_1$-$C_2$alkyl) or $C_1$-$C_2$fluoroalkyl, and in which one ring $CH_2$ moiety of a $C_4$-$C_6$cycloalkylmethyl- is replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or preferably is replaced by an oxygen or sulfur atom or by a N[C(O)$C_1$-$C_3$alkyl] or N[C(O)$C_1$-$C_2$fluoroalkyl] moiety);

HetA or HetA-$CH_2$—, wherein Het A is a heteroaryl, attached at a ring-carbon, which is optionally substituted by 1, 2 or 3 (in particular 1 or 2, e.g. 1) ring-carbon substituents independently being $C_1$-$C_3$alkyl (in particular $C_1$-$C_2$alkyl), $C_1$-$C_2$fluoroalkyl (in particular $C_1$fluoroalkyl), $C_1$-$C_3$alkyl-C(O)—, $C_1$-$C_2$fluoroalkyl-C(O)—, hydroxy (including any oxo tautomer), $C_2$-$C_3$alkenyl (in particular ethenyl or prop-1-enyl), $C_2$-$C_3$alkynyl (in particular ethynyl or prop-1-ynyl), $C_1$-$C_3$alkoxy (in particular $C_1$-$C_2$alkoxy), $C_1$-$C_2$fluoroalkoxy (in particular $C_1$fluoroalkoxy), halogen (in particular fluorine or chlorine), cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

or $R^{38}$ and $R^{39}$ taken together are —$(CH_2)_{n37}$— or —$(CH_2)_{n38}$—$X^{32}$—$(CH_2)_{n39}$—.

In the above even more preferred embodiment, preferably Y is $CR^{38}R^{39}$ and/or preferably $X^{32}$ is O.

In one particularly preferable embodiment (which e.g. can apply to all aspects and/or embodiments of the invention when Q is Q2), $R^{38}$ and $R^{39}$, independently of each other, are hydrogen or $C_1$-$C_3$alkyl (preferably hydrogen or $C_1$-$C_2$alkyl, more preferably hydrogen or methyl, most preferably hydrogen). In this embodiment, preferably, Y is $CR^{38}R^{39}$.

In another preferable embodiment (which e.g. can apply to all aspects and/or embodiments of the invention), $R^{38}$ is hydrogen, and $R^{39}$ is $C_1$-$C_3$alkylthio$C_1$-$C_3$alkyl. In this embodiment, $R^{39}$ preferably is $C_1$-$C_2$alkylthio-$CH_2CH_2$— or more preferably is $C_1$-$C_2$alkylthio-CH(Me)$CH_2$—. In this embodiment, preferably, Y is $CR^{38}R^{39}$.

In another preferable embodiment (which e.g. can apply to all aspects and/or embodiments of the invention when Q is Q2), $R^{38}$ is hydrogen and $R^{39}$ is $C_4$-$C_6$cycloalkylmethyl- or $C_4$-$C_6$cycloalkylmethyl- substituted by one or two ring substituents which independently are $C_1$-$C_3$alkyl (in particular $C_1$-$C_2$alkyl) or $C_1$-$C_2$fluoroalkyl, and in which one ring $CH_2$ moiety is replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or more preferably is replaced by an oxygen or sulfur atom or by a N[C(O)$C_1$-$C_3$alkyl] or N[C(O)$C_1$-$C_2$fluoroalkyl] moiety). In this embodiment, preferably, Y is $CR^{38}R^{39}$.

Within the above preferable embodiment, then preferably $R^{38}$ is hydrogen and $R^{39}$ is heterocyclyl-methyl-, wherein the heterocyclyl is V, wherein V is one of the following sub-formulae $V_1$, $V_2$, $V_3$, $V_4$, $V_5$, $V_6$, $V_7$, $V_{33}$, $V_{34}$, $V_{37}$, $V_{38}$, $V_{41}$, $V_{42}$, $V_{43}$, $V_{44}$, $V_{47}$, $V_{87}$, $V_{89}$, $V_{90}$ or $V_{107}$:

(V$_1$)

(V$_2$)

(V$_3$)

(V$_4$)

(V$_5$)

(V$_6$)

-continued (V_7) 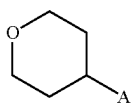

(V_8) 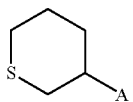

(V_9) 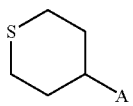

(V_10) 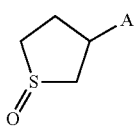

(V_38) 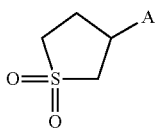

(V_41) 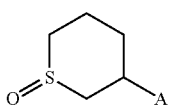

(V_42) 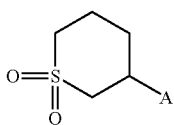

(V_43) 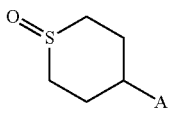

(V_44) 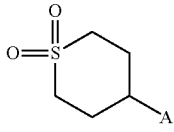

(V_47) 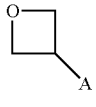

(V_87) 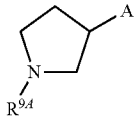

(V_89) 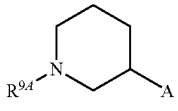

-continued (V_90) 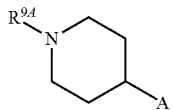

(V_107) 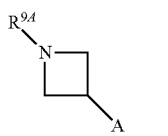

wherein: A is the position of attachment to the -methyl- moiety; and $R^{9A}$ is hydrogen, $C_1$-$C_2$alkyl (e.g. methyl), $C_1$-$C_2$fluoroalkyl (e.g. $C_1$fluoroalkyl), —C(O)$C_1$-$C_3$alkyl (e.g. —C(O)— methyl), —C(O)$C_1$-$C_2$fluoroalkyl (e.g. —C(O)$C_1$fluoroalkyl) or $C_1$-$C_2$alkoxy.

More preferably, V is one of the sub-formulae $V_1$, $V_2$, $V_4$, $V_6$, $V_7$, $V_{33}$, $V_{34}$, $V_{41}$, $V_{42}$, $V_{43}$, $V_{44}$, $V_{87}$, $V_{89}$ or $V_{90}$. Even more preferably, V is one of the sub-formulae $V_2$, $V_6$, $V_7$, $V_{33}$, $V_{34}$, $V_{41}$, $V_{42}$, $V_{43}$, $V_{44}$, $V_{87}$, $V_{89}$ or $V_{90}$.

Yet more preferably, V is one of the sub-formulae $V_2$, $V_7$, $V_{87}$ or $V_{90}$. Further more preferably, V is one of the sub-formulae $V_2$, $V_7$ or $V_{90}$.

Most preferably, V is sub-formula $V_7$.

Preferably, $R^{9A}$ is —C(O)$C_1$-$C_3$alkyl (e.g. —C(O)methyl) or —C(O)$C_1$-$C_2$fluoroalkyl (e.g. —C(O)$C_1$fluoroalkyl).

In one preferable embodiment of the invention (which e.g. can apply to all aspects and/or embodiments of the invention), $R^{38}$ is hydrogen, and $R^{39}$ is tetrahydro-2H-pyran-4-yl

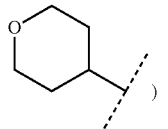

or (tetrahydro-2H-pyran-4-yl)-methyl-. In this embodiment, preferably, Y is $CR^{38}R^{39}$. When $R^{39}$ is (tetrahydro-2H-pyran-4-yl)-methyl-, then $R^{39}$ is $V_7$-methyl- wherein $V_7$ is

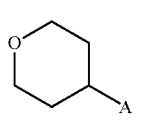

wherein A is the position of attachment to the -methyl- moiety.

In another preferable embodiment (which e.g. can apply to all aspects and/or embodiments of the invention when Q is Q2), $R^{38}$ is hydrogen and $R^{39}$ is HetA or HetA-$CH_2$— as defined herein. In this embodiment, more preferably, $R^{38}$ is hydrogen and $R^{39}$ is HetA as defined herein. In this embodiment, preferably, Y is $CR^{38}R^{39}$.

Preferably, e.g. in all aspects and/or embodiments of the invention when Q is Q2, and $R^{39}$ is HetA or HetA-$CH_2$, HetA is a heteroaryl (in particular monocyclic heteroaryl), attached at a ring-carbon, which is optionally substituted by 1, 2 or 3 (in particular 1 or 2, e.g. 1) ring-carbon substituents independently being $C_1$-$C_2$alkyl, $C_1$fluoroalkyl, $C_1$-$C_2$alkyl-C(O)—, $C_1$fluoroalkyl-C(O)—, hydroxy (including any oxo tautomer), ethynyl, prop-1-ynyl, $C_1$-$C_2$alkoxy, $C_1$fluoroalkoxy, fluorine, chlorine, bromine, cyano or nitro, provided that any chlorine, bromine, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent.

More preferably, e.g. in all aspects and/or embodiments of the invention when Q is Q2, and $R^{39}$ is HetA or HetA-CH$_2$, HetA is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular CF$_3$), $C_1$-$C_2$alkyl-C(O)— (in particular Me-C(O)—), $C_1$fluoroalkyl-C(O)—, ethynyl, prop-1-ynyl, fluorine or cyano; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_2$alkyl (e.g. methyl), $C_1$fluoroalkyl, methyl-C(O)— or $C_1$fluoroalkyl-C(O)— substituent.

More preferably, e.g. in all aspects and/or embodiments of the invention when Q is Q2, and $R^{39}$ is HetA or HetA-CH$_2$, HetA is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular CF$_3$), fluorine or cyano; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one methyl substituent.

Preferably, e.g. in all aspects and/or embodiments of the invention when Q is Q2, and $R^{39}$ is HetA or HetA-CH$_2$, HetA is an optionally substituted monocyclic heteroaryl, attached at a ring-carbon. Such as monocyclic heteroaryl can be 5-membered or 6-membered monocyclic heteroaryl.

More preferably, e.g. in all aspects and/or embodiments of the invention when Q is Q2, and $R^{39}$ is HetA or HetA-CH$_2$, HetA is an optionally substituted monocyclic heteroaryl, attached at a ring-carbon, which is:
pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), tetrazol-5-yl, oxazolyl, thiazolyl, isoxazolyl, isothiazolyl or oxadiazolyl; optionally present (e.g. where chemically possible) as an agrochemically acceptable salt thereof (such as an agrochemically acceptable acid addition salt thereof).

Even more preferably, e.g. in all aspects and/or embodiments of the invention when Q is Q2, and $R^{39}$ is HetA or HetA-CH$_2$, HetA is an optionally substituted monocyclic heteroaryl, attached at a ring-carbon, which is: pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), or tetrazol-5-yl; optionally present (e.g. where chemically possible) as an agrochemically acceptable salt thereof (such as an agrochemically acceptable acid addition salt thereof).

Still more preferably, e.g. in all aspects and/or embodiments of the invention when Q is Q2, and $R^{39}$ is HetA or HetA-CH$_2$, HetA is an optionally substituted monocyclic heteroaryl, attached at a ring-carbon, which is: pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), or pyridazinyl (preferably pyridazin-3-yl); optionally present (e.g. where chemically possible) as an agrochemically acceptable salt thereof (such as an agrochemically acceptable acid addition salt thereof).

Yet more preferably, e.g. in all aspects and/or embodiments of the invention when Q is Q2, and $R^{39}$ is HetA or HetA-CH$_2$, HetA is an optionally substituted monocyclic heteroaryl, attached at a ring-carbon, which is: pyridin-3-yl, pyridin-2-yl, or pyrazolyl (preferably pyrazol-5-yl or pyrazol-4-yl, or most preferably pyrazol-3-yl); optionally present (e.g. where chemically possible) as an agrochemically acceptable salt thereof (such as an agrochemically acceptable acid addition salt thereof).

Most preferably, e.g. in all aspects and/or embodiments of the invention when Q is Q2, and $R^{39}$ is HetA or HetA-CH$_2$, HetA is an optionally substituted monocyclic heteroaryl, attached at a ring-carbon, which is: pyridin-2-yl or pyrazol-3-yl; optionally present (e.g. where chemically possible) as an agrochemically acceptable salt thereof (such as an agrochemically acceptable acid addition salt thereof).

It is particularly preferred (e.g. in all aspects and/or embodiments of the invention when Q is Q2 and $R^{39}$ is HetA or HetA-CH$_2$,) that, in HetA, any ring-carbon atom, which is directly bonded to the ring-carbon atom which is the point of attachment (e.g. or i.e. which is the point of attachment to the central carbon atom within the Y=CR$^{38}$R$^{39}$ moiety (for HetA), or which is the point of attachment to the —CH$_2$— moiety (for Het-CH$_2$—), is unsubstituted. Therefore, for example, preferably, when Het is an optionally substituted pyridin-2-yl (optionally present as an agrochemically acceptable salt thereof), then the ring-carbon atom at the 3-position of the ring (calculated with respect to the pyridine ring nitrogen atom) is unsubstituted.

Preferably, e.g. in all aspects and/or embodiments of the invention when Q is Q2, $R^{310}$, $R^{311}$, $R^{312}$ and/or $R^{313}$ are, independently of each other, hydrogen or $C_1$-$C_2$alkyl (in particular hydrogen or methyl). More preferably, two, three or all of $R^{310}$, $R^{311}$, $R^{312}$ and $R^{313}$ are hydrogen. Most preferably, $R^{310}$, $R^{311}$, $R^{312}$ and $R^{313}$ are hydrogen.

In one particular embodiment of the invention (which e.g. can apply to all aspects and/or embodiments of the invention): Y is O or CR$^{38}$R$^{39}$ (preferably CR$^{38}$R$^{39}$); and $R^{34}$ and $R^{35}$ taken together are —C(R$^{37c}$)=C(R$^{37d}$)—. In this particular embodiment, more preferably, Y is O or CR$^{38}$R$^{39}$ (preferably CR$^{38}$R$^{39}$) wherein $R^{38}$ and $R^{39}$ are, independently of each other, hydrogen or $C_1$-$C_3$alkyl (in particular, this $C_1$-$C_3$alkyl can be $C_1$-$C_2$alkyl such as methyl). In this particular embodiment, even more preferably Y is O or CH$_2$; or, most preferably, Y is CH$_2$. In this particular embodiment, preferably, $R^{33}$ and $R^{36}$, independently of each other, are hydrogen, $C_1$-$C_3$alkyl (in particular $C_1$-$C_2$alkyl such as methyl) or $C_1$-$C_3$alkoxyC$_1$-$C_3$alkyl (in particular $C_1$-$C_2$alkoxyC$_1$-$C_2$alkyl); provided that no more than one (in particular none) of $R^{33}$ and $R^{36}$ is alkoxyalkyl. In this particular embodiment, more preferably, $R^{33}$ and $R^{36}$, independently of each other, are hydrogen or $C_1$-$C_2$alkyl (preferably hydrogen or methyl).

In a further particularly preferred embodiment, $R^1$ is fluorine, X is methyl, $R^2$ is $OR^{2A}$, wherein $R^{2A}$ is selected from methyl, ethyl, $CH_2CH_2OCH_3$, 2,2,2-trifluoroethyl and difluoromethyl (most preferably $R^{2A}$ is selected from methyl, ethyl and difluoromethyl), and either Q is Q1, wherein $R^3$, $R^4$, and $R^5$ are hydrogen, and $R^6$ is hydrogen or propargyl (which is ethynyl-$CH_2$—), and G is hydrogen, or Q is Q2, wherein Y is $CR^{38}R^{39}$ and $R^{38}$ and $R^{39}$ are each independently hydrogen or methyl (preferably both hydrogen or both methyl, more preferably both hydrogen), $R^{34}$ and $R^{35}$ taken together are —$C(R^{37c})$=$C(R^{37d})$— wherein $R^{37c}$ and $R^{37d}$ are as described herein e.g. hereinbefore.

Preferably, in this particularly preferred embodiment, when Q is Q2, G is hydrogen.

Preferably, in this particularly preferred embodiment, when Q is Q2, $R^{33}$ and $R^{36}$, independently of each other, are hydrogen, $C_1$-$C_3$alkyl (in particular $C_1$-$C_2$alkyl such as methyl), or $C_1$-$C_3$alkoxy$C_1$-$C_3$alkyl (in particular $C_1$-$C_2$alkoxy$C_1$-$C_2$alkyl); provided that no more than one (in particular none) of $R^{33}$ and $R^{36}$ is alkoxyalkyl. In this particularly preferred embodiment, more preferably, $R^{33}$ and $R^{36}$, independently of each other, are hydrogen or $C_1$-$C_2$alkyl (preferably hydrogen or methyl).

In a specific preferred embodiment, the compound of the invention (compound of formula (I)) is as described herein in the following tables (e.g. is a compound as described herein in one of Tables 1 to 46), optionally present (e.g. where chemically possible) as an agrochemically acceptable salt (e.g. agrochemically acceptable metal, sulfonium or ammonium salt) thereof.

Preferably, the compound of the invention (compound of formula (I)) is compound A8, A9, A10, A11, A12, A13, A14, A16, or P1, optionally present (e.g. where chemically possible) as an agrochemically acceptable salt (e.g. agrochemically acceptable metal, sulfonium or ammonium salt) thereof.

Preferably, the compound of the invention (compound of formula (I)) is compound A8, A9 or A10, optionally present (e.g. where chemically possible) as an agrochemically acceptable salt (e.g. agrochemically acceptable metal, sulfonium or ammonium salt) thereof.

Alternatively, preferably, the compound of the invention (compound of formula (I)) is compound A14 or A16, optionally present (e.g. where chemically possible) as an agrochemically acceptable salt thereof.

Alternatively, in one particular embodiment, the compound of the invention (compound of formula (I)) is compound P1, optionally present (e.g. where chemically possible) as an agrochemically acceptable salt (e.g. agrochemically acceptable metal, sulfonium or ammonium salt) thereof.

Especially particularly preferably, the compound of the invention (compound of formula (I)) is compound A8, A9, A10, A14 or A16 (preferably compound A8, A9, A10 or A16, more preferably A8, A9 or A16, most preferably A8 or A16), optionally present (e.g. where chemically possible) as an agrochemically acceptable salt (e.g. agrochemically acceptable metal, sulfonium or ammonium salt) thereof.

In an further, alternative, aspect of the invention, there is provided a compound B2, of the following structure:

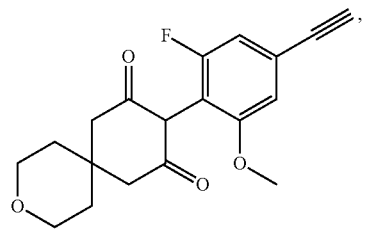 [SMILES: C#Cc1cc(F)c(C2C(=O)CC3(CCOCC3)CC2=O)c(OC)c1]

optionally present (e.g. where chemically possible) as an agrochemically acceptable salt thereof.

Processes for Preparation of Compounds, e.g. Compounds of Formula (I)

Compounds of formula I, in which Q is Q1 may in general be made by the general methods described below.

A compound of formula I, wherein Q is Q1, G is $C_1$-$C_8$alkyl, $C_2$-$C_8$fluoroalkyl, phenyl$C_1$-$C_8$alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, nitro, $SC_1$-$C_3$alkyl, $S(O)C_1$-$C_3$alkyl, or $S(O)_2C_1$-$C_3$alkyl), heteroaryl$C_1$-$C_8$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano, nitro, S, S(O), or $S(O)_2$), $C_2$-$C_7$alkenyl-$CH_2$—, $C_2$-$C_7$alkenyl-CH(Me)-, $C_2$-$C_7$alkenyl-$CMe_2$-, $C_2$-$C_4$fluoroalkenyl-$CH_2$—, $C_2$-$C_7$alkynyl-$CH_2$—, —$C(X^a)$—$R^a$, —$C(X^b)$—$X^c$—$R^b$, —$C(X^d)$—$N(R^c)$—$R^d$, —$SO_2$—$R^e$, —$P(X^e)(R^f)$—$R^g$ or —$CH_2$—$X^f$—$R^h$, may be prepared by treating a compound of formula (A), which is a compound of formula I wherein Q is Q1 and G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di($C_1$-$C_8$alkyl) sulfate, or with a $C_3$-$C_8$alkenyl halide, or with a $C_3$-$C_8$alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$, wherein $X^a$ is oxygen, or an isocyanate, $R^cN$=C=O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$(X^d)$—$N(R^c)$—$R^d$ (wherein $X^d$ is sulfur and with the proviso that neither $R^c$ or $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^cN$=C=S, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base. Where substituents $R^3$ and $R^4$ are not equal to substituents $R^5$ and $R^6$, these reactions may produce, in addition to a compound of formula I, wherein Q is Q1, a second compound of formula (IA) wherein Q is Q1. This invention covers both a compound of formula I and a compound of formula (IA) wherein Q is Q1, together with mixtures of these compounds in any ratio.

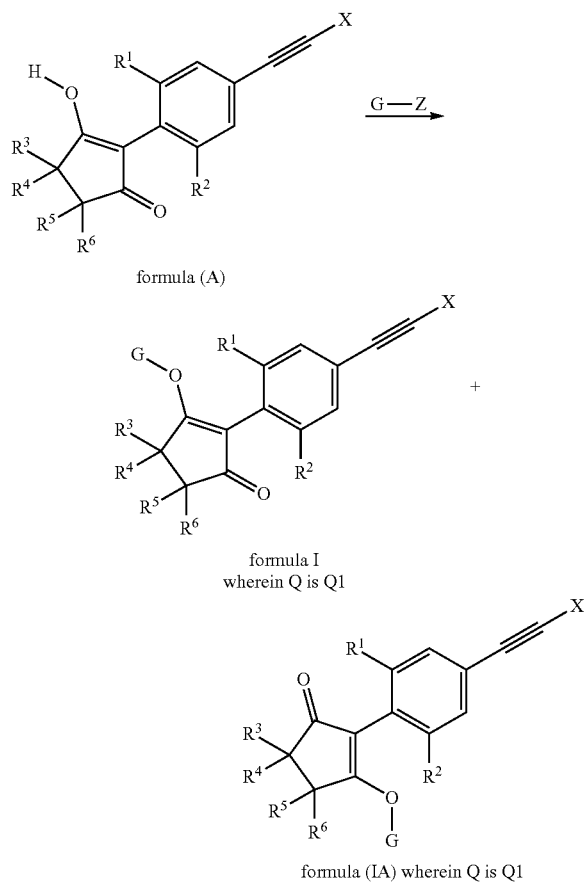

formula (A)

formula I
wherein Q is Q1 formula (IA) wherein Q is Q1

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide; a suitable metal hydride is sodium hydride; and suitable organic bases include trialkylamines, such as trimethylamine and triethylamine, pyridines or other amine bases such as 1,4-diazabicyclo[2.2.2]-octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197-201.

A compound of formula (A) may be prepared via the cyclisation of a compound of formula (B), preferably in the presence of an acid or base, and optionally in the presence of a suitable solvent, by analogous methods to those described by T. Wheeler, U.S. Pat. No. 4,209,532. Compounds of formula (B) have been particularly designed as intermediates in the synthesis of compounds of formula I wherein Q is Q1. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane. A compound of formula (B) wherein R is alkyl (preferably methyl or ethyl) may also be cyclised under basic conditions in the presence of at least one equivalent of a strong base in a solvent such as tetrahydrofuran, toluene, dimethylsulfoxide or N,N-dimethylformamide. Suitable bases include potassium tert-butoxide, lithium diisopropylamide, sodium bis(trimethylsilyl)amide or sodium hydride. A compound of formula (B), wherein R is alkyl, may be produced from a compound of formula (B), wherein R is H, by esterification under known conditions, for example by treatment with an alcohol, R—OH, in the presence of an acid catalyst.

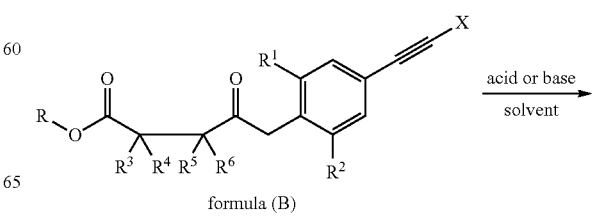

formula (B)

-continued

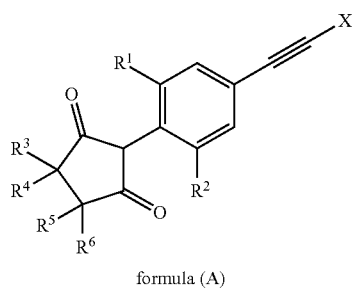

formula (A)

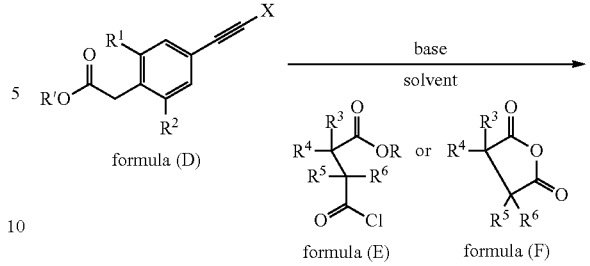

formula (D)     formula (E)    formula (F)

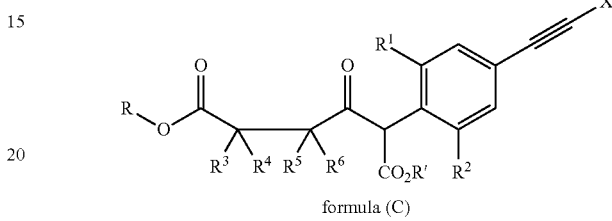

formula (C)

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation, by similar processes to those described by, for example, T. Wheeler, U.S. Pat. No. 4,209,532. Alternatively, a compound of formula (B), wherein R is alkyl or H may be prepared from a compound of formula (C), wherein R' is alkyl preferably $C_1$-$C_3$ alkyl, through a Krapcho decarboxylation procedure under known conditions using known reagents (see for example G. Quallich, P. Morrissey, *Synthesis*, (1993), (1), 51-53).

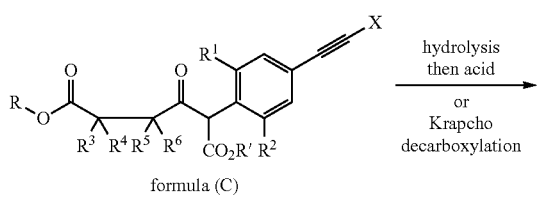

formula (C)

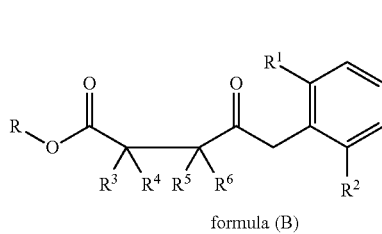

formula (B)

A compound of formula (C), wherein R is alkyl and R' is as previously described, may be prepared by treating a compound of formula (D) with a suitable carboxylic acid chloride of formula (E) wherein R is alkyl under basic conditions. Suitable bases include potassium tert-butoxide, sodium bis(trimethyl-silyl)amide and lithium diisopropylamide and the reaction is preferably conducted in a suitable solvent, such as tetrahydrofuran or toluene, at a temperature between −78° C. and 30° C. Under similar conditions a compound of formula (C), wherein R is H, may be prepared from a suitable anhydride of formula (F).

Compounds of formula (E) and formula (F) are known or can be prepared from known reagents using known methods.

Compounds of formula (D), wherein X is methyl and R' is as previously described, can be prepared by reacting compounds of formula (G) with propyne in the presence of a suitable catalyst, optionally a suitable additive, optionally in a suitable solvent at a suitable temperature. Suitable catalysts include transition metal salts or complexes of transition metal salts (for example palladium acetate, bis (triphenylphosphine) palladium(II) dichloride, tetrakis(triphenylphosphine)palladium(0), bis(triphenylphosphine) nickel(II) dichloride and tris(acetylacetonato) iron(III)), in an amount typically 0.001-25% with respect to a compound of formula (G). Suitable additives include copper salts, for example copper(I) iodide in an amount typically 0.001-50% with respect to a compound of formula (G), and tetraalkyl ammonium salts. Suitable bases include diethylamine, triethylamine, piperidine and pyrrolidine, and suitable solvents include 1,4-dioxane, N,N-dimethylacetamide or N,N-dimethylformamide. Preferably the reaction is carried out using 0.05-10% bis(triphenylphosphine) palladium(II) dichloride (with respect to a compound of formula (G)), 0.05-10% triphenylphosphine (with respect to a compound of formula (G)), 0.05-25% copper(I) iodide (with respect to a compound of formula (G)), 5-200% tetrabutyl ammonium iodide (with respect to a compound of formula (G)), triethylamine and N,N-dimethylformamide at a temperature between 25° C. to 150° C. Such a reaction is an example of a Sonogashira coupling and similar reactions are known in the literature (see for example F. Labrie, S. Gauthier, J. Cloutier, J. Mailhot, S. Potvin, S. Dion, J-Y. Sanceau, WO 2008/124922; M. S. Viciu, S. P. Nolan, *Modern Arylation Methods* (2009), 183-220; R. Chinchilla, C. Najera, *Chemical Reviews* (2007), 107(3), 874-922; I. P. Beletskaya, G. V. Latyshev, A. V. Tsvetkov, N. V. Lukashev, *Tetrahedron Letters* (2003), 44(27), 5011-5013 and J. Mao, G. Xie, M. Wu, J. Guo, S. Ji, *Advanced Synthesis & Catalysis* (2008), 350(16), 2477-2482).

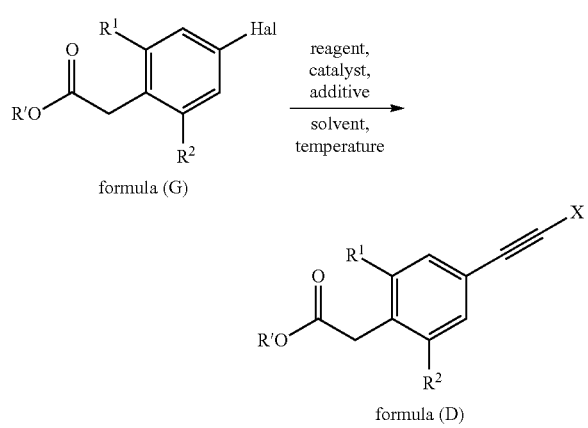

formula (G)

formula (D)

In an alternative approach a compound of formula (D) may be prepared from a compound of formula (G) by reaction with a propynyl transfer reagent such as 1-propynyllithium, 1-propynylmagnesium bromide, 1-propynylmagnesium chloride, 1-propynylmagnesium iodide, 1-propynylzinc chloride, 1-propynylzinc bromide, 1-propynylzinc iodide, tributylpropynylstannane, 1-propyne-1-boronic acid (or ester thereof), 2-butynoic acid or 1-(trimethylsilyl)propyne, with a transition metal catalyst system under suitable conditions (see for example P. Wessig, G. Mueller, C. Pick, A. Matthes, Synthesis (2007), (3), 464-477; J. H. Chaplin, G. S. Gill, D. W. Grobelny, B. L. Flynn, G. Kremmidiotis, WO07/087684; A. Akao, T. Tsuritani, S. Kii, K. Sato, N. Nonoyama, T. Mase, N. Yasuda, Synlett (2007), (1), 31-36. A. Coelho Coton, E. Sotelo Perez, F. Guitian Rivera, A. Gil Gonzalez, WO 2011/048247; C. H. Oh, S. H. Jung, Tetrahedron Letters (2000), 41(44), 8513-8516; D. Zhao, C. Gao, X. Su, Y. He, J. You, Y. Xue, Chemical Communications (2010), 46(47), 9049-9051; C. Yang, S. P. Nolan, Organometallics (2002), 21(6), 1020-1022). In another set of preferred conditions a compound of formula (G) is reacted with 1-propynylmagnesium bromide in the presence of 0.05-10% bis(triphenylphosphine) palladium(II) dichloride (with respect to a compound of formula (G)), in tetrahydrofuran at a temperature between 25° C. and 100° C., as described by J. H. Chaplin, G. S. Gill, D. W. Grobelny, B. L. Flynn, G. Kremmidiotis, WO 07/087684.

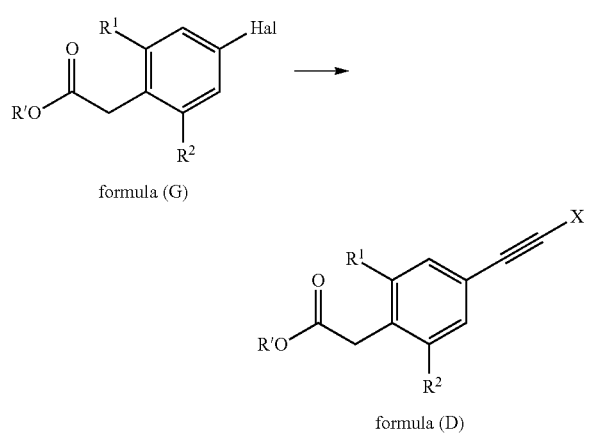

formula (G)

formula (D)

In another set of preferred conditions to prepare a compound of formula (D) in which X=methyl, a compound of formula (G) is reacted with 2-butynoic acid in the presence of bis(triphenylphosphine) palladium(II) dichloride (typically in an amount of 0.1 to 5 mole % with respect to the compound of formula (G)), in a suitable organic solvent such as dimethylsulfoxide, preferably at a temperature of from 25 to 125° C.; e.g. as described by J. Moon, M. Jang and S. Lee, Journal of Organic Chemistry (2009), page 1403 onwards. This is a decarboxylative coupling reaction.

Compounds of formula (G) are known, or can be prepared by known methods using known reagents.

Compounds of formula (D), wherein X is chlorine and R' is $C_1$-$C_4$alkyl, can be prepared from compounds of formula (H) or compounds of formula (I). In one approach a compound of formula (H) is first deprotonated with a base such as butyllithium, sodium hydride, lithium diisopropylamide or ethylmagnesium bromide, then reacted with a chlorine source such as N-chloro succinimide, chlorine or carbon tetrachloride. The specific chlorine source is selected to provide the required chloro-acetylene. Similar reactions and conditions are reported in the literature (see for example M. Tajbakhsh, S. Habibzadeh, Letters in Organic Chemistry (2007), 4(7), 512-514; D. Sud, T. J. Wigglesworth, N. R. Branda, Angewandte Chemie, International Edition (2007), 46(42), 8017-8019; M. A. P. Martins, D. J. Emmerich, C. M. P. Pereira, W. Cunico, M. Rossato, N. Zanatta, H. G. Bonacorso, Tetrahedron Letters (2004), 45(25), 4935-4938; A. Poloukhtine, V. Rassadin, A. Kuzmin, V. V. Popik, Journal of Organic Chemistry (2010), 75(17), 5953-5962; C. R. Hickenboth, J. D. Rule, J. S. Moore, Tetrahedron (2008), 64(36), 8435-8448; F. H. M. Graichen, A. C. Warden, S. Kyi, M. S. O'Shea, Australian Journal of Chemistry (2010), 63(4), 719-722; and M. L. Narayana, M. L. N. Rao, M. Periasamy, Synthetic Communications (1995), 25(15), 2295-9).

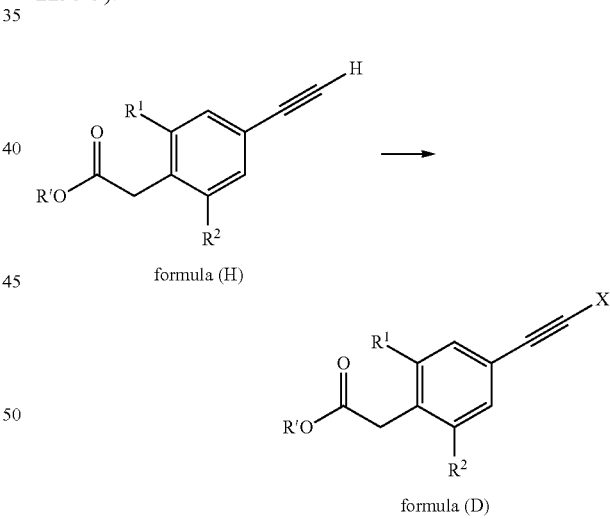

formula (H)

formula (D)

In another approach a compound of formula (D), wherein X is chlorine and R' is $C_1$-$C_4$alkyl, can be prepared from a compound of formula (H) by treatment with a mixture of reagents that are known to promote chlorination, such as potassium carbonate, tetrabutylammonium bromide and carbon tetrachloride (see for example T. Matsuda, S. Kadowaki, Y. Yamaguchi, M. Murakami, Chemical Communications (2008), (24), 2744-2746), pyridine and chlorine (see for example R. B. Gutsulyak, V. N. Britsuk, L. A. Kostrikina, Y. Serguchev, Ukrainskii Khimicheskii Zhurnal (1993), 59(10), 1062-7), silver nitrate and N-chloro succinimide, N-chloro succinimide and hexamethylphosphoramide (see for example G. Pangon, J. L. Philippe, P. Cadiot, *Comptes Rendus des Seances de l'Academie des Sciences, Serie C: Sciences Chimiques* (1973), 277(18), 879-81), and/or perchloric acid and acetic acid (see for example J. P. Montheard, M. Camps, M. Chatzopoulos, M. O. A. Yahia, R. Guilluy, D. Deruaz, *Journal of Chemical Research, Synopses* (1983), (9), 224-5). Conditions are selected to provide the required halo-acetylene. When X is chlorine, preferred conditions include reacting a compound of formula (H) with 1-5 equivilents of N-chloro succinimide and 0.05-50% silver acetate (with respect to a compound of formula (H)) in acetone at a temperature between 25° C. and 100° C.

Compounds of formula (I), wherein R' is $C_1$-$C_4$alkyl and R" is $C_1$-$C_4$alkyl, can also be directly converted to compounds of formula (D) by treatment with isocyanuric chloride or N-chloro succinimide and silver nitrate (see for example M. H. Vilhelmsen, A. S. Andersson, M B. Nielsen, *Synthesis* (2009), (9), 1469-1472).

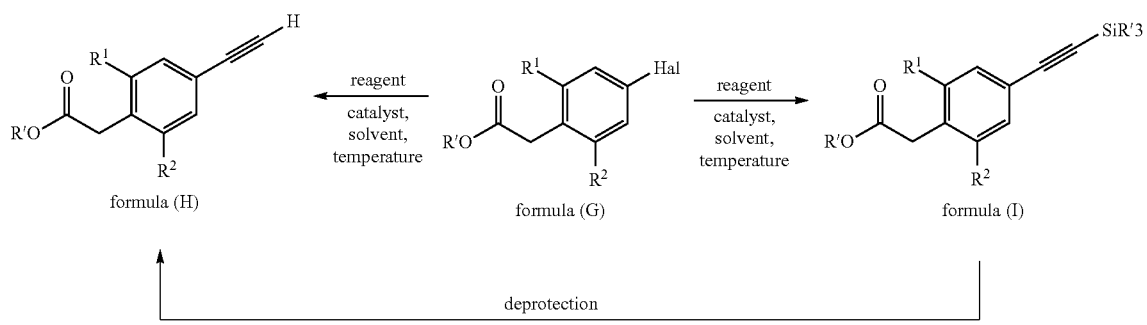

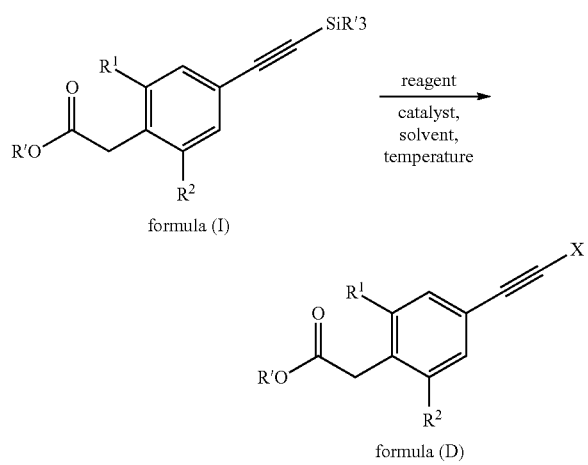

A compound of formula (I), wherein R' is $C_1$-$C_4$alkyl, can be prepared by reacting a compound of formula G with a trialkylsilylacetylene, under similar conditions described previously to convert a compound of formula (G) to a compound of formula (D) (wherein X is methyl).

A compound of formula (H) can either be prepared by deprotection of a compound of formula (I) under known conditions, or by reacting a compound of formula (G) with an ethynyl transfer reagent such as tributylstannylacetylene, lithium acetylide ethylenediamine complex, ethynylzinc bromide or ethynylmagnesium chloride in the presence of a suitable catalyst system, under conditions similar to those described previously (see for example C. Fischer, J. Methot, H. Zhou, A. J. Schell, B. Munoz, A. A. Rivkin, S. P. Ahearn, S. Chichetti, R. N. Maccoss, S. D. Kattar, M. Christopher, C. Li, A. Rosenau, W. C. Brown, WO 2010/071741; M. Behler, A. Eluntlaut, C. Ferman, A. Chapuf, CN 101195641; G. Wang, G. Zhu, E. Negishi, *Journal of Organometallic Chemistry* (2007), 692(21), 4731-4736 and E. Negishi, M. Kotora, C. Xu, *Journal of Organic Chemistry* (1997), 62(25), 8957-8960).

In a further approach, a compound of formula (D) (wherein X is chlorine) can either be prepared from a compound of formula (J) or a compound of formula (K), by treatment with a suitable base, in a suitable solvent, at a suitable temperature. A compound of formula (J) can be converted to a compound of formula (D) under conditions similar to those described in the literature, for example treatment using potassium tert-butoxide in tert-butanol at a temperature between 25° C. and 150° C., or lithium 2,2,6,6-tetramethylpiperidine in tetrahydrofuran at a temperature between −25° C. and 50° C. (see for example E. Bartmann, R. Hittich, H. Plach, U. Finkenzeller, U.S. Pat. No. 5,188,759 and *Indian Journal of Chemistry, Section B: Organic Chemistry Including Medicinal Chemistry*, 1978, vol. 16, 1051-1054). A compound of formula (K) can also be converted to a compound of formula (D) under conditions similar to those described in the literature, for example by treatment with cesium carbonate in N,N-dimethylformamide at a temperature between 25° C. and 150° C., sodium tert-butoxide in toluene at a temperature between 25° C. and 150° C., 1,8-diazabicyclo[5.4.0]undec-7-ene in dimethylsulfoxide at a temperature between 0° C. and 50° C. and potassium tert-butoxide in tetrahydrofuran at a temperature between −78° C. and 25° C. (see for example B. C. G. Soederberg, S. P. Gorugantula, C. R. Howerton, J. L. Petersen, S. W. Dantale, *Tetrahedron* (2009), 65(36), 7357-7363; S-C. Lo, R. E. Harding, E. Brightman, P. L. Burn, I. D. W. Samuel, *Journal of Materials Chemistry* (2009). 19(20), 3213-3227; S. Wang, T. Kohn, Z. Fu, X. Y. Jiao, S. Lai, M. Schmitt, *Tetrahedron Letters* (2008), 49(51), 7284-7286 and M. L. G. Borst, R. E. Bulo, D. J. Gibney, Y. Alem, F. J. J. de Kanter, A. W. Ehlers, M. Schakel, M. Lutz, A. L. Spek, K. Lammertsma, *Journal of the American Chemical Society* (2005), 127(48), 16985-16999). Compounds of formula (J) and (K) (wherein X is chlorine) can be prepared from known compounds using known methods and reagents.

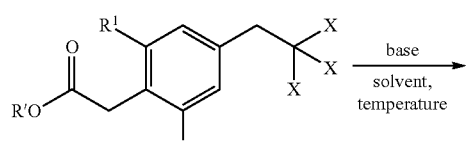

formula (J)

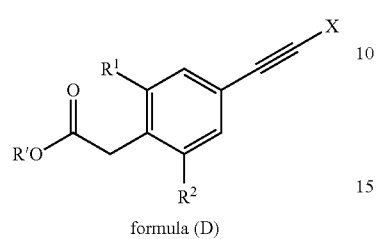

formula (D)

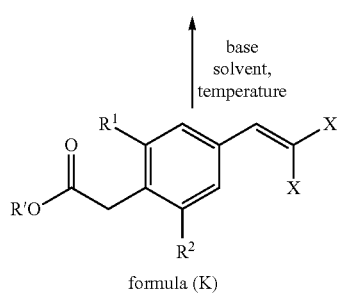

formula (K)

In a further approach a compound of formula (A), wherein X is methyl, can be prepared directly from a compound of formula (L), under similar conditions described previously to convert a compound of formula (G) to a compound of formula (D).

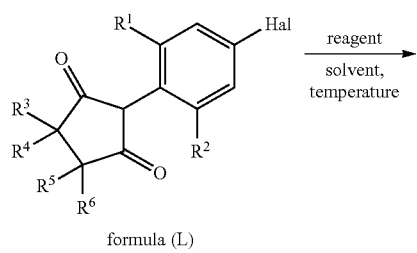

formula (L)

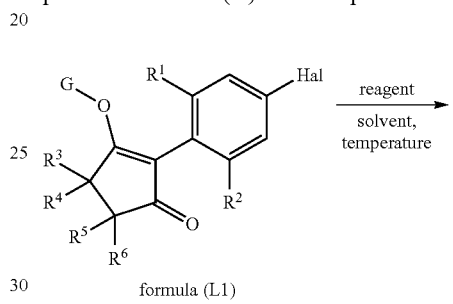

formula (A)

In a still further approach, a compound of formula I, wherein X is methyl and G is preferably $C_1$-$C_3$ alkyl, can be prepared directly from a compound of formula (L1), under similar conditions described previously to convert a compound of formula (G) to a compound of formula (D).

formula (L1)

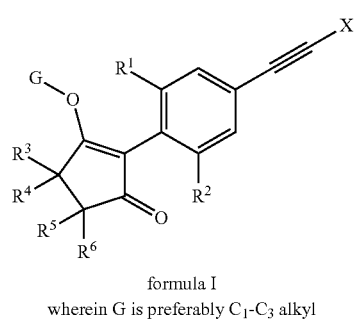

formula I
wherein G is preferably $C_1$-$C_3$ alkyl

A compound of formula (L) can be prepared from a compound of formula (G) using similar procedures to those outlined previously.

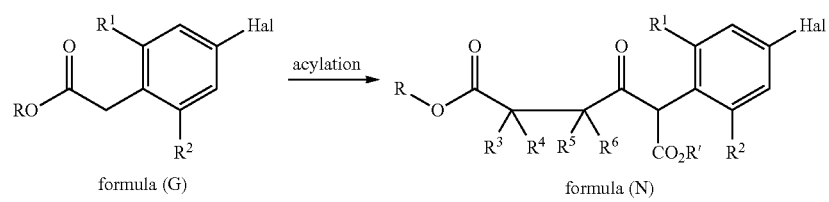

formula (G)　　　　　　　　formula (N)

hydrolysis and decarboxylation

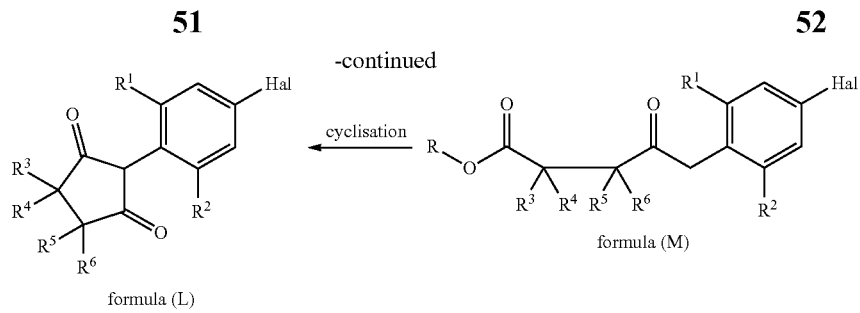

A compound of formula (A), wherein X is chlorine, can be prepared from a compound of formula (L), via either a compound of formula (O) or a compound of formula (P), wherein R' is $C_1$-$C_4$alkyl, under similar conditions to those described previously.

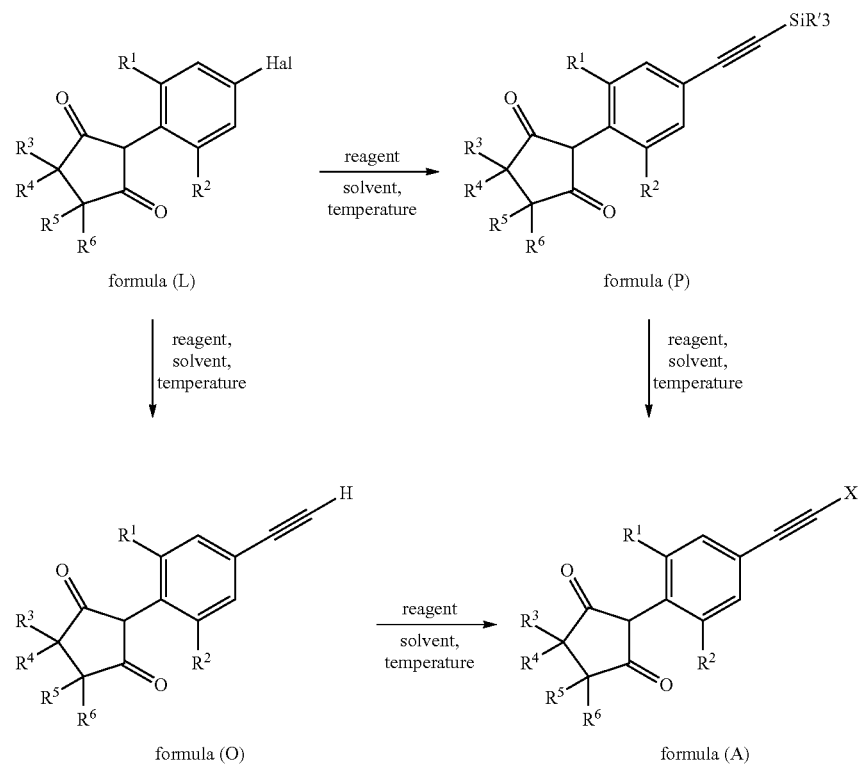

A compound of formula (A), wherein X is chlorine, can also be prepared from a compound of formula (Q*) under conditions similar to those described for converting a compound of formula (K) to a compound of formula (D).

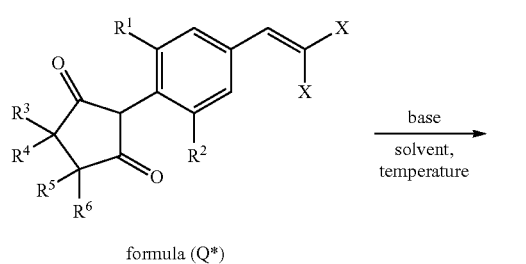

A compound of formula (Q*), wherein X is chlorine may be prepared from an aldehyde of formula (R) by treatment with triphenylphosphine in the presence of carbon tetrachloride in a suitable solvent at a suitable temperature. Carbon tetrachloride is selected to provide the required dichloroalkene, and similar reactions are known in the literature (see for example A. Poloukhtine, V. V. Popik, *Journal of the American Chemical Society* (2007), 129(40), 12062-12063; L. N. Michaelides, B. Darses, D. J. Dixon, *Organic Letters* (2011), 13(4), 664-667 and F. Gavina, S. V. Luis, P. Ferrer, A. M. Costero, J. A. Marco, *Journal of Chemical Research, Synopses* (1986), (9), 330-1).

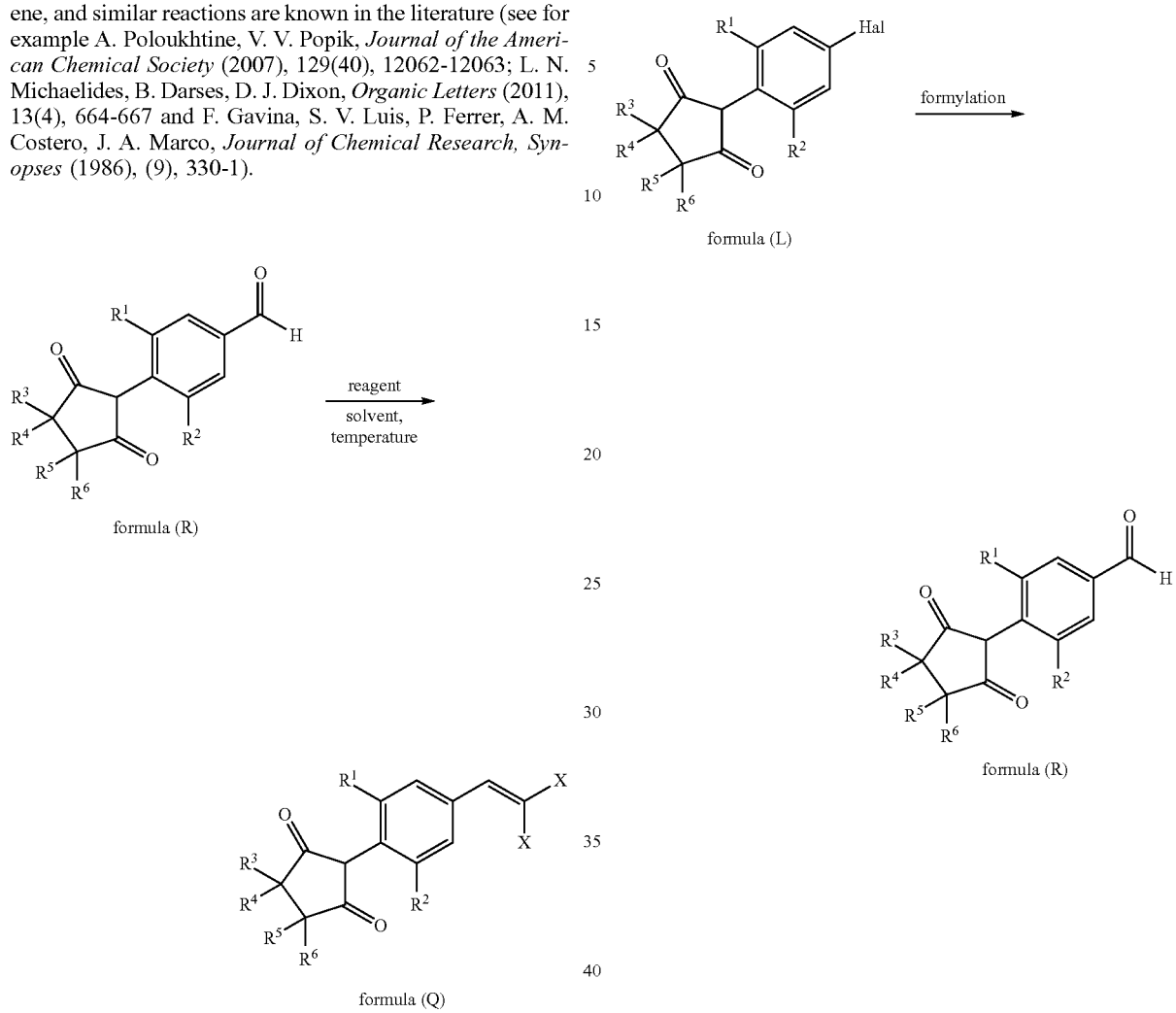

A compound of formula (R) may be prepared by the formylation of a compound of formula (L) (wherein Hal is chlorine, bromine or iodine, preferably bromine or iodine). Suitable conditions for effecting the formylation of aryl halides are known, and include, for example, the treatment of an aryl halide with a suitable organometallic reagent, such as isopropyl magnesium chloride, n-butyllithium, sec-butyllithium or tert-butyllithium, or by treatment with a suitable alkali metal or alkali earth metal, such as lithium or magnesium, in a suitable solvent such as diethyl ether, dimethoxyethane or tetrahydrofuran. The resulting arylmetal reagent is then reacted with a suitable formylating agent such as N,N-dimethylformamide or N-formylmorpholine. Alternatively a compound of formula (R) may be prepared from a compound of formula (L) (wherein Hal can also be a pseudohalogen such as triflate) by treatment with a carbonylating agent, such as carbon monoxide, in the presence of a suitable catalyst system, base, and reducing agent (see for example L. Ashfield and C. Barnard, *Org. Process Res. Dev.*, 11 (1), 39-43, 2007).

In an alternative approach a compound of formula I, wherein X is methyl and G is preferably methyl or ethyl, may be prepared from a boronic acid or boronic ester of formula (S) by treatment with either 1-bromo-1-propyne or 1-iodo-1-propyne in the presence of a suitable catalyst system, suitable base, suitable solvent at a suitable temperature. Similar reactions are known in the literature, and preferred conditions involve reacting a compound of formula (S) with 1-iodo-propyne in the presence of 0.005-25% palladium(II) chloride with respect to a compound of formula (S), and 1-10 equivalents potassium carbonate in a mixture of toluene, water and methanol at a temperature between 50° C.-150° C., as described by Y. Shi, X. Li, J. Liu, W. Jiang, L. Sun, *Tetrahedron Letters* (2010), 51(28), 3626-3628. A compound of formula (T), wherein G is preferably methyl or ethyl and R' is $C_1$-$C_4$alkyl, may be prepared under similar conditions using either 1-bromo-2-(trimethylsilyl)acetylene or 1-iodo-2-(trimethylsilyl)acetylene as the coupling partner. Compounds of formula (A) and (P) may be prepared from compounds of formula I and (T) respectively, by hydrolysis of the enol ether.

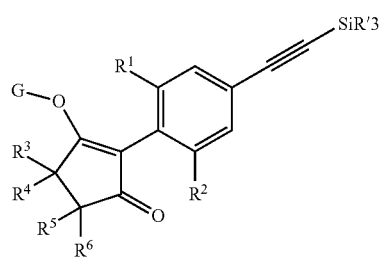

formula (T)

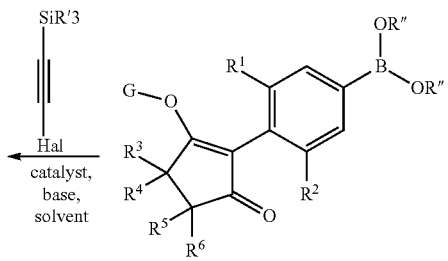

formula (S)

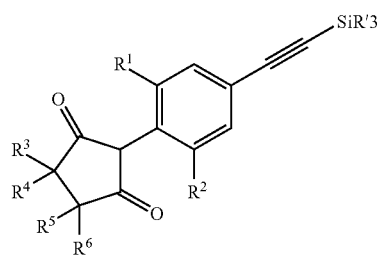

formula (P)

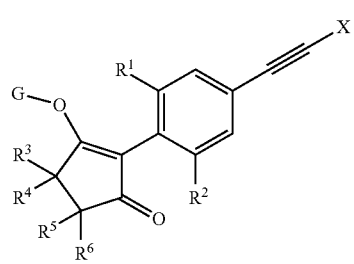

formula I

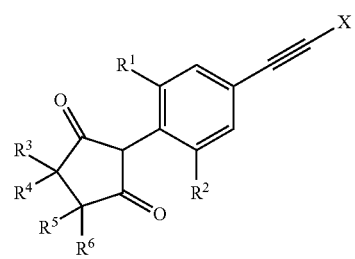

formula (A)

In one approach a compound of formula (S) may be prepared from a compound of formula (L), wherein Hal is preferably iodine or bromine, by treatment with a suitable base such as sodium hydride, potassium hydride or isopropylmagnesium chloride, in a suitable solvent such as tetrahydrofuran or diethyl ether, followed by a metal-halogen exchange reaction, preferably by treatment with an alkyllithium reagent such as n-butyllithium, sec-butyllithium or tert-butyllithium, or an organomagnesium reagent such as isopropyl magnesium chloride, and subsequent treatment with a trialkylborate, B(OR″)$_3$, preferably trimethylborate, to give the corresponding boronate ester of formula (S).

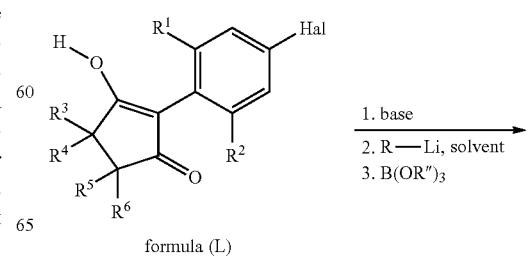

formula (L)

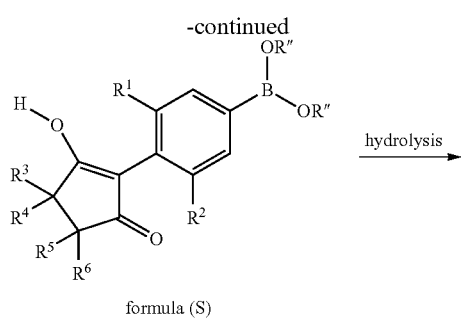

formula (S)

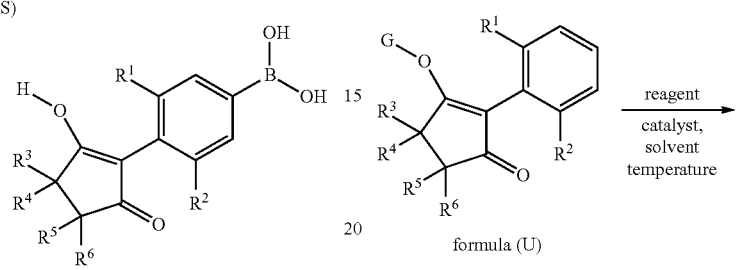

formula (U)

In an alternative approach a compound of formula (S) may be prepared from a compound of formula (U), wherein G is preferably methyl or ethyl, by C—H borylation with a suitable borylating agent, a suitable catalyst system, in a suitable solvent at a suitable temperature. Suitable catalysts include 1,5-cyclooctadiene)(methoxy)iridium(I) dimer in combination with 4,4'-di-tert-butyl-2,2'-dipyridyl, suitable borylating agents include bis(pinacolato)diboron or pinacol borane, and suitable solvents include hexane, octane, tetrahydrofuran and methyl tert-butyl ether. Similar examples are known in the literature (see for example J. F. Hartwig, *Chemical Society Reviews* (2011), 40(4), 1992-2002 and T. Ishiyama, N. Miyaura, *Pure and Applied Chemistry* (2006), 78(7), 1369-1375). Preferred conditions include treating a compound of formula (U) with 0.05-10% 1,5-cyclooctadiene)(methoxy)iridium(I) dimer (with respect to a compound of formula (U)), 0.05-10% 4,4'-di-tert-butyl-2,2'-dipyridyl (with respect to a compound of formula (U)), and 1-2 equivalents bis(pinacolato)diboron (with respect to a compound of formula (U)) in methyl tert-butyl ether at a temperature between 50° C.-150° C., optionally under microwave irradiation, as described by P. Harrisson, J. Morris, T. B. Marder, P. G. Steel, *Organic Letters* (2009), 11(16), 3586-3589.

formula (S)

Compounds of formula (U) can be prepared from compounds of formula (W) using similar procedures described above, starting from compounds of formula (Y) which are known compounds.

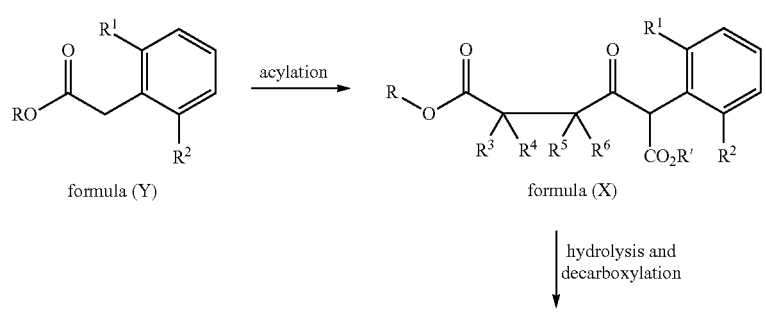

formula (Y)  formula (X)

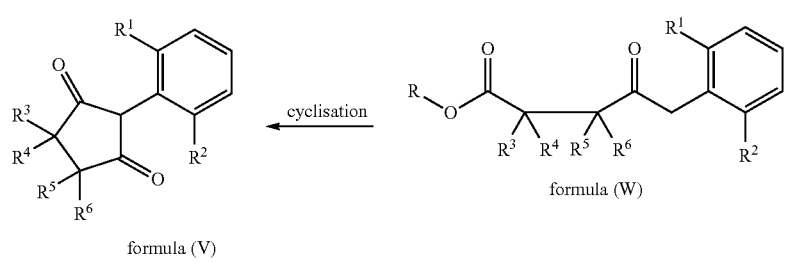

formula (V)  formula (W)

Additionally, a compound of formula (A), wherein X is methyl, may be prepared by the Pinacol rearrangement of a compound of formula (Z) or a compound of formula (AA), wherein X is methyl and R' is $C_1$-$C_4$ alkyl preferably methyl, under protic or Lewis acidic conditions (see, for example, Eberhardt, U. et. al., Chem. Ber. (1983), 116(1), 119-35, and Wheeler, T. N. U.S. Pat. No. 4,283,348). Preferred conditions include reacting a compound of formula (Z) or (AA) with trifluoroacetic acid at room temperature.

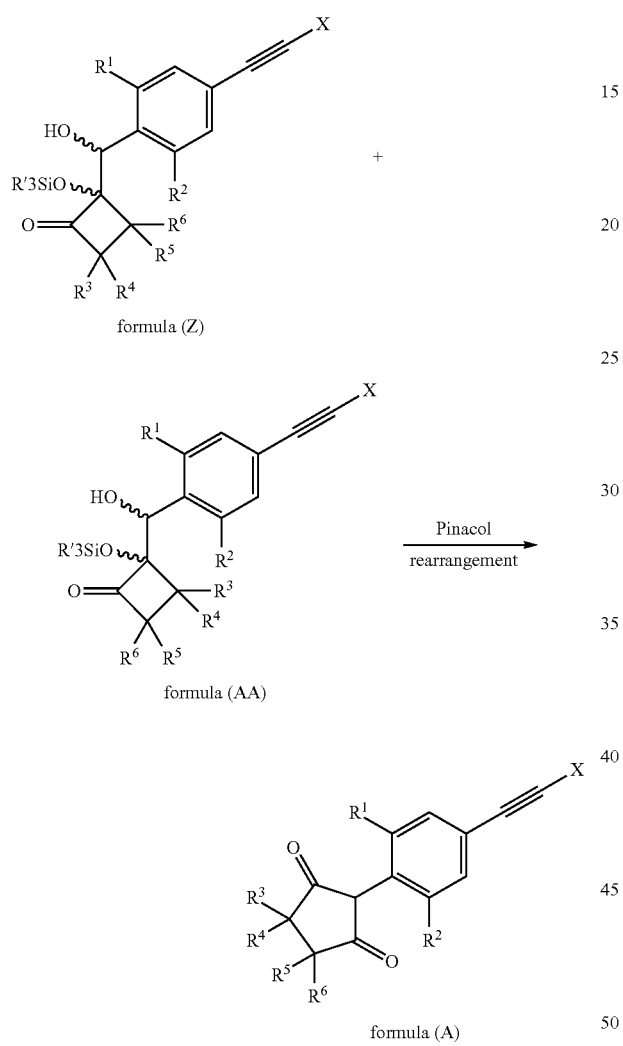

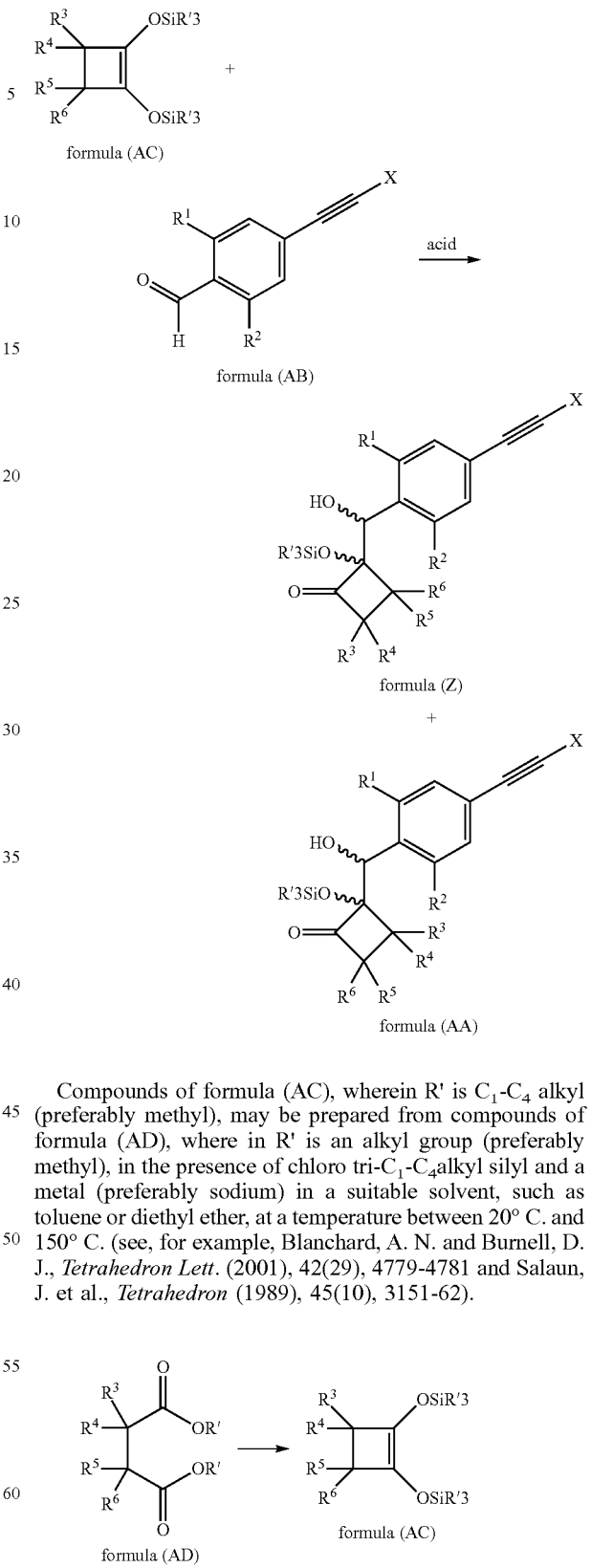

A compound of formula (Z) and a compound of formula (AA), wherein X is methyl and R' is $C_1$-$C_4$ alkyl (preferably methyl), may be prepared by treating a compound of formula (AC) with a compound of formula (AB) in the presence of an acid such as boron trifluoride, titanium chloride or magnesium iodide, optionally in a suitable solvent such as dichloromethane, at a temperature between −80° C. and 30° C. (see, for example, Li, W.-D. Z. and Zhang, X.-X., Org. Lett. (2002), 4(20), 3485-3488; Shimada, J. et al., J. Am. Chem. Soc. (1984), 106(6), 1759-73; Eberhardt, U. et. al., Chem. Ber. (1983), 116(1), 119-35 and Wheeler, T. N. U.S. Pat. No. 4,283,348). A compound of formula (AB), wherein X is methyl, is known or can be prepared from known reagents using known methods.

Compounds of formula (AC), wherein R' is $C_1$-$C_4$ alkyl (preferably methyl), may be prepared from compounds of formula (AD), where in R' is an alkyl group (preferably methyl), in the presence of chloro tri-$C_1$-$C_4$alkyl silyl and a metal (preferably sodium) in a suitable solvent, such as toluene or diethyl ether, at a temperature between 20° C. and 150° C. (see, for example, Blanchard, A. N. and Burnell, D. J., Tetrahedron Lett. (2001), 42(29), 4779-4781 and Salaun, J. et al., Tetrahedron (1989), 45(10), 3151-62).

Compounds of formula (AD) are either known compounds or can be prepared from known reagents using known methods.

Similarly, compounds of formula (P) can also be prepared from compounds of formula (AC), wherein R' is $C_1$-$C_4$alkyl (preferably methyl), and compounds of formula (AE), wherein R' is $C_1$-$C_4$alkyl (preferably methyl), using similar procedures and conditions described previously. Compounds of formula (AE) are known or can be prepared from known reagents using known methods.

Similarly, compounds of formula (L) can also be prepared from compounds of formula (AC), wherein R' is $C_1$-$C_4$alkyl (preferably methyl), and halogenated compounds of formula (AH), using similar procedures and conditions described previously. Compounds of formula (AH) are known or can be prepared from known reagents using known methods.

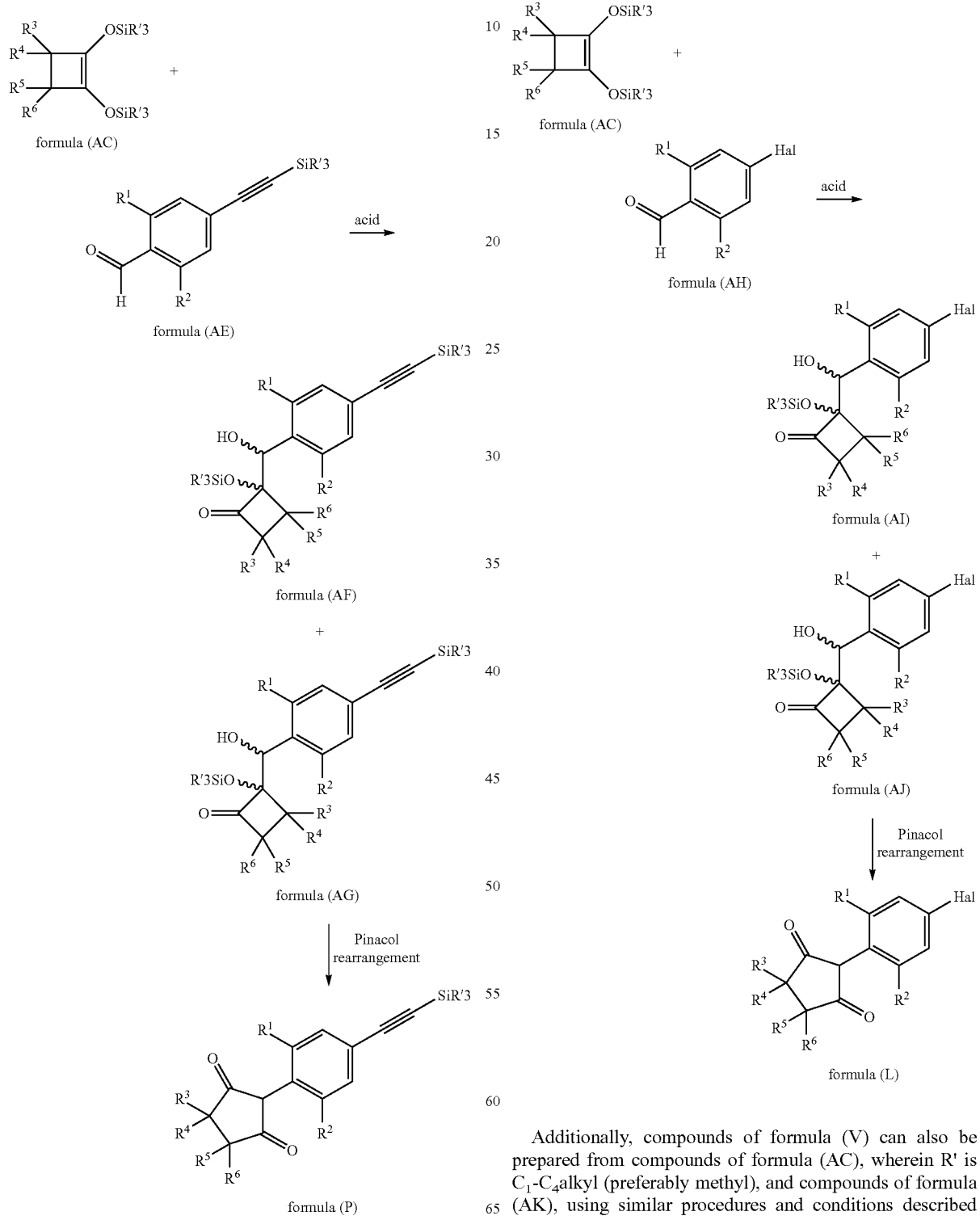

Additionally, compounds of formula (V) can also be prepared from compounds of formula (AC), wherein R' is $C_1$-$C_4$alkyl (preferably methyl), and compounds of formula (AK), using similar procedures and conditions described previously. Compounds of formula (AH) are known or can be prepared from known reagents using known methods.

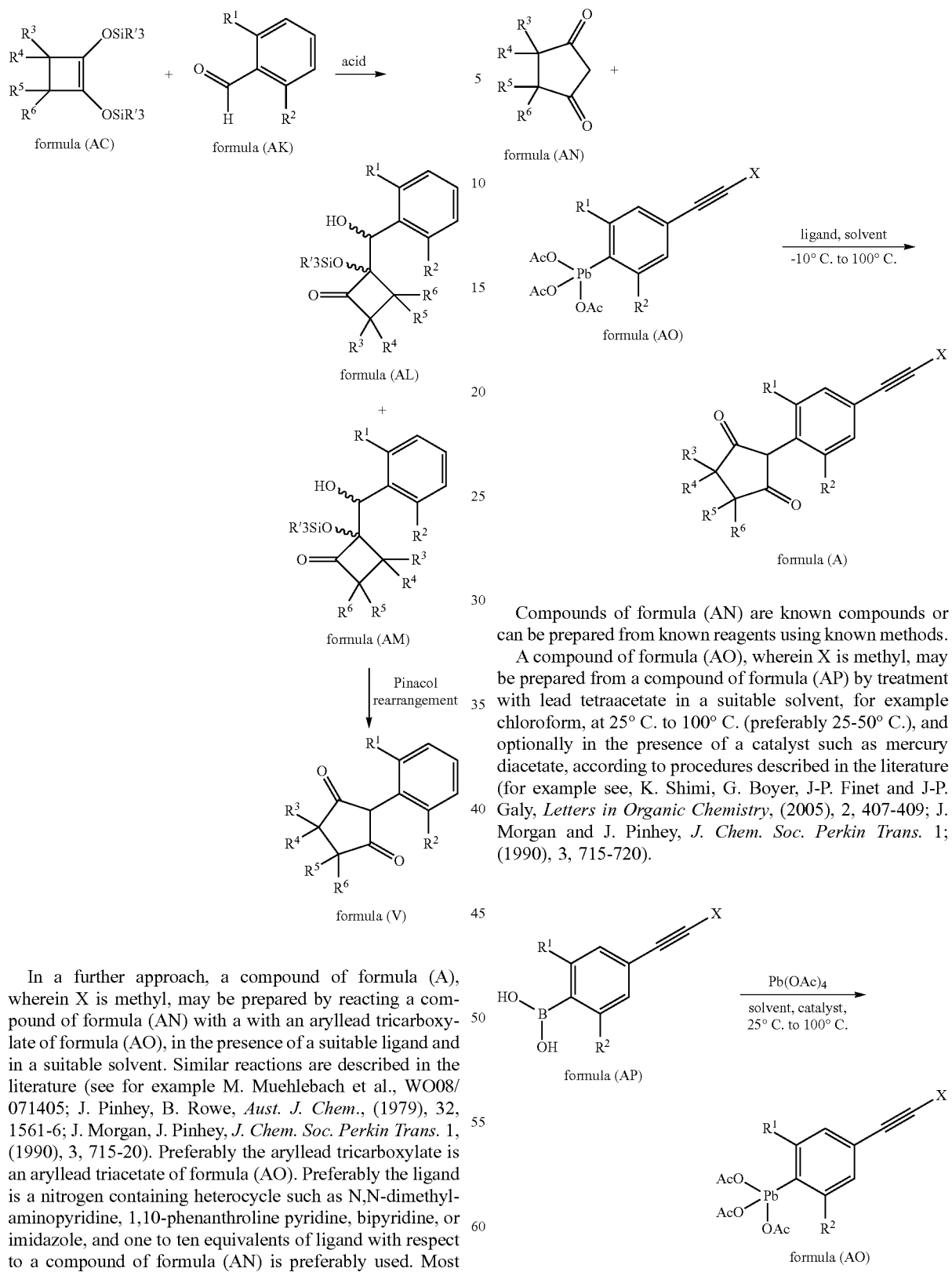

Compounds of formula (AN) are known compounds or can be prepared from known reagents using known methods.

A compound of formula (AO), wherein X is methyl, may be prepared from a compound of formula (AP) by treatment with lead tetraacetate in a suitable solvent, for example chloroform, at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, *Letters in Organic Chemistry*, (2005), 2, 407-409; J. Morgan and J. Pinhey, *J. Chem. Soc. Perkin Trans. 1*; (1990), 3, 715-720).

In a further approach, a compound of formula (A), wherein X is methyl, may be prepared by reacting a compound of formula (AN) with a with an aryllead tricarboxylate of formula (AO), in the presence of a suitable ligand and in a suitable solvent. Similar reactions are described in the literature (see for example M. Muehlebach et al., WO08/071405; J. Pinhey, B. Rowe, *Aust. J. Chem.*, (1979), 32, 1561-6; J. Morgan, J. Pinhey, *J. Chem. Soc. Perkin Trans. 1*, (1990), 3, 715-20). Preferably the aryllead tricarboxylate is an aryllead triacetate of formula (AO). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (AN) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.

An aryl boronic acid of formula (AP), wherein X is methyl, may be prepared from an aryl halide of formula (AQ), wherein X is methyl and Hal is bromine or iodine, by known methods (see, for example, W. Thompson and J.

Gaudino, *J. Org. Chem.*, (1984), 49, 5237-5243 and R. Hawkins et al., *J. Am. Chem. Soc.*, (1960), 82, 3053-3059). Thus an aryl halide of formula (AQ) may be treated with an alkyl lithium or alkyl magnesium halide at low temperature, and the aryl magnesium or aryl lithium reagent obtained is allowed to react with a trialkyl borate, B(OR")$_3$, preferably trimethylborate, to give an aryl dialkylboronate which may be hydrolysed to the desired boronic acid of formula (AP) under acidic conditions. Alternatively the same overall transformation of compound (AQ) to compound (AP) may be achieved through a palladium-catalysed borylation reaction under known conditions using known reagents (see for example T. Ishiyama, M. Murata, N. Miyaura, *J. Org. Chem.* (1995), 60, 7508-7501; and K. L. Billingsley, T. E. Barder, S. L. Buchwald, *Angew. Chem. Int. Ed.* (2007), 46, 5359-5363), followed by hydrolysis of the intermediate boronate ester.

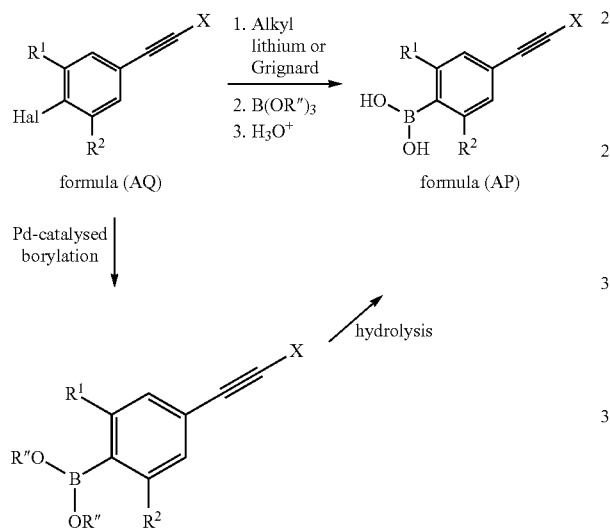

In an alternative approach, a compound of formula (A), wherein X is methyl, may be prepared by the reaction of a compound of formula (AR), wherein Ar is an aryl moiety (preferably phenyl) with an arylboronic acid of formula (AP) in the presence of a suitable palladium catalyst, a suitable base, an optionally in the presence of a suitable ligand or additive, and in a suitable solvent.

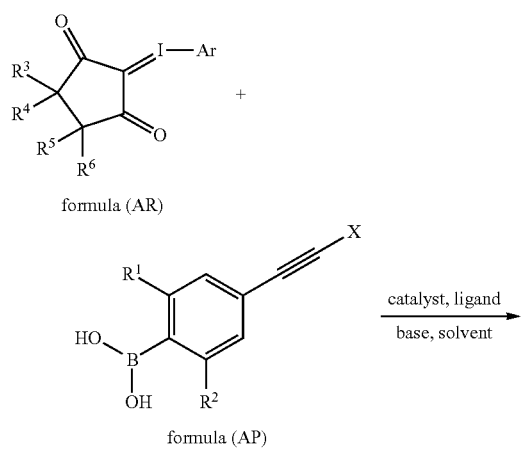

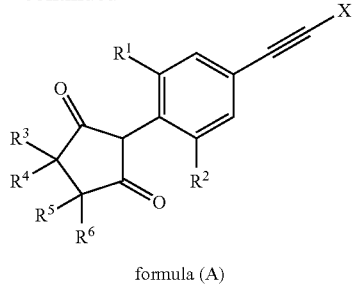

formula (A)

Suitable palladium catalysts include, for example palladium(II) dihalides, palladium(II) acetate and palladium(II) sulfate, and is preferably palladium(II) acetate. Suitable ligands include triphenylphosphine, tricyclopentylphosphine, tricyclohexylphosphine, 2-dicyclohexylphosphino-2', 6'-dimethoxybiphenyl, 2-dicyclohexylphosphino-2',4',6'-triisopropylbiphenyl, 1,1'-bis(diphenylphosphino)ferrocene and 1,2-bis(diphenylphosphino)ethane. The reaction may also be carried out in the presence of other additives, such as tetralkylammonium salts, for example, tetrabutylammonium bromide. Suitable bases include alkali metal hydroxides, especially lithium hydroxide. A suitable solvent is aqueous 1,2-dimethoxyethane.

A compound of formula (AR) may be prepared from a compound of formula (AN) by treatment with a hypervalent iodine reagent such as a (diacetoxy)iodobenzene or iodosylbenzene and a base such as aqueous sodium carbonate, lithium hydroxide or sodium hydroxide in a solvent such as water or an aqueous alcohol such as aqueous ethanol according to the procedures of K. Schank and C. Lick, *Synthesis* (1983), 392; R. Moriarty et al, *J. Am. Chem. Soc.*, (1985), 107, 1375, or of Z. Yang et al., *Org. Lett.*, (2002), 4 (19), 3333:

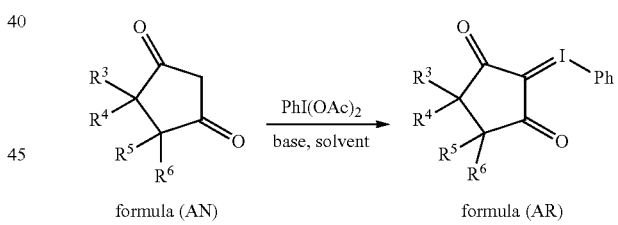

In a further approach, a compound of formula I (wherein Q is Q1, X is methyl and G is preferably methyl or ethyl) may be prepared by reacting a compound of formula (AS) (wherein G is preferably $C_{1-4}$ alkyl, and Hal is a halogen, preferably bromine or iodine), with an arylboronic acid of formula (AP) in the presence of a suitable palladium catalyst for example 0.001-50% palladium(II) acetate with respect to compound (AS), and a base for example 1 to 10 equivalents potassium phosphate with respect to compound (AS), and preferably in the presence of a suitable ligand (for example 0.001-50% (2-dicyclohexylphosphino)-2',6'-dimethoxybiphenyl with respect to compound (AS), and in a suitable solvent, for example toluene, preferably between 25° C. and 200° C. Similar couplings are known in the literature (see for example, Y. Song, B. Kim and J.-N. Heo, *Tetrahedron Letters* (2005), 46 (36), 5987-5990). A compound of formula I wherein Q is Q1 can be converted to a compound of formula (A) by hydrolysis under known conditions.

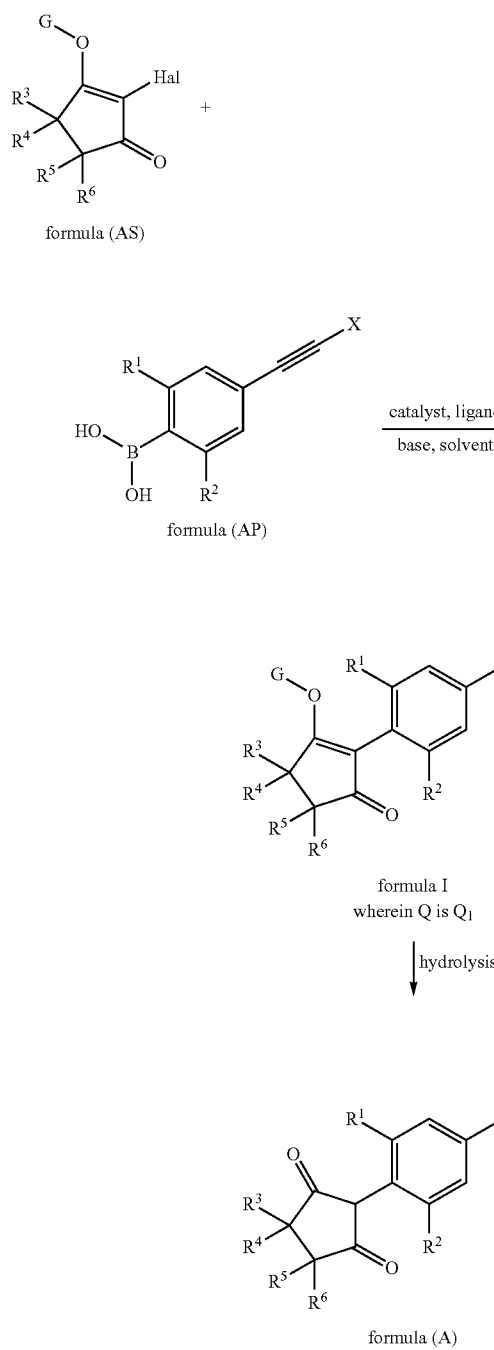

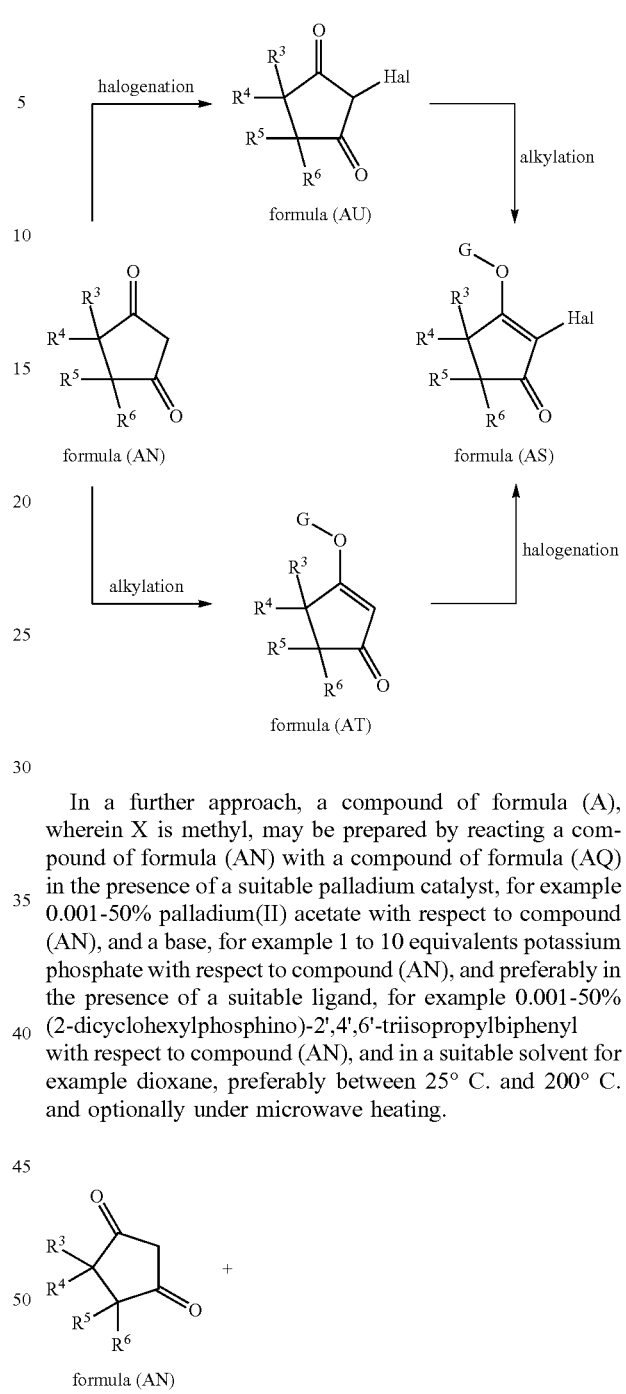

In a further approach, a compound of formula (A), wherein X is methyl, may be prepared by reacting a compound of formula (AN) with a compound of formula (AQ) in the presence of a suitable palladium catalyst, for example 0.001-50% palladium(II) acetate with respect to compound (AN), and a base, for example 1 to 10 equivalents potassium phosphate with respect to compound (AN), and preferably in the presence of a suitable ligand, for example 0.001-50% (2-dicyclohexylphosphino)-2′,4′,6′-triisopropylbiphenyl with respect to compound (AN), and in a suitable solvent for example dioxane, preferably between 25° C. and 200° C. and optionally under microwave heating.

A compound of formula (AS) may be prepared by halogenating a compound of formula (AN), followed by reaction of the resulting halide of formula (AU) with a $C_1$-$C_4$ alkyl halide or tri-$C_1$-$C_4$-alkylorthoformate under known conditions, for example by the procedures of R. Shepherd and A. White (*J. Chem. Soc. Perkin Trans.* 1 (1987), 2153-2155) and Y.-L. Lin et al. (*Bioorg. Med. Chem.* (2002), 10, 685-690). Alternatively, a compound of formula (AS) may be prepared by reacting a compound of formula (AN) with a $C_1$-$C_4$ alkyl halide or a tri-$C_1$-$C_4$-alkylorthoformate, and halogenating the resulting enol ether of formula (AT) under known conditions (see for example Y. Song, B. Kim and J.-N. Heo, *Tetrahedron Letters* (2005), 46(36), 5987-5990).

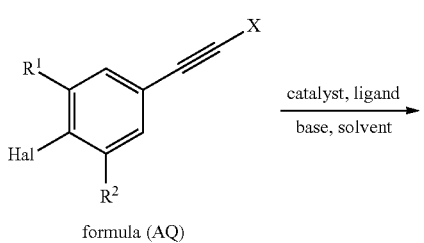

-continued

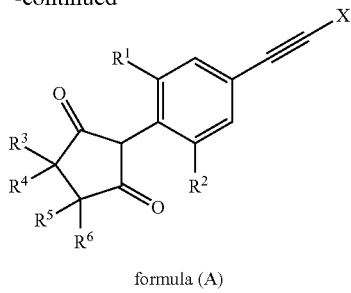

formula (A)

Similar couplings are known in the literature (see for example, S. Buchwald et al., J. Am. Chem. Soc. (2000), 122, 1360-1370; B. Hong et al. WO 2005/000233). Alternatively, a compound of formula (A) may be prepared by reacting a compound of formula (AN) with a compound of formula (AQ) in the presence of a suitable copper catalyst, for example 0.001-50% copper(I) iodide with respect to compound (AN), and a base, for example 1 to 10 equivalents cesium carbonate with respect to compound (AN), and preferably in the presence of a suitable ligand for example 0.001-50% L-proline with respect to compound (AN), and in a suitable solvent, for example dimethylsulfoxide, preferably between 25° C. and 200° C. Similar couplings are known in the literature (see for example, Y. Jiang et al., *Synlett*, (2005), 18, 2731-2734, and X. Xie et al., *Organic Letters* (2005), 7(21), 4693-4695).

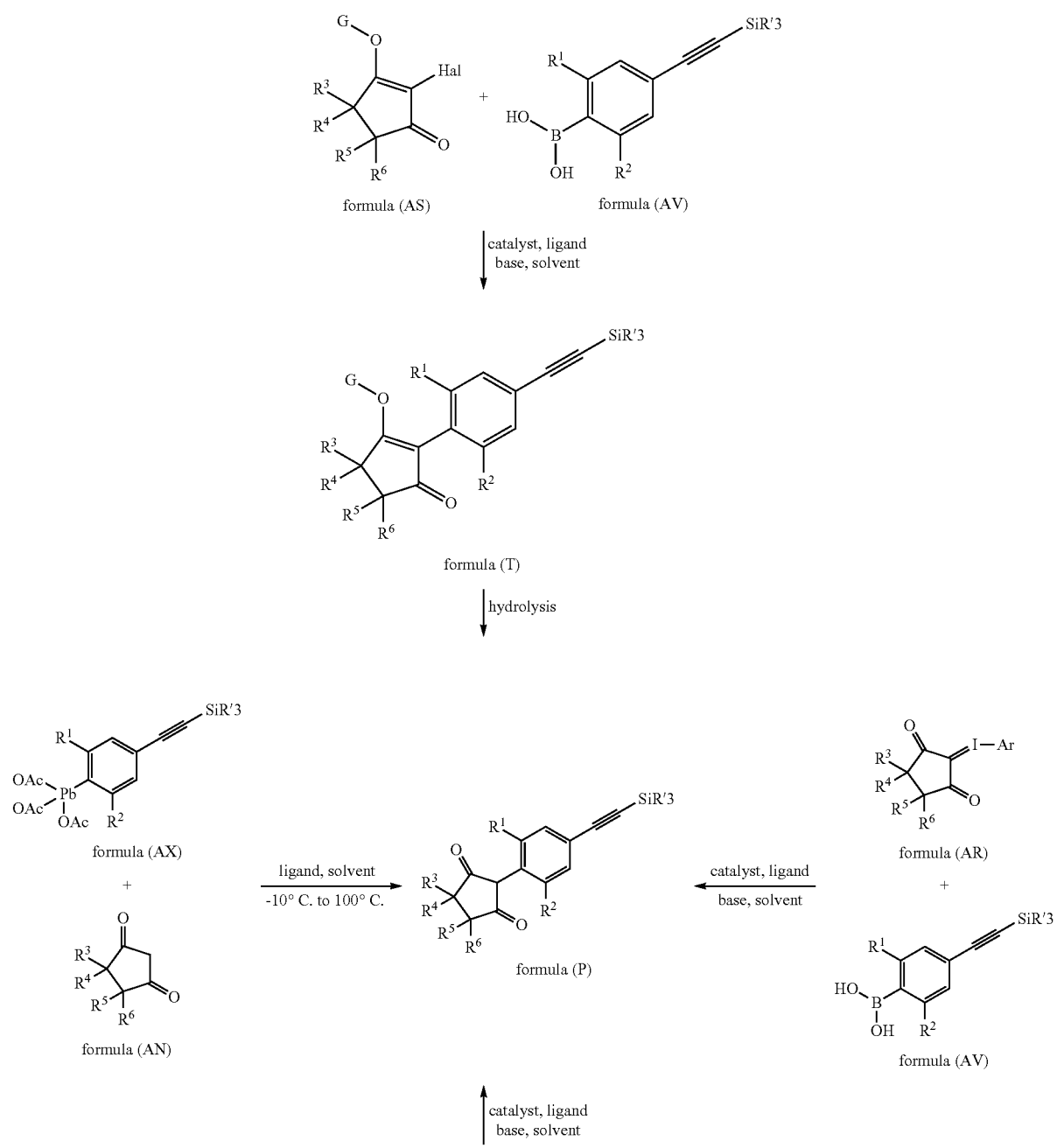

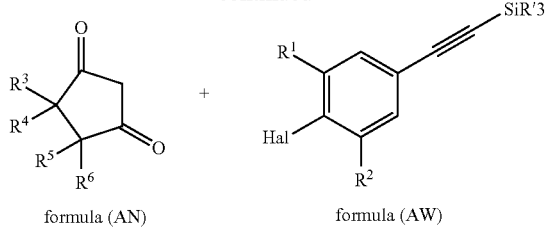
Similarly, a compound of formula (P) can also be prepared using similar methods described previously, starting from compounds (AV), (AW) and (AX) which are known or can be prepared from known reagents using known methods.
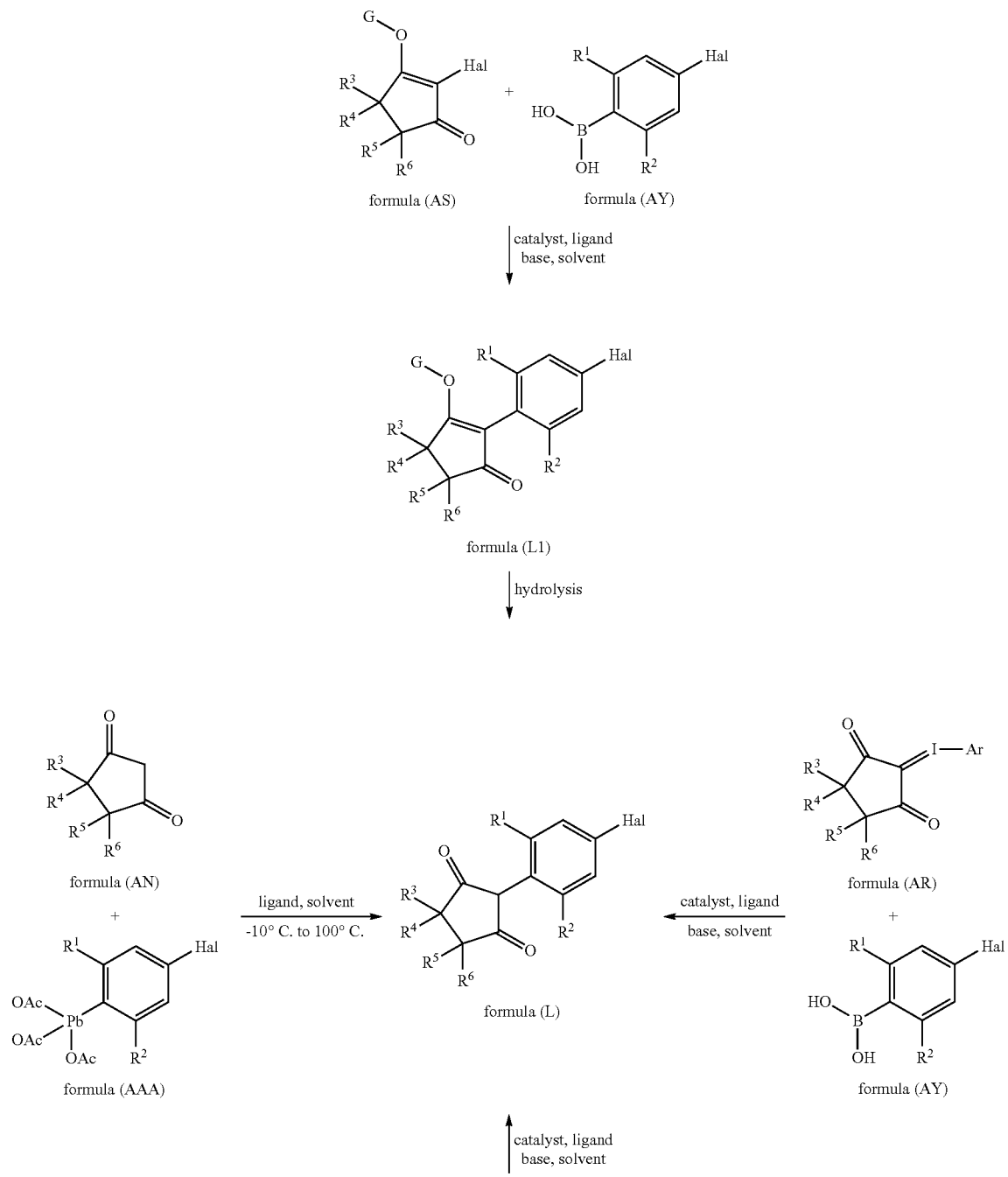

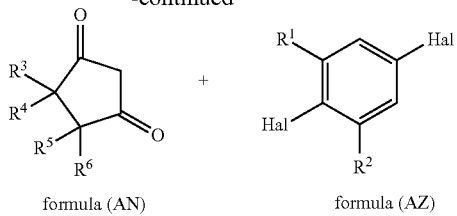

Similarly, a compound of formula (L) can also be prepared using similar methods described previously, starting from compounds (AY), (AZ) and (AAA) which are known or can be prepared from known reagents using known methods.

Additionally, a compound of formula (V) can also be prepared using similar methods described previously, starting from compounds (AAB), (AAC) and (AAD) which are known or can be prepared from known reagents using known methods.

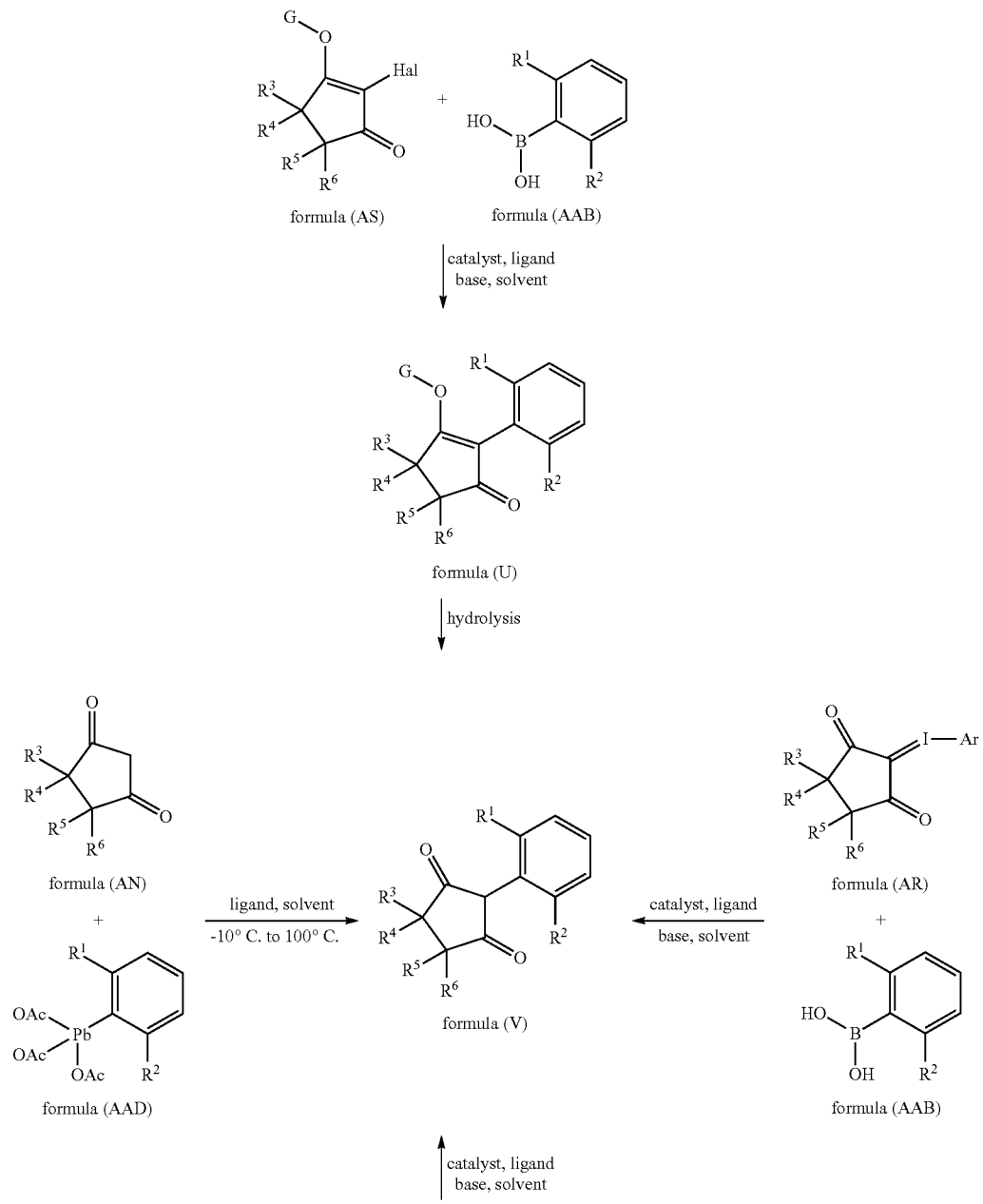

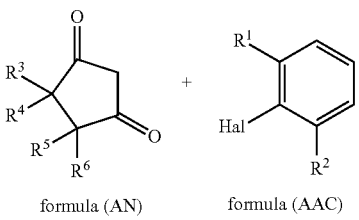

formula (AN)     formula (AAC)

Furthermore, a compound of formula (L) can be prepared by reacting a compound of formula (AN) with a halonitrobenzene of formula (AAE) (under conditions similar to those described for coupling a compound of formula (AN) and a compound of formula (AQ)), to produce a compound of formula (AAF), which is then reduced under standard conditions (for a similar example see T. N. Wheeler, CA1113959). The aniline (AAG) is then converted to the aryl halide (L) under Sandmeyer conditions (for a similar example see T. N. Wheeler, CA1113959).

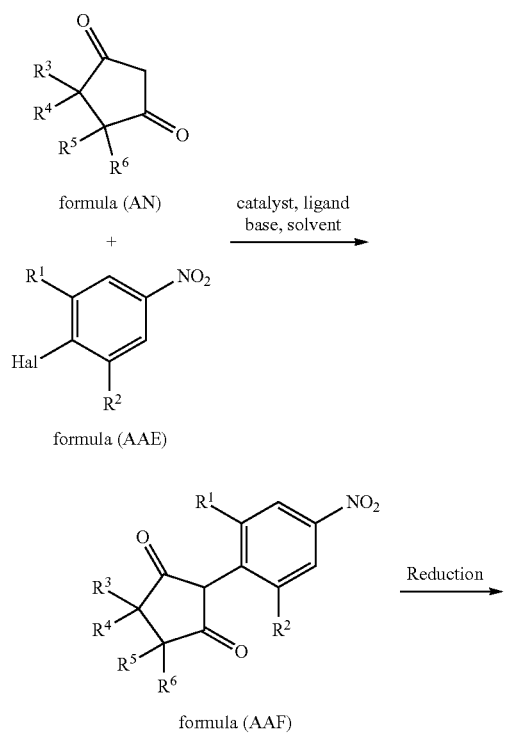

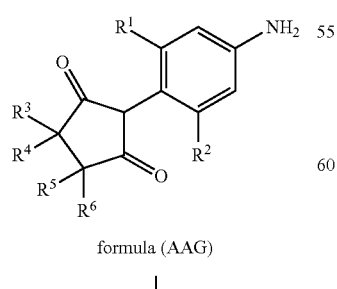

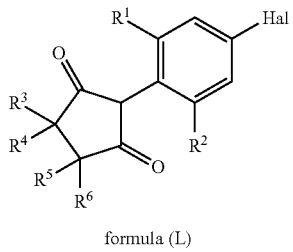

formula (L)

In a further approach, a compound of formula (A), wherein X is methyl, may be prepared by derivatisation of a compound of formula (AAH), which is a compound of formula I, wherein X is methyl, G is hydrogen and $R^4$ and $R^5$ together form a bond. Compounds of formula (AAH) are α, β-unsaturated cyclic diones and undergo reactions in the presence of reagents known to effect transformations of α, β-unsaturated ketones to give additional compounds of formula (A).

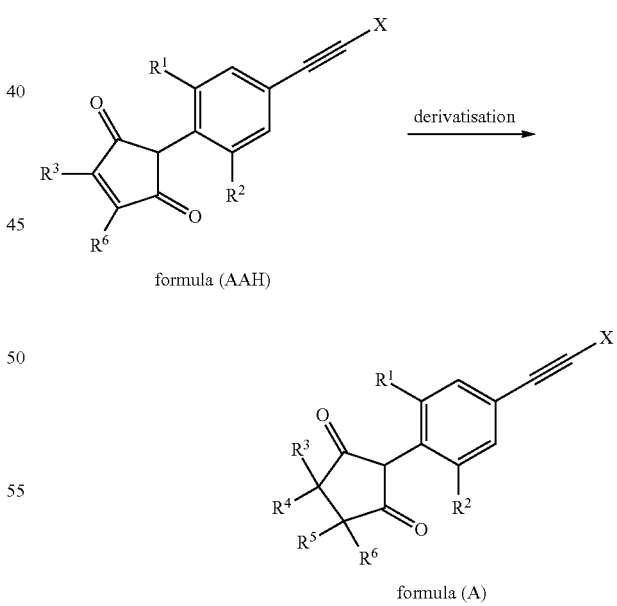

For example, a compound of formula (AAH), wherein X is methyl, may be reacted with a suitable nucleophile, Nuc-H, optionally in the presence of a suitable base and a suitable solvent to give compounds of formula (A), wherein X is methyl and $R^5$ is the group Nuc resulting from nucleophilic attack and $R^4$ is hydrogen.

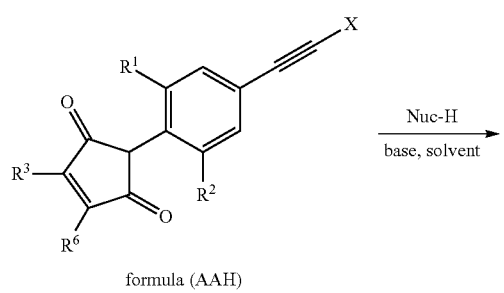

formula (AAH)

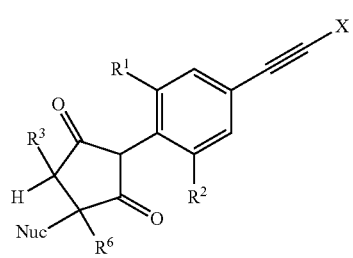

formula (A) wherein X is methyl,
R⁵ is Nuc and R⁴ is H

Suitable nucleophiles, Nuc-H, include, but are not limited to, optionally substituted $C_1$-$C_6$alkylthiols, optionally substituted arylthiols, optionally substituted heteroarylthiols optionally substituted $C_1$-$C_6$alkyl alcohols and optionally substituted $C_3$-$C_7$cyclic alcohols (including $C_3$-$C_6$ alicyclic alcohols, 4-6 membered heterocyclic alcohols, phenols and heteroaromatic alcohols).

A compound of formula (AAH), wherein X is methyl, will also participate in cycloaddition reactions under suitable conditions to afford additional compounds of formula (A). For example, a compound of formula (AAH), wherein X is methyl, may be reacted with a suitable 1,3-diene of formula (AAI), wherein $R_a$ represents a suitable substituent (such as $C_1$-$C_4$alkyl, $C_1$-$C_4$alkoxy or tri-$C_1$-$C_4$alkylsilyloxy), and n is 0, 1 or 2, under suitable conditions to give a compound of formula (A) wherein $R^4$ and $R^5$ together with the atoms to which they are joined form an unsaturated six-membered ring.

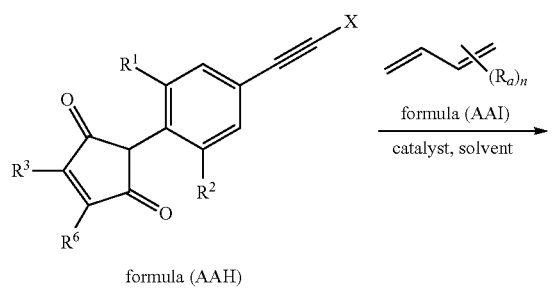

formula (AAH)

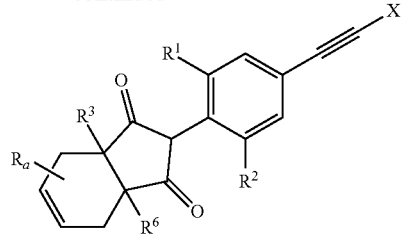

formula (A) wherein X is methyl and
R⁴ and R⁵ are joined to form an
unsaturated 6-membered ring Suitable 1,3-dienes include 1,3-butadiene (or an equivalent, for instance 2,5-dihydrothiophene-1,1-dioxide), and substituted 1,3-butadienes. Similarly, a compound of formula (AAH), wherein X is methyl, may also be reacted with cyclic dienes of formula (AAJ) such as cyclopentadiene (W is —$CH_2$— and $R_b$ is hydrogen), substituted cyclopentadienes, cyclohexa-1,3-diene (W is —$CH_2$—$CH_2$— and $R_b$ is hydrogen), substituted cyclopentadienes, furan (W is oxygen and $R_b$ is hydrogen) and substituted furans.

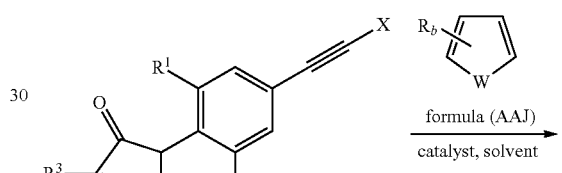

formula (AAH)

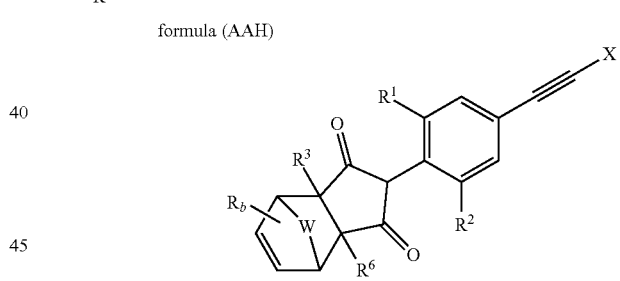

formula (A) wherein X is methyl and R⁴ and
R⁵ are joined to form an unsaturated ring
which is further bridged Those skilled in the art will appreciate that cyclic dienes of formula (AAJ) bearing a wide variety of substituents $R_b$ Will undergo cycloaddition reactions with a compound of formula (AAH) to give new compounds of formula (A), under appropriate conditions for example, in the presence or absence of Lewis acid catalysts, such as aluminium chloride, bismuth(III) chloride, bismuth(III) trifluoromethanesulfonate, boron trifluoride, cerium(III) chloride, copper(I) trifluoromethanesulfonate, diethylaluminium chloride, hafnium(IV) chloride, iron(II) chloride, lithium perchlorate, lithium trifluoromethanesulfonate, magnesium bromide, magnesium iodide, scandium(III) trifluoromethanesulfonate, tin(IV) chloride, titanium(IV) chloride, titanium(IV) isopropoxide, trimethyl aluminium, N-trimethylsilyl-bis(trifluoromethanesulfonyl)imide, trimethylsilyl trifluoromethane-sulfonate, ytterbium(III) trifluoromethanesulfonate, zinc iodide and zirconium(IV) chloride, and in the presence or absence of solvents such as chloroform, dichloromethane, diethyl ether, ethanol, methanol, perfluorinated alkanes such as perfluorohexane, toluene, water, and ionic liquids such as 1-butyl-3-methylimidazolium tetrafluoroborate and 1-butyl-3-methylimidazolium hexafluorophosphate, and at normal atmospheric pressure or under high pressure conditions, as described, for example by G. Silvero et al., *Tetrahedron* (2005), 61, 7105-7111; I. Hemeon et al., *Synlett*, (2002), 11, 1815-1818; S. Otto and J. Engberts, *Pure Appl. Chem.* (2000), 72 (7), 1365-1372; R. Breslow, *Acc. Chem. Res.*, (1991), 24 (6), 159-164; K. Hara et al., *Org. Lett.*, (2005), 7 (25), 5621-5623; J, Aubé et al., *Synlett*, (2000), 6, 877-879, B. Garrigues and A. Oussaid, *J. Organometallic Chem.*, (1989), 585, 253-255; B. Mathieu and L. Ghosez, *Tetrahedron Lett.*, (1997), 38 (31), 5497-5500; M. Ordoñez et al., *Tetrahedron Asymmetry*, (1996), 7 (9), 2675-2686; S. Kobayashi et al., *Tetrahedron Lett.*, (1993), 34 (23), 3755-3758; C. Cativiela et al., U. Pindur et al., *Chem. Rev.*, (1993), 93, 741-761; *Tetrahedron*, (1992), 48 (31), 6467-6476; J. Aubé et al., *J. Am. Chem. Soc.*, (1992), 114, 5466-5467; S. Danishefsky and M. Bednarski, *Tetrahedron Lett.*, (1985), 26 (21), 2507-2508 and references therein); Q. Chu, W. Zhang and D. Curran, *Tetrahedron Lett.*, (2006), 47, 9287-9290; K. Ishihara and K. Nakano, *J. Am. Chem. Soc.*, (2005), 127 (30), 10504-10505; and A. Northrup and D. MacMillan, (2002), *J. Am. Chem. Soc.*, 124 (11), 2458-2460).

The reaction of compounds of formula (AAH) with compounds of formula (AAI) or with compounds of formula (AAJ) provides compounds of formula (A) wherein $R^4$ and $R^5$ are joined to form an unsaturated ring. Such compounds are alkenes, which may undergo reactions typical of alkenes (for example reduction, halogenation or cross-coupling) to produce further compounds of formula (A).

A compound of formula (AAH), wherein X is methyl, may also act as a dipolarophile and will therefore undergo a range of 3+2 cycloaddition reactions with suitable dipolar reagents under suitable conditions. For example, a compound of formula (AAH) may react with a nitrile oxide of formula (AAK), wherein $R_c$ is a suitable substituent (for example $C_1$-$C_4$alkyl or aryl), or with a nitrone of formula (AAL), wherein $R_e$, $R_f$ and $R_d$ are suitable substituents, for example hydrogen or $C_1$-$C_4$alkyl, under appropriate conditions to give further compounds of formula (A), wherein $R^4$ and $R^5$ together with the atoms to which they are attached form an isoxazoline or isoxazolidine ring respectively.

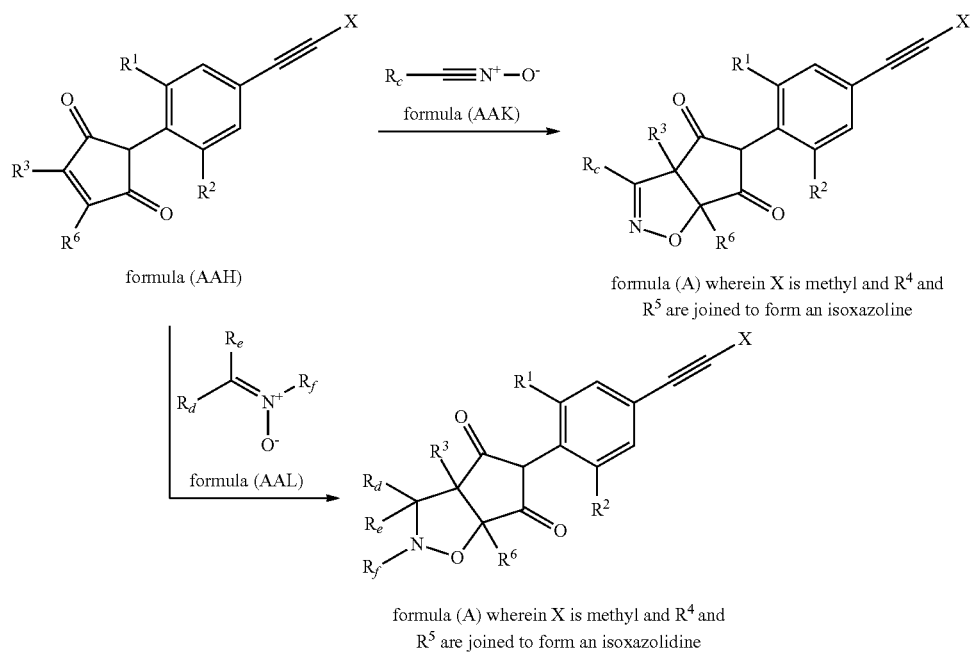

Suitable conditions for effecting 3+2 cycloadditions are described, for example, by L. Deng and Y. Hu, *Synth. Commun.* (2007), 37, 157-163; E. Kantorowski et al., *J. Org. Chem.*, (1998), 63, 5272-5274; and by V. Jäger and I. Müller, *Tetrahedron* (1985), 41 (17), 3519-3528.

In a further approach, a compound of formula (A), wherein X is methyl and $R^5$ is Nuc (and Nuc is as previously defined) may be prepared by the hydrolysis of a compound of formula I, wherein G is $C_1$-$C_4$alkyl, under acidic conditions.

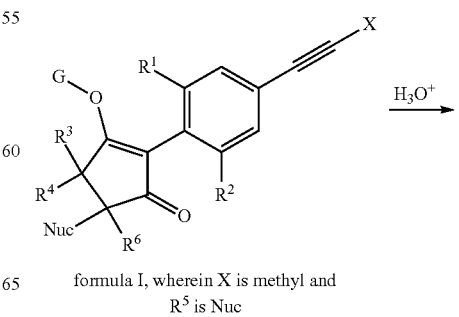

formula I, wherein X is methyl and $R^5$ is Nuc

-continued

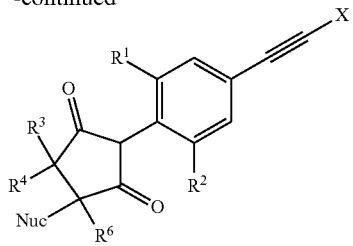

formula (A) wherein X is methyl and
R⁵ is Nuc

A compound of formula I (wherein X is methyl, G is C₁-C₄alkyl and R⁵ is Nuc) may be prepared from a compound of formula I (wherein X is methyl, G is C₁-C₄alkyl, R⁵ is Hal and Hal is chlorine, bromine or iodine), by treatment with a nucleophile, Nuc-H, optionally in the presence of a suitable base and in a suitable solvent. Suitable conditions for effecting nucleophilic substitution reactions are described, for example, by J. March, Advanced Organic Chemistry Third Edition, ed J. Wiley and Sons, 1985.

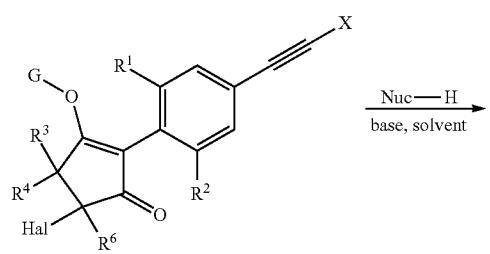

formula I wherein X is methyl
and R⁵ is Hal

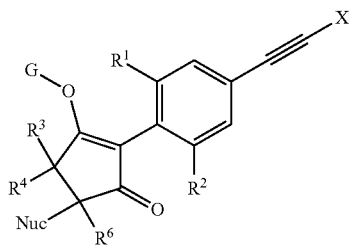

formula I, wherein X is methyl
and R⁵ is Nuc

A compound of formula I, wherein Q is Q1, X is methyl and R⁵ is Hal, may be prepared from a compound of formula I, wherein X is methyl and R⁵ is hydrogen, by halogenation.

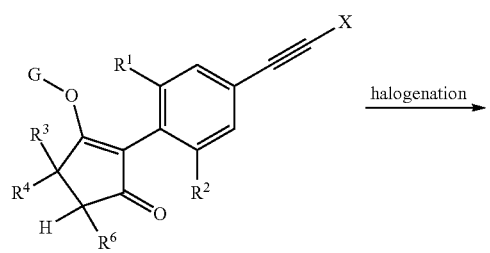

formula I, wherein Q is Q₁,
X is methyl and R⁵ is hydrogen

-continued

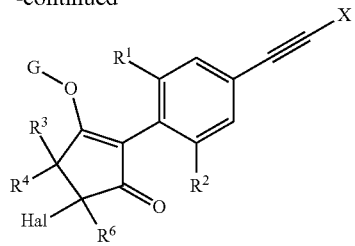

formula I wherein Q is Q₁, X is methyl
and R₅ is Hal

For example, a compound of formula I, wherein Q is Q1, X is methyl, Hal is chlorine and G is hydrogen or C₁-C₄alkyl, may be prepared by reacting a compound of formula I, wherein X is methyl and R⁵ is hydrogen, with copper(II) chloride and lithium chloride according to the procedure of E. Kosower et al., *J. Org. Chem.*, (1963), 28, 630. Alternatively a compound of formula (AM), wherein X is methyl, Hal is bromine and G is C₁-C₄alkyl, may be prepared treating a compound of formula I, wherein R⁵ is hydrogen, with dibutylboryl trifluoromethanesulfonate and N-bromosuccinimide, by methods similar to those described by P. Page et al., *Tetrahedron* (1995), 51 (4), 1285-1294).

Alternatively, a compound of formula (A), wherein X is methyl and R⁴ and R⁵ are hydrogen, may be prepared by reduction of a compound of formula (AAH) under conditions which are compatible with the substrate, for example in the presence of sodium borohydride and cuprous chloride, as described by M. Narisada, I. Horibe, F. Watanabe and K. Takeda, *Journal of Organic Chemistry* (1989), 54(22), 5308-13.

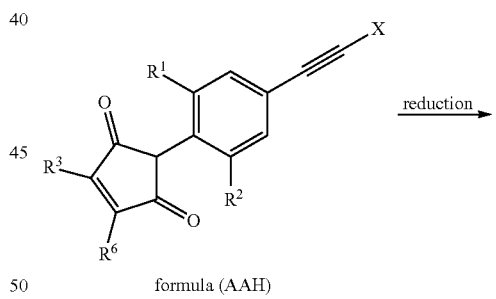

formula (AAH)

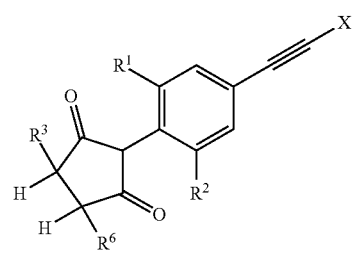

formula (A) wherein X is methyl and
R⁴ and R⁵ is hydrogen

A compound of formula (AAH), wherein X is methyl, may be prepared by oxidising a compound of formula (AAM) in a suitable solvent such as toluene, acetone, chloroform, dichloromethane or 1,4-dioxane. A wide range of oxidants is suitable for effecting this transformation, including inorganic oxidants such as chromium trioxide, pyridinium dichromate, manganese dioxide and aluminium alkoxides such as aluminium isopropoxide, as well as organic oxidants such as 2,3-dichloro-5,6-dicyano-p-benzoquinone and hypervalent iodine oxidants such as 1,1,1,-tris(acetyloxy)-1,1-dihydro-1,2-benziodoxol-3-(1H)-one (Dess-Martin periodinane). Suitable procedures are described, for example, by K. Saito and H. Yamachika, U.S. Pat. No. 4,371,711, and by G. Piancatelli et al., *Tetrahedron* (1978), 34, 2775. The use of chromium trioxide in a mixture of sulfuric acid and acetone (Jones reagent) is preferred.

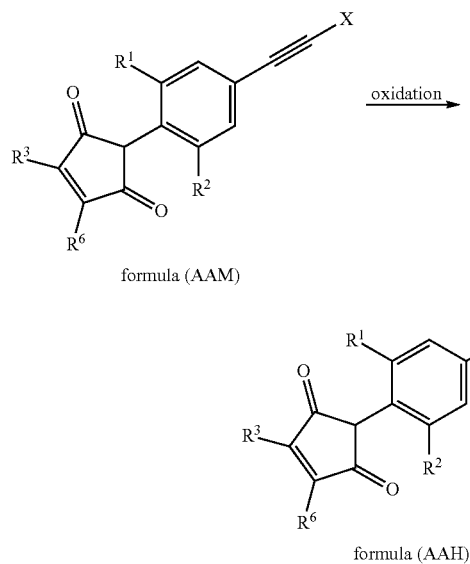

A compound of formula (AAM), wherein X is methyl, may be prepared from a compound of formula (AAN) by treatment with a suitable acid catalyst in the presence of water and optionally in the presence of a suitable solvent.

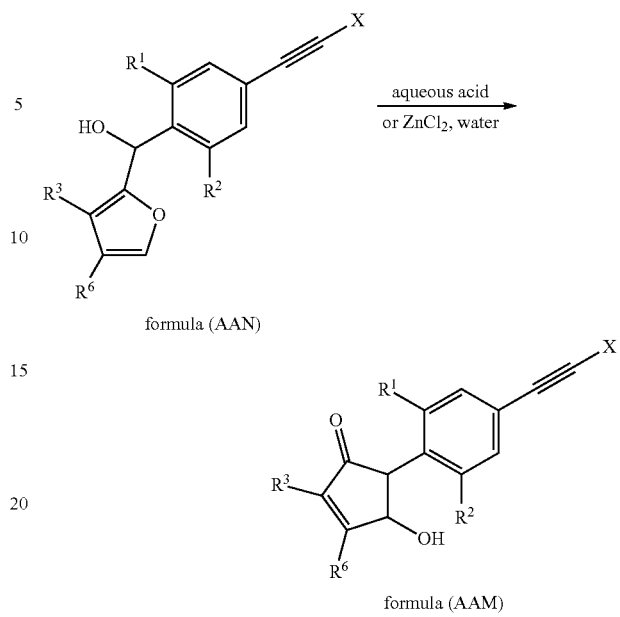

For example, a compound of formula (AAN), wherein X is methyl, may be converted to a compound of formula (AAM) in the presence of an aqueous solution of an acid such as phosphoric acid or polyphosphoric acid under conditions described, for example by K. Saito and H. Yamachika, U.S. Pat. No. 4,371,711. Alternatively a compound of formula (AAM), wherein X is methyl, may be prepared from a compound of formula (AAN) by rearrangement in the presence of a Lewis acid catalyst such as zinc chloride according to the procedure of G. Piancatelli et al., *Tetrahedron*, (1978), 34, 2775.

A compound of formula (AAN), wherein X is methyl, may be prepared by the addition of a suitable organometallic reagent such as an arylmagnesium halide of formula (AAQ) wherein X is methyl and Hal is a halide such as chloride, bromide or iodide, or an aryllithium reagent of formula (AAP) or a diarylzinc reagent of formula (AAO) to a furan-2-carboxaldehyde of formula (AAR) according to known procedures (see, for example G. Panda et al., *Tetrahedron Lett.*, (2005), 46, 3097).

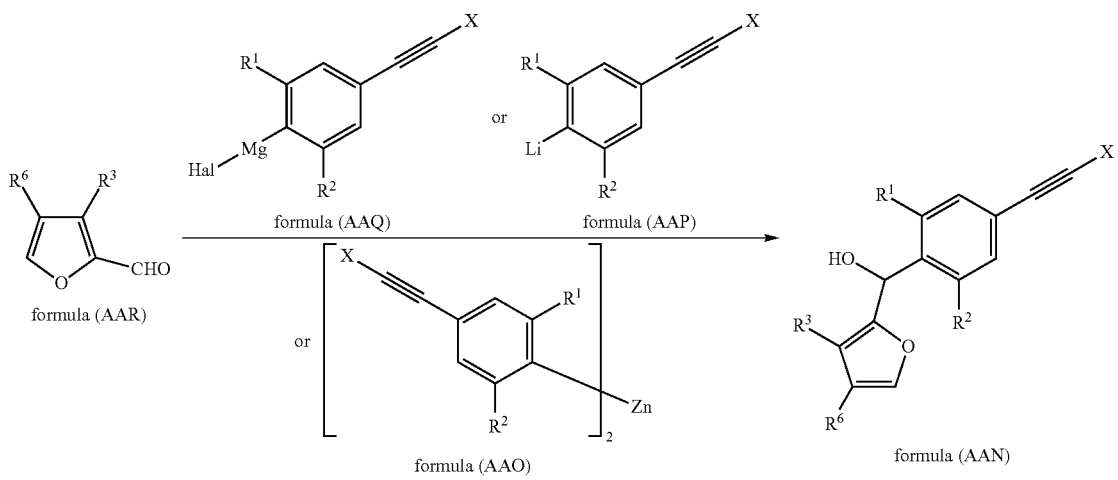

The organometallic reagents of formula (AAQ), formula (AAP) and formula (AAO), wherein X is methyl, may be made by known methods from a compound of formula (AQ).

Additionally, a compound of formula I, wherein Q is Q1, X is methyl and $R^5$ is hydrogen, can be prepared by the reduction of a compound of formula (AAS), wherein $R_f$ and $R_g$ are suitable substituents, under similar conditions to those described to convert a compound of formula (AAH) to a compound of formula (A), wherein X is methyl and $R^4$ and $R^5$ are hydrogen.

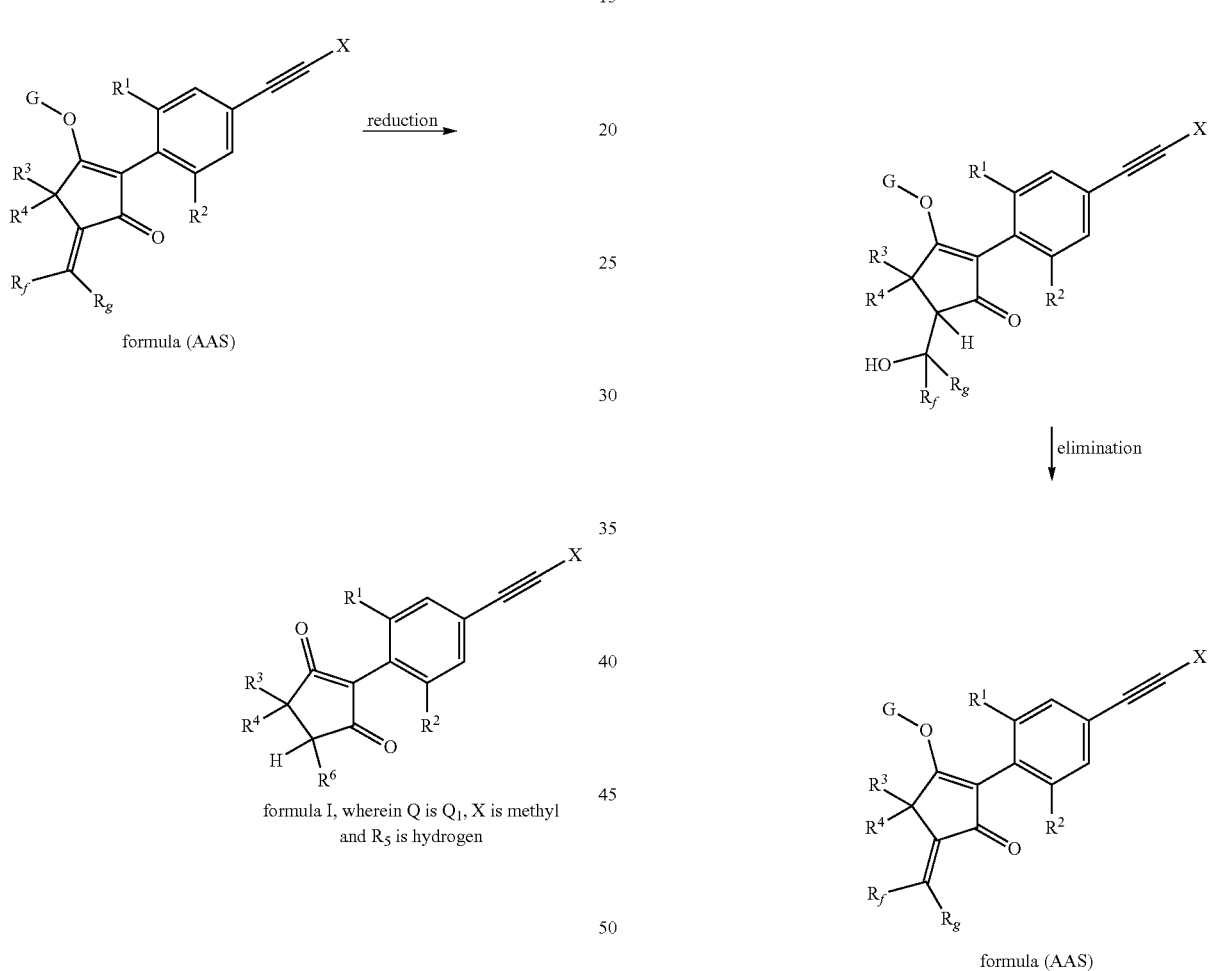

formula (AAS)

reduction formula I, wherein Q is $Q_1$, X is methyl and $R_5$ is hydrogen

A compound of formula (AAS), wherein Q is Q1, X is methyl, can be prepared, for example, from a compound of formula I (wherein Q is Q1, X is methyl, $R^5$ and $R^6$ are hydrogen and G is preferably methyl) and compound of formula (AAT), under basic conditions, followed by elimination. Suitable bases include lithium diisopropylamide, sodium hexamethyldisilazide, potassium tert-butoxide and the reaction is preferably conducted in a suitable solvents such as tetrahydrofuran, at a temperature between −80° C. and 30° C. (see, for example, Drege, E. et al. *Tetrahedron Letters* (2005), 46(42), 7263-7266 and Drege, E. et al., *Eur. J. Org. Chem.* (2006), (21), 4825-4840). Compounds of formula (AAT) are known compounds, or can be prepared from known compounds using known methods.

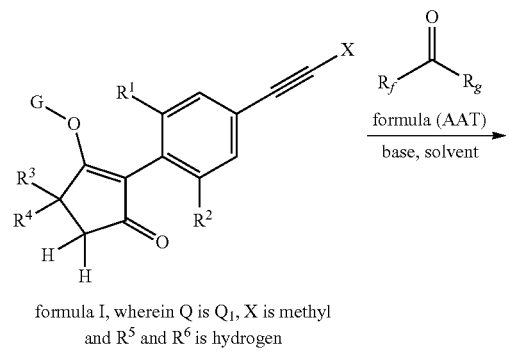

formula I, wherein Q is $Q_1$, X is methyl and $R^5$ and $R^6$ is hydrogen

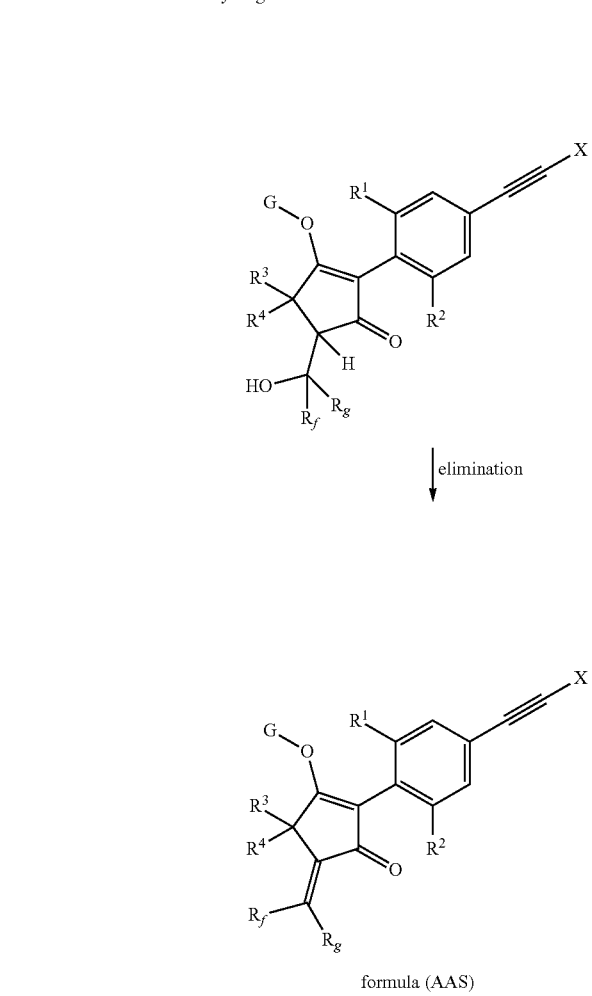

elimination formula (AAS)

Furthermore, a compounds of formula I, wherein Q is Q1, X is methyl, can be obtained by reacting compounds of formula I (wherein Q is Q1, X is methyl, $R^5$ is hydrogen and G is preferably methyl), with compounds of formula (AAU) wherein LG is a leaving group such as halogen (preferably iodide or bromide) or an activated alcohol (preferably mesylate, tosylate or triflate) under under basic conditions. Suitable bases include lithium diisopropylamide, sodium hexamethyldisilazide, potassium tert-butoxide and the reaction is preferably conducted in a suitable solvent such as tetrahydrofuran at a temperature between −80° C. and 30° C. Similar reactions are described by Gulias, M. et al. *Org. Lett.* (2003), 5(11), 1975-1977. Compounds of formula (AAU) are known compounds, or can be prepared from known compounds using known reagents.

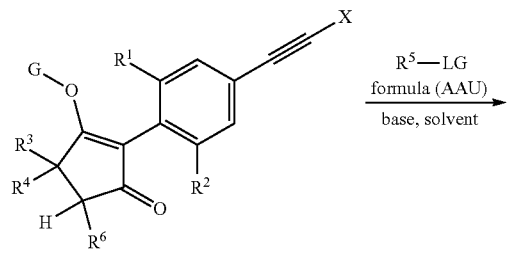

formula I, wherein Q is Q₁, X is methyl and R⁵ is hydrogen

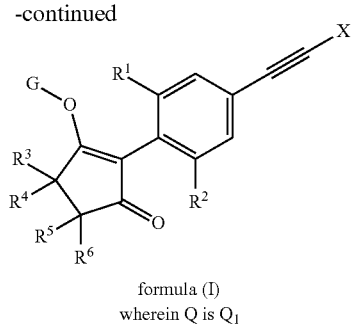

formula (I)
wherein Q is Q₁

Using similar chemistry, a compound of formula (P) can be prepared by the derivitisation of a compound of formula (AAV), a compound of formula (AAX) or a compound of formula (AAY). Compounds of formula (AAV), (AAX) and (AAY) can be prepared by routes analogous to those described previously.

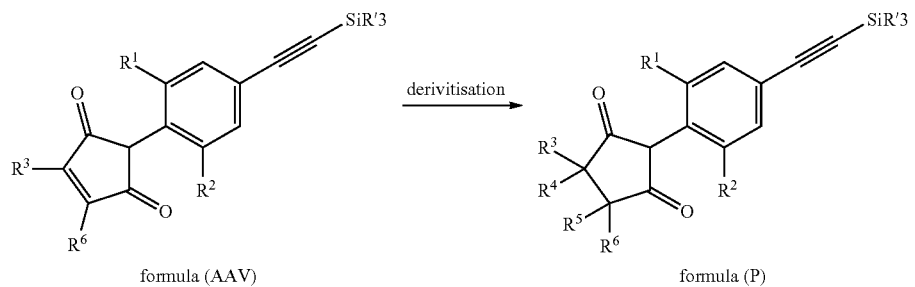

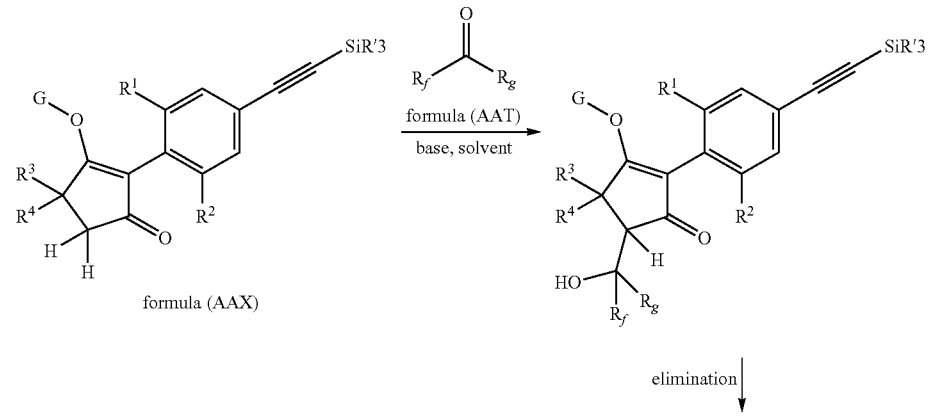

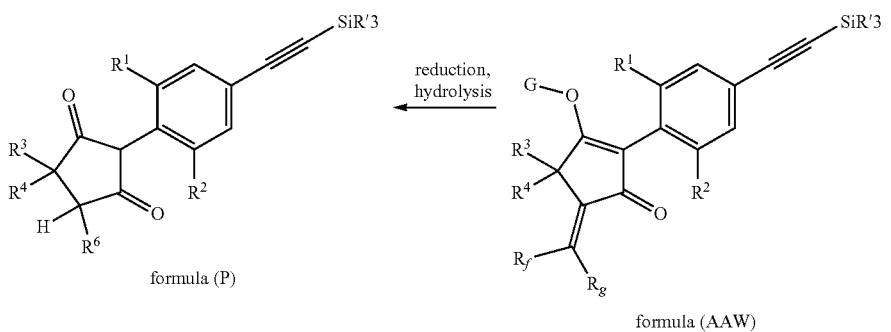

-continued

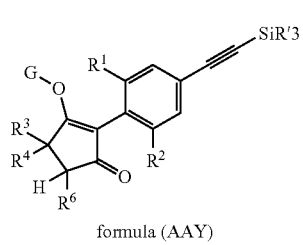

formula (AAY)

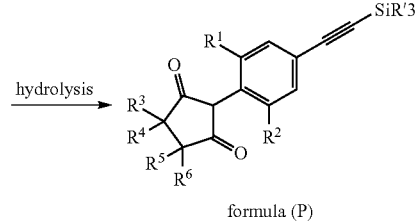

formula (P)

Similarly, using similar chemistry, a compound of formula (L) can be prepared by the derivitisation of a compound of formula (AAZ), a compound of formula (AAAB) or a compound of formula (AAAC), using similar chemistry to that described above. Compounds of formula (AAZ), (AAAB) and (AAAC) can be prepared by routes analogous to those described previously.

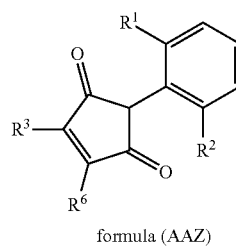

formula (AAZ)

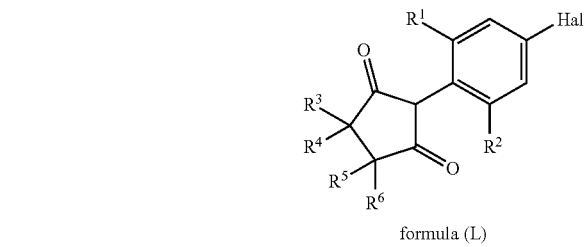

formula (L)

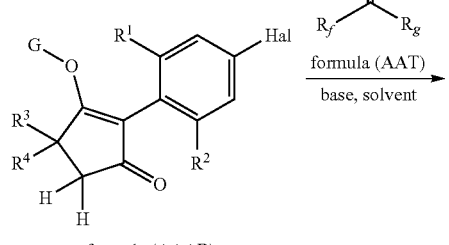

formula (AAAB)

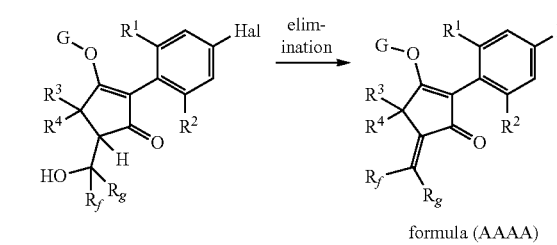

formula (AAAA)

↓ reduction, hydrolysis

-continued

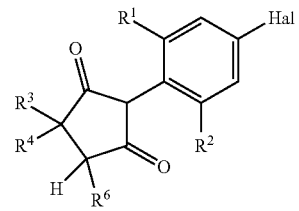

formula (L)

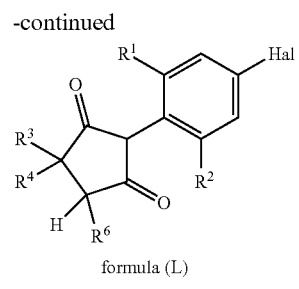

formula (AAAC)

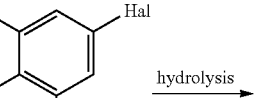

hydrolysis

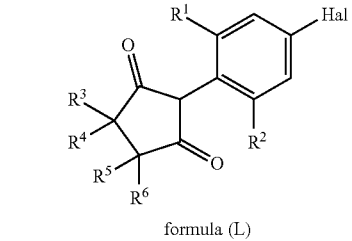

formula (L)

Finally, using similar chemistry a compound of formula (V) can be prepared by the derivitisation of a compound of formula (AAAD), a compound of formula (AAAF) or a compound of formula (U) wherein $R^5$ is hydrogen. Compounds of formula (AAAD), (AAAF) and (U) can be prepared by routes analogous to those described previously.

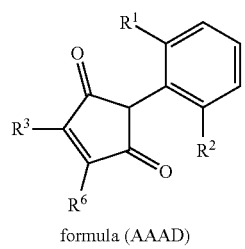

formula (AAAD)

derivitisation →

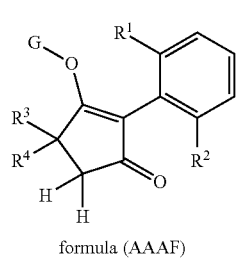

formula (AAAF)

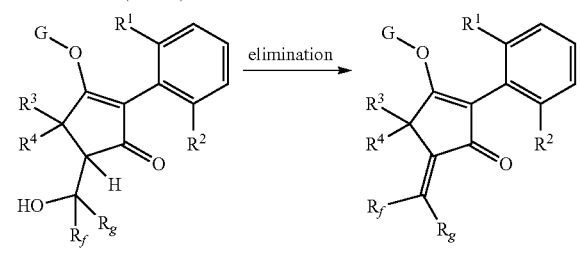

formula (AAT)
base, solvent elimination → formula (AAAE)

↓ reduction, hydrolysis

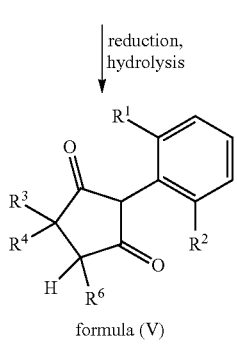

formula (V)

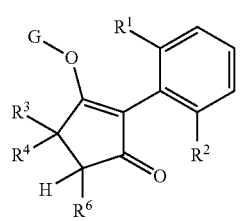

formula (U),
wherein R⁵ is hydrogen

R⁵—LG
formula (AAU)
base, solvent

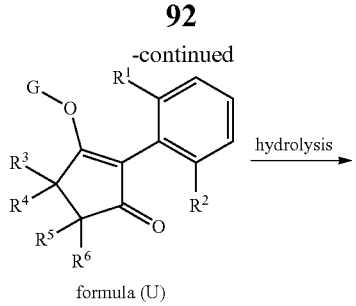

formula (U)

hydrolysis →

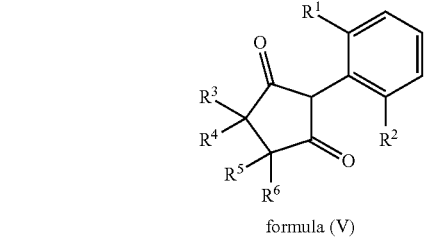

formula (V)

Compounds of formula I, in which Q is Q2 may in general be made by the general methods described below.

A compound of formula I, wherein Q is Q2 and G is: $-C(X^a)-R^a$, $-C(X^b)-X^c-R^b$, $-C(X^d)-N(R^c)-R^d$, $-SO_2-R^e$, $-P(X^e)(R^f)-R^g$, $-CH_2-X^f-R^h$; or phenyl-$CH_2-$ or phenyl-$CH(C_1-C_2alkyl)$- (in each of which the phenyl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano, nitro, $SC_1-C_3$alkyl, $S(O)C_1-C_3$alkyl, or $S(O)_2C_1-C_3$alkyl), or heteroaryl-$CH_2-$ or heteroaryl-$CH(C_1-C_2alkyl)$- (in each of which the heteroaryl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano, nitro S, S(O), or $S(O)_2$), or phenyl-$C(O)-CH_2-$ (wherein the phenyl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano, nitro, $SC_1-C_3$alkyl, $S(O)C_1-C_3$alkyl, or $S(O)_2C_1-C_3$alkyl); or $C_1-C_6$alkoxy-$C(O)-CH_2-$, $C_1-C_6$alkoxy-$C(O)-CH=CH-$, $C_2-C_7$alken-1-yl-$CH_2-$, $C_2-C_7$alken-1-yl-CH($C_1-C_2$alkyl)-, $C_2-C_4$fluoroalken-1-yl-$CH_2-$, $C_2-C_7$alkyn-1-yl-$CH_2-$, or $C_2-C_7$alkyn-1-yl-CH($C_1-C_2$alkyl)-; may be prepared by treating a compound of formula (2A), which is a compound of formula I wherein Q is Q2 and G is H, (a) with a reagent G1-Z, wherein G1-Z is an alkylating agent (wherein G1 is an organic group according to G within the compound of formula (I), wherein Q is Q2, and which is linked by a non-carbonyl, non-thiocarbonyl carbon atom) such as an organic halide (in which Z=halogen such as chlorine, bromine or iodine); wherein the organic halide (e.g. chloride) can typically be a substituted alkyl halide (e.g. chloride) such as a chloromethyl alkyl ether Cl—$CH_2$—$X^f$—$R^h$ wherein $X^f$ is oxygen, a chloromethyl alkyl sulfide Cl—$CH_2$—$X^f$—$R^h$ wherein $X^f$ is sulphur, a suitable optionally substituted benzyl halide (e.g. chloride) such as Cl—$CH_2$-[optionally substituted phenyl], [optionally substituted phenyl]-$C(O)$—$CH_2$-[halogen e.g. Cl], $C_1-C_6$alkoxy-$C(O)$—$CH_2$-[halogen e.g. Cl], $C_1-C_6$alkoxy-$C(O)$—CH=CH-[halogen e.g. Cl], a suitable alkenyl or alkynyl halide (e.g. chloride) such as $C_2-C_7$alken-1-yl-$CH_2$-[halogen e.g. Cl] or $C_2-C_7$alkyn-1-yl-$CH_2$-[halogen e.g. Cl], or another organic halide suitable for preparing a (non-carbonyl, non-thiocarbonyl carbon)-linked G (or G1) group; or (b) [e.g. to prepare carbonyl-carbon-linked or thiocarbonyl-carbon-linked G groups] with an acylating agent such as a carboxylic acid, HO—C($X^a$)$R^a$, wherein $X^a$ is oxygen, an acid chloride, Cl—C($X^a$)$R^a$, wherein $X^a$ is oxygen, or an acid anhydride, [$R^a$C($X^a$)]$_2$O, wherein $X^a$ is oxygen, or an isocyanate, $R^c$N=C=O, or a carbamoyl chloride, Cl—C($X^d$)—N($R^c$)—$R^d$ (wherein $X^d$ is oxygen and with the proviso that neither $R^c$ or $R^d$ is hydrogen), or a thiocarbamoyl chloride Cl—($X^d$)—N($R^c$)—$R^d$ (wherein $X^d$ is sulfur and with the proviso that neither $R^c$ or $R^d$ is hydrogen), or a chloroformate, Cl—C($X^b$)—$X^c$—$R^b$ (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithio-formate Cl—C($X^b$)—$X^c$—$R^b$ (wherein $X^b$ and $X^c$ are sulfur), or an isothiocyanate, $R^c$N=C=S; or (c) by sequential treatment with carbon disulfide and an alkylating agent; or (d) with a phosphorylating agent such as a phosphoryl chloride, Cl—P($X^e$)($R^f$)—$R^g$; or (e) with a sulfonylating agent such as a sulfonyl chloride Cl—SO$_2$—$R^e$, preferably in the presence of at least one equivalent (i.e. mole equivalent) of base.

Where substituent $R^{33}$ and $R^{34}$ are not equal to substituents $R^{35}$ and $R^{36}$, and/or where $R^{34}$ and $R^{35}$ taken together is an asymmetric —C($R^{37c}$)=C($R^{37d}$)— chain, these reactions may produce, in addition to a compound of formula I, a second compound of formula (IAA).

This invention covers both a compound of formula (I), wherein Q is Q2, and a compound of formula (IAA), together with mixtures of these compounds in any ratio.

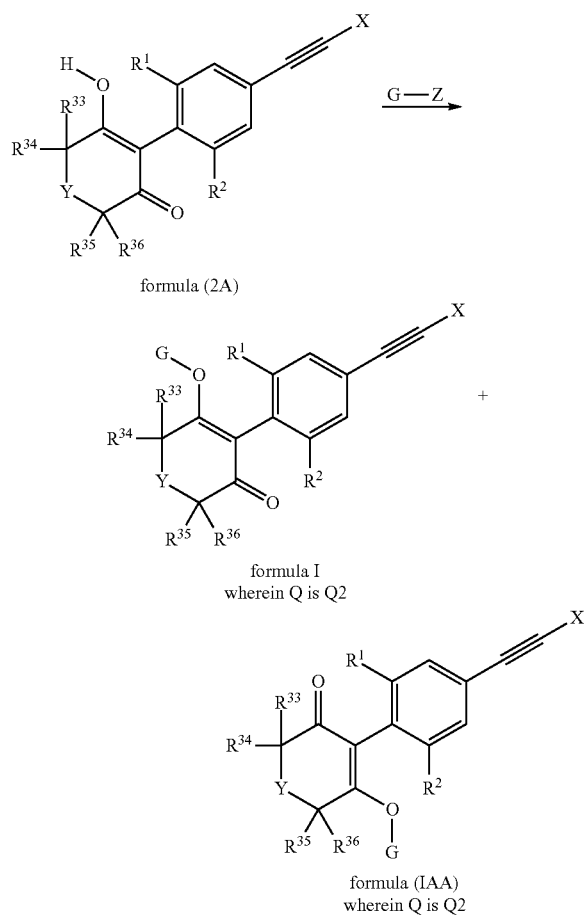

formula (2A)

formula I
wherein Q is Q2 formula (IAA)
wherein Q is Q2

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected e.g. by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (2A) may be treated with an acylating agent preferably in the presence of at least one equivalent (i.e. mole equivalent) of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxy-ethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected e.g. using a phosphoryl halide or thiophosphoryl halide and a base e.g. by procedures analogous to those described by L. Hodakowski, U.S. Pat. No. 4,409,153.

Sulfonylation of a compound of formula (2A) may be achieved e.g. using an alkyl or aryl sulfonyl halide, preferably in the presence of at least one equivalent (i.e. mole equivalent) of base, for example by the procedure of C. Kowalski and K. Fields, J. Org. Chem., (1981), 46, 197-201.

Compounds of formula (2A), wherein Y is S(O) or S(O)$_2$ may be prepared from compounds of formula (2A) wherein Y is S by oxidation, e.g. according to a procedure analogous to that of E. Fehnel and A. Paul, J. Am. Chem. Soc., (1955), 77, 4241-4244.

A compound of formula (2A), wherein Y is O, S, C(O) or CR$^{38}$R$^{39}$ may be prepared via the cyclisation of a compound of formula (2B), preferably in the presence of an acid or base, and optionally in the presence of a suitable solvent, e.g. by analogous methods to those described by T. Wheeler, U.S. Pat. No. 4,209,532. The compounds of the formula (2B) have been particularly designed as intermediates in the synthesis of the compounds of the formula I wherein Q is Q2, and a further aspect of the present invention provides a compound of formula (2B) (shown below). Compounds of formula (2B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane. A compound of formula (2B) wherein R is alkyl (preferably methyl or ethyl) may also be cyclised under basic conditions in the presence of at least one equivalent (i.e. mole equivalent) of a strong base in a solvent such as tetrahydrofuran, toluene, dimethylsulfoxide or N,N-dimethylformamide. Suitable bases include potassium tert-butoxide, lithium diisopropylamide, sodium bis(trimethylsilyl)amide or sodium hydride. A compound of formula (2B), wherein R is alkyl, may be produced from a compound of formula (2B), wherein R is H, by esterification under known conditions (for example by treatment with an alcohol, R—OH, in the presence of an acid catalyst).

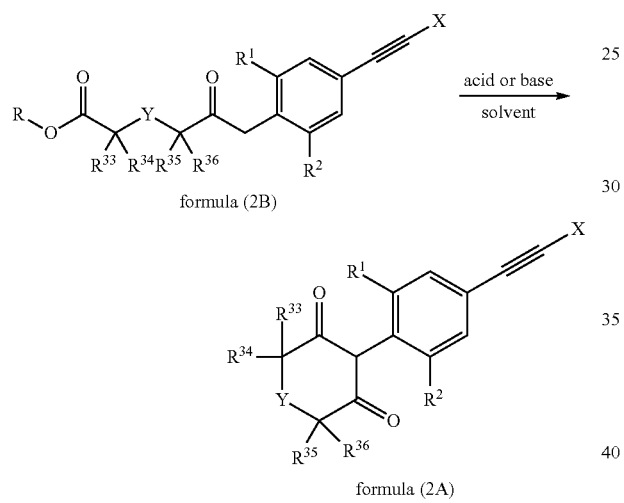

formula (2B)

acid or base
solvent formula (2A)

A compound of formula (2B), wherein R is H, may be prepared by hydrolysis of a compound of formula (2C) wherein R is H or alkyl and R' is alkyl (preferably methyl or ethyl), followed by acidification of the reaction mixture to effect decarboxylation, e.g. by similar processes to those described by, for example, T. Wheeler, U.S. Pat. No. 4,209,532. Alternatively, a compound of formula (2B), wherein R is alkyl or H may be prepared from a compound of formula (2C), wherein R' is alkyl (preferably methyl), through a Krapcho decarboxylation procedure, e.g. under known conditions using known reagents (see for example G. Quallich, P. Morrissey, Synthesis, (1993), (1), 51-53).

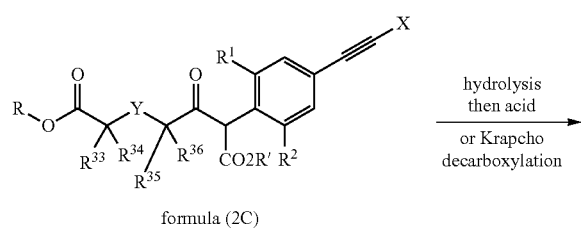

formula (2C)

hydrolysis
then acid
or Krapcho
decarboxylation

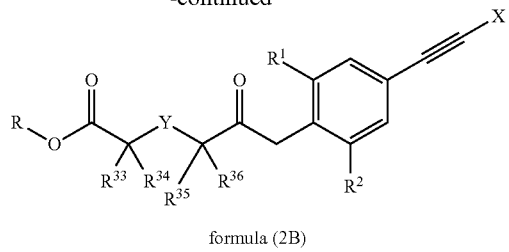

formula (2B)

A compound of formula (2C) wherein R is alkyl may be prepared by treating a compound of formula (2D) with a suitable carboxylic acid chloride of formula (2E) wherein R is alkyl under basic conditions. Suitable bases include potassium tert-butoxide, sodium bis(trimethyl-silyl)amide and lithium diisopropylamide and the reaction is preferably conducted in a suitable solvent (such as tetrahydrofuran or toluene) at a temperature between −78° C. and 30° C. Under similar conditions a compound of formula (2C), wherein R is H, may be prepared from a suitable anhydride of formula (2F).

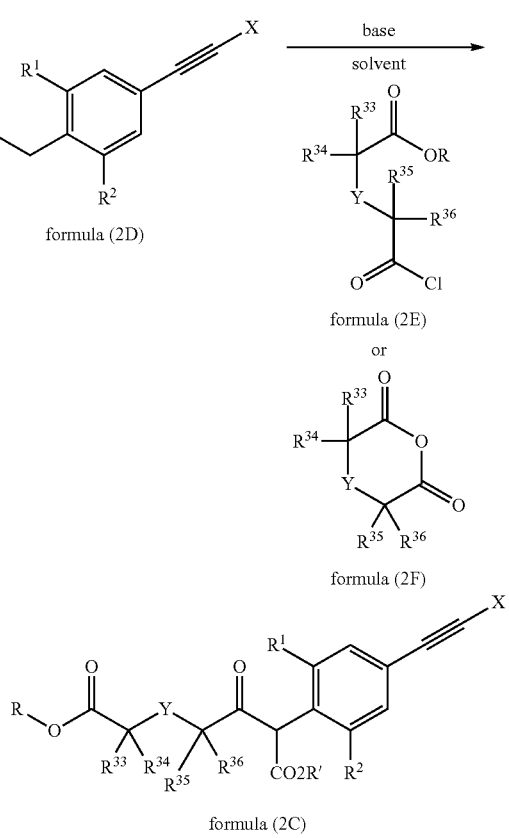

Compounds of formula (2E) and formula (2F) are known (see, for example T. Terasawa and T. Okada, J. Org. Chem., (1977), 42 (7), 1163-1169; G. Bennett, W. Houlihan, R. Mason; R. Engstrom, J. Med. Chem., (1976), 19 (5), 709-14; L. J. J. Hronowski, Lucjan W. A. Szarek, Canadian Journal of Chemistry (1988), 66(1), 61-70; S. F. Birch, V. E. Gripp, D. T. McAllan, W. S. Nathan, Journal of the Chemical Society (1952), 1363-8; S. Kitamura, T. D. Aicher, Gonzales, Steve; Y. Le Huerou, S. A. Pratt, Y. Nakada, WO 2008011130; O. Jentzer, M. Guglieri, WO 2009092795), or may be made by similar methods from commercially available starting materials.

Compounds of formula (2D), wherein X is methyl and R' is $C_1$-$C_4$alkyl, can be prepared by reacting compounds of formula (2G) with propyne in the presence of a suitable catalyst, optionally a suitable additive, optionally in a suitable solvent at a suitable temperature. Suitable catalysts include transition metal salts or complexes of transition metal salts (for example palladium acetate, bis(triphenylphosphine) palladium(II) dichloride, tetrakis(triphenylphosphine)palladium(0), bis(triphenylphosphine) nickel(II) dichloride and tris(acetylacetonato) iron(III)), in an amount of typically 0.001-25 mole % with respect to a compound of formula (2G). Suitable additives include copper salts, for example copper(I) iodide in an amount of typically 0.001-50 mole % with respect to a compound of formula (2G), and tetraalkyl ammonium salts. Suitable bases include diethylamine, triethylamine, piperidine and pyrrolidine, and suitable solvents include 1,4-dioxane, N,N-dimethylacetamide or N,N-dimethylformamide. Preferably the reaction is carried out using 0.05-10 mole % bis(triphenylphosphine) palladium(II) dichloride (with respect to a compound of formula (2G)), 0.05-10 mole % triphenylphosphine (with respect to a compound of formula (2G)), 0.05-25 mole % copper(I) iodide (with respect to a compound of formula (2G)), 5-200 mole % tetrabutyl ammonium iodide (with respect to a compound of formula (2G)), triethylamine and N,N-dimethylformamide at a temperature between 25° C. to 150° C. Such a reaction is an example of a Sonogashira coupling and similar reactions are known in the literature (see for example F. Labrie, S. Gauthier, J. Cloutier, J. Mailhot, S. Potvin, S. Dion, J-Y. Sanceau, WO 2008124922; M. S. Viciu, S. P. Nolan, Modern Arylation Methods (2009), 183-220; R. Chinchilla, C. Najera, Chemical Reviews (2007), 107(3), 874-922; I. P. Beletskaya, G. V. Latyshev, A. V. Tsvetkov, N. V. Lukashev, Tetrahedron Letters (2003), 44(27), 5011-5013 and J. Mao, G. Xie, M. Wu, J. Guo, S. Ji, Advanced Synthesis & Catalysis (2008), 350(16), 2477-2482). In an alternative approach a compound of formula (2D) may be prepared from a compound of formula (2G) by reaction with a propynyl transfer reagent such as 1-propynyllithium, 1-propynylmagnesium bromide, 1-propynylmagnesium chloride, 1-propynylmagnesium iodide, 1-propynylzinc chloride, 1-propynylzinc bromide, 1-propynylzinc iodide, tributylpropynylstannane, 1-propyne-1-boronic acid (or ester thereof), 2-butynoic acid or 1-(trimethylsilyl)propyne, with a transition metal catalyst system under suitable conditions (see for example P. Wessig, G. Mueller, C. Pick, A. Matthes, Synthesis (2007), (3), 464-477; J. H. Chaplin, G. S. Gill, D. W. Grobelny, B. L. Flynn, G. Kremmidiotis, WO07087684; A. Akao, T. Tsuritani, S. Kii, K. Sato, N. Nonoyama, T. Mase, N. Yasuda, Synlett (2007), (1), 31-36. A. Coelho Coton, E. Sotelo Perez, F. Guitian Rivera, A. Gil Gonzalez, WO 2011048247; C. H. Oh, S. H. Jung, Tetrahedron Letters (2000), 41(44), 8513-8516; D. Zhao, C. Gao, X. Su, Y. He, J. You, Y. Xue, Chemical Communications (2010), 46(47), 9049-9051; C. Yang, S. P. Nolan, Organometallics (2002), 21(6), 1020-1022). In another set of preferred conditions a compound of formula (2G) is reacted with 1-propynylmagnesium bromide in the presence of 0.05-10 mole % bis(triphenylphosphine) palladium(II) dichloride (with respect to a compound of formula (2G)), in tetrahydrofuran at a temperature between 25° C. and 100° C., as described by J. H. Chaplin, G. S. Gill, D. W. Grobelny, B. L. Flynn, G. Kremmidiotis, WO 07087684. Compounds of formula (2G) are known, or can be prepared by known methods using known reagents.

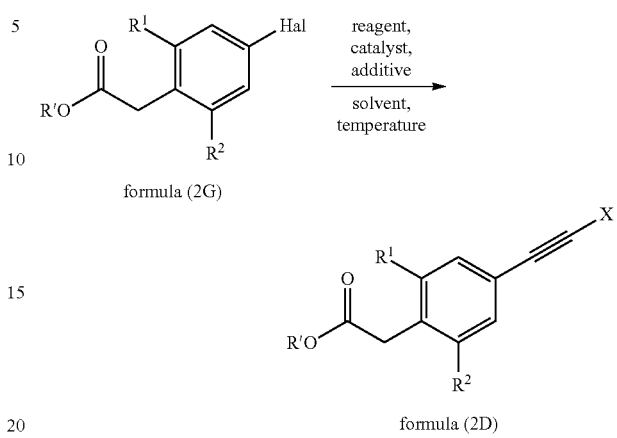

Compounds of formula (2D), wherein X is chlorine and R' is $C_1$-$C_4$alkyl, can be prepared from compounds of formula (2H) or compounds of formula (2I). In one approach a compound of formula (2H) is first deprotonated with a base such as butyllithium, sodium hydride, lithium diisopropylamide or ethylmagnesium bromide, then reacted with a chlorine source such as N-chloro succinimide, chlorine or carbon tetrachloride. The specific chlorine source is selected to provide the required chloro-acetylene. Similar reactions and conditions are reported in the literature (see for example M. Tajbakhsh, S. Habibzadeh, Letters in Organic Chemistry (2007), 4(7), 512-514; D. Sud, T. J. Wigglesworth, N. R. Branda, Angewandte Chemie, International Edition (2007), 46(42), 8017-8019; M. A. P. Martins, D. J. Emmerich, C. M. P. Pereira, W. Cunico, M. Rossato, N. Zanatta, H. G. Bonacorso, Tetrahedron Letters (2004), 45(25), 4935-4938; A. Poloukhtine, V. Rassadin, A. Kuzmin, V. V. Popik, Journal of Organic Chemistry (2010), 75(17), 5953-5962; C. R. Hickenboth, J. D. Rule, J. S. Moore, Tetrahedron (2008), 64(36), 8435-8448; F. H. M. Graichen, A. C. Warden, S. Kyi, M. S. O'Shea, Australian Journal of Chemistry (2010), 63(4), 719-722; and M. L. Narayana, M. L. N. Rao, M. Periasamy, Synthetic Communications (1995), 25(15), 2295-9).

In another approach a compound of formula (2D), wherein X is chlorine and R' is $C_1$-$C_4$alkyl, can be prepared from a compound of formula (2H) by treatment with a mixture of reagents that are known to promote chlorination, such as potassium carbonate, tetrabutylammonium bromide and carbon tetrachloride (see for example T. Matsuda, S. Kadowaki, Y. Yamaguchi, M. Murakami, Chemical Communications (2008), (24), 2744-2746), pyridine and chlorine (see for example R. B. Gutsulyak, V. N. Britsuk, L. A. Kostrikina, Y. Serguchev, Ukrainskii Khimicheskii Zhurnal (1993), 59(10), 1062-7), silver nitrate and N-chloro succinimide, N-chloro succinimide and hexamethylphosphoramide (see for example G. Pangon, J. L. Philippe, P. Cadiot, Comptes Rendus des Seances de l'Academie des Sciences, Serie C: Sciences Chimiques (1973), 277(18), 879-81), and/or perchloric acid and acetic acid (see for example J. P. Montheard, M. Camps, M. Chatzopoulos, M. O. A. Yahia, R.

Guilluy, D. Deruaz, Journal of Chemical Research, Synopses (1983), (9), 224-5). Conditions are selected to provide the required chloro-acetylene. When X is chlorine, preferred conditions include reacting a compound of formula (2H) with 1-5 mole equivalents of N-chloro succinimide and 0.05-50 mole % silver acetate (with respect to a compound of formula (2H)) in acetone at a temperature between 25° C. and 100° C.

Compounds of formula (2I), wherein R' is $C_1$-$C_4$alkyl and R' is $C_1$-$C_4$alkyl, can also be directly converted to compounds of formula (2D), e.g. by treatment with isocyanuric chloride or N-chloro succinimide and silver nitrate (see for example M. H. Vilhelmsen, A. S. Andersson, M B. Nielsen, Synthesis (2009), (9), 1469-1472).

In a further approach, a compound of formula (2D) (wherein X is chlorine) can either be prepared from a compound of formula (2J) or a compound of formula (2K), by treatment with a suitable base, in a suitable solvent, at a suitable temperature. A compound of formula (2J) can be converted to a compound of formula (2D) under conditions similar to those described in the literature, for example treatment using potassium tert-butoxide in tert-butanol at a temperature between 25° C. and 150° C., or lithium 2,2,6,6-tetramethylpiperidine in tetrahydrofuran at a temperature between −25° C. and 50° C. (see for example E. Bartmann, R. Hittich, H. Plach, U. Finkenzeller, U.S. Pat. No. 5,188,759 and Indian Journal of Chemistry, Section B: Organic Chemistry Including Medicinal Chemistry, 1978, vol. 16,

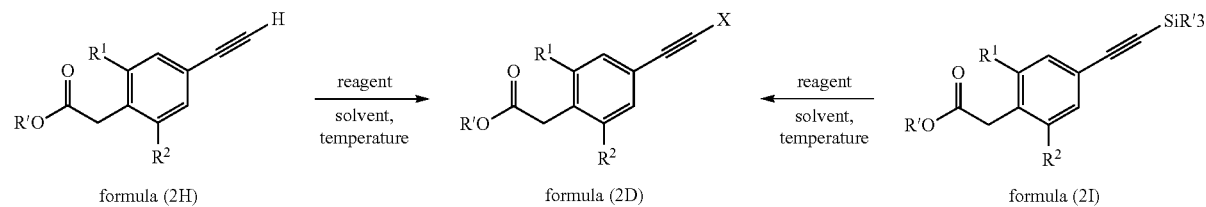

A compound of formula (2I), wherein R' is $C_1$-$C_4$alkyl and R' is $C_1$-$C_4$alkyl, can be prepared by reacting a compound of formula (2G) with a trialkylsilylacetylene, under similar conditions described previously to convert a compound of formula (2G) to a compound of formula (2D) (wherein X is methyl).

A compound of formula (2H) can either be prepared by deprotection of a compound of formula (2I) under known conditions, or by reacting a compound of formula (2G) with an ethynyl transfer reagent such as tributylstannylacetylene, lithium acetylide ethylenediamine complex, ethynylzinc bromide or ethynylmagnesium chloride in the presence of a suitable catalyst system, e.g. under conditions similar to those described previously (see for example C. Fischer, J. Methot, H. Zhou, A. J. Schell, B. Munoz, A. A. Rivkin, S. P. Ahearn, S. Chichetti, R. N. Maccoss, S. D. Kattar, M. Christopher, C. Li, A. Rosenau, W. C. Brown, WO 2010071741; M. Behler, A. Eluntlaut, C. Ferman, A. Chapuf, CN 101195641; G. Wang, G. Zhu, E. Negishi, Journal of Organometallic Chemistry (2007), 692(21), 4731-4736 and E. Negishi, M. Kotora, C. Xu, Journal of Organic Chemistry (1997), 62(25), 8957-8960).

1051-1054). A compound of formula (2K) can also be converted to a compound of formula (2D) under conditions similar to those described in the literature, for example by treatment with cesium carbonate in N,N-dimethylformamide at a temperature between 25° C. and 150° C., sodium tert-butoxide in toluene at a temperature between 25° C. and 150° C., 1,8-diazabicyclo[5.4.0]undec-7-ene in dimethylsulfoxide at a temperature between 0° C. and 50° C., or potassium tert-butoxide in tetrahydrofuran at a temperature between −78° C. and 25° C. (see for example B. C. G. Soederberg, S. P. Gorugantula, C. R. Howerton, J. L. Petersen, S. W. Dantale, Tetrahedron (2009), 65(36), 7357-7363; S-C. Lo, R. E. Harding, E. Brightman, P. L. Burn, I. D. W. Samuel, Journal of Materials Chemistry (2009). 19(20), 3213-3227; S. Wang, T. Kohn, Z. Fu, X. Y. Jiao, S. Lai, M. Schmitt, Tetrahedron Letters (2008), 49(51), 7284-7286 and M. L. G. Borst, R. E. Bulo, D. J. Gibney, Y. Alem, F. J. J. de Kanter, A. W. Ehlers, M. Schakel, M. Lutz, A. L. Spek, K. Lammertsma, Journal of the American Chemical Society (2005), 127(48), 16985-16999). Compounds of formula (2J) and (2K) (wherein X is chlorine) can be prepared from known compounds using known methods and reagents.

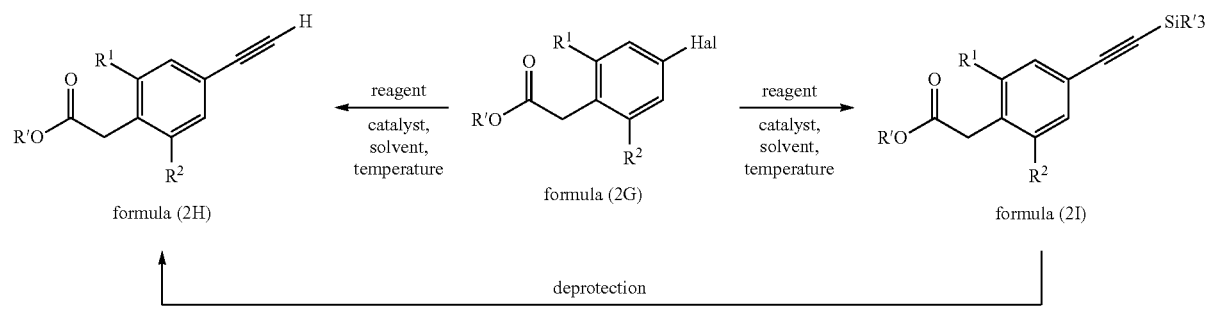

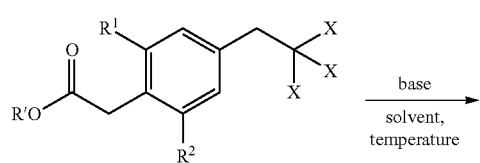

formula (2J)

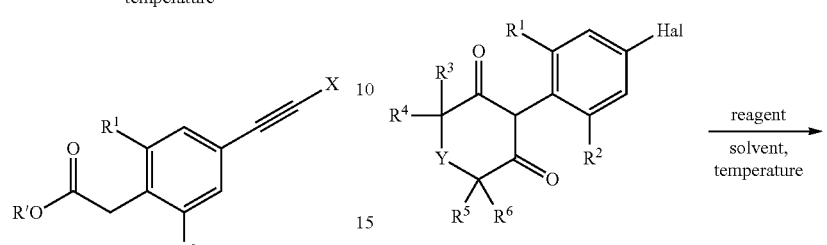

In a further approach a compound of formula (2A), wherein X is methyl, can be prepared directly from a compound of formula (2L), under similar conditions described previously to convert a compound of formula (2G) to a compound of formula (2D).

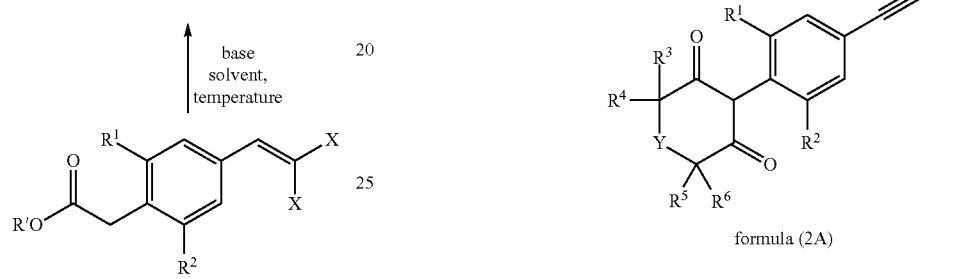

A compound of formula (2L) can be prepared from a compound of formula (2G) using similar procedures to those outlined previously.

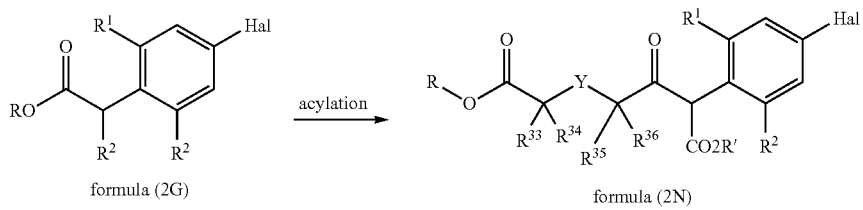

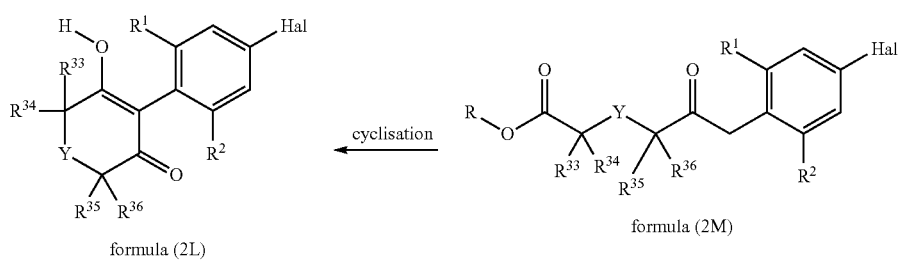

A compound of formula (2A), wherein X is chlorine, can be prepared from a compound of formula (2L), via either a compound of formula (2O) or a compound of formula (2P) (wherein R' is $C_1$-$C_4$alkyl), e.g. under similar conditions to those described previously.

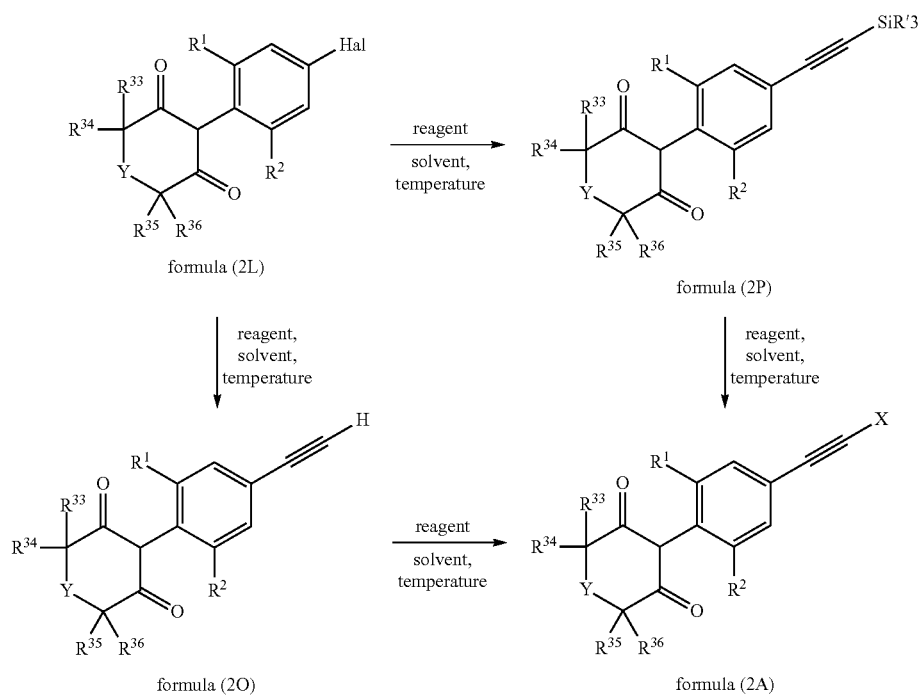

A compound of formula (2A), wherein X is chlorine, can also be prepared from a compound of formula (2Q), e.g. under conditions similar to those described for converting a compound of formula (2K) to a compound of formula (2D).

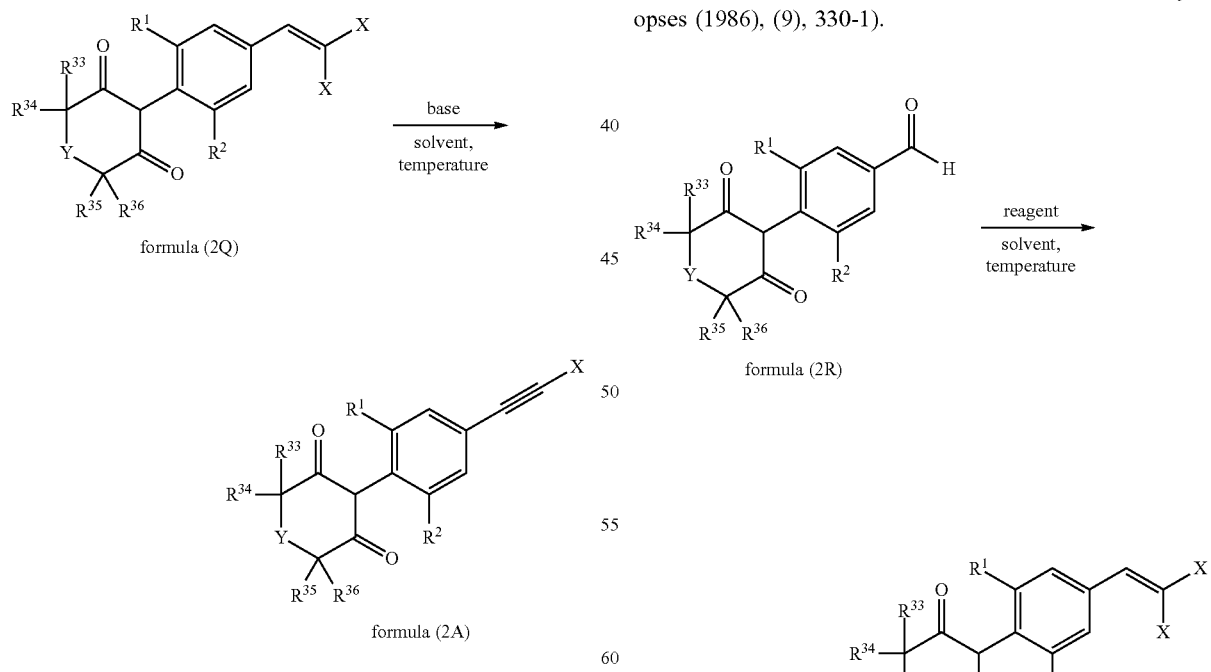

A compound of formula (2Q), wherein X is chlorine may be prepared from an aldehyde of formula (2R) by treatment with triphenylphosphine in the presence of carbon tetrachloride in a suitable solvent at a suitable temperature. Carbon tetrachloride is selected to provide the required dichloroalkene, and similar reactions are known in the literature (see for example A. Poloukhtine, V. V. Popik, Journal of the American Chemical Society (2007), 129(40), 12062-12063; L. N. Michaelides, B. Darses, D. J. Dixon, Organic Letters (2011), 13(4), 664-667 and F. Gavina, S. V. Luis, P. Ferrer, A. M. Costero, J. A. Marco, Journal of Chemical Research, Synopses (1986), (9), 330-1).

A compound of formula (2R) may be prepared by the formylation of a compound of formula (2L) (wherein Hal is chlorine, bromine or iodine, preferably bromine or iodine). Suitable conditions for effecting the formylation of aryl halides are known, and include, for example, the treatment of an aryl halide with a suitable organometallic reagent, such as isopropyl magnesium chloride, n-butyllithium, sec-butyllithium or tert-butyllithium, or by treatment with a suitable alkali metal or alkali earth metal such as lithium or magnesium in a suitable solvent, such as diethyl ether, dimethoxyethane or tetrahydrofuran. The resulting arylmetal reagent is then reacted with a suitable formylating agent such as N,N-dimethylformamide or N-formylmorpholine. Alternatively a compound of formula (2R) may be prepared from a compound of formula (2L) (wherein Hal can also be a pseudohalogen such as triflate) by treatment with a carbonylating agent (such as carbon monoxide in the presence of a suitable catalyst system, base, and reducing agent (see for example L. Ashfield and C. Barnard, Org. Process Res. Dev., 11 (1), 39-43, 2007).

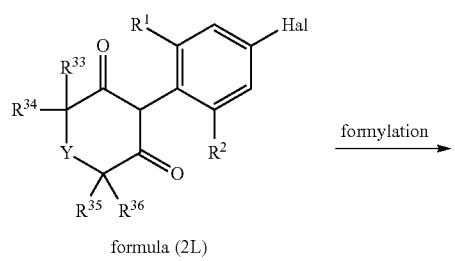

formula (2L)

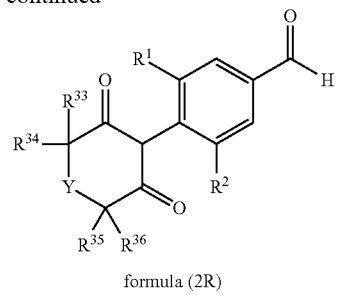

formula (2R)

In an alternative approach, a compound of formula I, wherein Q is Q2, X is methyl, and wherein G is preferably substituted alkyl (e.g. optionally substituted phenyl-$CH_2$— or heteroaryl-$CH_2$—), or hydrogen, or methyl or ethyl (the latter two are not within formula I but can be converted to G=H later), may be prepared from a boronic acid or boronic ester of formula (2S) by treatment with either 1-bromo-1-propyne or 1-iodo-1-propyne, preferably in the presence of a suitable catalyst system, a suitable base and/or a suitable solvent and/or at a suitable temperature. Similar reactions are known in the literature, and preferred conditions involve reacting a compound of formula (2S) with 1-iodo-propyne in the presence of 0.005-25 mole % palladium(II) chloride (with respect to a compound of formula (2S)) and 1-10 equivalents (i.e. mole equivalents) of potassium carbonate, preferably in a mixture of toluene, water and methanol at a temperature between 50° C.-150° C., as described by Y. Shi, X. Li, J. Liu, W. Jiang, L. Sun, Tetrahedron Letters (2010), 51(28), 3626-3628. A compound of formula (2T), wherein G is preferably methyl or ethyl and R″ is $C_1$-$C_4$alkyl, may be prepared under similar conditions using either 1-bromo-2-(trimethylsilyl)acetylene or 1-iodo-2-(trimethylsilyl)acetylene as the coupling partner. Compounds of formula (2A) and (2P) may be prepared from compounds of formula I, wherein Q is Q2, and (2T) respectively, by hydrolysis of the enol ether.

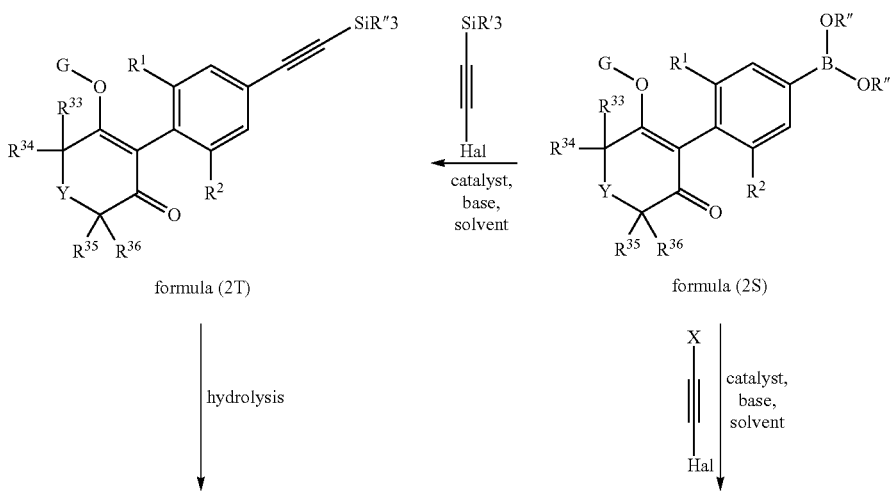

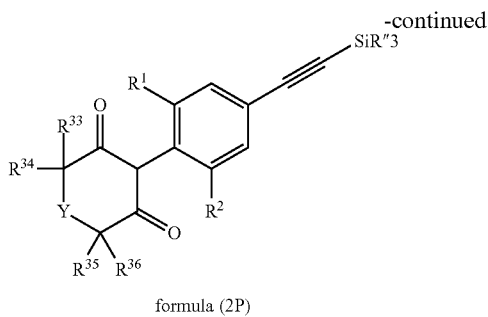

formula (2P)

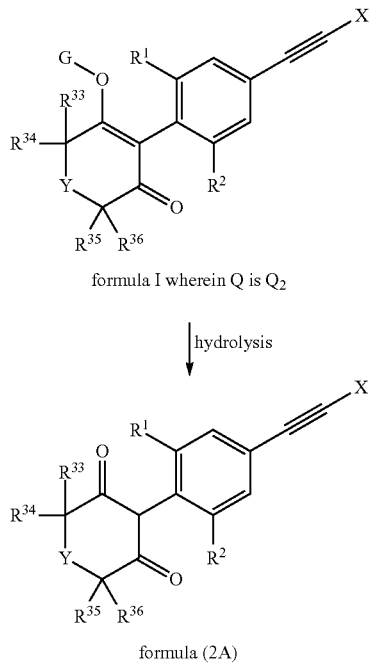

formula I wherein Q is Q₂

↓ hydrolysis formula (2A)

In one approach, a compound of formula (2S) may be prepared from a compound of formula (2L) (wherein Hal is preferably iodine or bromine), preferably by treatment with a suitable base, such as sodium hydride, potassium hydride or isopropylmagnesium chloride, in a suitable solvent, such as tetrahydrofuran or diethyl ether, followed by a metal-halogen exchange reaction, preferably by treatment with an alkyllithium reagent such as n-butyllithium, sec-butyllithium or tert-butyllithium, or an organomagnesium reagent such as isopropyl magnesium chloride, and subsequent treatment with a trialkylborate, B(OR")₃, preferably trimethylborate, to give the corresponding boronate ester of formula (2S).

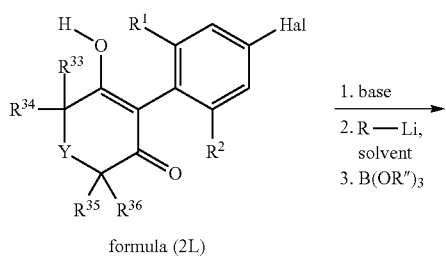

formula (2L)

1. base
2. R—Li, solvent
3. B(OR")₃

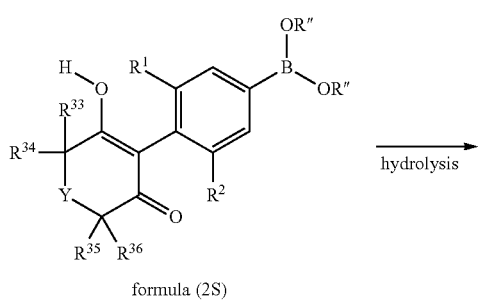

formula (2S)

hydrolysis →

-continued

[boronic acid structure]

In an alternative approach, a compound of formula (2U) may be prepared from a compound of formula (2V), wherein G is preferably substituted alkyl (e.g. optionally substituted phenyl-CH₂— or heteroaryl-CH₂—), or methyl or ethyl (the latter two are not within the G definition in formula I but can be converted to G=H later), by C—H borylation with a suitable borylating agent, a suitable catalyst system, in a suitable solvent at a suitable temperature. Suitable catalysts include 1,5-cyclooctadiene)(methoxy)iridium(I) dimer in combination with 4,4'-di-tert-butyl-2,2'-dipyridyl, suitable borylating agents include bis(pinacolato)diboron or pinacol borane, and suitable solvents include hexane, octane, tetrahydrofuran and methyl tert-butyl ether. Similar examples are known in the literature (see for example J. F. Hartwig, Chemical Society Reviews (2011), 40(4), 1992-2002 and T. Ishiyama, N. Miyaura, Pure and Applied Chemistry (2006), 78(7), 1369-1375). Preferred conditions include treating a compound of formula (2V) with 0.05-10 mole % 1,5-cyclooctadiene)(methoxy)iridium(I) dimer (with respect to a compound of formula (2V)), 0.05-10 mole % 4,4'-di-tert-butyl-2,2'-dipyridyl (with respect to a compound of formula (2V)), and 1-2 equivalents (i.e. mole equivalents) of bis(pinacolato)diboron (with respect to a compound of formula (2V)) in methyl tert-butyl ether at a temperature between 50° C.-150° C., optionally under microwave irradiation, as described by P. Harrisson, J. Morris, T. B. Marder, P. G. Steel, Organic Letters (2009), 11(16), 3586-3589.

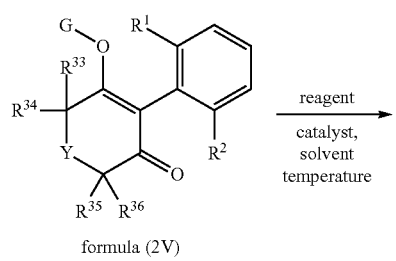

formula (2V)

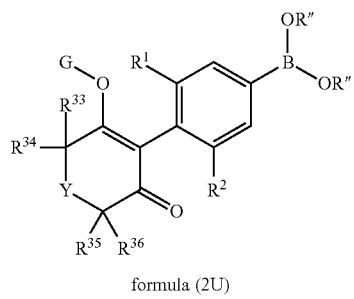

formula (2U)

Compounds of formula (2W) can be prepared from compounds of formula (2X) using similar procedures described previously, starting from compounds of formula (2Z) which are known compounds.

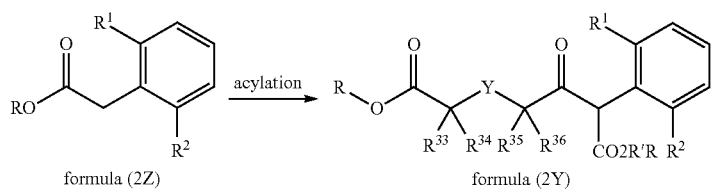

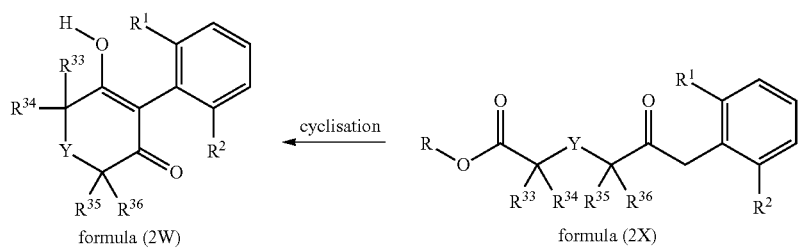

In a further approach to the compounds of the invention, a compound of formula (2A), wherein X is methyl, may be prepared via the rearrangement of a compound of formula (2AA), in the presence of a reagent which promotes rearrangement. Preferably, the reagent which promotes rearrangement is (i) a metal alkoxide (e.g. sodium or potassium methoxide), preferably in an amount equal to or greater than 100 mole % with respect to compound of formula (2AA), or is (ii) a cyanide anion, for example 0.001-25 mole % potassium cyanide or 0.001-25 mole % sodium cyanide with respect to a compound of formula (2AA), or is (iii) a cyanohydrin, preferably 0.001-25 mole % acetone cyanohydrin with respect to a compound of formula (2AA). This reaction is preferably performed in a suitable solvent (e.g. organic solvent, e.g. N, N-dimethylformamide) and/or at a suitable temperature (typically 25-150° C.). More preferably, a compound of formula (2A) wherein X is methyl is prepared by treating a compound of formula (2AA) with 1-3 equivalents (i.e. mole equivalents) of sodium methoxide in N, N-dimethylformamide at a temperature between 50° C. and 100° C.

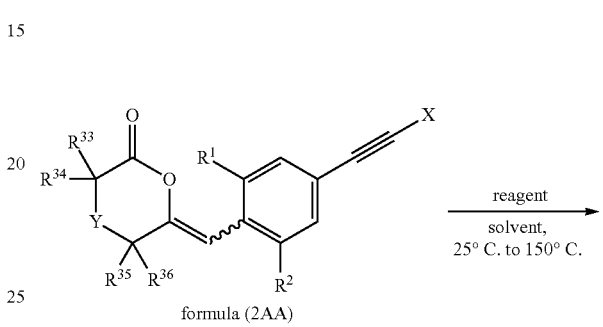

formula (2AA)

-continued

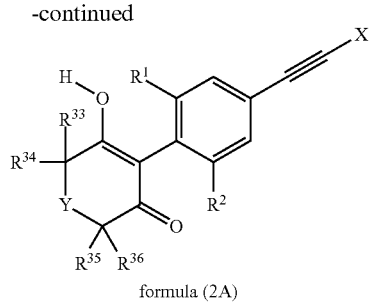

formula (2A)

In one approach to a compound of formula (2AA), the compound of formula (2AA), wherein X is methyl, may be prepared from a compound of formula (2AB) by treatment with a catalyst system which promotes lactonisation, such as palladium(II) dichloride, gold(I) chloride or silver carbonate, preferably 0.001-50 mole % silver carbonate with respect to a compound of formula (2AB), in the presence of a suitable solvent, for example acetonitrile, at a suitable temperature (typically 25° C. to 150° C.), and optionally under microwave irradiation. Similar lactonisations are known in the literature (see for example WO 2008/071405, P. Huang and W. Zhou, Tetrahedron Asymmetry (1991), 2 (9), 875-878; and H. Harkat, J-M. Weibel, P. Pale, Tetrahedron Letters (2006), 47(35), 6273-6276).

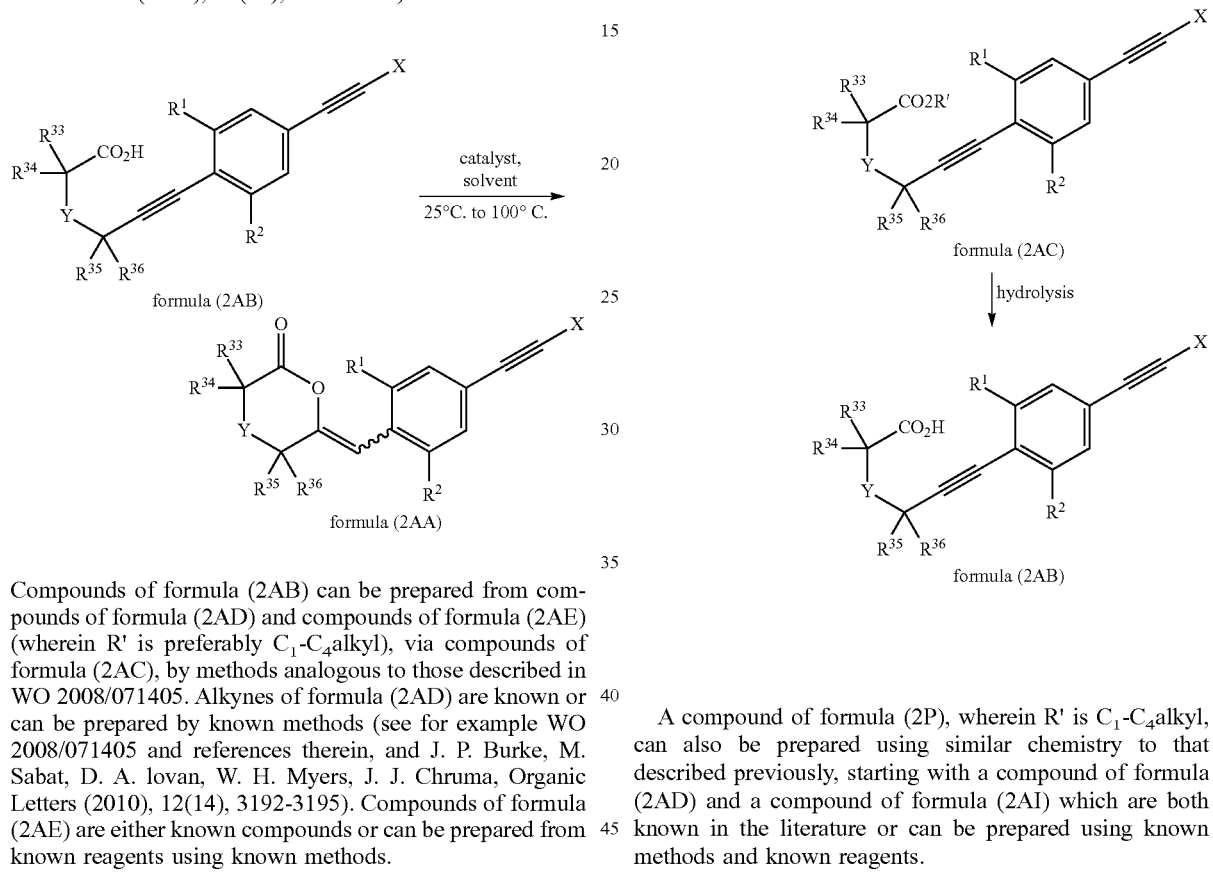

Compounds of formula (2AB) can be prepared from compounds of formula (2AD) and compounds of formula (2AE) (wherein R' is preferably $C_1$-$C_4$alkyl), via compounds of formula (2AC), by methods analogous to those described in WO 2008/071405. Alkynes of formula (2AD) are known or can be prepared by known methods (see for example WO 2008/071405 and references therein, and J. P. Burke, M. Sabat, D. A. Iovan, W. H. Myers, J. J. Chruma, Organic Letters (2010), 12(14), 3192-3195). Compounds of formula (2AE) are either known compounds or can be prepared from known reagents using known methods.

A compound of formula (2P), wherein R' is $C_1$-$C_4$alkyl, can also be prepared using similar chemistry to that described previously, starting with a compound of formula (2AD) and a compound of formula (2AI) which are both known in the literature or can be prepared using known methods and known reagents.

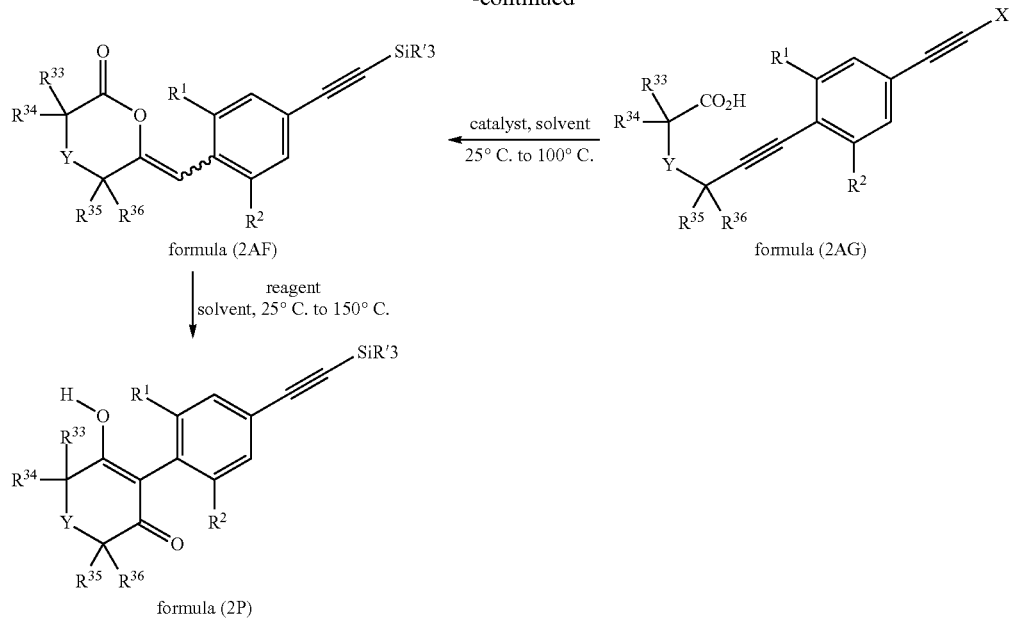
Similarly, a compound of formula (2L) can be prepared from a compound of formula (2AJ) using similar chemistry to that described previously.
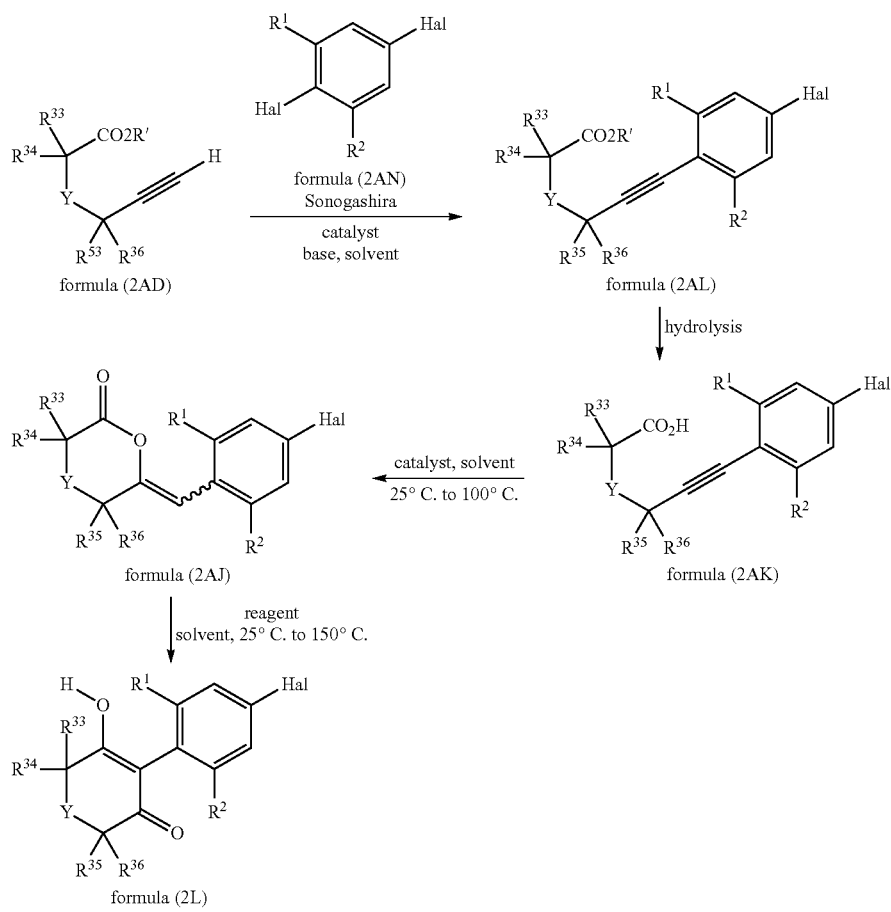

Similarly, a compound of formula (2W) can be prepared from a compound of formula (2AO) using similar chemistry to that described previously.

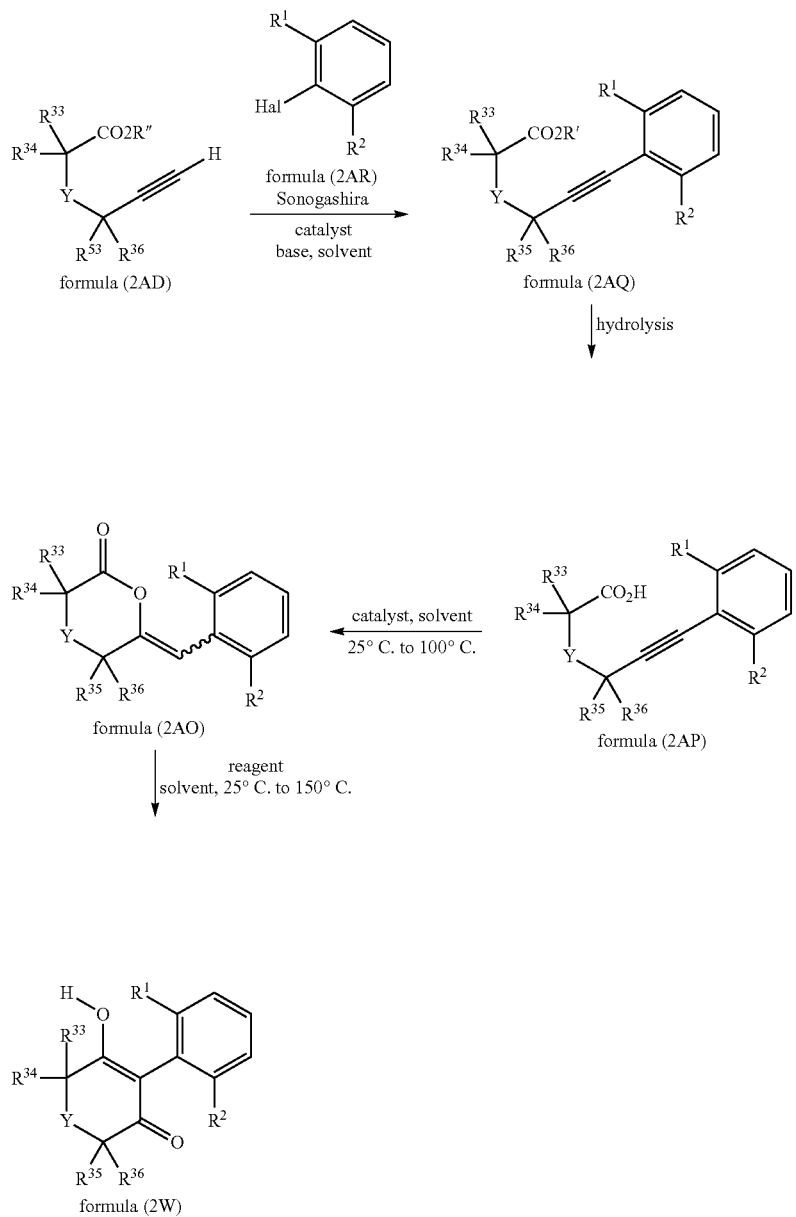

In a second approach, a compound of formula (2AA), wherein X is methyl, may be prepared via the Baeyer-Villiger oxidation of a compound of formula (2AS), preferably in a suitable solvent and/or at a suitable temperature (in particular from 0° C. to 100° C.), and optionally in the presence of a suitable catalyst system (such as selenium dioxide). Suitably, an oxidant comprising peracetic acid or hydrogen peroxide is used. Preferred conditions are hydrogen peroxide and catalytic selenium dioxide (0.001-25 mole %) in tert-butanol at a temperature of from 0° C. to 100° C., as described by J. A. Guzman, V. Mendoza, E. Garcia, C. F. Garibay, L. Z. Olivares, L. A. Maldonado, Synthetic Communications (1995), 25(14), 2121-33.

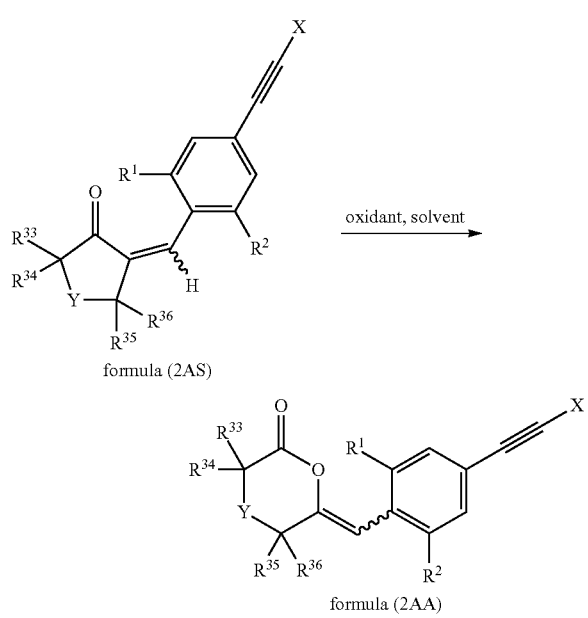

formula (2AS)

formula (2AA)

A compound of formula (2AS), wherein X is methyl, may be prepared from a compound of formula (2AU) by condensation with a benzaldehyde of formula (2AT), in the presence of a suitable base and optionally in the presence of a suitable solvent (for similar examples see WO 2010/136431; A. Lagrange, S. Forestier, G. Lang and B. Luppi, EP368717 A1; D. C. Rowlands, U.S. Pat. No. 2,776,239; E. Tamate, Journal of the Chemical Society of Japan, (1957), 78, 1293-7; R. Hernandez, D. Melian, T. Prange, E. Suarez, Heterocycles (1995), 41(3), 439-54; and J. Sotiropoulos, N. El Batouti, A. M. Lamazouere, Journal of Heterocyclic Chemistry (1987), 24(4), 907-12).

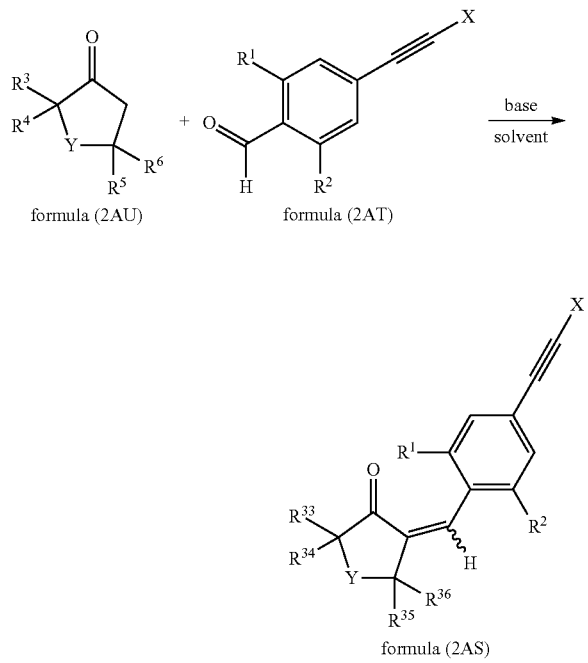

formula (2AU)

formula (2AT)

formula (2AS)

Preferably the base is a metal hydroxide, such as sodium hydroxide or potassium hydroxide, metal alkoxide such as sodium methoxide, sodium ethoxide or potassium tert-butoxide, or metal amide such as sodium amide. Preferably the solvent is dimethoxyethane, dioxane, tetrahydrofuran, diethyl ether or an alkyl alcohol, such as methanol, ethanol, isopropanol or tert-butanol.

Compounds of formula (2AU), wherein Y is O and or $CR^{38}R^{39}$, are known compounds (see for example X. Ye, M. D. Johnson, T. Diao, M. H. Yates, S. S. Stahl, Green Chemistry (2010), 12(7), 1180-1186; M. Newman and W. Reichle, Org. Synth. Coll. Vol. V., (1973), 1024; Y. Zal'kind, E. Venus-Danilova and V. Ryabtseva, Russian Journal of General Chemistry, (1950), 20, 2222-9; M. Bertrand, J. Dulcere, G. Gil, J. Grimaldi and P. Sylvestre-Panthet, Tetrahedron Letters (1976), (18), 1507-8), or may be prepared from known compounds by known methods.

Compounds of formula (2AU), wherein Y is C(O), are known compounds (see for example N. J. Turro, D. R. Morton, E. Hedaya, M. E. Kent, P. D'Angelo, P. Schissel, Tetrahedron Letters (1971), (27), 2535-8; P. A. Krapcho, D. R. Rao, M. P. Silvon, B. Abegaz, Journal of Organic Chemistry (1971), 36(25), 3885-90; S. N. Crane, T. J. Jenkins, D. J. Burnell, Journal of Organic Chemistry (1997), 62(25), 8722-8729; S. N. Crane, D. J. Burnell, Journal of Organic Chemistry (1998), 63(4), 1352-1355; S. N. Crane, D. J. Burnell, Journal of Organic Chemistry (1998), 63(16), 5708-5710; C. E. Elliott, D. O. Miller, D. J. Burnell, Journal of the Chemical Society, Perkin Transactions 1 (2002), (2), 217-226), or may be prepared from known compounds by known methods.

Compounds of formula (2AU), wherein Y is S, S(O) or $S(O)_2$ are known compounds (see for example E. R. Buchman, H. Cohen, Journal of the American Chemical Society (1944), 66, 847-8; A. W. D. Avison, F. Bergel, J. W. Haworth, U.S. Pat. No. 2,408,519: K. G. Mason, M. A. Smith, E. S. Stern, E J. A. Elvidge, Journal of the Chemical Society [Section] C: Organic (1967), (21), 2171-6; T. A. Magee, Thomas A. DE 2033454; I. Tabushi, Y. Tamaru, Z. Yoshida, T. Sugimoto, Journal of the American Chemical Society (1975), 97(10), 2886-91; P. E. Aldrich, G. H. Berezin, B. I. Dittmar, I. Bruce, D E 2516554; I. Tabushi, Y. Tamaru, Z. Yoshida, Bulletin of the Chemical Society of Japan (1978), 51(4), 1178-82; D. N. Reinhoudt, J. Geevers, W. P. Trompenaars, S. Harkema, G. J. Van Hummel, Journal of Organic Chemistry (1981), 46(2), 424-34; F. Duus, Synthesis (1985), (6-7), 672-4; J. Schatz, Science of Synthesis (2002), 9, 287-422), or may be prepared from known compounds by known methods.

A compound of formula (2AT), wherein X is methyl, can be prepared from known compounds by known methods.

A compound of formula (2P), wherein R' is $C_1$-$C_4$alkyl, can also be prepared from a compound of formula (2AF), by rearrangement under conditions similar to those described for the conversion of a compound of formula (2AA) to a compound of formula (2A). A compound of formula (2AW) is known, or can be prepared by known methods using known reagents.

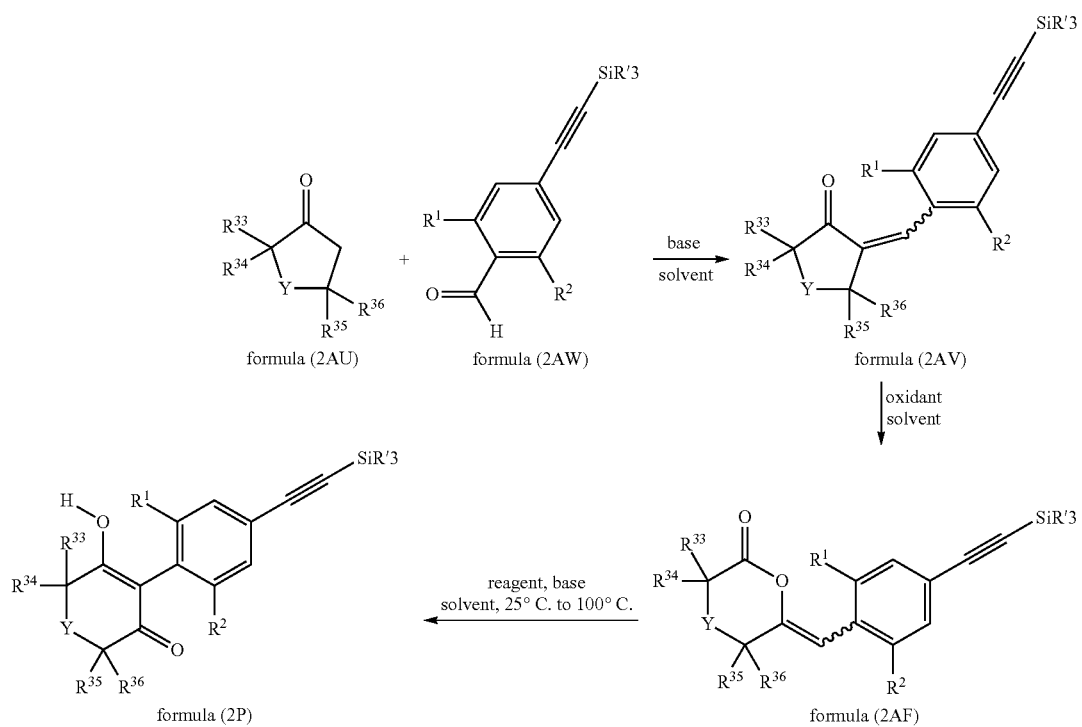

Similarly, a compound of formula (2L) can also be prepared from a compound of formula (2AJ) by rearrangement under similar conditions. Compounds of formula (2AY) are known compounds, or can be prepared from known reagents using known methods.

Similarly, a compound of formula (2W) can also be prepared from a compound of formula (2AO) by rearrangement under similar conditions. Compounds of formula (2AAA) are known compounds, or can be prepared from known reagents using known methods.

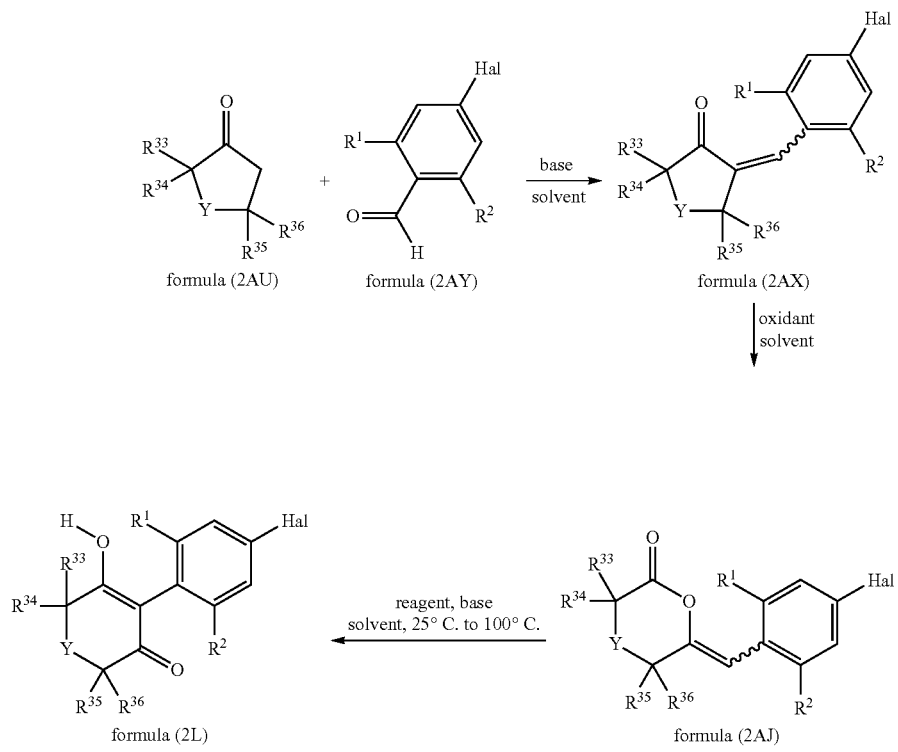

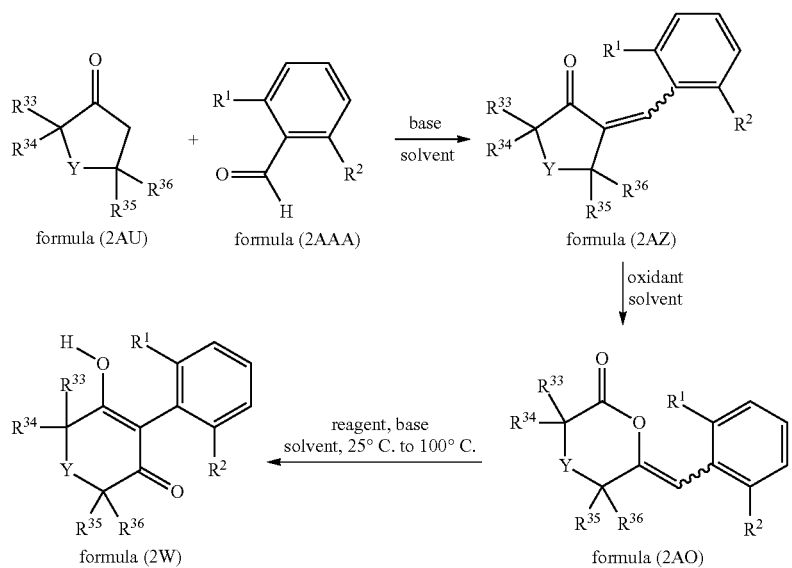

In a further approach, a compound of formula (2A), wherein X is methyl, can be prepared by a rearrangement of an epoxide of formula (2AAB) catalysed by the presence of an acid, in the presence of a suitable solvent (e.g. organic solvent).

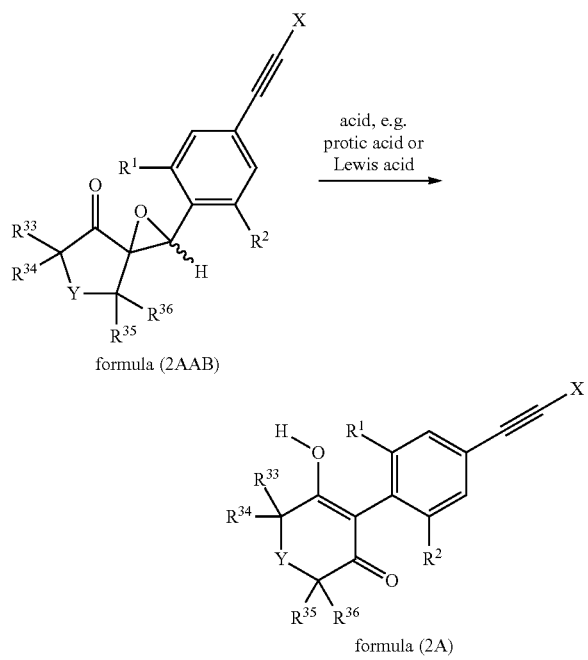

For the rearrangement of (2AAB) to (2A), suitable acids include a Brönsted acid (protic acid), such as a mineral acid or an organic acid, for example sulfuric acid, hydrochloric acid, hydrogen chloride, p-toluenesulfonic acid, methanesulfonic acid, acetic acid or formic acid, or a Lewis acid, such as a metal halide, for example boron trifluoride, aluminium chloride, iron chloride, tin(IV) chloride, zinc chloride, zinc bromide, or lithium perchlorate, or a metal triflate such as scandium triflate or ytterbium triflate. Mixtures of such acids can also be used. The conversion of a compound of formula (2AAB) into a compound of formula (2A) may be considered to be an example of a semi-Pinacol rearrangement (see for example WO 2010/136431 A1 (Syngenta Limited); M. Paulson, M. Daliya and C. Asokan, Synth. Commun. (2007), 37(5), 661-665; S. Sankararaman and J. Nesakumar, J. Chem. Soc, Perkin Trans. 1, (1999), (21), 3173-3175; K. Rehse and R. Bienfait, Archiv der Pharmazie, (1984), 317(5), 385-93; H. Kamath, A. Sahasrabudhe, B. Bapat and S. Kulkarni, Indian J. Chem., Section B: (1981), 20B(12), 1094-6; G. Buchanan and D. Jhaveri, J. Org. Chem. (1961), 26 4295-9; and H. House, Richard L. Wasson, J. Am. Chem. Soc., (1956), 78, 4394-400). For the rearrangement of (2AAB) to (2A), a suitable solvent (e.g. organic solvent) is preferably chosen to be compatible with the acid used, and can include a chlorinated hydrocarbon, an alcohol, an ether, an aromatic solvent or an organic acid, for example dichloromethane, dichloroethane, diethyl ether, acetic acid, formic acid, toluene, benzene, methanol, ethanol, isopropanol or tetrahydrofuran. Preferably the reaction, i.e. the rearrangement of (2AAB) to (2A), is performed using methanesulfonic acid in toluene at a temperature between 25° C. and 150° C.

A compound of formula (2AAB) can be prepared by the epoxidation of a compound of formula (2AS). Epoxidation may be effected by treatment of a compound of formula (2AS) with a suitable oxidising agent such as an organic peroxide or metal hyperchlorite, for example dimethyldioxirane, sodium hypochlorite, hydrogen peroxide, tert-butyl peroxide or trifluoroperacetic acid, optionally in combination with a suitable base, such as an alkali metal hydroxide or carbonate, alkaline earth metal hydroxide or carbonate, or an amine base such as 1,8-diazabicyclo[5.4.0]-undec-7-ene, optionally in a suitable solvent, such as an alcohol or halogenated hydrocarbon, for example methanol, ethanol or dichloromethane, and at a suitable temperature. The reaction can also be performed under biphasic conditions, in which a phase-transfer reagent is also typically used in 0.001-50 mole %. The phase transfer reagent is preferably a quaternary ammonium salt, a crown ether, a polyethylene glycol, or phosphonium salt. Similar reactions are known in the literature (see for example WO 2010/136431 A1 (Syngenta Limited); I. K. Korobitsyna, O. P. Studzinskii, The Russian Journal of Organic Chemistry (1969), 5(8), 1493-5; A. Halasz, Z. Jambor, A. Levai, C. Nemes, T. Patonay and G. Toth, J. Chem. Soc, Perkin Trans. 1, (1996), (4), 395-400; N. Yousif, F. Gad, A. Fahmy, M. Amine and H. Sayed, Phosphorus, Sulfur and Silicon and the Related Elements (1996), 117, 11-19; T. Ooi, D. Ohara, M. Tamura and K. Maruoka, J. Am. Chem. Soc., (2004), 126(22), 6844-6845; A. Amr, H. Hayam and M. Abdulla, Archiv der Pharmazie, (2005), 338(9), 433-440; K. Drauz, S. M. Roberts, T. Geller and A. Dhanda, U.S. Pat. No. 6,538,105 B1; and L. S. Chagonda and B. A. Marples, J. Chem. Soc. Perkin 1, 1988, 875-879). Preferably, epoxidation is carried out using hydrogen peroxide and a metal hydroxide (especially lithium hydroxide or sodium hydroxide), in methanol at a temperature of between −10° C. and 60° C.

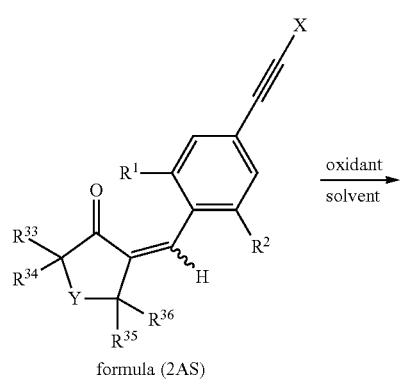

formula (2AS)

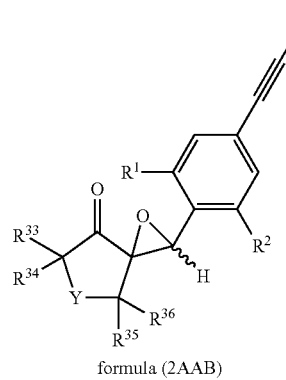

formula (2AAB)

Alternatively a compound of formula (2AAB), wherein X is methyl, may be prepared by reacting a compound of formula (2AAC) (wherein halogen is chlorine, bromine or iodine, preferably chlorine or bromine) with a compound of formula (2AT), in the presence of a suitable base, optionally in a suitable solvent, at a suitable temperature.

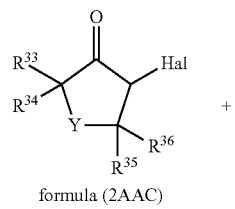

formula (2AAC)

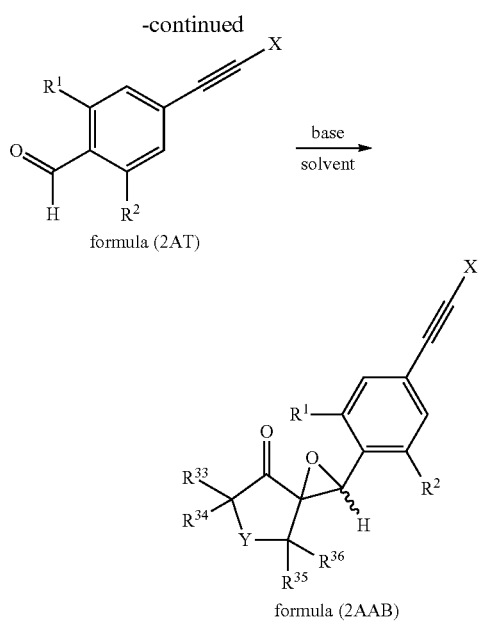

formula (2AT)

formula (2AAB)

Suitable bases include alkali or alkali earth metal hydroxides, such as sodium hydroxide, lithium hydroxide or potassium hydroxide, alkali or alkali earth metal alkoxides, such as sodium methoxide, sodium ethoxide, potassium tert-butoxide or sodium tert-butoxide, alkali or alkali earth metal carbonates such as potassium carbonate or sodium carbonate, or sodium bicarbonate, metal amides such as lithium diisopropylamide, lithium hexamethyldisilazide or lithium 2,2,6,6-tetramethylpiperidide, organometallics such as butyl lithium or ethylmagnesium bromide, or metal hydrides such as sodium hydride or potassium hydride. Suitable solvents include chlorinated hydrocarbons, ethers, alcohols, aromatics and various polar aprotic solvents, for example 1,2-dimethoxyethane, tetrahydrofuran, 1,4-dioxane, diethyl ether, dibutyl ether, dichloromethane, dichloroethane, acetonitrile, dimethyl sulfoxide, N, N-dimethylformamide, benzene, toluene, methanol, ethanol, isopropanol or tert-butanol, and is chosen to be compatible with the base under the reaction conditions. The reaction can also be performed under biphasic conditions, in which a phase-transfer reagent is also typically used in 0.001-50 mole %. The phase transfer reagent is preferably a quaternary ammonium salt, a crown ether, a polyethylene glycol, or phosphonium salt. Most preferably the reaction is performed using lithium diisopropylamide in tetrahydrofuran at a temperature range of −100° C. to 60° C. The conversion of a compound of formula (2AAC) into a compound of formula (2AAB) may be considered to be an example of a Darzens condensation (see for example WO 2010/136431 A1 (Syngenta Limited); W. N. Wassef, M. M. El-Barky, Journal of Chemical Research, Synopses (1990), (12), 402-3; J. Li, X. Liu, X. Li, Youji Huaxue (2007), 27(11), 1428-1431; Y. Tong, Y. Cheng, X. Guo, S. Wu, Hecheng Huaxue (2007), 15(1), 102-104; C. Parmenon, J. Guillard, D. Caignard, N. Hennuyer, B. Staels, V. Audinot-Bouchez, J. Boutin, C. Dacquet, A. Ktorza, M. Viaud-Massuard, Bioorganic & Medicinal Chemistry Letters (2008), 18(5), 1617-1622; H. Xiao, X. Han, J. Xiong, Faming Zhuanli Shenqing Gongkai Shuomingshu (2007), p 11; J. M. Concellon, E. Bardales, R. Llavona, Journal of Organic Chemistry (2003), 68(4), 1585-1588).

Compounds of formula (2AAC), wherein Y is O or $CR^{38}R^{39}$ are either known compounds (see for example WO 2010136431; B. Sreedhar, P. S. Reddy, M. Madhavi, Synthetic Communications (2007), 37(23), 4149-4156; R. R. Agarwal, S. S. Deshapande, Journal of the Indian Chemical Society (1949), 26, 483-6; H. Richet, R. Dulou, R., G. Dupont, Bulletin de la Societe Chimique de France (1947), 693-9; H. Richet, Ann. Chim. [12](1948), 3 317-54; I. K. Korobitsyna, Yu. K. Yur'ev, Yu. A. Cheburkov, E. M. Lukina, Russian Journal of General Chemistry (1955), 25, 734-8; I. K. Korobitsyna, Yu. K. Yur'ev, Yu. A. Cheburkov, E. M. Lukina, Russian Journal of General Chemistry (1955), 25, 690-702; F. Leonard, A. Wajngurt, H. Horn, Journal of Organic Chemistry (1956), 21, 1400-4; I. K. Korobitsyna, I. G. Zhukova, V. A. Kuvshinova, N. N. Gaidamovich, Yu. K. Yur'ev, Doklady Akademii Nauk SSSR (1957), 114, 327-30; I. K. Korobitsyna, I. G. Zhukova, I. G, Yu. K. Yur'ev, Russian Journal of General Chemistry (1959), 29, 2190-6; I. K. Korobitsyna, L. L. Rodina, L. M. Stashkova, Chemistry of Heterocyclic Compounds (1966), (6), 843-7; G. Hoehne, F. Marschner, K. Praefcke, P. Weyerstahl, Chem. Ber. (1975), 108(2), 673-82; H. Saimoto, T. Hiyama, H. Nozaki, Bull. Chem. Soc. Jpn., (1983), 56(10), 3078-87; A. M. Zvonok, N. M. Kuz'menok, I. G. Tishchenko, L. S. Stanishevskii, Russian Journal of General Chemistry (1985), 21(6), 1330-4) or can be prepared from compounds of formula (2AU) under known conditions.

Compounds of formula (2AAC), wherein Y is S, S(O) and $S(O)_2$, are either known compounds (see for example M. Polievka, L. Uhlar, V. Patek, Petrochemia (1973), 13(5-6), 156-60; N. N. Novitskaya, B. V. Flekhter, G. M. Prokhorov, A. S. Lukmanova, G. A. Tolstikov, G. V. Leplyanin, S. A. Lange, M. V. Strashnov, SU 468920 A1; P. H. McCabe, W. Routledge, Tetrahedron Letters (1976), (1), 85-6; T. S. Chou, C. Y. Tsai, Tetrahedron Letters (1992), 33(29), 4201-4), or can be prepared from compounds of formula (2AU) under known conditions. Compounds of formula (2AAC), wherein Y is C(O), can be prepared from compounds of formula (2AU) under similar halogenation conditions.

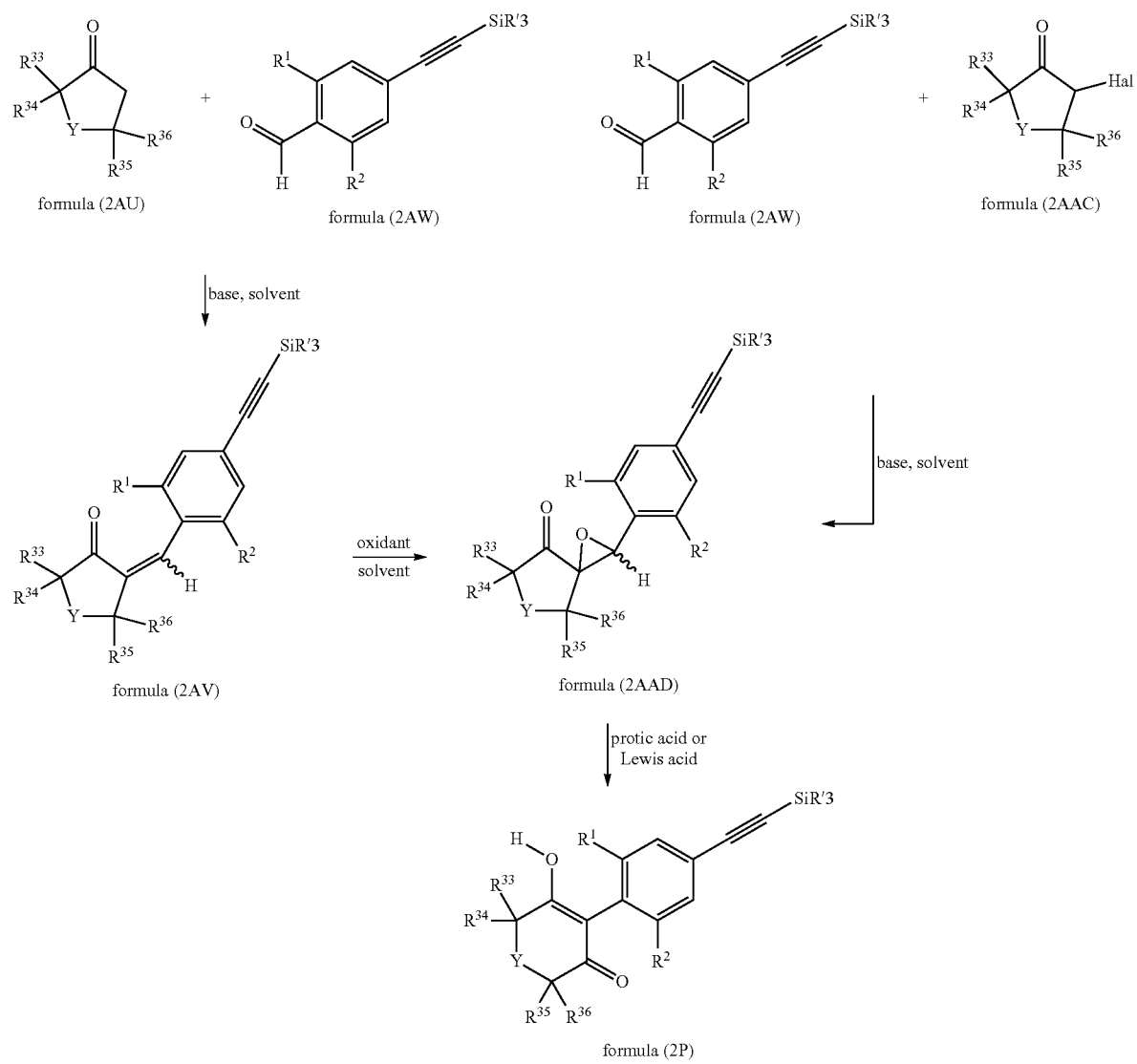

Compounds of formula (2P), wherein R' is $C_1$-$C_4$alkyl, can also be prepared from compounds of formula (2AAD), using similar procedures and conditions described previously. Compounds of formula (2AAD) can either be prepared from compounds of formula (2AU) and (2AW), via compounds of formula (2AV), or from compounds of formula (2AAC) and (2AW).

Similarly, a compound of formula (2L) can also be prepared from a compound of formula (2AAE). A compound of formula (2AY) is known in the literature or can be prepared from known reagents using known methods.

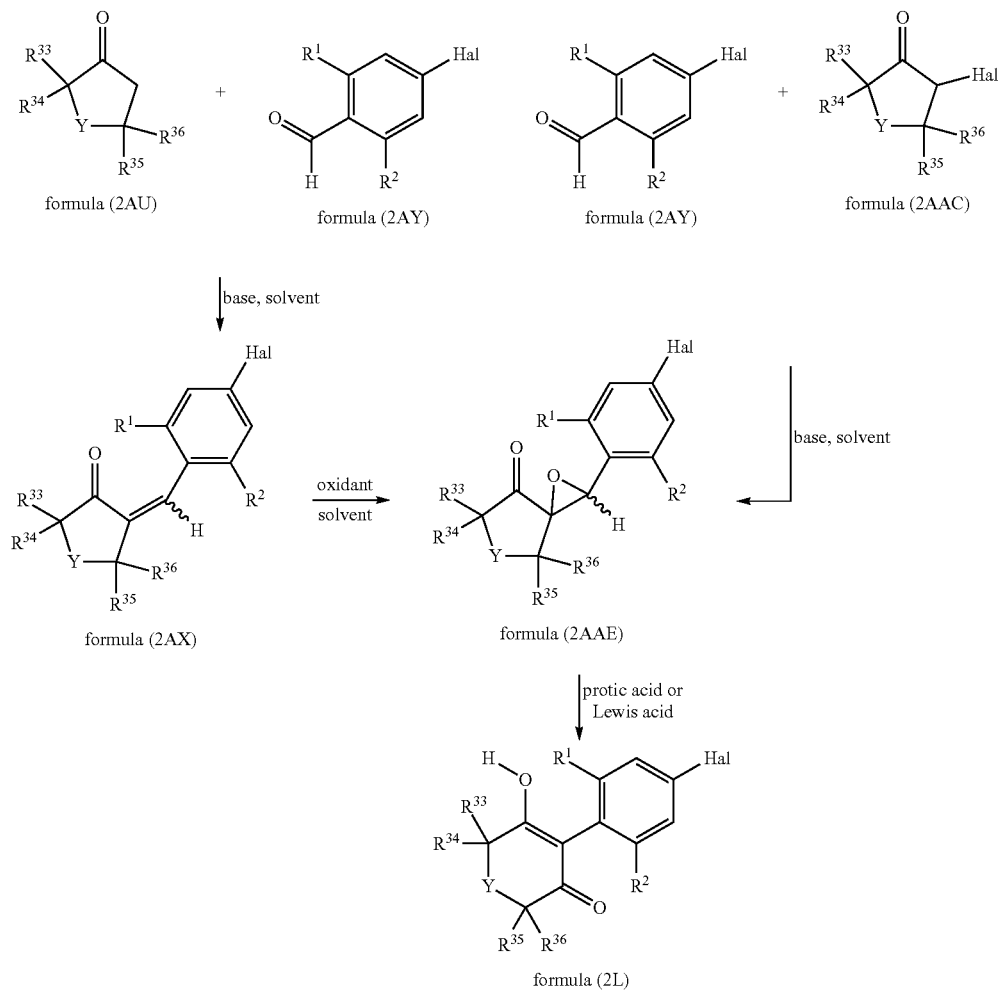

Similarly, a compound of formula (2W) can also be prepared from a compound of formula (2AAF), which can be prepared using similar chemistry to that described previously.

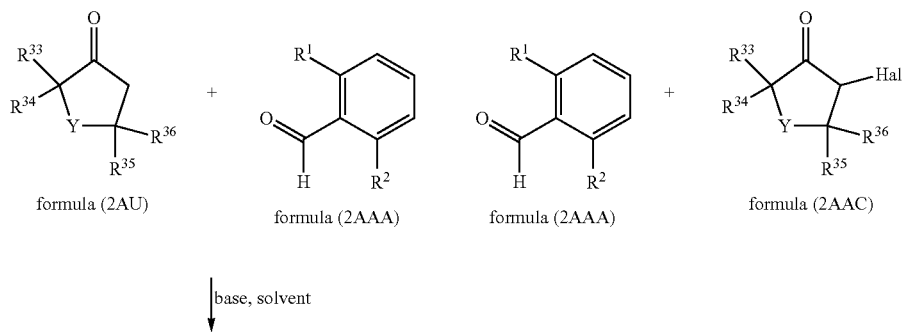

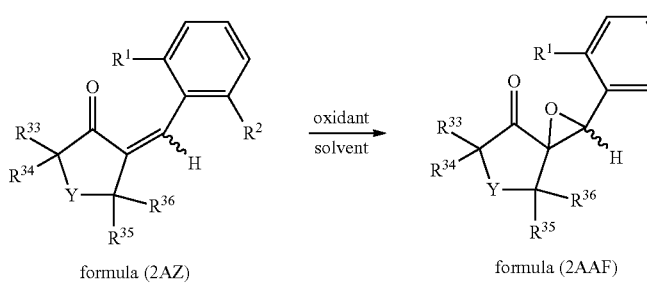

formula (2AZ) → formula (2AAF)

oxidant, solvent base, solvent 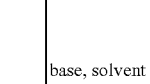

protic acid or Lewis acid

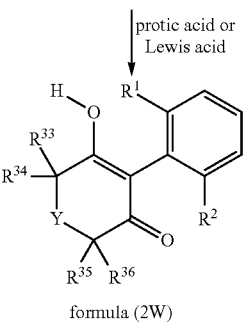

formula (2W)

In a further approach, a compound of formula (2A), wherein X is methyl, may be prepared by reacting a compound of formula (2AAH) with a with an aryllead tricarboxylate, in the presence of a suitable ligand and in a suitable solvent. Similar reactions are described in the literature (see for example M. Muehlebach et al., WO08/071405; J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (2AAG). Preferably the ligand is a nitrogen containing heterocycle such as N,N-dimethylaminopyridine, 1,10-phenanthroline pyridine, bipyridine, or imidazole, and one to ten equivalents (i.e. mole equivalents) of ligand with respect to a compound of formula (2AAG) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.

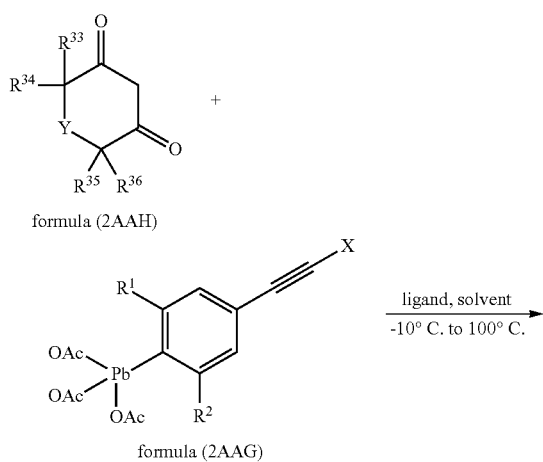

formula (2AAH)

+ formula (2AAG)

ligand, solvent
−10° C. to 100° C.
→

-continued

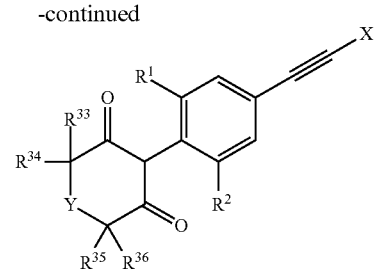

formula (2A)

Compounds of formula (2AAH), wherein Y is O, are known compounds or may be prepared by routes analogous to those described in the literature (see, for example, M. Muehlebach et al., WO08/071405; M. Morgan and E. Heyningen, J. Am. Chem Soc., (1957), 79, 422-424; I. Korobitsyna and K. Pivnitskii, Russian Journal of General Chemistry, (1960), 30, 4016-4023; T. Terasawa, and T. Okada, J. Org. Chem., (1977), 42 (7), 1163-1169; R. Anderson et al. U.S. Pat. No. 5,089,046; R. Altenbach, K. Agrios, I. Drizin and W. Carroll, Synth. Commun., (2004), 34 (4) 557-565; R. Beaudegnies et al., WO2005/123667; W. Li, G. Wayne, J. Lallaman, S. Chang, and S. Wittenberger, J. Org. Chem. (2006), 71, 1725-1727; R. Altenbach, M. Brune, S. Buckner, M. Coghlan, A. Daza, A. Fabiyi, M. Gopalakrishnan, R. Henry, A. Khilevich, M. Kort, I. Milicic, V. Scott, J. Smith, K. Whiteaker, and W. Carroll, J. Med. Chem, (2006), 49(23), 6869-6887; Carroll et al., WO 2001/083484 A1; J. K. Crandall, W. W. Conover, J. Org. Chem. (1978), 43(18), 3533-5; I. K. Korobitsyna, O. P. Studzinskii, Chemistry of Heterocyclic Compounds (1966), (6), 848-854).

Compounds of formula (2AAH), wherein Y is S, are known compounds or may be prepared by routes analogous to those described in the literature (see, for example, E. Fehnel and A. Paul, J. Am. Chem Soc., (1955), 77, 4241-4244; E. Er and P. Margaretha, Helvetica Chimica Acta (1992), 75(7), 2265-69; H. Gayer et al., DE 3318648 A1).

Compounds of formula (2AAH), wherein Y is C(O), are known compounds or may be prepared by routes analogous to those described in the literature (see, for example, R. Götz and N. Götz, WO2001/060776 R. Götz et al. WO 2000/075095; M. Benbakkar et al., Synth. Commun. (1989) 19(18) 3241-3247; A. Jain and T. Seshadri, Proc. Indian Acad. Sci. Sect. A, (1955), 42, 279); N. Ahmad et al., J. Org. Chem., (2007), 72(13), 4803-4815); F. Effenberger et al., Chem. Ber., (1986), 119, 3394-3404 and references therein).

Compounds of formula (2AAH), wherein Y is $CR^{38}R^{39}$ are known compounds of may be prepared by routes analogous to those described in the literature (see for example, M. Muehlebach et al., WO08/110307; M. Muehlebach et al., WO08/110308; S. Spessard and B. Stoltz, Organic Letters, (2002), Vol. 4, No. 11, 1943-1946; F. Effenberger et al., *Chem. Ber.*, (1984), 117, 3280-3296; W. Childers et al., Tetrahedron Lett., (2006), 2217-2218; W. Childers et al., US2006/0004108; H. Schneider and C. Luethy, EP1352890; D. Jackson, A. Edmunds, M. Bowden and B. Brockbank, WO2005/105745 and WO2005/105717; R. Beaudegnies, C. Luethy, A. Edmunds, J. Schaetzer and S. Wendeborn, WO2005/123667; J-C. Beloeil, J-Y. Lallemand, T. Prange, Tetrahedron, (1986), Vol. 42. No. 13, 3491-3502; G. Stork and R. Danheiser, J. Org. Chem., (1973), 38 (9), 1775-1776; H. Favre et al., Can. J. Chem. (1956), 34 1329-39; R. Shriner and H. Todd, Org. Synth. Coll. Vol. II, (1943), 200-202).

A compound of formula (2AAI), wherein X is methyl, may be prepared from a compound of formula (2AAJ) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

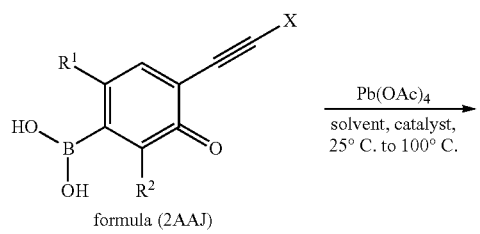

formula (2AAJ)

Pb(OAc)₄
solvent, catalyst,
25° C. to 100° C.

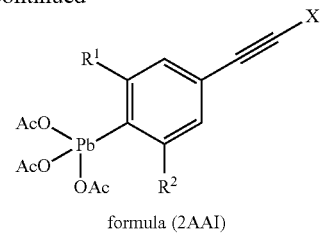

formula (2AAI)

An aryl boronic acid of formula (2AAJ), wherein X is methyl, may be prepared from an aryl halide of formula (2AE), wherein Hal is bromine or iodine by known methods (see, for example, W. Thompson and J. Gaudino, J. Org. Chem, (1984), 49, 5237-5243 and R. Hawkins et al., J. Am. Chem. Soc., (1960), 82, 3053-3059). Thus an aryl halide of formula (2AE) may be treated with an alkyl lithium or alkyl magnesium halide at low temperature, and the aryl magnesium or aryl lithium reagent obtained is allowed to react with a trialkyl borate, $B(OR'')_3$, preferably trimethylborate, to give an aryl dialkylboronate which may be hydrolysed to the desired boronic acid of formula (2AAJ), where X is methyl, under acidic conditions.

Alternatively the same overall transformation of compound (2AE) to compound (2AAJ), wherein X is methyl, may be achieved through a palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

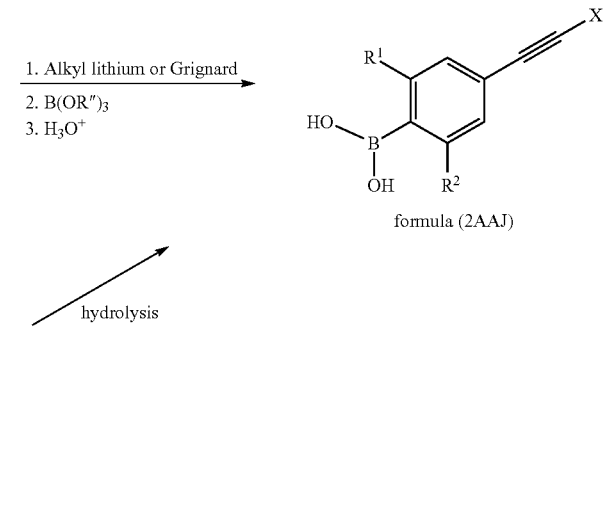

In an alternative approach, a compound of formula (2A), wherein X is methyl, may be prepared by the reaction of a compound of formula (2AAK), wherein Ar is an aryl moiety (preferably phenyl) with an arylboronic acid of formula (2AAJ), wherein X is methyl, in the presence of a suitable palladium catalyst, a suitable base, an optionally in the presence of a suitable ligand or additive, and in a suitable solvent.

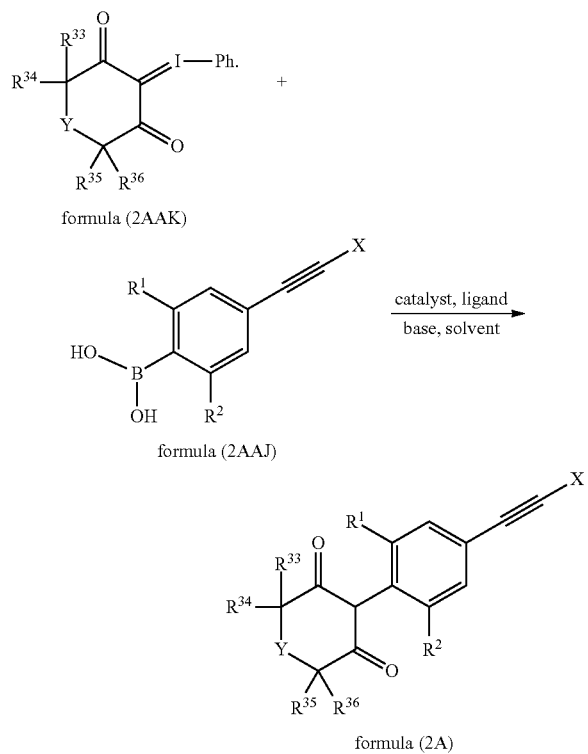

formula (2AAK)

formula (2AAJ)

formula (2A)

Suitable palladium catalysts include, for example palladium(II) dihalides, palladium(II) acetate and palladium(II) sulfate, and is preferably palladium(II) acetate. Suitable ligands include triphenylphosphine, tricyclopentylphosphine, tricyclohexylphosphine, 2-dicyclohexylphosphino-2',6'-dimethoxybiphenyl, 2-dicyclohexylphosphino-2',4',6'-triisopropylbiphenyl, 1,1'-bis(diphenylphosphino)ferrocene and 1,2-bis(diphenylphosphino)ethane. The reaction may also be carried out in the presence of other additives, such as tetralkylammonium salts, for example, tetrabutylammonium bromide. Suitable bases include alkali metal hydroxides, especially lithium hydroxide. A suitable solvent is aqueous 1,2-dimethoxyethane.

A compound of formula (2AAK) may be prepared from a compound of formula (2AAH) by treatment with a hypervalent iodine reagent such as a (diacetoxy)iodobenzene or iodosylbenzene, and a base such as aqueous sodium carbonate, lithium hydroxide or sodium hydroxide, in a solvent such as water or an aqueous alcohol such as aqueous ethanol according to the procedures of K. Schank and C. Lick, Synthesis (1983), 392; R. Moriarty et al, J. Am. Chem. Soc, (1985), 107, 1375, or of Z. Yang et al., Org. Lett., (2002), 4 (19), 3333:

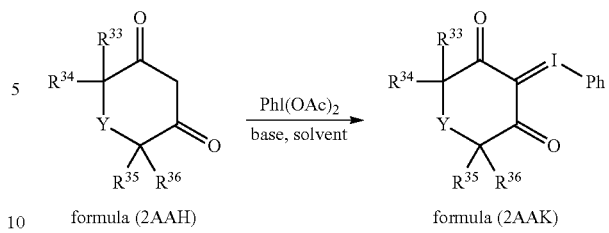

formula (2AAH)     formula (2AAK)

In a further approach, a compound of formula I, wherein Q is Q2 and X is methyl, may be prepared by reacting a compound of formula (2AAL) (wherein G is preferably $C_{1-4}$ alkyl, and Hal is a halogen, preferably bromine or iodine), with an arylboronic acid of formula (2AAJ) in the presence of a suitable palladium catalyst, for example 0.001-50 mole % palladium(II) acetate with respect to compound (2AAL), and a base, for example 1 to 10 equivalents (i.e. mole equivalents) of potassium phosphate with respect to compound (2AAL), and preferably in the presence of a suitable ligand for example 0.001-50 mole % (2-dicyclohexylphosphino)-2',6'-dimethoxybiphenyl with respect to compound (2AAL), and in a suitable solvent, for example toluene, preferably between 25° C. and 200° C. Similar couplings are known in the literature (see for example, Y. Song, B. Kim and J.-N. Heo, Tetrahedron Letters (2005), 46 (36), 5987-5990). A compound of formula I, wherein Q is Q2 and X is preferably methyl, can be converted to a compound of formula (2A) by hydrolysis of the enol ether under known conditions.

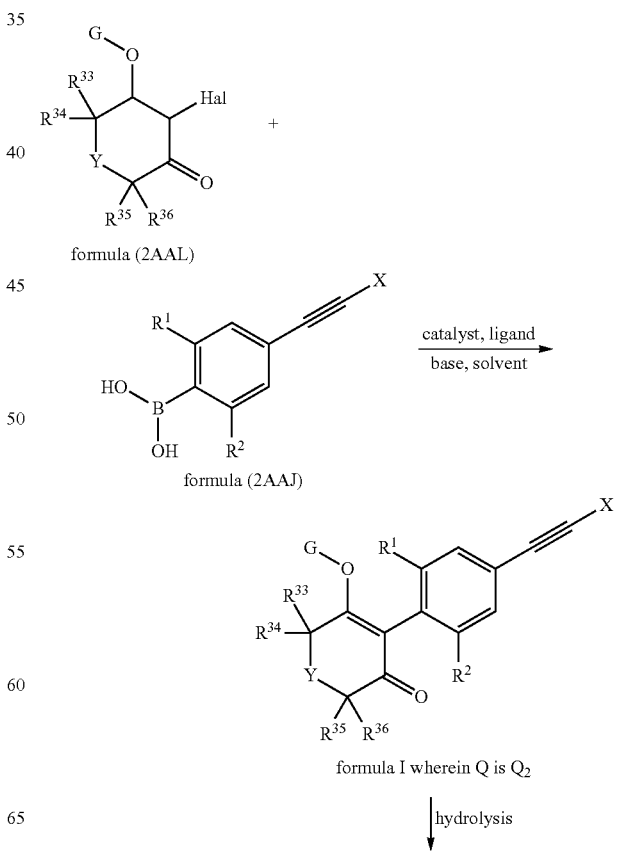

formula (2AAL)

formula (2AAJ)

formula I wherein Q is $Q_2$

↓ hydrolysis

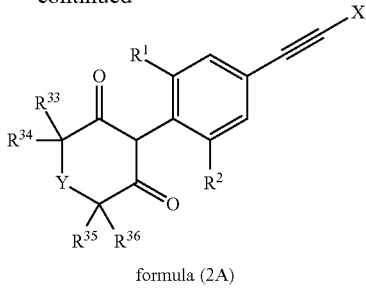

formula (2A)

A compound of formula (2AAL) may be prepared by halogenating a compound of formula (2AAH), followed by reaction of the resulting halide of formula (2AAN) with a $C_1$-$C_4$alkyl halide or tri-$C_1$-$C_4$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690).

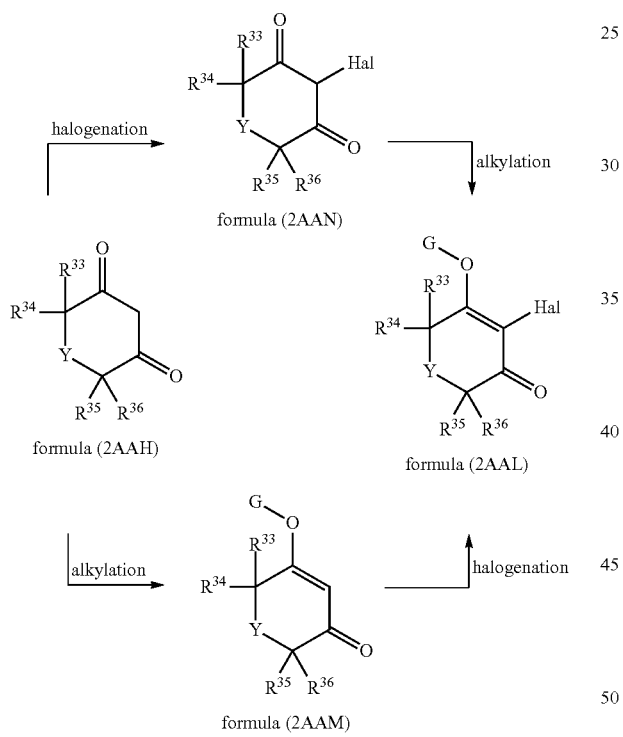

Alternatively, a compound of formula (2AAL) may be prepared by reacting a compound of formula (2AAH) with a $C_1$-$C_4$alkyl halide or a tri-$C_1$-$C_4$-alkylorthoformate, and halogenating the resulting enol ether of formula (2AAM) under known conditions (see for example Y. Song, B. Kim and J.-N. Heo, Tetrahedron Letters (2005), 46(36), 5987-5990).

In a further approach, a compound of formula (2A), wherein X is methyl, may be prepared by reacting a compound of formula (2AAH) with a compound of formula (2AE) in the presence of a suitable palladium catalyst, for example 0.001-50 mole % palladium(II) acetate with respect to compound (2AAH), and a base, for example 1 to 10 equivalents (i.e. mole equivalents) of potassium phosphate with respect to compound (2AAH), and preferably in the presence of a suitable ligand for example 0.001-50 mole % (2-dicyclohexylphosphino)-2',4',6'-triisopropylbiphenyl with respect to compound (2AAH), and in a suitable solvent, for example dioxane, preferably between 25° C. and 200° C. and optionally under microwave heating.

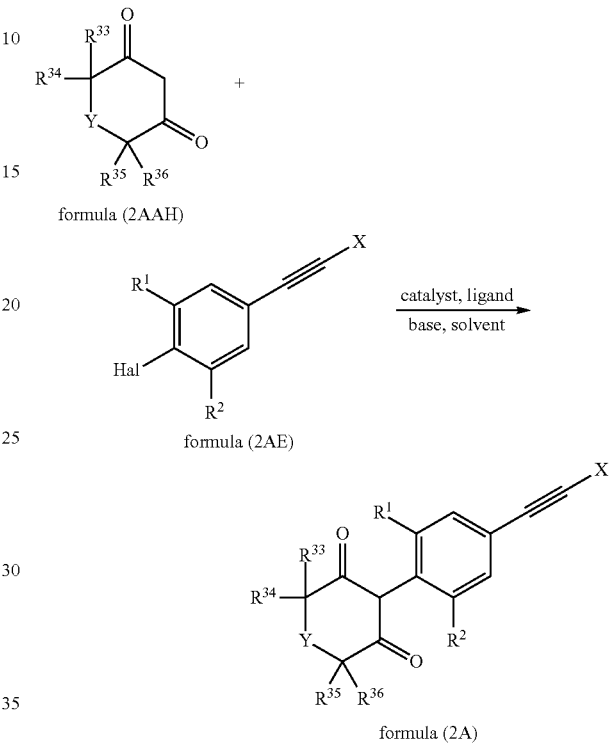

Similar couplings are known in the literature (see for example, S. Buchwald et al., J. Am. Chem. Soc. (2000), 122, 1360-1370; B. Hong et al. WO 2005/000233). Alternatively, a compound of formula (2A) may be prepared by reacting a compound of formula (2AAH) with a compound of formula (2AE) in the presence of a suitable copper catalyst, for example 0.001-50 mole % copper(I) iodide with respect to compound (2AAH), and a base, for example 1 to 10 equivalents (i.e. mole equivalents) of cesium carbonate with respect to compound (2AAH), and preferably in the presence of a suitable ligand, for example 0.001-50 mole % L-proline with respect to compound (2AAH), and in a suitable solvent, for example dimethylsulfoxide, preferably between 25° C. and 200° C. Similar couplings are known in the literature (see for example, Y. Jiang et al., Synlett, (2005), 18, 2731-2734, and X. Xie et al., Organic Letters (2005), 7(21), 4693-4695).

A compound of formula (2P), wherein R" is $C_1$-$C_4$alkyl, can also be prepared using using similar methods described previously, starting from silylated precursors (2AAO), (2AAP) and (2AAI). Compounds (2AAO), (2AAP) and (2AAI) are known compounds, or can be prepared using similar methods to those described previously.

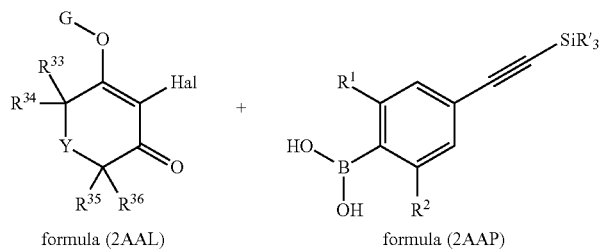
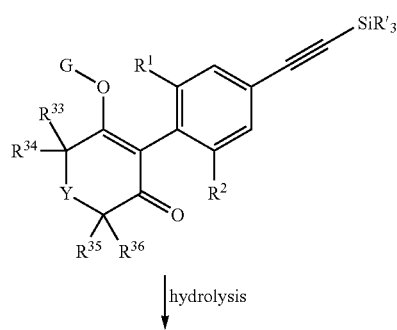
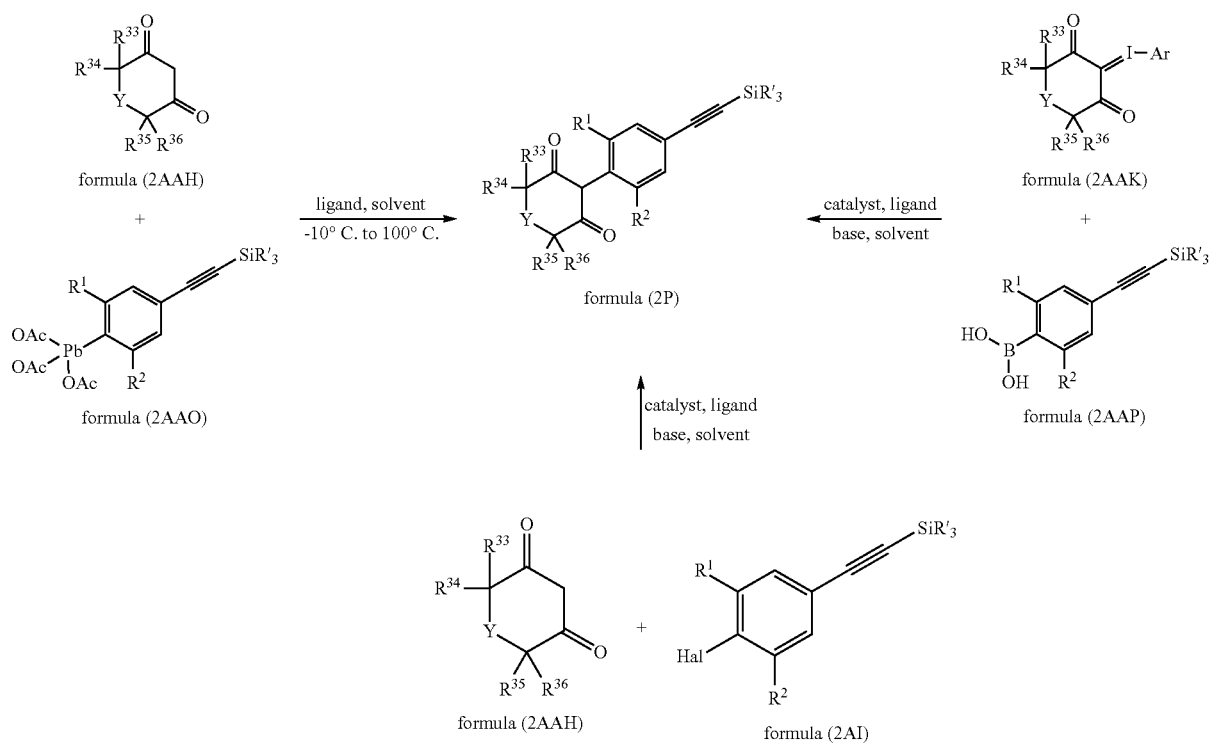
Similarly, a compound of formula (2L) can also be prepared from suitable halogenated precursors, using similar methods to those described previously.

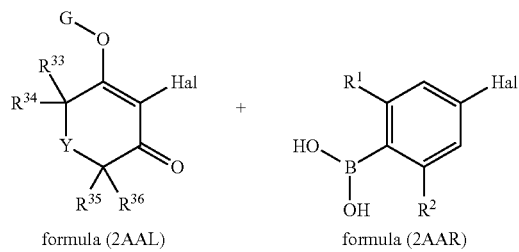
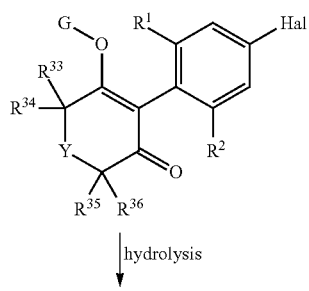
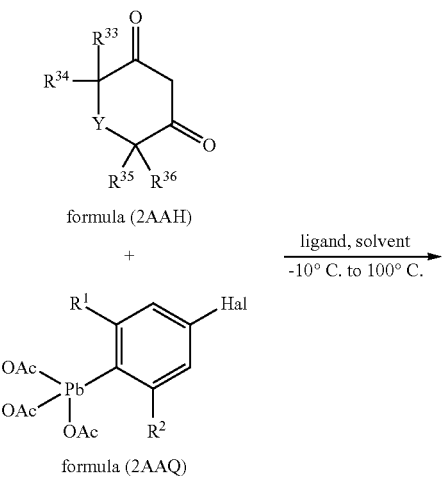
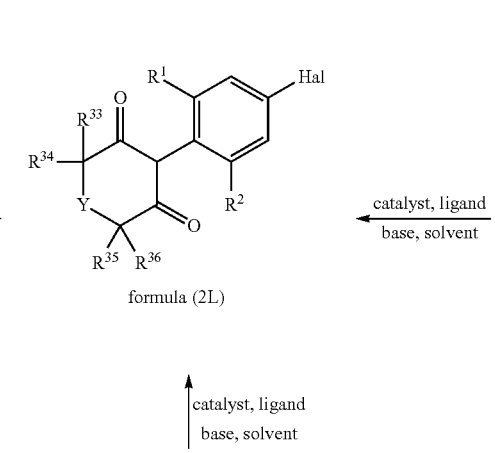
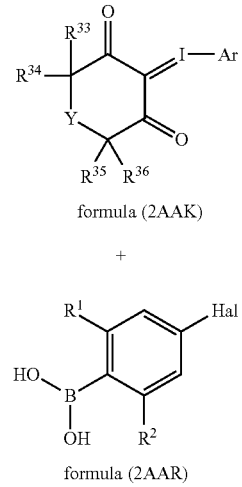
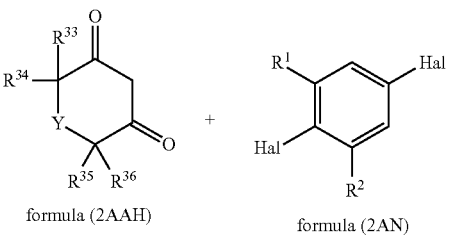
Similarly, a compound of formula (2W) can also be prepared from suitable precursors, using similar methods to those described previously.

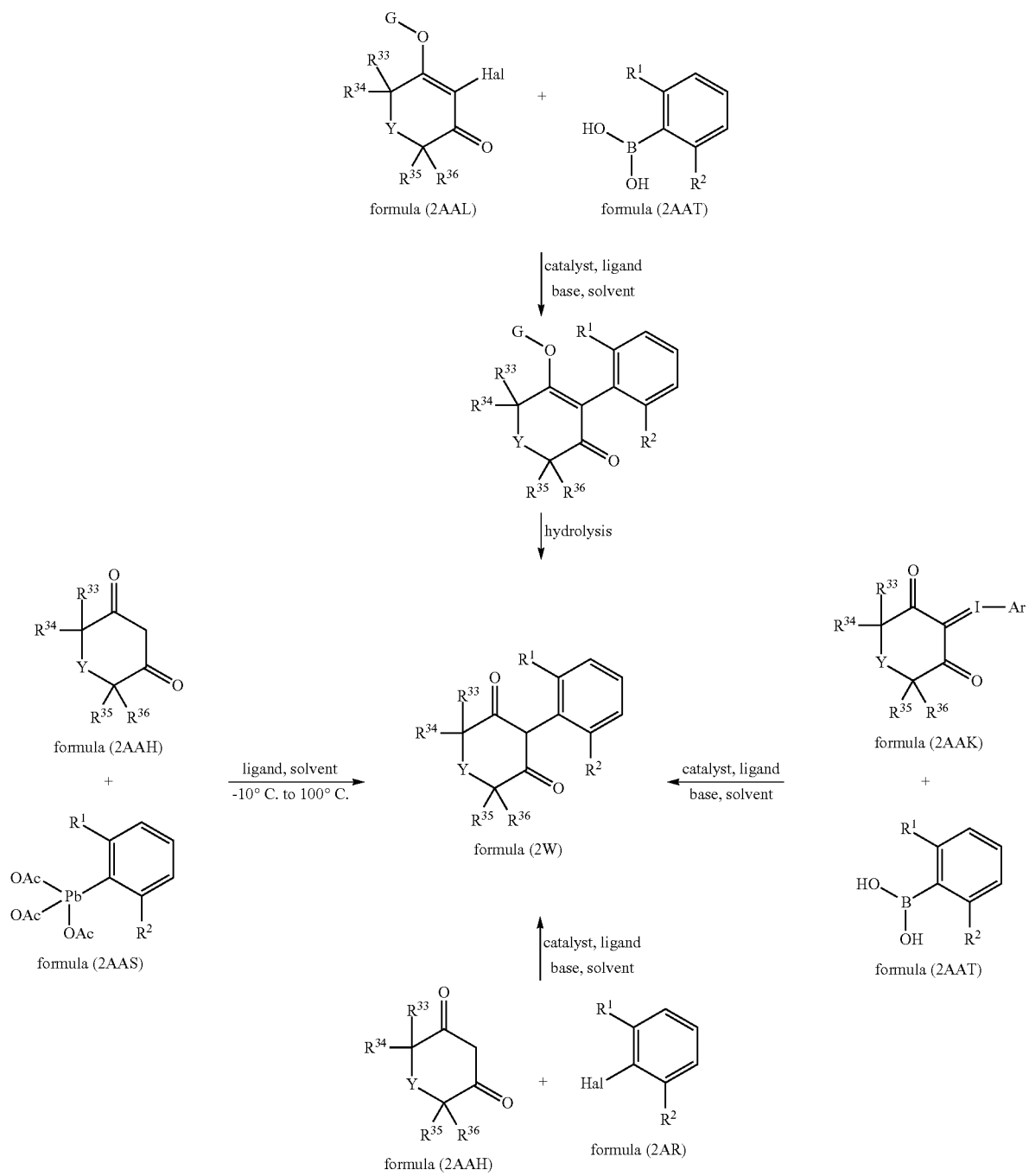

Furthermore, a compound of formula (2L) can be prepared by reacting a compound of formula (2AAH) with a halonitrobenzene of formula (2AAX) (under conditions similar to those described for coupling a compound of formula (2AAH) and a compound of formula (2AE) to produce a compound of formula (2A)), to produce a compound of formula (2AAW) which is then reduced under standard conditions (for a similar example see T. N. Wheeler, CA1113959). The aniline (2AAV) is then converted to the aryl halide (2L) under Sandmeyer conditions (for a similar example see T. N. Wheeler, CA1113959). Alternatively, a compound of formula (2AAU), wherein X is chlorine, can be prepared by reacting the aniline of formula (2AAV) with 1,1-dichloroethylene, a suitable metal salt such as copper(II) chloride, a suitable metal or alkyl nitrite in a suitable solvent at a suitable temperature. Such a reaction is an example of a Meerwein arylation, and examples are known in the literature (see for example T. Himmler, US 20100234651 and J-P. A. M. Bongartz, J. T. M. Linders, L. Meerpoel, G. S. E. Van Lommen, E. Coesemans, M. Braeken, C. F. R. N. Buyck, M. J. M. Berwaer, K. A. G. J. M. De Waepenaert, P. W. M. Roevens, G. M. Boeckx, P. V. Davidenko, WO 2008148868).

A compound of formula (2A) can be prepared from a compound of formula (2AAU) under similar conditions to those described previously to convert a compound of formula (2J) to a compound of formula (2D).

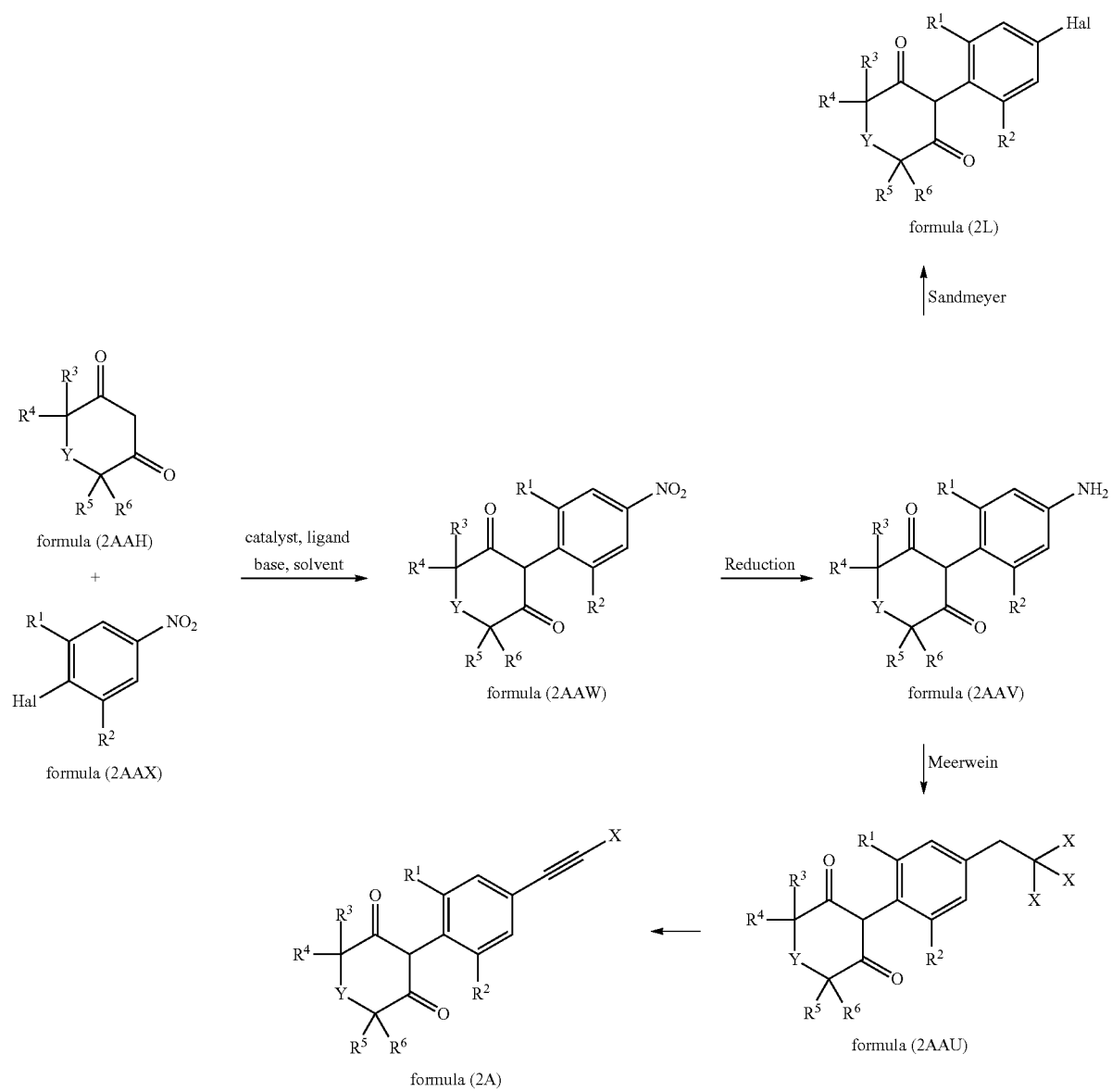

Herbicidal Compositions

In another aspect, the present invention provides a herbicidal composition, e.g. for use in a method of controlling weeds (e.g. monocotyledonous such as grassy weeds) in crops of useful plants, which composition comprises a compound of formula (I) as defined herein (e.g. a herbicidally effective amount thereof), and a substantially-inert agrochemically acceptable substance (e.g. an agrochemically acceptable carrier, diluent and/or solvent, an agrochemically acceptable adjuvant, an agrochemically acceptable emulsifier/surfactant/surface-active substance, and/or another agrochemically acceptable additive).

In a further aspect, the present invention provides a herbicidal composition, e.g. for use in a method of controlling weeds (e.g. monocotyledonous such as grassy weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt thereof.

The compounds of formula (I) according to the invention can be used as crop protection agents in unmodified form, as obtained by synthesis, but, for use as herbicides, they are generally formulated into herbicidal compositions (formulations), e.g. in a variety of ways, containing one or more substantially-inert agrochemically acceptable substances (e.g. an agrochemically acceptable carrier, diluent and/or solvent, an agrochemically acceptable adjuvant, an agrochemically acceptable emulsifier/surfactant/surface-active substance, and/or another agrochemically acceptable additive).

The formulations (herbicidal compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or micro-rods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc. Other suitable matrix materials for slow release formulations are starch, stearin, lignin.

The formulation ingredients (e.g. inert ingredients) suitable for the preparation of the compositions according to the invention are generally known per se.

As a liquid carrier and/or solvent (e.g. organic solvent), e.g. for use in the herbicidal composition(s) according to the invention, there may be used: water, an aromatic solvent such as toluene, m-xylene, o-xylene, p-xylene or a mixture thereof, cumene, an aromatic hydrocarbon blend with a boiling range between 140 and 320° C. (e.g. known under various trademarks such as Solvesso®, Shellsol A®, Caromax®, Hydrosol®), a paraffinic or isoparaffinic carrier such as paraffin oil, mineral oil, a de-aromatized hydrocarbon solvent with a boiling range between 50 and 320° C. (e.g. known for instance under the trademark Exxsol®), a non-dearomatized hydrocarbon solvent with a boiling range between 100 and 320° C. (e.g. known under the tradename Varsol®), an isoparaffinic solvent with a boiling range between 100 and 320° C. (e.g. known under tradenames like Isopar® or Shellsol T®), a hydrocarbon such as cyclohexane, tetrahydronaphthalene (tetralin), decahydronaphthalene, alpha-pinene, d-limonene, hexadecane, isooctane; an ester solvent such as ethyl acetate, n- or iso-butyl acetate, amyl acetate, i-bornyl acetate, 2-ethylhexyl acetate, a $C_6$-$C_{18}$ alkyl ester of acetic acid (e.g. known under the tradename Exxate®), lactic acid ethylester, lactic acid propylester, lactic acid butylester, benzyl benzoate, benzyl lactate, dipropyleneglycol dibenzoate, or a dialkyl ester of succinic, maleic or fumaric acid; a polar solvent such as N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, a $C_4$-$C_{18}$ fatty acid dimethylamide, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, or butylene carbonate; an alcoholic solvent or diluent such as methanol, ethanol, propanol, n- or iso-butanol, n- or iso-pentanol, 2-ethyl hexanol, n-octanol, tetrahydrofurfuryl alcohol, 2-methyl-2,4-pentanediol, 4-hydroxy-4-methyl-2-pentanone, cyclohexanol, benzyl alcohol, ethylene glycol, ethylene glycol butyl ether, ethylene glycol methyl ether, diethylene glycol, diethylene glycol butyl ether, diethylene glycol monoethyl ether, diethylene glycol monomethyl ether, propylene glycol, dipropylene glycol, dipropylene glycol monomethyl ether, or another similar glycol monoether solvent based on a ethylene glycol, propylene glycol or butylene glycol feedstock, triethylene glycol, polyethylene glycol (e.g. PEG 400), a polypropylenglycol with a molecular mass of 400-4000, or glycerol; glycerol acetate, glycerol diacetate, glycerol triacetate, 1,4-dioxane, diethylene glycol abietate, chlorobenzene, chlorotoluene; a fatty acid ester such as methyl octanoate, isopropyl myristate, methyl laurate, methyl oleate, a mixture of $C_8$-$C_{10}$ fatty acid methyl esters, rapeseed oil methyl ester, rapeseed oil ethyl ester, soybean oil methyl ester, soybean oil ethyl ester; a vegetable oil (e.g. rapeseed oil or soybean oil); a fatty acid such as oleic acid, linoleic acid, or linolenic acid; or an ester of phosphoric or phosphonic acid such as triethyl phosphate, a $C_3$-$C_{18}$-tris-alkyl phosphate, an alkylaryl phosphate, or bis-octyl-octyl phosphonate.

Water is generally the liquid carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations (herbicidal compositions), especially in those formulations (herbicidal compositions) which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkyl-naphthalenesulfonates, such as sodium dibutylnaphthalene-sulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further formulation ingredients (e.g. inert ingredients) which can typically be used in formulations (herbicidal compositions) include crystallisation inhibitors, viscosity-modifying substances, suspending agents, dyes, anti-oxidants, foaming agents, light absorbers, mixing aids, antifoams, complexing agents, neutralising or pH-modifying substances and/or buffers, corrosion-inhibitors, fragrances, wetting agents, absorption improvers, micronutrients, plasticisers, glidants, lubricants, dispersants, thickeners, antifreezes, microbiocides, compatibility agents and/or solubilisers; and/or also liquid and solid fertilisers.

The compositions (formulations) may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives/oil esters. The amount of oil additive (oil adjuvant) used in the composition according to the invention is generally from 0.01 to 10%, based on the spray mixture. For example, the oil additive (oil adjuvant) can be added to the spray tank in the desired concentration after the spray mixture has been prepared. Preferred oil additives (oil adjuvants) comprise mineral oils or an oil of vegetable origin, for example rapeseed oil, olive oil or sunflower oil, emulsifiable vegetable oil, such as AMIGO® (Loveland Products Inc.), $C_1$-$C_6$alkyl esters of oils of vegetable origin, for example the methyl esters, or an oil of animal origin, such as fish oil or beef tallow. A preferred oil additive (oil adjuvant) contains methylated rapeseed oil (rapeseed oil methyl ester). Another preferred oil additive (oil adjuvant) contains, for example, as active components essentially 80% by weight alkyl esters of fish oils and 15% by weight methylated rapeseed oil (rapeseed oil methyl ester), and also 5% by weight of customary emulsifiers and pH modifiers. Especially preferred oil additives (oil adjuvants) comprise $C_1$-$C_6$alkyl ester(s) of $C_8$-$C_{22}$ fatty acid(s), especially the methyl ester(s) of $C_8$-$C_{22}$ (especially $C_{12}$-$C_{18}$) fatty acid(s); preferably the methyl ester of lauric acid, of palmitic acid, or of oleic acid. Those esters are known as methyl laurate (CAS-111-82-0), methyl palmitate (CAS-112-39-0) and methyl oleate (CAS-112-62-9) respectively. A preferred fatty acid methyl ester derivative is AGNIQUE ME 18 RD-F® (e.g. available from Cognis). Those and other oil derivatives are also known from the Compendium of Herbicide Adjuvants, 5th Edition, Southern Illinois University, 2000.

The application and action of the above-mentioned oil additives (oil adjuvants) can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. As non-ionic sufactants, special preference is given to ethoxylated $C_{12}$-$C_{22}$ fatty alcohols preferably having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total oil additive (oil adjuvant) is generally from 1 to 50% by weight of the oil additive (oil adjuvant). Examples of oil additives (oil adjuvants) that consist of mixtures of oils and/or mineral oils and/or derivatives thereof with surfactants are TURBO-CHARGE®, ADIGOR® (both (Syngenta Crop Protection AG), ACTIPRON® (BP Oil UK Limited), AGRI-DEX® (Helena Chemical Company).

The above-mentioned surface-active substances may also be used in the formulations alone, that is to say without oil additives (oil adjuvants).

Furthermore, the addition of an organic solvent to the oil additive (oil adjuvant)/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further such oil additives (oil adjuvants) that are preferred according to the invention are SCORE® and ADIGOR® (both Syngenta Crop Protection AG).

In addition to the oil additives (oil adjuvants) listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

A particularly preferred oil adjuvant (oil additive), e.g. for use in the herbicidal compositionas of the invention, is an emulsifiable concentrate which consists of:

(i) ethoxylated alcohols, which preferably includes ethoxylated $C_{12}$-$C_{22}$ fatty alcohols (preferably having a degree of ethoxylation of from 5 to 40); and
(ii) a mixture of heavy aromatic hydrocarbons, which preferably includes (or more preferably includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and
(iii) methylated rapeseed oil (rapeseed oil methyl ester) (e.g. Agnique ME 18 RD-F™), as an adjuvant; preferably present at about 47% w/w and/or about 45% w/v of the oil adjuvant/oil additive/emulsifiable concentrate. One example of such a emulsifiable concentrate oil adjuvant (oil additive) is ADIGOR™, currently available in many countries from Syngenta.

When the above emulsifiable concentrate oil adjuvant is used, it is preferably added to the herbicidal composition after dilution (e.g. with water and/or in a spray tank), typically before application to weeds and/or to crops of useful plants and/or to the locus thereof. In one particular embodiment, the herbicidal composition, e.g. after dilution (e.g. with water and/or in a spray tank), contains the above emulsifiable concentrate oil adjuvant, and additionally ammonium sulphate and/or isopropyl alcohol.

Such adjuvant oils as described in the preceding paragraphs may be employed as a or the carrier liquid in which an active compound is dissolved, emulsified or dispersed as appropriate to the physical form of the active compound.

In an alternative particular embodiment, the herbicidal composition of the invention comprises an agrochemically acceptable adjuvant comprising 1,2-cyclohexane dicarboxylic acid di-isononyl ester (e.g. CAS Registry no. 166412-78-8), e.g. as available from BASF as Hexamoll™ DINCH™. "Isononyl" in this context is thought to mean one or more, preferably a mixture of two or more, branched isomers of $C_9H_{19}$. In one particular embodiment, the herbicidal composition, e.g. after dilution (e.g. with water and/or in a spray tank), contains 1,2-cyclohexane dicarboxylic acid di-isononyl ester, and additionally ammonium sulphate and/or isopropyl alcohol.

In an alternative particular embodiment, the herbicidal composition of the invention comprises an agrochemically acceptable adjuvant comprising an organic phosphate and/or organic phosphonate adjuvant. Preferably, the phosphate adjuvant is a tris-[$C_4$-$C_{12}$alkyl or 2-($C_2$-$C_6$alkoxy)ethyl-] ester of phosphoric acid, or more preferably is tris-(2-ethylhexyl) phosphate, tris-n-octyl phosphate and/or tris-[2-(n-butoxy)ethyl]phosphate, or most preferably is tris-(2-ethylhexyl) phosphate. Preferably, the phosphonate adjuvant is a bis-($C_3$-$C_{12}$alkyl) ester of a $C_3$-$C_{12}$alkyl-phosphonic acid, or more preferably is bis-(2-ethylhexyl) (2-ethylhexyl) phosphonate, bis-(2-ethylhexyl) (n-octyl)phosphonate and/or di-n-butyl (n-butyl)phosphonate.

The formulations (herbicidal compositions) generally contain from 0.1 to 99% by weight, especially from 0.1 to 95% by weight, of a compound of formula I and from 1 to 99.9% by weight of a substantially-inert agrochemically acceptable substance, which preferably includes a formulation adjuvant and/or from 0 to 30% or from 0 to 25% (e.g. from 0.5 to 30% or from 0.5 to 25%) by weight of a surface-active substance. Whereas herbicidal compositions (especially commercial products) will preferably be formulated as concentrates, the end user will normally employ dilute formulations (compositions), e.g. formulations (compositions) diluted with water, in particular when applying the herbicidal composition to weeds and/or to crops of useful plants and/or to the locus thereof.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied (preferably post-emergence) at a rate of from 1 to 2000 g/ha, preferably from 1 to 1000 g/ha and most preferably at from 1 to 500 g/ha or from 5 to 500 g/ha.

Preferred formulations/compositions have especially the following representative compositions:
(%=percent by weight of the composition):
Emulsifiable Concentrates:
active ingredient: 0.3 to 95%, preferably 0.5 to 60% such as 1 to 40%
surface-active agents: 1 to 30%, preferably 3 to 20% such as 5 to 15%
solvents as liquid carrier: 1 to 80%, preferably 1 to 60% such as 1 to 40%
Dusts:
active ingredient: 0.1 to 10%, preferably 0.1 to 5%
solid carriers: 99.9 to 90%, preferably 99.9 to 99%
Suspension Concentrates:
active ingredient: 1 to 75%, preferably 3 to 50% or 10 to 50%
water: 98 to 24%, preferably 95 to 30% or 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%
The following Examples further illustrate, but do not limit, the invention.

| F1. Emulsifiable concentrates | | | | |
|---|---|---|---|---|
| | a) | b) | c) | d) |
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP (N-methyl-2-pyrrolidone) | — | 10% | — | 20% |
| aromatic hydrocarbon mixture $C_9$-$C_{12}$ | 85% | 68% | 65% | 16% |

Emulsions of any desired concentration can be prepared from such concentrates by dilution with water.

F2. Solutions

|  | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP (N-methyl-2-pyrrolidone) | — | — | 50% | 10% |
| aromatic hydrocarbon mixture $C_9$-$C_{12}$ | 35% | 30% | — | — | mixture $C_9$-$O_{12}$

The solutions are suitable for application undiluted or after dilution with water.

F3. Wettable powders

|  | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

F4. Coated granules

|  | a) | b) | c) |
|---|---|---|---|
| active ingredient | 0.1% | 5% | 15% |
| highly dispersed silica | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

F5. Coated granules

|  | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorganic carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

F6. Extruded granules

|  | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

F7. Water-dispersible granules

|  | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | — | 4% | 5% | — |
| kaolin | 48% | 30% | 30% | — |

The active ingredient is mixed and ground with the adjuvants and the mixture is moistened with water. The resulting mixture is extruded and then dried in a stream of air.

F8. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F9. Suspension concentrates

|  | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-benzisothiazolin-3-one | 0.1% | 0.1% | 0.1% | 0.1% |
| silicone oil emulsion | 0.7% | 0.7% | 0.7% | 0.7% |
| water | 88% | 80% | 60% | 38% |

The finely ground active ingredient is intimately mixed with the adjuvants, yielding a suspension concentrate from which suspensions of any desired concentration can be prepared by dilution with water.

Herbicidal Uses—Crops of Useful Plants, Weeds, Application Rates, et al.

In a further aspect, the present invention provides a method of controlling weeds (preferably monocotyledonous weeds such as more preferably grassy monocotyledonous weeds) in crops of useful plants, which comprises applying a compound of the formula (I), or a herbicidal composition comprising such a compound, to the weeds and/or to the plants and/or to the locus thereof. (Preferably, in this further aspect, the herbicidal composition can be as described hereinabove or hereinbelow, e.g. as described in the "Herbicidal compositions", "Herbicidal uses", "Combinations and mixtures" and/or Claims sections hereinabove or hereinbelow.)

In a further aspect, the present invention provides a herbicidal composition, in particular for use in a method of controlling weeds (preferably monocotyledonous weeds such as more preferably grassy monocotyledonous weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt (e.g. agrochemically acceptable metal, sulfonium or ammonium salt) thereof.

In one embodiment, the herbicidal composition also comprises one or more further herbicides, e.g. as mixture partner(s) for the compound of formula (I), and/or a safener. See the combinations and mixtures section herein for more details of examples of these.

In all aspects of the invention (e.g. the methods of use of the invention), crops of useful plants, e.g. on or in which or at the locus of which the compounds or compositions according to the invention can be used, comprise (e.g. are), in particular: cereals (e.g. non-oat cereals, in particular non-oat non-sorghum non-millet cereals, more particularly wheat, barley, rye and/or triticale), rice, corn (maize), sugarcane, leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, linseed, sugarbeet, fodder beet, potato, vegetables (preferably dicotyledonous vegetables), flax, tobacco, plantation crops (such as conifer trees, olives and/or olive trees, oil palms, coffee, or vines), and/or fruit crops (in particular dicotyledonous and/or broadleaved fruit, and/or in particular pome fruit, stone fruit, bush fruit, citrus fruit, pineapple, banana, and/or strawberry); and/or turf and/or pastureland grass.

Preferably, in all aspects of the invention, the crops of useful plants, e.g. on or in which or at the locus of which the compounds or compositions according to the invention can be used, comprise (e.g. are) cereals (in particular non-oat cereals, more particularly non-oat non-sorghum non-millet cereals, even more particularly wheat, barley, rye and/or triticale), rice, sugarcane, leguminous crops [preferably soybean, peanut, and/or pulse crops (more preferably soybean)], cotton, rape (in particular oilseed rape or canola), sunflower, linseed, sugarbeet, fodder beet, potato, and/or vegetables (preferably dicotyledonous vegetables).

More preferably, in all aspects of the invention, the crops of useful plants, e.g. on or in which or at the locus of which the compounds or compositions according to the invention can be used, comprise (e.g. are): wheat (e.g. winter wheat, spring wheat, or durum wheat), barley (e.g. winter or spring barley), rye, triticale, sugarcane, leguminous crops [preferably soybean, peanut, and/or pulse crops (more preferably soybean)], cotton, rape (in particular oilseed rape or canola), sunflower, linseed, sugarbeet, fodder beet, potato, and/or vegetables (preferably dicotyledonous vegetables).

Even more preferably, in all aspects of the invention, the crops of useful plants, e.g. on or in which or at the locus of which the compounds or compositions according to the invention can be used, comprise (e.g. are): leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, sugarbeet, fodder beet, potato, and/or vegetables (preferably dicotyledonous vegetables).

Certain compounds of formula (I) according to the present invention are particularly efficacious vs grassy monocotyledonous weeds and appear to be selective for grassy (e.g. warm-climate grassy) monocotyledonous weed control in crops of soybean or sugarbeet (e.g. see Biological Examples 2 and 3 herein).

The term "crops" is to be understood as also including crops that have been rendered tolerant to herbicides or classes of herbicides (for example ALS, GS, EPSPS, PPO and HPPD inhibitors, and/or 2,4-D or dicamba) as a result of conventional methods of breeding or genetic engineering. Examples of crops that have been rendered tolerant e.g. to imid-azolinones (which are ALS inhibitors), such as imazamox, by conventional methods of breeding include Clearfield® summer rape (canola) and/or Clearfield® wheat and/or Clearfield® rice (all from BASF). Examples of crops that have been rendered tolerant to herbicides by genetic engineering methods include e.g. glyphosate-resistant or glufosinate-resistant maize or soybean varieties, in particular those commercially available under the trade name RoundupReady® or RoundupReady® 2 (both from Monsanto, both glyphosate-resistant) or LibertyLink® (from Bayer, glufosinate-resistant). Glufosinate-resistant rice (LibertyLink®) also has been published.

Other crops of useful plants include 2,4-D-tolerant soybean, e.g. soybean genetically-modified to be tolerant to the herbicide 2,4-D, or dicamba-tolerant soybean, e.g. soybean genetically-modified to be tolerant to the herbicide dicamba. Such 2,4-D-tolerant or dicamba-tolerant soybean crops can also, in particular, be tolerant to glyphosate or glufosinate. For example, crops of useful plants include soybeans containing a dicamba-tolerance trait combined (stacked) with a glyphosate-tolerance trait, such that these soybeans have tolerance to the herbicides glyphosate and dicamba (for example Genuity® Roundup Ready® 2 Xtend soybeans, currently under development by Monsanto).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

In all aspects of the invention, the weeds, e.g. to be controlled and/or growth-inhibited, may be either monocotyledonous (e.g. grassy) and/or dicotyledonous weeds. Preferably the weeds, e.g. to be controlled and/or growth-inhibited, comprise or are monocotyledonous weeds, more preferably grassy monocotyledonous weeds.

In all aspects of the invention, typically, the monocotyledonous (preferably grassy) weeds, e.g. to be controlled and/or growth-inhibited, comprise (e.g. are) weeds from the genus *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass"); and/or in particular: *Brachiaria platyphylla* (BRAPP), *Panicum dichotomiflorum* (PANDI), and/or *Sorghum vulgare*. Alternatively or additionally, the monocotyledonous (preferably grassy) weeds, e.g. to be controlled and/or growth-inhibited, comprise volunteer corn (volunteer maize) weeds.

In one preferred embodiment of all aspects of the invention, the monocotyledonous weeds, e.g. to be controlled and/or growth-inhibited, are grassy monocotyledonous weeds; in which case they typically comprise (e.g. are): weeds from the genus *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*; in particular: weeds from the genus *Agrostis, Alopecurus, Apera, Avena, Brachiaria, Bromus, Digitaria, Echinochloa, Eriochloa, Leptochloa, Lolium, Panicum, Phalaris, Poa, Rottboellia, Setaria* and/or *Sorghum*. Alternatively or additionally, the monocotyledonous (preferably grassy) weeds, e.g. to be controlled and/or growth-inhibited, comprise volunteer corn (volunteer maize) weeds.

In one particularly preferred embodiment of all aspects of the invention, the grassy monocotyledonous weeds, e.g. to be controlled and/or growth-inhibited, are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*; more particularly: weeds from the genus *Brachiaria, Digitaria, Echinochloa, Eriochloa, Leptochloa, Panicum, Setaria* and/or *Sorghum*. Alternatively or additionally, the grassy monocotyledonous weeds, e.g. to be controlled and/or growth-inhibited, comprise volunteer corn (volunteer maize) weeds. More preferably, the grassy monocotyledonous weeds, e.g. to be controlled and/or growth-inhibited, are "warm-season" (warm climate) grassy weeds comprising (e.g. being) weeds from the genus *Brachiaria, Cenchrus, Digitaria, Echinochloa, Eleusine, Eriochloa, Panicum, Setaria* and/or *Sorghum*; and/or the grassy monocotyledonous weeds, e.g. to be controlled and/or growth-inhibited, comprise volunteer corn (volunteer maize) weeds.

In a particular embodiment of all aspects of the invention, the grassy monocotyledonous weeds, e.g. to be controlled and/or growth-inhibited, are "cool-season" (cool climate) grassy weeds; in which case they typically comprise (e.g. are) weeds from the genus *Agrostis, Alopecurus, Apera, Avena, Bromus, Lolium* and/or *Poa*.

In non-oat cereal crops such as wheat and/or barley, control and/or growth inhibition of weeds from the genus *Alopecurus, Apera, Avena*, especially *Avena fatua, Bromus, Lolium, Phalaris*, and/or *Setaria* is preferred; in particular *Alopecurus, Avena* (especially *Avena fatua*), *Lolium* and/or *Setaria* (especially *Setaria viridis, Setaria lutescens, Setaria faberi* and/or *Setaria glauca*).

In all aspects of the invention, in a particular embodiment, the weeds, e.g. to be controlled and/or growth-inhibited e.g. by applying a compound of formula (I), may be grassy monocotyledonous weeds (in particular: *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum* weeds; more particularly *Alopecurus, Apera, Avena, Brachiaria, Bromus, Digitaria, Echinochloa, Eriochloa, Lolium, Panicum, Phalaris, Poa, Setaria* and/or *Sorghum* weeds), which are resistant to one or more ACCase inhibitor herbicides (ACCase=acetyl-coenzyme A carboxylase) selected from the group consisting of pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim and butroxydim;

and/or which are resistant to glyphosate;

and/or which are resistant to one or more ALS inhibitor herbicides (ALS=acetolactate synthase), such as one or more sulfonyl urea herbicides (e.g. iodosulfuron-methyl, mesosulfuron-methyl, tribenuron-methyl, triasulfuron, prosulfuron, sulfosulfuron, pyrazosulfuron-ethyl, bensulfuron-methyl, nicosulfuron, flazasulfuron, iofensulfuron, metsulfuron-methyl, or any other sulfonyl urea herbicide disclosed in The Pesticide Manual, 15th edition (2009) or 16th Edition (2012), ed. C. D. S. Tomlin, British Crop Protection Council) and/or one or more triazolopyrimidine herbicides (e.g. florasulam, pyroxsulam or penoxsulam) and/or one or more pyrimidinyl-(thio or oxy)-benzoate herbicides (e.g. bispyribac-sodium or pyriftalid) and/or one or more sulfonylaminocarbonyl-triazolinone herbicides (e.g. thiencarbazone-methyl, propoxycarbazone-sodium or flucarbazone-sodium) and/or one or more imidazolinone herbicides (e.g. imazamox).

Such resistant (in particular ACCase-inhibitor-resistant, glyphosate-resistant, and/or ALS-inhibitor-resistant) grassy weeds can particularly comprise *Alopecurus myosuroides, Apera spica-venti, Avena fatua, Avena sterilis, Brachiaria decumbens, Brachiaria plantaginea, Digitaria horizontalis, Digitaria insularis, Digitaria sanguinalis, Echinochloa colona, Echinochloa crus-galli, Eleusine indica, Lolium multiflorum, Lolium rigidum, Lolium perenne, Phalaris minor, Phalaris paradoxa, Setaria viridis, Setaria faberi, Setaria glauca*, and/or *Sorghum halepense*; or can more particularly comprise *Alopecurus myosuroides, Apera spica-venti, Avena fatua, Avena sterilis, Digitaria sanguinalis, Echinochloa colona, Echinochloa crus-galli, Lolium multiflorum, Lolium rigidum, Lolium perenne, Phalaris minor, Phalaris paradoxa, Setaria viridis, Setaria faberi* and/or *Sorghum halepense*.

In an even more particular embodiment of the invention, the compound of formula (I) can be applied to grassy monocotyledonous weeds (e.g. selected from one of the above-mentioned list(s) of grassy weeds):

(a1) which are resistant to one or more ACCase inhibitor herbicides (e.g. selected from the above-mentioned list of ACCase inhibitor herbicides) at least partly by means of mutation (e.g. substitution) of one or more amino acids on the ACCase target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 325-327 therein in particular Table 3, incorporated herein by reference, for examples of such resistant weeds and/or amino acid substitutions); and/or (a2) which are resistant to glyphosate at least partly by means of mutation (e.g. substitution) of one or more amino acids on the EPSPS target site in the weed targeted by glyphosate (e.g. see above-mentioned S. B. Powles and Qin Yu article, pp. 327-329); and/or (a3) which are resistant to one or more ALS inhibitor herbicides (e.g. selected from the above-mentioned list of ALS inhibitor herbicides) at least partly by mutation (e.g. substitution) of one or more amino acids on the ALS target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 322-324 therein in particular Table 2, incorporated herein by reference, for examples of such resistant weeds and/or amino acid substitutions); and/or (b) which are resistant to: one or more ACCase inhibitor herbicides (e.g. selected from the above-mentioned list), and/or glyphosate, and/or one or more ALS inhibitor herbicides (e.g. selected from the above-mentioned list); at least partly by metabolic-type herbicidal resistance e.g. at least partly by cytochrome P450-mediated herbicide metabolism (e.g. see S. B. Powles and Qin Yu, "Evolution in Action: Plants Resistant to Herbicides", *Annu. Rev. Plant Biol.*, 2010, 61, pp. 317-347, e.g. see Table 4 on page 328 therein, incorporated herein by reference, for examples of such resistant weeds).

Typically, dicotyledonous weeds, e.g. to be controlled, comprise (e.g. are) *Abutilon, Amaranthus, Chenopodium, Chrysanthemum, Galium, Ipomoea, Kochia, Nasturtium, Polygonum, Sida, Sinapsis, Solanum, Stellaria, Viola, Veronica* and/or *Xanthium*.

Areas under cultivation, and/or the locus (e.g. of weeds and/or of crops of useful plants), are to be understood as including land where the crop plants are already growing as well as land intended for the cultivation of those crop plants.

In all aspects of the invention, the rate of application (typically to the weeds and/or to the crops of useful plants and/or to the locus thereof) of the compound of formula (I) (which optionally may be an agrochemically acceptable salt thereof) is generally from 1 to 2000 g of the compound of formula (I) per hectare (ha) (measured as the salt-free compound, i.e. excluding the weight of any associated salt counterion(s)), in particular from 5 to 1000 g/ha or from 5 to 500 g/ha or from 10 to 500 g/ha, preferably from 10 to 400 g/ha or from 20 to 300 g/ha, of the compound of formula (I) (measured as the salt-free compound, i.e. excluding the weight of any associated salt counterion(s)). In a preferred embodiment, the above rates of application are for post-emergence application of the compound of formula (I) (which optionally may be an agrochemically acceptable salt thereof).

In all aspects of the invention, the compound of formula (I) can be applied (typically to the weeds and/or to the crops of useful plants and/or to the locus thereof) pre- and/or post-emergence, but preferably is applied post-emergence. Other Possible Uses—e.g. Possible Insecticidal and/or Acaricidal Uses The main use and purpose of the compounds of formula (I) according to the invention is their herbicidal use. However, at least some of the compounds of formula (I) may have activity against one or more types of pest (in particular pests associated with agriculture and/or food storage). For example, at least some of the compounds of formula (I) may have at least some insecticidal, acaricidal, molluscicidal and/or nematicidal activity.

At least some of the compounds of formula (I) may have activity against (and/or may help to control and/or combat) insect pests, such as one or more of: Coleoptera, Dictyoptera, Diptera, Hemiptera (including Homoptera), Hymenoptera, Isoptera, Lepidoptera, Orthoptera, Siphonaptera and/or Thysanoptera.

At least some of the compounds of formula (I) may have activity against (and/or may help to control and/or combat) acarine pests and/or pests from the order Acarina, such as one or more of: *Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and/or *Tetranychus* spp.

At least some of the compounds of formula (I) may have activity against (and/or may help to control and/or combat) other (i.e. non-insect, non-acarine) invertebrate pests, for example, nematode and/or mollusc pests.

Insects, acarines, nematodes and/or molluscs are hereinafter collectively referred to as pests.

Examples of pest species, on and/or to which the compounds of formula (I) can be tried and/or applied, include one or more of: *Myzus* spp. such as *Myzus persicae* (aphid), *Aphis* spp. such as *Aphis gossypii* (aphid) or *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus* spp. such as *Tetranychus urticae* (two-spotted spider mite) or *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), of the Kalotermitidae (for example *Neotermes* spp.), of the Rhinotermitidae (for example *Coptotermes formosanus, Reticulitermes flavipes, R. speratu, R. virginicus, R. hesperus*, or *R. santonensis*) or of the Termitidae (for example *Globitermes sulphureus*), *Solenopsis geminata* (fire ant), *Monomorium pharaonis* (pharaoh's ant), *Damalinia* spp. or *Linognathus* spp. (biting lice or sucking lice), *Meloidogyne* spp. (root knot nematodes), *Globodera* spp. or *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and/or *Deroceras reticulatum* (slug).

Combinations and Mixtures

In a further aspect, the present invention provides a herbicidal composition, e.g. for use in a method of controlling weeds (e.g. monocotyledonous such as grassy monocotyledonous weeds) in crops of useful plants, comprising a compound of formula (I) as defined herein (e.g. a herbicidally effective amount thereof), and an agrochemically acceptable carrier, diluent and/or solvent, and also comprising one or more further herbicides, and/or a safener.

In all aspects of the invention, the compound of the formula (I) is optionally present (e.g. where chemically possible) as an agrochemically acceptable salt thereof.

Examples of these mixtures/compositions, comprising one or more further herbicides and/or a safener, follow.

The compounds of formula (I) according to the invention can be used in combination with one or more further herbicides, e.g. as mixture partner(s) for the compound of formula (I). Preferably, in these mixtures (in particular in the specific mixtures disclosed hereinbelow), the compound of the formula (I) is one of those compounds listed in Tables 1 to 46, and/or one of the exemplified compounds (in particular one of compounds A1 to A7, A8, or P1 to P5), as disclosed herein e.g. hereinbelow, optionally present (e.g. where chemically possible) as an agrochemically acceptable salt thereof.

In particular, the following mixtures of the compound of formula (I) with one or more further herbicides are particularly disclosed:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chloransulam, compound of formula I+chloransulam-methyl, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+2,4-D+glyphosate, compound of formula I+2,4-D-dimethylammonium+glyphosate, compound of formula I+2,4-D-2-ethylhexyl+glyphosate, compound of formula I+a choline salt of 2,4-D+glyphosate (see e.g. Examples 2 and 3 of WO2010/123871A1), compound of formula I+3, 4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl]methylamine salt of dicamba (see e.g. US2012/0184434A1), compound of formula I+dicamba+glyphosate, compound of formula I+dicamba-dimethylammonium+glyphosate, compound of formula I+dicamba-potassium+glyphosate, compound of formula I+dicamba-sodium+glyphosate, compound of formula I+dicamba-diglycolamine+glyphosate, compound of formula I+a N,N-bis-[aminopropyl]methylamine salt of dicamba+glyphosate (see e.g. US2012/0184434A1), compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula (I)+fenoxaprop, compound of formula (I)+fenoxaprop-ethyl, compound of formula I+fenoxaprop-P, compound of formula I+fenoxaprop-P-ethyl, compound of formula I+fenoxasulfone (CAS Reg. No. 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glufosinate-P, compound of formula I+glyphosate, compound of formula I+glyphosate-diammonium, compound of formula I+glyphosate-isopropylammonium, compound of formula I+glyphosate-potassium, compound of formula I+halosulfuron, compound of formula I+halosulfuron-methyl, compound of formula I+haloxyfop, compound of formula I+haloxyfop-P, compound of formula (I)+haloxyfop-methyl, compound of formula (I)+haloxyfop-P-methyl, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS Reg. No. 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS Reg. No. 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS Reg. No. 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS Reg. No. 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS Reg. No. 335104-84-2), compound of formula I+topramezone (CAS Reg. No. 210631-68-8), compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula I+4-hydroxy-3-[[2-(3-methoxypropyl)-6-(difluoromethyl)-3-pyridinyl]carbonyl]-bicyclo[3.2.1]oct-3-en-2-one, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, and compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+aminocyclopyrachlor (which is 6-amino-5-chloro-2-cyclopropylpyrimidine-4-carboxylic acid, CAS Reg. No. 858956-08-8), compound of formula I+aminocyclopyrachlor-methyl (which is methyl 6-amino-5-chloro-2-cyclopropylpyrimidine-4-carboxylate, CAS Reg. No. 858954-83-3), compound of formula I+aminocyclopyrachlor-potassium (which is potassium 6-amino-5-chloro-2-cyclopropylpyrimidine-4-carboxylate, CAS Reg. No. 858956-35-1), compound of formula I+saflufenacil (which is N'-{2-chloro-4-fluoro-5-[1,2,3,6-tetrahydro-3-methyl-2,6-dioxo-4-(trifluoromethyl)pyrimidin-1-yl]benzoyl}-N-isopropyl-N-methylsulfamide, CAS Reg. No. 372137-35-4), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), compound of formula I+clacyfos (which is dimethyl [(1RS)-1-(2,4-dichlorophenoxyacetoxy)ethyl]phosphonate, also named lvxiancaolin or lüxiancaolin, CAS Reg. No. 215655-76-8), compound of formula I+cyclopyrimorate (which is 6-chloro-3-(2-cyclopropyl-6-methylphenoxy)pyridazin-4-yl morpholine-4-carboxylate, CAS Reg. No. 499231-24-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6).

The mixture partners for the compound of formula (I) are optionally in the form of an ester (in particular an agrochemically acceptable ester) or a salt (in particular an agrochemically acceptable salt) thereof (e.g. where chemically possible). The above-mentioned mixture partners for the compound of formula (I), are generally mentioned e.g. in The Pesticide Manual, 15th Edition (2009) or 16th Edition (2012), ed. C. D. S. Tomlin, British Crop Production Council.

In the present patent specification, "CAS Reg. No." or "CAS RN" means the Chemical Abstracts Service Registry Number of the stated compound.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl] methylamine salt of dicamba (see e.g. US2012/0184434A1), compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula (I)+fenoxaprop, compound of formula (I)+fenoxaprop-ethyl, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/

059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in cereals, more preferred is a mixture comprising: a compound of formula (I)+amidosulfuron, compound of formula (I)+aminopyralid, compound of formula (I)+beflubutamid, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluroxypyr, compound of formula I+fluroxypyr-meptyl, compound of formula I+fluroxypyr-butometyl, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula I+topramezone, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl, compound of formula (I)+tritosulfuron, compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+diquat, compound of formula (I)+diquat dibromide, compound of formula (I)+esprocarb, compound of formula (I)+ethoxysulfuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula (I)+metamifop, compound of formula I+metazosulfuron (NC-620, CAS Reg. No. 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H, 6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2', 4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl) pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl) pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3, 5-triazin-2-yl)carbonyl]-6-fluorophenyl]-N-methyl-1,1-difluoromethanesulfonamide, CAS Reg. No. 874195-61-6); wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, more preferred is a mixture comprising: a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula I+metazosulfuron (NC-620, CAS Reg. No. 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5 (4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in soybean, the following mixtures are preferred:

compound of formula (I)+acifluorfen, compound of formula (I)+acifluorfen-sodium, compound of formula (I)+ametryn, compound of formula (I)+atrazine, compound of formula (I)+bentazone, compound of formula (I)+bicyclopyrone, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chloransulam, compound of formula (I)+chloransulam-methyl, compound of formula (I)+chlorimuron, compound of formula (I)+chlorimuron-ethyl, compound of formula (I)+clethodim, compound of formula (I)+clomazone, compound of formula (I)+cyanazine, compound of formula (I)+2,4-D (especially for applications to 2,4-D-tolerant soybean, e.g. genetically-modified), compound of formula (I)+2,4-D-dimethylammonium (especially for applications to 2,4-D-tolerant soybean, e.g. genetically-modified), compound of formula (I)+2,4-D-2-ethylhexyl (especially for applications to 2,4-D-tolerant soybean, e.g. genetically-modified), compound of formula (I)+a choline salt of 2,4-D (see e.g. Examples 2 and 3 of WO2010/123871A1) (especially for applications to 2,4-D-tolerant soybean, e.g. genetically-modified), compound of formula (I)+2,4-D+glyphosate (especially for applications to 2,4-D-tolerant and/or glyphosate-tolerant soybean, e.g. genetically-modified), compound of formula (I)+2,4-D-dimethylammonium+glyphosate (especially for applications to 2,4-D-tolerant and/or glyphosate-tolerant soybean, e.g. genetically-modified), compound of formula (I)+2,4-D-2-ethylhexyl+glyphosate (especially for applications to 2,4-D-tolerant and/or glyphosate-tolerant soybean, e.g. genetically-modified), compound of formula I+a choline salt of 2,4-D+glyphosate (see e.g. Examples 2 and 3 of WO2010/123871A1) (especially for applications to dicamba-tolerant and/or glyphosate-tolerant soybean, e.g. genetically-modified), compound of formula (I)+dicamba (especially for applications to dicamba-tolerant soybean, e.g. genetically-modified), compound of formula (I)+dicamba-dimethylammonium (especially for applications to dicamba-tolerant soybean, e.g. genetically-modified), compound of formula (I)+dicamba-potassium (especially for applications to dicamba-tolerant soybean, e.g. genetically-modified), compound of formula (I)+dicamba-sodium (especially for applications to dicamba-tolerant soybean, e.g. genetically-modified), compound of formula (I)+dicamba-diglycolamine (especially for applications to dicamba-tolerant soybean, e.g. genetically-modified), compound of formula (I)+a N,N-bis-[aminopropyl]methylamine salt of dicamba (see e.g. US2012/0184434A1) (especially for applications to dicamba-tolerant soybean, e.g. genetically-modified), compound of formula (I)+dicamba+glyphosate (especially for applications to dicamba-tolerant and/or glyphosate-tolerant soybean, e.g. genetically-modified), compound of formula (I)+dicamba-dimethylammonium+glyphosate (especially for applications to dicamba-tolerant and/or glyphosate-tolerant soybean, e.g. genetically-modified), compound of formula (I)+dicamba-potassium+glyphosate (especially for applications to dicamba-tolerant and/or glyphosate-tolerant soybean, e.g. genetically-modified), compound of formula (I)+dicamba-sodium+glyphosate (especially for applications to dicamba-tolerant and/or glyphosate-tolerant soybean, e.g. genetically-modified), compound of formula (I)+dicamba-diglycolamine+glyphosate (especially for applications to dicamba-tolerant and/or glyphosate-tolerant soybean, e.g. genetically-modified), compound of formula (I)+a N,N-bis-[aminopropyl]methylamine salt of dicamba+glyphosate (especially for applications to dicamba-tolerant and/or glyphosate-tolerant soybean, e.g. genetically-modified), compound of formula (I)+diclosulam, compound of formula (I)+dimethenamid, compound of formula (I)+dimethenamid-P, compound of formula (I)+diquat, compound of formula (I)+diquat dibromide, compound of formula (I)+diuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula (I)+fluazifop, compound of formula (I)+fluazifop-butyl, compound of formula (I)+fluazifop-P, compound of formula (I)+fluazifop-P-butyl, compound of formula (I)+flufenacet, compound of formula (I)+flumetsulam, compound of formula (I)+flumioxazin, compound of formula (I)+fluthiacet, compound of formula (I)+fluthiacet-methyl, compound of formula (I)+fomesafen, compound of formula (I)+glufosinate, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+imazethapyr, compound of formula (I)+lactofen, compound of formula (I)+mesotrione, compound of formula (I)+metolachlor, compound of formula (I)+S-metolachlor, compound of formula (I)+metribuzin, compound of formula (I)+oxyfluorfen, compound of formula (I)+paraquat, compound of formula (I)+paraquat dichloride, compound of formula (I)+pendimethalin, compound of formula (I)+pyroxasulfone, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula (I)+saflufenacil, compound of formula (I)+sethoxydim, compound of formula (I)+sulfentrazone, compound of formula (I)+thifensulfuron, compound of formula (I)+thifensulfuron-methyl, compound of formula (I)+tribenuron, compound of formula (I)+tribenuron-methyl, compound of formula (I)+trifluralin, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H, 6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), or compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference);

wherein the mixture partners for the compound of formula (I) may optionally be in the form of an ester (in particular an agrochemically acceptable ester) or a salt (in particular an agrochemically acceptable salt) thereof (e.g. where chemically possible).

In the above-mentioned compositions or mixtures comprising a compound of formula (I) (in particular a compound from Tables 1 to 46, and/or one of Compounds A1 to A7, A8, or P1 to P5 herein, optionally present (e.g. where chemically possible) as an agrochemically acceptable salt thereof) and one or more further herbicides, the weight ratio of the compound of formula (I) to each further herbicide can vary over a large range and is, typically, from 500:1 to 1:500 or from 300:1 to 1:500 or from 500:1 to 1:200, especially from 200:1 to 1:200 or from 150:1 to 1:200 or from 200:1 to 1:100, more especially from 100:1 to 1:100 or from 100:1 to 1:50, even more especially from 30:1 to 1:30. Typically, these weight ratios are measured as the free compound(s), i.e. excluding the weight of any associated salt counterion (s).

The compounds of formula I according to the invention can be used in combination with a safener. Preferably, in these mixtures, the compound of the formula I is one of those compounds listed (disclosed) in Tables 1 to 46, and/or one of the exemplified compounds (in particular one of compounds A1 to A7, A8, or P1 to P5) herein e.g. hereinbelow, optionally present (e.g. where chemically possible) as an agrochemically acceptable salt thereof. The following mixtures with safeners, especially, come into consideration: compound of formula I+cloquintocet-mexyl, compound of formula I+cloquintocet acid or an agrochemically acceptable salt thereof, compound of formula I+fenchlorazole-ethyl, compound of formula I+fenchlorazole acid or an agrochemically acceptable salt thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292.

Preferably, in a composition or mixture comprising a compound of formula (I) (in particular, a compound from Tables 1 to 46, and/or one of Compounds A1 to A7, A8, or P1 to P5 herein, optionally present (e.g. where chemically possible) as an agrochemically acceptable salt thereof) and a safener, the safener comprises (e.g. is) benoxacor, cloquintocet acid or an agrochemically acceptable salt thereof, cloquintocet-mexyl, cyprosulfamide, mefenpyr-diethyl, isoxadifen-ethyl and/or N-(2-methoxybenzoyl)-4-[(methylaminocarbonyl)amino]benzenesulfonamide. In one particular embodiment, the safener comprises (e.g. is) cloquintocet acid or an agrochemically acceptable salt thereof, cloquintocet-mexyl, mefenpyr-diethyl and/or isoxadifen-ethyl; in particular for use on non-oat cereals such as wheat, barley, rye and/or triticale. Cloquintocet-mexyl is particularly valuable and is the most preferred safener, especially for use on non-oat cereals such as wheat, barley, rye and/or triticale.

The ratio of safener relative to the herbicide is largely dependent upon the mode of application. However, typically, the weight ratio of the compound of formula (I) to the safener can vary over a large range and is, typically, from 200:1 to 1:200, especially from 50:1 to 1:50 such as from 50:1 to 1:20, more especially from 20:1 to 1:20, even more especially from 20:1 to 1:10. As stated above, preferably, the safener comprises (e.g. is) benoxacor, cloquintocet-mexyl, cloquintocet acid or an agrochemically acceptable salt thereof, cyprosulfamide, mefenpyr-diethyl, isoxadifen-ethyl and/or N-(2-methoxybenzoyl)-4-[(methylaminocarbonyl) amino]benzenesulfonamide; in which case, more preferably, the weight ratio of the compound of formula (I) to the safener is from 50:1 to 1:20 or from 20:1 to 1:10, even more preferably from 15:1 to 1:2. Typically, these weight ratios are measured as the free compound(s), i.e. excluding the weight of any associated salt counterion(s). In the above typical or preferred embodiments, preferably, the compound of formula (I) is a compound from Tables 1 to 46, and/or one of Compounds A1 to A7, A8, or P1 to P5 herein, optionally present (e.g. where chemically possible) as an agrochemically acceptable salt thereof.

Application rates of herbicide (in particular compound of formula (I)) and/or safener: The rate of application of safener relative to the herbicide (in particular compound of formula (I)) is largely dependent upon the mode of application. In the case of field and/or soil and/or plant treatment (e.g. in a field or glasshouse): for example from 0.001 to 5.0 kg (e.g. from 1 to 1000 g) of safener per ha, preferably from 0.001 to 0.5 kg (in particular from 1 to 250 g or from 2 to 200 g or from 5 to 200 g) of safener per ha, are applied; and/or generally from 0.001 to 2 kg of herbicide (e.g. compound of formula (I)) per ha, but preferably from 0.005 to 1 kg (more preferably from 5 to 500 g or from 10 to 400 g or from 10 to 300 g or from 20 to 200 g) of herbicide (in particular compound of formula (I)) per ha, are applied. ha=hectare. Typically, these application rates are measured as the free compound, i.e. excluding the weight of any associated salt counterion(s). In field and/or plant treatment, the application of the herbicide (in particular compound of formula (I)) is preferably post-emergence.

The above-mentioned safeners and herbicides are described, for example, in the Pesticide Manual, Twelfth Edition, British Crop Protection Council, 2000; or The Pesticide Manual, 15th edition (2009) or 16th edition (2012), ed. C. D. S. Tomlin, British Crop Production Council. R-29148 is described, for example by P. B. Goldsbrough et al., Plant Physiology, (2002), Vol. 130 pp. 1497-1505 and references therein. PPG-1292 is known from WO 2009/211761. N-(2-methoxybenzoyl)-4-[(methylaminocarbonyl) amino]-benzenesulfonamide is known e.g. from EP365484.

In one particular embodiment, the composition or mixture comprising the compound of formula (I) and one or more further herbicides (e.g. as mentioned hereinabove) can be applied together with one of the safeners mentioned herein, e.g. hereinabove.

The compounds and/or herbicidal compositions according to the invention are suitable for all methods of application customary in agriculture, such as, for example, pre-emergence application, post-emergence application and seed dressing. Post-emergence application is preferred. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field and/or soil and/or plant treatment (e.g. in a field or glasshouse), generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

In the invention, in the case of field and/or soil and/or plant treatment (e.g. post-emergence application), generally from 1 to 2000 g of herbicide (in particular compound of formula (I))/ha, but preferably from 5 to 1000 g of herbicide (in particular compound of formula (I))/ha, more preferably from 10 to 400 g of herbicide (in particular compound of formula (I))/ha, is applied. If a safener is used, in the case of field and/or soil and/or plant treatment (e.g. post-emergence application), generally from 0.5 to 1000 g of safener/ha, preferably from 2 to 500 g of safener/ha, more preferably from 5 to 200 g of safener/ha, is applied.

The following examples illustrate further but do not limit the invention.

PREPARATION EXAMPLES

Those skilled in the art will appreciate that certain compounds described herein, e.g. hereinbelow, are β-ketoenols, and as such may exist as a single tautomer or as a mixture of keto-enol and diketone tautomers as described, for example, by J. March, Advanced Organic Chemistry, third edition, John Wiley and Sons. The compounds shown hereinbelow, and in Tables T1, T2 and P1 hereinbelow, as well as those compounds shown hereinbelow in Tables 1 to 46, are drawn as an arbitrary single enol tautomer, but it should be inferred that this description covers both the diketone form and any possible enols which could arise through tautomerism. Where more than one tautomer is observed in proton ($^1$H) NMR, the data shown are for the mixture of tautomers. Furthermore, some of the compounds shown below may be drawn as single enantiomers for the purposes of simplicity, but unless specified as single enantiomers, these structures should be construed as representing a mixture of enantiomers (e.g. a racemic mixture). Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer (or the drawn structure) is the enol form.

ABBREVIATIONS USED HEREIN s=singlet; brs or br s=broad singlet; d=doublet; t=triplet; m=multiplet.
NMR nuclear magnetic resonance
LC-MS liquid chromatography-mass spectrometry
DMSO dimethylsulfoxide
THF tetrahydrofuran
RT room temperature (in the context of experimentals and/or temperatures)
RT retention time (in the context of LCMS)
LC-MS Analysis
Note: Compounds characterised by HPLC-MS were analysed using an Agilent 1100 Series HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minute run time, according to the following gradient table:

| Time (mins) | Solvent A (%) | Solvent B (%) | Flow (ml/mn) |
| --- | --- | --- | --- |
| 0.00 | 90.0 | 10.0 | 2.00 |
| 0.25 | 90.0 | 10.0 | 2.00 |
| 2.00 | 10.0 | 90.0 | 2.00 |
| 2.50 | 10.0 | 90.0 | 2.00 |
| 2.6 | 90.0 | 10.0 | 2.00 |
| 3.0 | 90.0 | 10.0 | 2.00 |

Solvent A: H$_2$O with 0.1% HCOOH
Solvent B: 0.1% HCOOH in CH$_3$CN

The characteristic values obtained for each compound were the retention time (RT, recorded in minutes) and the molecular ion, typically the cation MH+.

Example 1

Preparation of
4-Bromo-2-fluoro-6-methoxy-benzaldehyde

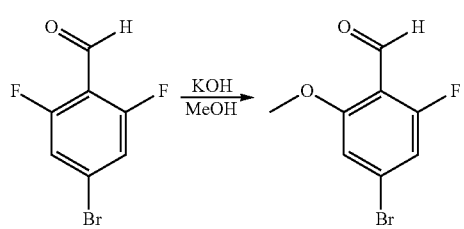

Flaked potassium hydroxide (59.575 g) was added portionwise to stirred and cooled (ice-bath) methanol (600 mL) keeping the temperature below 20° C. This solution was transferred to a dropping funnel. The starting material, 4-bromo-2,6-difluoro-benzaldehyde (commercially available, Chemical Abstracts Reg. No. 537013-51-7, 200 g), was dissolved in methanol (1210 mL) at 25° C. The mixture was warmed to 40° C. and the potassium methoxide solution added from the dropping funnel over 20 minutes with stirring. An initial exotherm was observed which was controlled by external cooling. The reaction temperature was increased to 55° C. and heating was continued for 1 hour.

The reaction mixture was cooled to room temperature and the methanol was removed under vacuum. The resultant residue was partitioned between water (1.6 L) and ethyl acetate (1.6 L). The phases were separated and the aqueous layer extracted with further ethyl acetate (2×0.5 L). The combined organic phases were washed with water (0.5 L) and concentrated under vacuum leaving a yellow solid.

This solid was triturated with cold iso-hexane, filtered and dried in vacuo to give a yellow solid as a 4:1 mixture of the desired compound 4-bromo-2-fluoro-6-methoxy-benzaldehyde [1H-NMR (400 MHz, CDCl$_3$) 10.36 δ (delta): (s, 1H), 6.94-6.97 (m, 2H), 3.94 (s, 3H)] and 4-bromo-2,6-dimethoxy-benzaldehyde.

The following compounds may be made using the same method:
4-Bromo-2-fluoro-6-(2-methoxy-ethoxy)-benzaldehyde was made using 2-methoxyethanol. $^1$H-NMR (400 MHz, CDCl$_3$) 10.39 (d, 1H), 6.93-6.99 (m, 2H), 4.18-4.26 (m, 2H), 3.73-3.84 (m, 2H), 3.45 (s, 3H).
4-Bromo-2-fluoro-6-(2,2,2-trifluoro-ethoxy)-benzaldehyde. $^1$H-NMR (400 MHz, CDCl$_3$) δ (delta): 10.37 (d, 1H), 7.09 (dd, 1H), 6.95 (s, 1H), 4.47 (q, 2H).
2,4-dibromo-6-methoxy-benzaldehyde. $^1$H-NMR (400 MHz, CDCl$_3$) δ (delta): 10.34 (s, 1H), 7.44 (s, 1H), 7.11 (s, 1H), 3.92 (s, 3H).

Example 2

Preparation of
4-Bromo-2-fluoro-6-methoxy-benzaldehyde

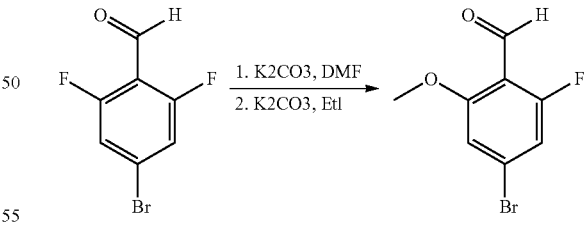

To a stirred solution of 4-bromo-2,6-difluoro-benzaldehyde (commercially available, CAS 537013-51-7, 1.00 g) in N,N-dimethylformamide (5 mL) at ambient temperature was added potassium carbonate (1.10 g) followed by water (0.408 g). The resulting suspension was heated at 90° C. After 1 hour further water (0.08 mL) was added and heating continued for another 1 hour.

The reaction mixture was cooled to ambient temperature and potassium carbonate (0.595 g) added with stirring followed by iodomethane (1.4 mL). This mixture was stirred at ambient temperature overnight.

Partitioned the reaction mixture between water and diethyl ether and extracted the aqueous layer with further diethyl ether (2×). The combined organics were washed with water, brine and dried with anhydrous magnesium sulfate. This mixture was filtered and concentrated under vacuum to give a red-orange solid. This solid was dissolved in dichloromethane, passed through a plug of silica and concentrated to give 4-bromo-2-fluoro-6-methoxy-benzaldehyde as a cream solid.

$^1$H-NMR (400 MHz, CDCl$_3$) δ (delta): 10.37 (s, 1H), 6.94-6.97 (m, 2H), 3.94 (s, 3H).

The following compounds may be made using the same method:

4-Bromo-2-ethoxy-6-fluoro-benzaldehyde was made using ethyl iodide. $^1$H-NMR (400 MHz, CDCl$_3$) δ (delta): 10.38 (d, 1H), 6.85-6.96 (m, 2H), 4.15 (q, 2H), 1.49 (t, 3H).

Example 3

Preparation of 4-Bromo-2-fluoro-6-hydroxy-benzaldehyde

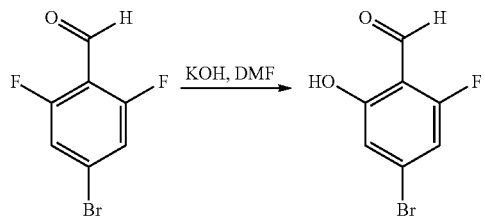

To a stirred solution of 4-bromo-2,6-difluoro-benzaldehyde (commercially available, Chemical Abstracts Reg. No. 537013-51-7, 2.000 g) in N,N-dimethylformamide (10 mL) was added a solution of potassium hydroxide (1.015 g) in water (4 mL) at ambient temperature. The yellow solution was heated at 60° C. for 2 hours. The reaction mixture was cooled and poured onto iced water and extracted with diethylether. The aqueous layer was separated and taken to pH 2 by addition of concentrated hydrochloric acid. Unexpectedly no solid crashed out of aqueous even when cooled.

It was noted that upon standing a yellow solid had crashed out of the organic phase. This solid was collected by filtration and dissolved in water. The aqueous filtrate was taken to pH 2 by addition of concentrated hydrochloric acid and the resulting pale yellow solid was filtered and dried to give 4-bromo-2-fluoro-6-hydroxy-benzaldehyde. $^1$H-NMR (400 MHz, CDCl$_3$) δ (delta): 11.57 (s, 1H), 10.20 (s, 1H), 6.99 (s, 1H), 6.86 (dd, 1H).

Example 4

Preparation of 4-Bromo-2-difluoromethoxy-6-fluoro-benzaldehyde

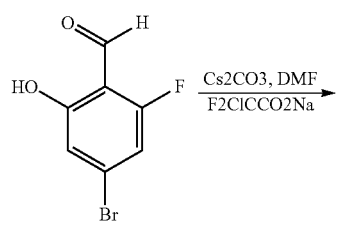

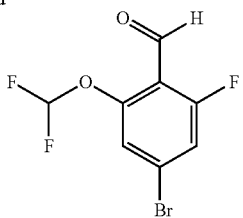

To a solution of 4-bromo-2-fluoro-6-hydroxy-benzaldehyde (see e.g. Example 3, 1.451 g) in N,N-dimethylformamide (4.7 mL) at ambient temperature was added cesium carbonate (3.022 g) giving a yellow suspension which was stirred for 5 minutes. Sodium 2-chloro-2,2-difluoro-acetic acid (2.339 g) was added to the suspension followed by water (0.86 mL). This mixture was heated at 85° C. for 2.5 hours. The reaction mixture was cooled, poured into ice-water and extracted with diethyl ether (×2). The combined organic layers were washed with water, dried with magnesium sulfate and concentrated in vacuo to leave a brown oil. The brown oil was purified by column chromatography on silica eluting with 0-15% ethyl acetate in iso-hexane to give 4-bromo-2-(difluoromethoxy)-6-fluoro-benzaldehyde as a yellow oil. $^1$H-NMR δ (delta) (400 MHz, CDCl$_3$) δ (delta): 10.31 (s, 1H), 7.27-7.33 (m, 1H), 6.44-6.83 (m, 1H).

Example 11

Preparation of (4-bromo-2-fluoro-6-methoxy-phenyl)-(2-furyl)methanol

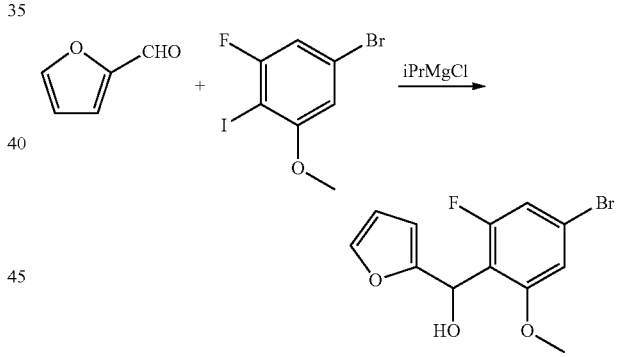

A solution of 5-bromo-1-fluoro-2-iodo-3-methoxy-benzene (10.0 g) was dissolved in anhydrous tetrahydrofuran (50 mL) and cooled to −65° C. under nitrogen. To this was added isopropylmagnesium chloride (2.0M in tetrahydrofuran, 19 mL) over 40 minutes. When the addition was complete the brown solution was stirred at −70° C. for 20 minutes then allowed to warm to room temperature and stirred for 2.5 hr. The reaction mixture was re-cooled to −65° C. and a solution of furan-2-carbaldehyde (3.04 mL) in tetrahydrofuran (10 mL) was added drop wise. On completion of the addition the solution was stirred for 20 minutes, then cooling was removed and the reaction was stirred for 4 hr. The reaction was quenched with saturated aqueous ammonium chloride (50 mL) and partitioned between water (10 mL) and ethyl acetate (50 mL). The aqueous phase was extracted with further ethyl acetate (×2). The combined organic phases were washed with brine, dried over magnesium sulfate and concentrated to afford a brown gum which was purified by column chromatography on silica to give (4-bromo-2-fluoro-6-methoxy-phenyl)-(2-furyl)methanol as a yellow gum. ¹H-NMR (400 MHz, CDCl₃) δ (delta): 7.37-7.36 (m, 1H), 6.95 (dd, 1H), 6.90 (t, 1H), 6.31 (dd, 1H), 6.12 (s, 1H), 6.11 (d, 1H), 3.87 (s, 3H), 3.66 (dd, 1H).

Example 12

Preparation of 2-(4-bromo-2-fluoro-6-methoxy-phenyl)cyclopent-4-ene-1,3-dione

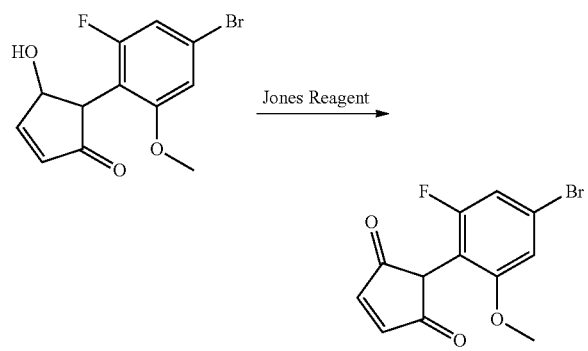

Concentrated sulfuric acid (10.94 mL) was added to water (54.70 mL) with cooling in an icebath. This was then added to trioxochromium (0.9990 g) cooled in an ice bath to give an about 1.67M solution of Jones' Reagent. The prepared Jones' reagent was added dropwise over 10 minutes to a cooled (ice bath) solution of 5-(4-bromo-2-fluoro-6-methoxy-phenyl)-4-hydroxy-cyclopent-2-en-1-one (2.735 g) in acetone (35.56 mL). The reaction was stirred for 30 minutes in ice then the cooling was removed and the reaction stirred for 3 h. 2-Propanol (30 mL) was added and the mixture was stirred at room temperature for 1.5 hr. The acetone was removed in vacuo and water and ethyl acetate were added. The phases were separated and the aqueous phase was extracted with further ethyl acetate (2×50 mL). The combined organic phases were washed with water (2×50 mL), brine (50 mL), dried over magnesium sulphate and concentrated in vacuo to give a yellow oil. Diethyl ether was added and the material was concentrated in vacuo to give 2-(4-bromo-2-fluoro-6-methoxy-phenyl)cyclopent-4-ene-1,3-dione as a yellow solid. ¹H-NMR (400 MHz, CDCl₃) δ (delta): 7.35 (s, 2H), 6.95 (brs, 1H), 6.80 (brs, 1H), 3.67 (brs, 3H)

Example 13

Preparation of 2-(4-bromo-2-fluoro-6-methoxy-phenyl)cyclopentane-1,3-dione

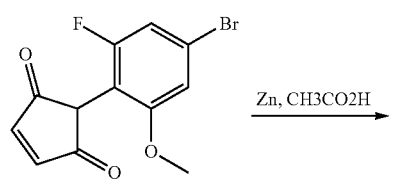

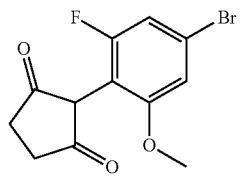

To a solution of 2-(4-bromo-2-fluoro-6-methoxy-phenyl)cyclopent-4-ene-1,3-dione (see e.g. Example 12, 2.639 g) in acetic acid (26.39 mL) was added zinc (2.019 g) and the mixture stirred at room temperature.

After 1.25 hr, the reaction was diluted with ethyl acetate (100 mL) and 2M aqueous hydrochloric acid (100 mL) was added. The mixture was stirred at room temperature until the majority of zinc solid had dissolved. The mixture was partitioned and the aqueous phase was extracted with further ethyl acetate (×2). The combined organic phases were washed with brine, dried over magnesium sulphate and concentrated. Toluene (100 mL) was added and the solution was concentrated to give 2-(4-bromo-2-fluoro-6-methoxy-phenyl)cyclopentane-1,3-dione as a yellow solid. ¹H-NMR (400 MHz, CD₃OD) δ (delta): 6.99 (t, 1H), 6.95 (dd, 1H), 3.77 (s, 3H), 2.65 (s, 4H).

Example 14

Preparation of 2-(4-bromo-2-fluoro-6-methoxy-phenyl)-3-methoxy-cyclopent-2-en-1-one

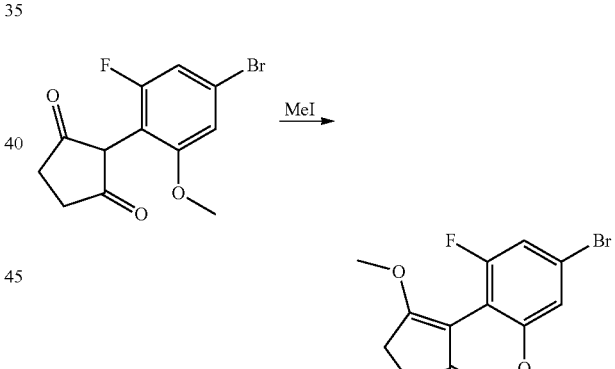

To a solution of 2-(4-bromo-2-fluoro-6-methoxy-phenyl)cyclopentane-1,3-dione (see e.g. Example 13, 2.71 g) in acetone (162 mL) at room temperature was added potassium carbonate (1.87 g) followed by iodomethane (2.80 mL). The mixture was stirred at room temperature for 18 hours.

The acetone was removed in vacuo and the residue partitioned between water and ethyl acetate (100 mL). The phases were separated and the aqueous was extracted with further ethyl acetate (2×50 mL). The combined organic phases were washed with brine, dried over magnesium sulphate, filtered and concentrated to give 2-(4-bromo-2-fluoro-6-methoxy-phenyl)-3-methoxy-cyclopent-2-en-1-one as a brown oil. ¹H-NMR (400 MHz, CDCl₃) δ (delta): 6.92 (dd, 1H), 6.85 (d, 1H), 3.85 (s, 3H), 3.79 (s, 3H), 2.81-2.79 (m, 2H), 2.63-2.60 (m, 2H).

Example 15

Preparation of 2-(2-fluoro-6-methoxy-4-prop-1-ynyl-phenyl)-3-methoxy-5-prop-2-ynyl-cyclopent-2-en-1-one

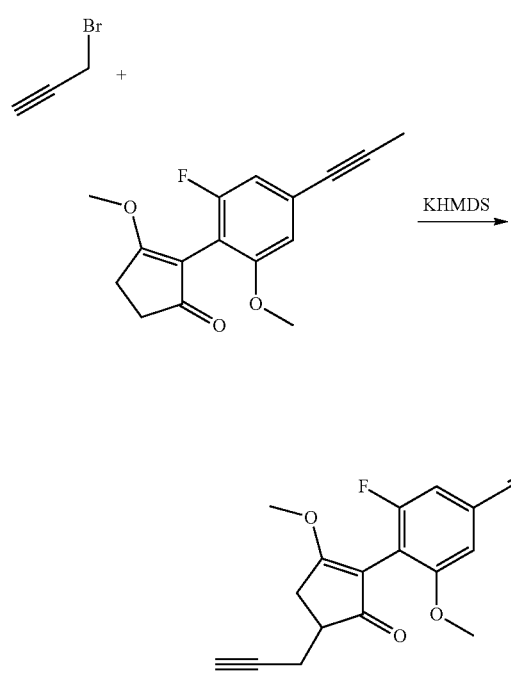

To a solution of 2-(2-fluoro-6-methoxy-4-prop-1-ynyl-phenyl)-3-methoxy-cyclopent-2-en-1-one (0.205 g) in anhydrous tetrahydrofuran (5 mL) under nitrogen at −78° C. was added potassium hexamethyldisilazide (KHMDS, 1M in tetrahydrofuran, 0.8969 mL) dropwise and the reaction was stirred at this temperature for 1 hour 45 minutes. A solution of 3-bromoprop-1-yne (80 wt % in toluene, 0.09990 mL) was diluted in anhydrous tetrahydrofuran (1 mL) under a nitrogen atmosphere and then added dropwise to the reaction mixture. The reaction was stirred at −78° C. for 15 minutes, then the cooling bath was removed and the solution stirred at room temperature for 18 hours.

The reaction was quenched with saturated aqueous ammonium chloride solution (10 mL) and partitioned with ethyl acetate (10 mL) and water (2 mL). The aqueous phase was extracted further with ethyl acetate (×2). The combined organic phases were washed with brine, dried with magnesium sulfate and concentrated to afford an orange gum which was purified by column chromatography on silica to give 2-(2-fluoro-6-methoxy-4-prop-1-ynyl-phenyl)-3-methoxy-5-prop-2-ynyl-cyclopent-2-en-1-one as a yellow solid (112.7 mg).

$^1$H-NMR (400 MHz, CDCl$_3$) (a mixture of atropisomers) δ (delta): 6.77 (dd, 1H), 6.73 (brs, 1H), 3.79-3.77 (m, 3H), 3.69 (s, 3H), 3.14-3.07 (m, 1H), 2.75 (dd, 1H), 2.67-2.63 (m, 1H), 2.58-2.49 (m, 2H), 2.06 (s, 3H), 2.01-1.99 (m, 1H).

Example 16

Preparation of 2-(2-fluoro-6-methoxy-4-prop-1-ynyl-phenyl)-4-prop-2-ynyl-cyclopentane-1,3-dione (Table T1, Compound A8)

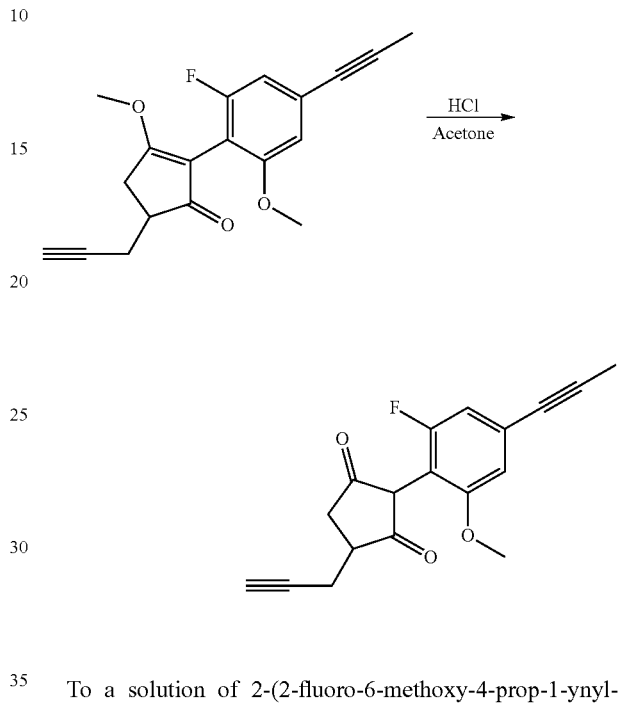

To a solution of 2-(2-fluoro-6-methoxy-4-prop-1-ynyl-phenyl)-3-methoxy-5-prop-2-ynyl-cyclopent-2-en-1-one (see e.g. Example 14, 0.117 g) in acetone (2 mL) in a microwave vial was added 2M aqueous hydrochloric acid (0.5 mL) and the resultant solution heated in a microwave reactor at 100° C. for 30 minutes. After standing at room temperature overnight the reaction mixture was poured into dichloromethane and water. The phases were separated and the aqueous was extracted with further dichloromethane. The combined organic extracts were concentrated to afford 2-(2-fluoro-6-methoxy-4-prop-1-ynyl-phenyl)-4-prop-2-ynyl-cyclopentane-1,3-dione as a yellow solid.

Example 17

Sample Preparation of a Benzoate Ester (a Compound of Formula (I) in which G=Phenyl-C(O)—), Starting from a Compound of Formula (I) in which G=H To a solution of a suitable cyclic dione (a compound of formula (I) in which G=H) and 4-(dimethylamino)pyridine in dichloromethane is added pyridine and benzoyl chloride. The reaction is stirred at room temperature for 1 hour, and then is concentrated and purified by column chromatography on silica, e.g. eluting with 5-55% ethyl acetate in iso-hexane to give the benzoate ester product, which is a compound of formula (I) in which G=phenyl-C(O)—.

Example 23

Preparation of 4-(4-Bromo-2-fluoro-6-methoxy-phenyl)-10-oxa-tricyclo[5.2.1.0-2,6-]dec-8-ene-3,5-dione (Diels-Alder cycloaddition)

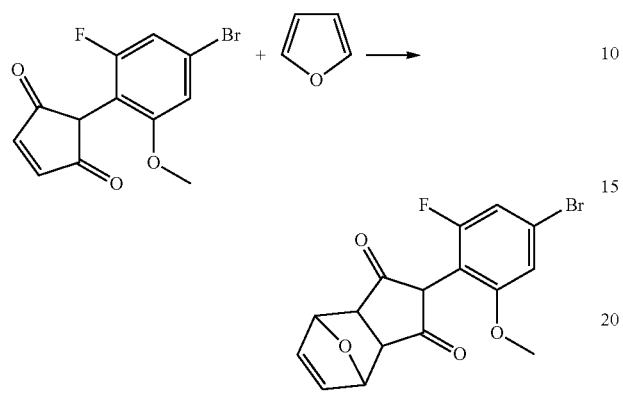

To 2-(4-bromo-2-fluoro-6-methoxy-phenyl)cyclopent-4-ene-1,3-dione (1 g, see e.g. Example 12) and magnesium diiodide (0.279 g) in dichloromethane (4 mL) was added furan (0.729 mL). The solution was stirred at room temperature in the dark (foil wrap). After 18 hours further furan (0.729 mL) was added and stirring continued. Three further portions of furan (0.729 mL) were added at 72 hours, 120 hours and 216 hours.

After 288 hours the reaction mixture was dissolved in methanol, concentrated on to silica in vacuo and purified by chromatography on silica eluting with ethyl acetate in iso-hexane to give 4-(4-bromo-2-fluoro-6-methoxy-phenyl)-10-oxa-tricyclo[5.2.1.0-2,6-]dec-8-ene-3,5-dione (580 mg).

$^1$H NMR (400 MHz, DMSO-d6) δ (delta): 7.03-7.10 (m, 2H), 6.54 (s, 2H), 4.88-4.94 (m, 2H), 3.69-3.78 (m, 3H), 2.63-2.76 (m, 2H).

Example 24

Preparation of 4-(4-Bromo-2-fluoro-6-methoxy-phenyl)-10-oxa-tricyclo[5.2.1.0-2,6-]decane-3,5-dione

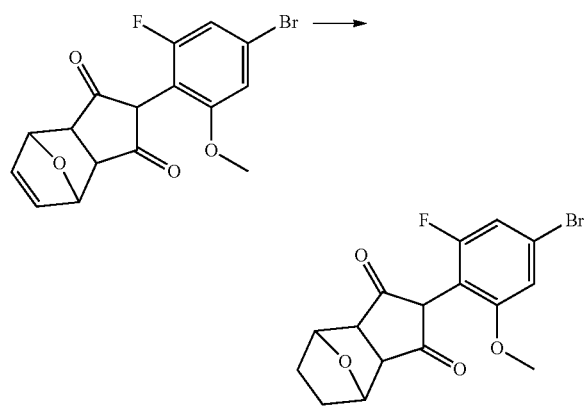

A mixture of 4-(4-bromo-2-fluoro-6-methoxy-phenyl)-10-oxa-tricyclo[5.2.1.0-2,6-]dec-8-ene-3,5-dione (0.200 g) and 2-nitrobenzenesulfonyl chloride (0.362 g) was vigorously stirred in acetonitrile (2.72 mL) at 0° C. Hydrazine hydrate (0.159 mL) was added slowly over 1 minute and the reaction was slowly warmed to room temperature.

After 28 hours further 2-nitrobenzenesulfonyl chloride (180 mg) and hydrazine hydrate (0.08 mL) was added and stirring continued.

After a further 20 hours the reaction mixture was filtered, washed with water and diethyl ether to give 4-(4-bromo-2-fluoro-6-methoxy-phenyl)-10-oxa-tricyclo[5.2.1.0-2,6-]decane-3,5-dione (0.126 g).

$^1$H NMR (400 MHz, d$_4$-methanol) δ (delta): 6.89-7.01 (m, 2H), 4.54-4.64 (m, 2H), 3.76 (s, 3H), 2.83 (br. s., 2H), 1.73-1.84 (m, 2H), 1.58-1.68 (m, 2H).

Example 25

Preparation of [diacetoxy-(4-bromo-2-fluoro-6-methoxy-phenyl)plumbyl]acetate

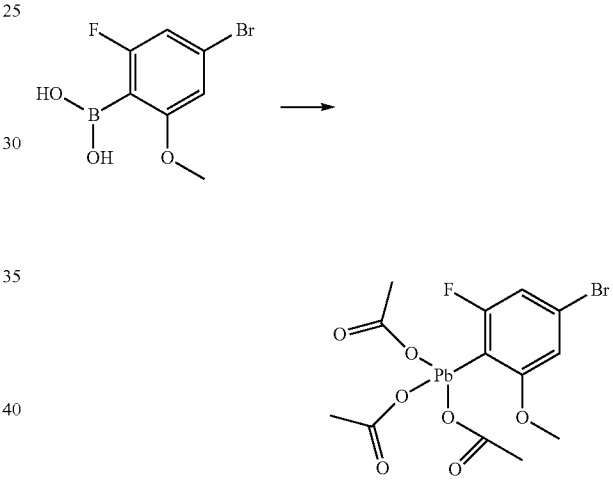

A nitrogen flushed mixture of mercury(II)acetate (0.305 g) and lead(IV)acetate (10.2 g) in chloroform (47 mL) was warmed to 40° C. with stirring. The heat source was removed and (4-bromo-2-fluoro-6-methoxy-phenyl)boronic acid (4.76 g, commercially available, Chemical Abstracts Reg. No. 957035-32-4) was added in portions over 1 minute. This mixture was heated at 40° C. for 4 hours and left to cool. Chloroform (25 mL) was added and the mixture cooled in an ice bath with stirring. Potassium carbonate (23.8 g) was added gradually and the mixture stirred for 10 minutes under nitrogen. The resulting dark orange suspension was filtered through chloroform-washed Celite™ and washed through with further chloroform (40 ml). The filtrate was concentrated to leave a yellow solid which was triturated with iso-Hexane and chloroform and filtered, washed with a little cold iso-hexane and air-dried to give [diacetoxy-(4-bromo-2-fluoro-6-methoxy-phenyl)plumbyl]acetate (7.39 g) as a pale yellow solid.

$^1$H NMR (500 MHz, CDCl$_3$) δ (delta): 7.00-7.06 (m, 1H) 6.75-6.82 (m, 1H) 3.80-3.83 (m, 3H) 1.76-2.12 (m, 9H)

Example 26

Preparation of 2-(4-Bromo-2-fluoro-6-methoxyphenyl)-cyclohexane-1,3-dione

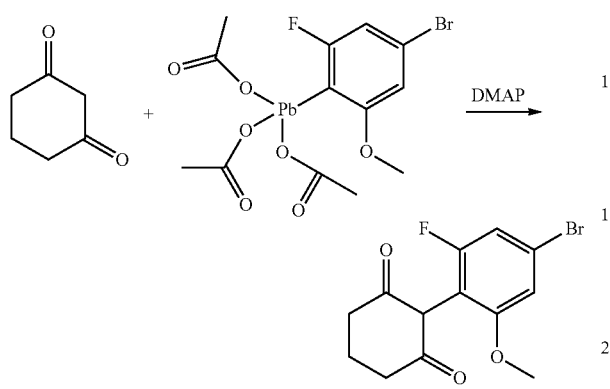

To a mixture of cyclohexane-1,3-dione (0.33 g) and DMAP (4-dimethylaminopyridine) (1.8 g) in chloroform (16 mL), under nitrogen, was added toluene (4 mL) followed by [diacetoxy-(4-bromo-2-fluoro-6-methoxy-phenyl)plumbyl] acetate (2.1 g). The mixture was heated under nitrogen at 80° C. (internal temperature) for 3 hrs.
The reaction was diluted with chloroform (25 mL) and cooled with an ice-water-bath. Gradually it was acidified with aqueous 2M hydrochloric (10 mL), then the mixture was stirred vigorously for 10 mins. The mixture was filtered through water-washed 'Celite'™ then washed through with chloroform. The organic layer was separated, concentrated under reduced pressure and purified by chromatography on silica eluting with methanol in dichloromethane to give 2-(4-bromo-2-fluoro-6-methoxy-phenyl)-cyclohexane-1,3-dione (230 mg) as a colourless foamy solid.
$^1$H NMR (500 MHz, CDCl$_3$) δ (delta): 6.88-6.92 (m, 1H) 6.53 (dd, 1H) 3.69-3.72 (m, 3H) 2.39-2.49 (m, 4H) 1.91-2.03 (m, 2H)

Example 27

Preparation of (E)-6-Methylsulfanylhept-3-en-2-one

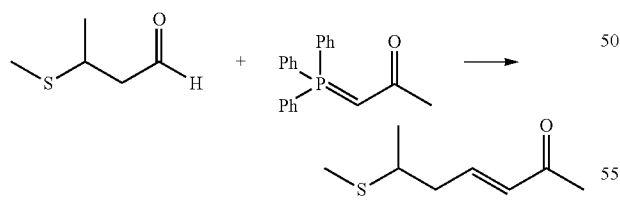

To a solution of 3-methylsulfanylbutanal (CAS 16630-52-7, 6.4 g) in dichloromethane (120 mL) was added 1-(triphenylphosphoranylidene)-2-propanone (CAS 1439-36-7, 17 g) in a single portion. The reaction mixture was heated and stirred at reflux for 7 hour and left to cool overnight. The cooled reaction mixture was concentrated to leave a pale yellow solid which was triturated with a 1:1 mixture of ether:isohexane (100 mL). The resulting solid was collected by filtration and washed with further 1:1 ether:iso-hexane (50 mL). The filtrate was concentrated to a yellow oil and purified by chromatography on silica eluting with ethyl acetate in iso-hexane to give (E)-6-methylsulfanylhept-3-en-2-one (5.409 g) as a yellow liquid.
$^1$H NMR (400 MHz, CDCl$_3$) δ (delta): 6.82 (dt, 1H), 6.12 (d, 1H), 2.84 (sxt, 1H), 2.37-2.56 (m, 2H), 2.27 (s, 3H), 2.08-2.14 (m, 3H), 1.27-1.34 (m, 3H)

Example 28

Preparation of Ethyl 2-(2-methylsulfanylpropyl)-4,6-dioxo-cyclohexanecarboxylate

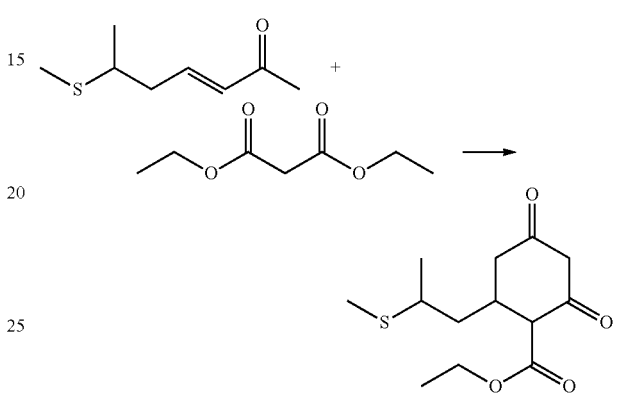

To ice cooled ethanol (50 mL) was added sodium metal (1.045 g) in small portions under nitrogen, and the resulting solution was stirred for 15 minutes. Diethyl propanedioate (6.613 g) in ethanol (25 mL) was added drop wise to this cooled solution over 20 minutes. The reaction was allowed to warm to ambient temperature and stirred for a further 1 hour. The mixture was cooled in an ice bath and a solution of (E)-6-methylsulfanylhept-3-en-2-one (5.409 g) in ethanol (25 mL) was added drop wise. The reaction was allowed to warm to ambient temperature, stirred for 4 hours and then left to stand overnight. The reaction was concentrated to a yellow slurry which was poured into a cooled solution of 2M hydrochloric acid and stirred for 5 minutes. This was extracted with dichloromethane (×2) and the combined organic layers were dried over anhydrous magnesium sulfate, concentrated and purified by chromatography on silica eluting with ethyl acetate in iso-hexane to give ethyl 2-(2-methylsulfanylpropyl)-4,6-dioxo-cyclohexanecarboxylate (3.227 g) as a yellow oil.
$^1$H NMR (400 MHz, CDCl$_3$) δ (delta): 5.38-5.43 (m, 1H), 4.13-4.31 (m, 2H), 3.86-3.96 (m, 2H), 3.05-3.18 (m, 1H), 2.53-2.88 (m, 2H), 2.12-2.37 (m, 1H), 1.99-2.09 (m, 3H), 1.44-1.75 (m, 2H), 1.22-1.41 (m, 6H)

Example 29

Preparation of 5-(2-Methylsulfanylpropyl)cyclohexane-1,3-dione

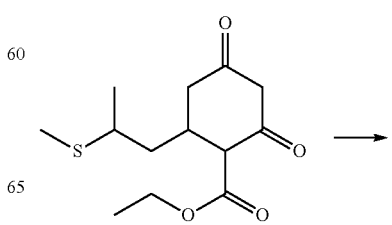

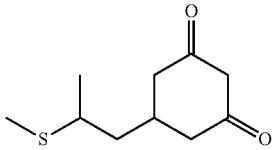

A mixture of 3-ethoxy-5-(2-methylsulfanylpropyl)cyclohex-2-en-1-one (5.846 g) was heated and stirred in 5M hydrochloric acid (30 mL) for 6 hours and left to stand overnight. The reaction mixture was extracted with ethyl acetate (×2). The combined organic layers were dried over anhydrous magnesium sulfate, concentrated and purified by chromatography on silica eluting with ethyl acetate in iso-hexane to give 5-(2-methylsulfanylpropyl)cyclohexane-1,3-dione (1.734 g) as a white solid $^1$H NMR (400 MHz, CDCl$_3$) δ (delta): 7.55 (br s, 1H), 3.41 (d, 1H), 2.65-2.82 (m, 2H), 2.33-2.55 (m, 3H), 2.01-2.16 (m, 4H), 1.42-1.67 (m, 2H), 1.24-1.33 (m, 3H)

Example 30

Preparation of (E)-6-Methylsulfanyl hex-3-en-2-one

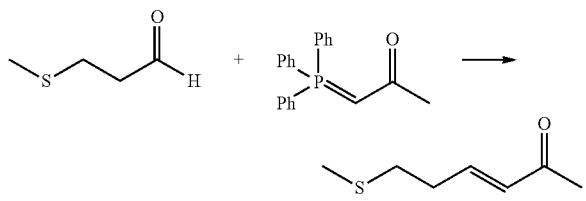

To a solution of 3-methylsulfanylpropanal (CAS 3268-49-3, 5.6 g) in dichloromethane (120 mL) was added 1-(triphenylphosphoranylidene)-2-propanone (CAS 1439-36-7, 17 g) in a single portion. The reaction mixture was heated and stirred at reflux for 5 hours. The cooled reaction mixture was concentrated to leave a pale yellow solid which was triturated with a 1:1 mixture of ether:iso-hexane (100 mL). The resulting solid was collected by filtration and washed with further 1:1 ether:iso-hexane (50 mL). The filtrate was concentrated to a yellow oil and purified by chromatography on silica eluting with ethyl acetate in iso-hexane to give (E)-6-methylsulfanylhex-3-en-2-one (5.890 g) as a colourless liquid.

$^1$H NMR (400 MHz, CDCl$_3$) δ (delta): 6.81 (dt, 1H), 6.08-6.15 (m, 1H), 2.61-2.67 (m, 2H), 2.49-2.58 (m, 2H), 2.24-2.27 (m, 3H), 2.10-2.15 (m, 3H)

Example 31

Preparation of Ethyl 2-(2-methylsulfanylethyl)-4,6-dioxo-cyclohexanecarboxylate

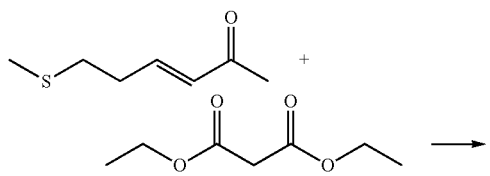

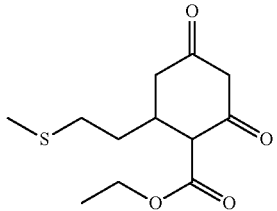

To ice cooled ethanol (50 mL) was added sodium metal (1.249 g) in small portions under nitrogen and the resulting solution was stirred for 15 minutes. Diethyl propanedioate (7.901 g) in ethanol (25 mL) was added drop wise to this cooled solution over 20 minutes. The reaction was allowed to warm to ambient temperature and stirred for a further 2 hours. The mixture was cooled in an ice bath and a solution of (E)-6-methylsulfanylhex-3-en-2-one (5.890 g) in ethanol (25 mL) was added drop wise. The reaction was allowed to warm to ambient temperature, stirred for 4 hours and then left to stand overnight. The reaction was concentrated to a yellow slurry which was poured into a cooled solution of 2M hydrochloric acid and stirred for 5 minutes. This was extracted with dichloromethane (×2) and the combined organic layers dried over anhydrous magnesium sulfate and concentrated to give ethyl 2-(2-methylsulfanylethyl)-4,6-dioxo-cyclohexanecarboxylate (11.446 g) as a yellow oil.

$^1$H NMR (400 MHz, CDCl$_3$) δ (delta): 5.48-5.56 (m, 1H), 4.13-4.33 (m, 2H), 3.38-3.48 (m, 1H), 3.11-3.21 (m, 1H), 2.44-2.75 (m, 3H), 2.17-2.26 (m, 1H), 2.09 (s, 3H), 1.63-1.86 (m, 2H), 1.30 (t, 3H)

Example 32

Preparation of 5-(2-Methylsulfanylethyl)cyclohexane-1,3-dione

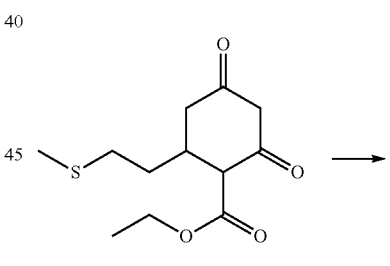

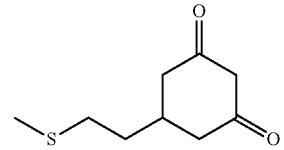

A solution of ethyl 2-(2-methylsulfanylethyl)-4,6-dioxo-cyclohexanecarboxylate (11.446 g) in propan-2-ol (32 mL) was stirred with 2M sodium hydroxide solution (115.2 mL) for 4 hours. The reaction was concentrated to remove the propan-2-ol and the remaining aqueous solution was taken to pH 1 by the addition of conc. hydrochloric acid. This solution was heated to 70° C. for 1.5 hours, then left to cool overnight. The resulting solid was collected by filtration and washed with water then iso-hexane and air dried to leave a pale yellow powder. The powder was washed further with water (×4) and air dried to give 5-(2-methylsulfanylethyl)cyclohexane-1,3-dione (6.583 g) as a yellow solid ¹H NMR (400 MHz, CDCl₃) δ (delta): 5.48 (s, 1H), 3.41 (d, 1H), 2.77 (dd, 3H), 2.45-2.61 (m, 2H), 2.25-2.43 (m, 2H), 2.08-2.18 (m, 3H), 1.63-1.74 (m, 2H).

Additional compounds in Table T1 and Table P1 below illustrate the present invention, and are particular and/or preferred embodiments of the compounds of formula (I) according to the present invention. For the most part, these compounds can generally be prepared by method(s) similar to those disclosed in the Examples hereinabove and/or disclosed in the "Processes for preparation of compounds" section hereinabove using appropriate starting materials, and/or in an analogous manner.

TABLE T1

| Compound Number | Structure | ¹H NMR δ (delta) (CDCl₃ unless stated), or other physical data |
|---|---|---|
| A8 | 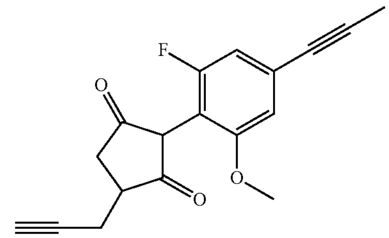 [SMILES: C#CCC1CC(=O)C(c2c(F)cc(C#CC)cc2OC)C1=O] | ¹H NMR (d₄-methanol) δ (delta): 6.79 (s, 1H), 6.73-6.70 (m, 1H), 3.75 (m, 3H), 2.92-2.82 (m, 2H), 2.68-2.46 (m, 3H), 2.28 (dt, 1H), 2.03 (s, 3H). 1H missing due to cyclic dione proton exchange. |
| A9 | 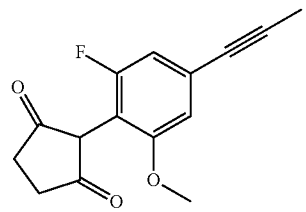 [SMILES: CC#Cc1cc(F)c(C2C(=O)CCC2=O)c(OC)c1] | ¹H NMR (d₄-methanol) δ (delta): 6.81 (s, 1H) 6.73 (d, 1H) 3.70-3.82 (m, 3H) 2.66 (s, 4H) 1.95-2.09 (m, 3H)). 1H missing due to cyclic dione proton exchange. |
| A10 | 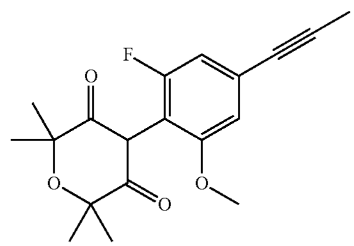 [SMILES: CC#Cc1cc(F)c(C2C(=O)C(C)(C)OC(C)(C)C2=O)c(OC)c1] | ¹H NMR (CDCl₃ + 2 drops of d₄-methanol) δ (delta): 6.82-6.73 (m, 2H), 3.72-3.78 (m, 3H), 2.05 (s, 3H), 1.48-1.53 (m, 12H). 1H missing due to cyclic dione proton exchange. |
| A11 | 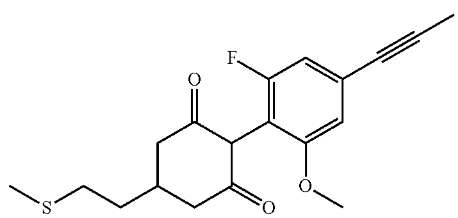 | ¹H NMR (500 MHz) δ (delta): 6.84 (d, 1H) 6.65 (dd, 1H) 5.63 (s, 1H) 3.77-3.81 (m, 3H) 2.72-2.80 (m, 1H)) 2.63-2.70 (m, 1H) 2.54-2.62 (m, 2H) 2.37-2.46 (m, 2H) 2.27 (dd, 1H) 2.09-2.14 (m, 3H) 1.99 (s, 3H) 1.75-1.86 (m, 2H). |
| A12 | 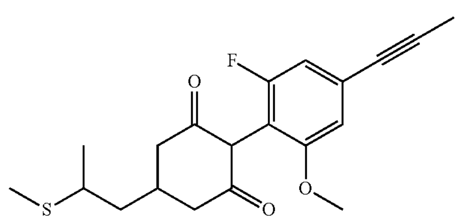 [SMILES: CC#Cc1cc(F)c(C2C(=O)CC(CCSC)CC2=O)c(OC)c1] | ¹H NMR (500 MHz) δ (delta): 6.84 (d, 1H) 6.60-6.68 (m, 1H) 5.67 (d, 1H) 3.77-3.81 (m, 3H) 2.61-2.80 (m, 3H) 2.47-2.57 (m, 1H) 2.34-2.45 (m, 1H) 2.17-2.30 (m, 1H) 2.08 (d, 3H) 1.96-2.02 (m, 3H) 1.60-1.80 (m, 2H) 1.30-1.35 (m, 3H). |
| A13 | 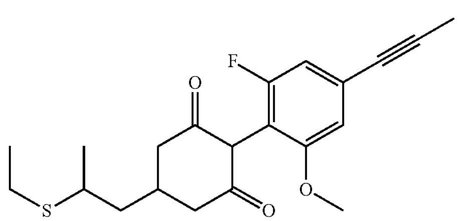 [SMILES: CC#Cc1cc(F)c(C2C(=O)CC(CC(C)SCC)CC2=O)c(OC)c1] | |

TABLE T1-continued

| Compound Number | Structure | $^1$H NMR δ (delta) (CDCl$_3$ unless stated), or other physical data |
|---|---|---|
| A14 | 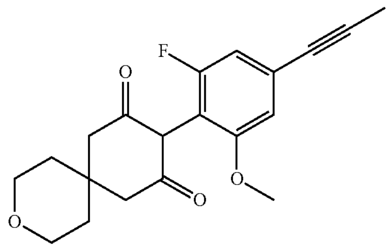 [SMILES: CC#Cc1cc(F)c(C2C(=O)CC3(CCOCC3)CC2=O)c(OC)c1] | $^1$H NMR (500 MHz) δ (delta): 6.83 (s,1H), 6.63 (dd, 1H), 5.98 (br s, 1H), 3.80 (s, 3H), 3.72 (m, 4H), 2.58 (m, 4H), 1.93 (s, 3H), 1.68-1.78 (m, 4H). |
| A16 | 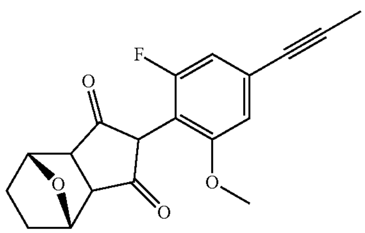 [SMILES: CC#Cc1cc(F)c(C2C(=O)C3C(C2=O)[C@H]2CC[C@@H]3O2)c(OC)c1] | $^1$H NMR (d$_4$-methanol) δ (delta): 6.66-6.82 (m, 2H), 4.52-4.64 (m, 2H), 3.74 (d, 3H), 2.82 (d, 2H), 2.02 (s, 3H), 1.73-1.85 (m, 2H), 1.58-1.68 (m, 2H). 1H missing due to cyclic dione proton exchange. |
| A17 | 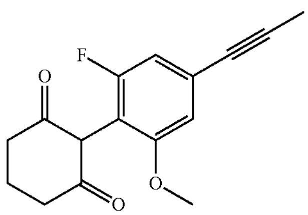 [SMILES: CC#Cc1cc(F)c(C2C(=O)CCCC2=O)c(OC)c1] | $^1$H NMR (500 MHz) δ (delta): 6.83 (d, 1H) 6.64 (dd, 1H) 5.93 (br s, 1H) 3.77-3.83 (m, 3H) 2.63 (br s, 2H) 2.51 (br s, 2H) 2.04-2.15 (m, 2H) 1.97-2.00 (m, 3H). |

It should be noted that certain compounds of the invention may exist as a mixture of isomers, including sometimes atropisomers, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

TABLE T2

The following compound B2 is not a compound of formula (I) according to the present invention. However, a further, independent, aspect of the invention provides a compound B2, optionally present as an agrochemically acceptable salt (e.g. metal, sulfonium or ammonium salt) thereof:

| Compound Number | Structure | $^1$H NMR δ (delta) (CDCl$_3$ unless stated), or other physical data |
|---|---|---|
| B2 | 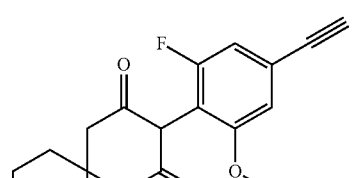 | Compound synthesized and tested (see Biological Examples) |

TABLE P1

Additional compounds in Table P1 below illustrate the
present invention, and are preferred embodiments of the compounds
of formula (I) according to the present invention.

| Compound Number | Structure | $^1$H NMR δ (delta) (CDCl$_3$ unless stated), or other physical data |
|---|---|---|
| P1 | 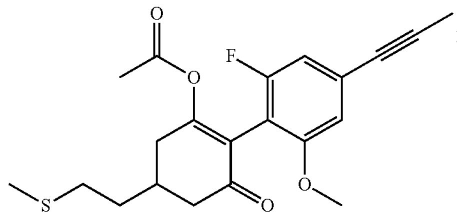 [SMILES: CC#Cc1cc(F)c(C2=C(OC(C)=O)CC(CCSC)CC2=O)c(OC)c1] | $^1$H NMR (500 MHz, CDCl$_3$) 1.75-1.88 (m, 2H), 1.97(d, 3H), 2.00-2.06 (m, 3H), 2.10-2.15 (m, 3H), 2.30-2.39 (m, 1H), 2.49 (d, 1H), 2.54-2.62 (m, 2H), 2.65-2.84 (m, 3H), 3.76-3.81 (m, 3H), 6.58 (dt, 1H), 6.78 (s, 1H) |

The compounds of the following Tables 1 to 46 are also particular and/or preferred embodiments of the compounds of formula (I) according to the present invention.

For the most part, these compounds can generally be prepared by method(s) similar to those disclosed in the Examples hereinabove and/or disclosed in the "Processes for preparation of compounds" section hereinabove using appropriate starting materials, and/or in an analogous manner.

Table 1 covers 28 compounds of the following formula

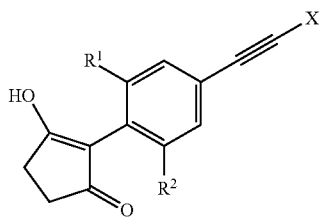

wherein X, R$^1$ and R$^2$ are as defined in Table 1.

TABLE 1

| Compound Number | R$^1$ | R$^2$ | X |
|---|---|---|---|
| 1.01 | fluorine | methoxy | methyl |
| 1.02 | fluorine | ethoxy | methyl |
| 1.03 | fluorine | trifluoromethoxy | methyl |
| 1.04 | fluorine | difluoromethoxy | methyl |
| 1.05 | fluorine | 2,2,2-trifluoroethoxy | methyl |
| 1.06 | fluorine | 2-methoxyethoxy | methyl |
| 1.07 | fluorine | ethynyl | methyl |
| 1.08 | fluorine | methoxy | chlorine |
| 1.09 | fluorine | ethoxy | chlorine |
| 1.10 | fluorine | trifluoromethoxy | chlorine |
| 1.11 | fluorine | difluoromethoxy | chlorine |
| 1.12 | fluorine | 2,2,2-trifluoroethoxy | chlorine |
| 1.13 | fluorine | 2-methoxyethoxy | chlorine |
| 1.14 | fluorine | ethynyl | chlorine |
| 1.15 | bromine | methoxy | methyl |
| 1.16 | bromine | ethoxy | methyl |
| 1.17 | bromine | trifluoromethoxy | methyl |
| 1.18 | bromine | difluoromethoxy | methyl |
| 1.19 | bromine | 2,2,2-trifluoroethoxy | methyl |
| 1.20 | bromine | 2-methoxyethoxy | methyl |
| 1.21 | bromine | ethynyl | methyl |
| 1.22 | bromine | methoxy | chlorine |
| 1.23 | bromine | ethoxy | chlorine |
| 1.24 | bromine | trifluoromethoxy | chlorine |
| 1.25 | bromine | difluoromethoxy | chlorine |

TABLE 1-continued

| Compound Number | R$^1$ | R$^2$ | X |
|---|---|---|---|
| 1.26 | bromine | 2,2,2-trifluoroethoxy | chlorine |
| 1.27 | bromine | 2-methoxyethoxy | chlorine |
| 1.28 | bromine | ethynyl | chlorine |

Table 2 covers 28 compounds of the following formula

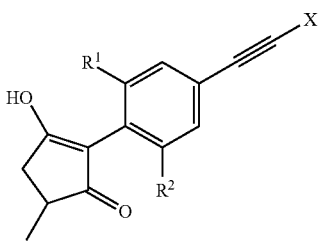

wherein X, R$^1$ and R$^2$ are as defined in Table 1.

Table 3 covers 28 compounds of the following formula

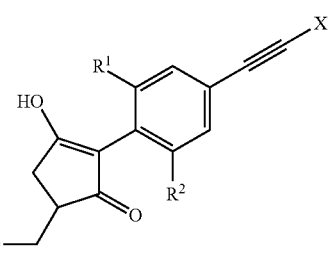

wherein X, R$^1$ and R$^2$ are as defined in Table 1.

Table 4 covers 28 compounds of the following formula

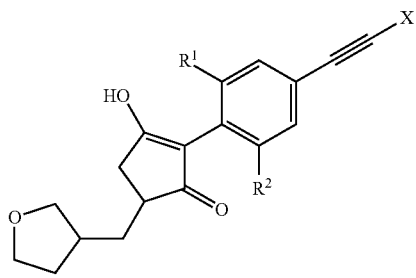

wherein X, R$^1$ and R$^2$ are as defined in Table 1.

Table 5 covers 28 compounds of the following formula

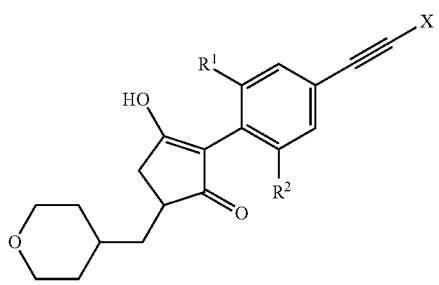

wherein X, R$^1$ and R$^2$ are as defined in Table 1.

Table 6 covers 28 compounds of the following formula

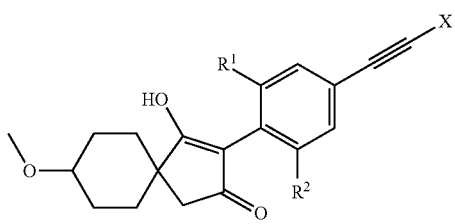

wherein X, R$^1$ and R$^2$ are as defined in Table 1.

Table 7 covers 28 compounds of the following formula

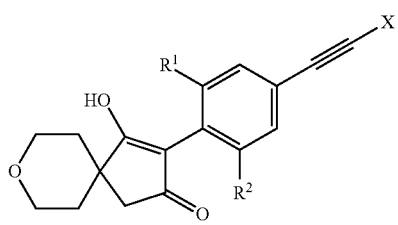

wherein X, R$^1$ and R$^2$ are as defined in Table 1.

Table 8 covers 28 compounds of the following formula

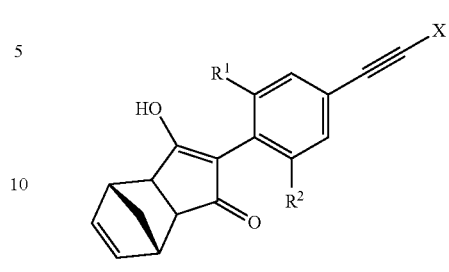

wherein X, R$^1$ and R$^2$ are as defined in Table 1.

Table 9 covers 28 compounds of the following formula

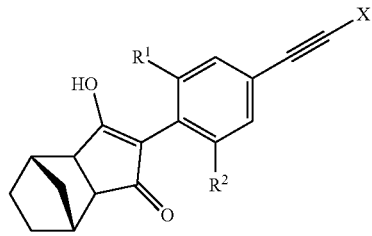

wherein X, R$^1$ and R$^2$ are as defined in Table 1.

Table 10 covers 28 compounds of the following formula

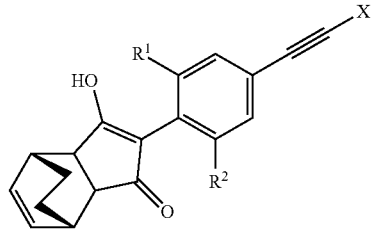

wherein X, R$^1$ and R$^2$ are as defined in Table 1.

Table 11 covers 28 compounds of the following formula

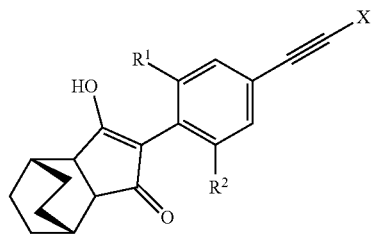

wherein X, R$^1$ and R$^2$ are as defined in Table 1.

Table 12 covers 28 compounds of the following formula

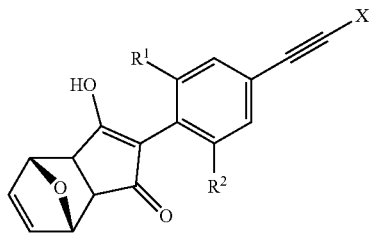

wherein X, R¹ and R² are as defined in Table 1.

Table 13 covers 28 compounds of the following formula

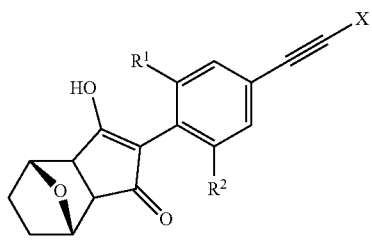

wherein X, R¹ and R² are as defined in Table 1.

Table 14 covers 28 compounds of the following formula

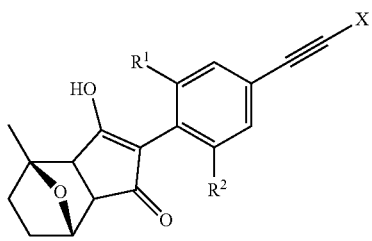

wherein X, R¹ and R² are as defined in Table 1.

Table 15 covers 28 compounds of the following formula

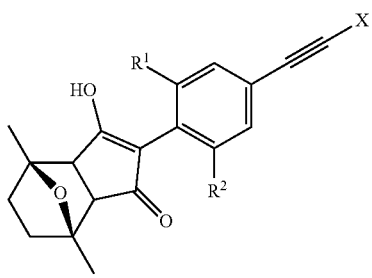

wherein X, R¹ and R² are as defined in Table 1.

Table 16 covers 28 compounds of the following formula

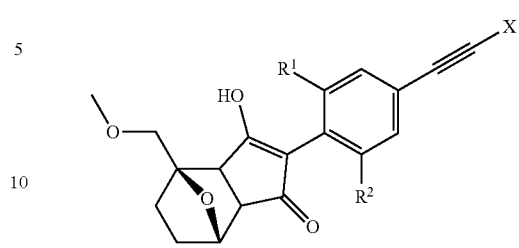

wherein X, R¹ and R² are as defined in Table 1.

Table 17 covers 28 compounds of the following formula

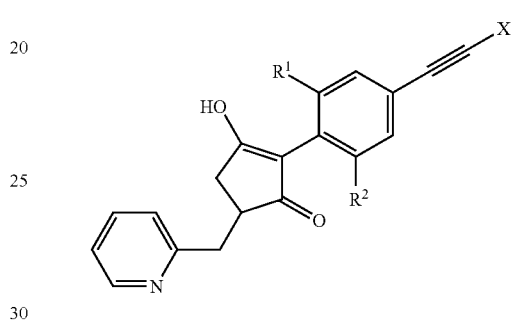

wherein X, R¹ and R² are as defined in Table 1.

Table 18 covers 28 compounds of the following formula

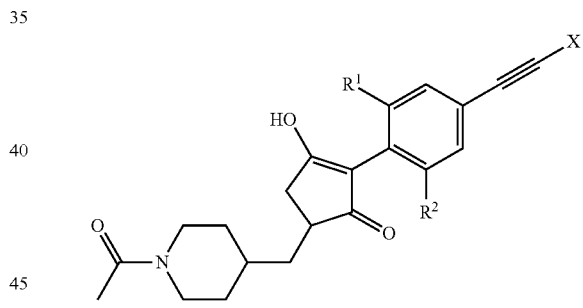

wherein X, R¹ and R² are as defined in Table 1.

Table 19 covers 28 compounds of the following formula

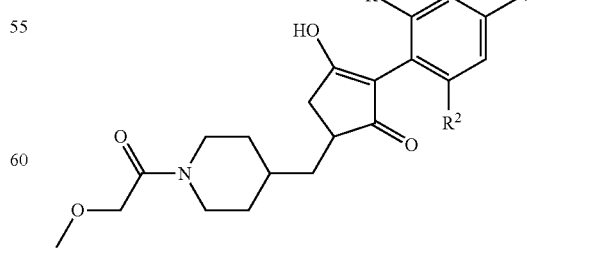

wherein X, R¹ and R² are as defined in Table 1.

Table 20 covers 28 compounds of the following formula

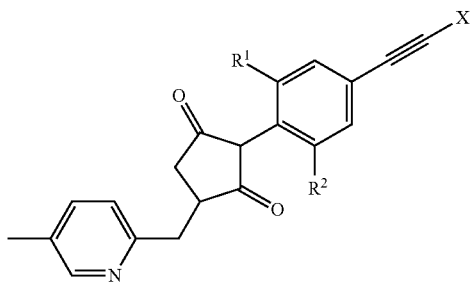

wherein X, R¹ and R² are as defined in Table 1.

Table 21 covers 28 compounds of the following formula

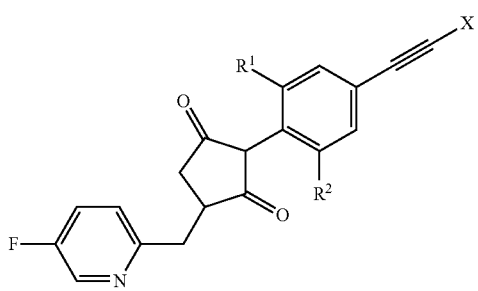

wherein X, R¹ and R² are as defined in Table 1.

Table 22 covers 28 compounds of the following formula

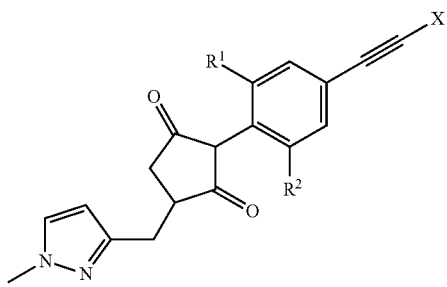

wherein X, R¹ and R² are as defined in Table 1.

Table 23 covers 28 compounds of the following formula

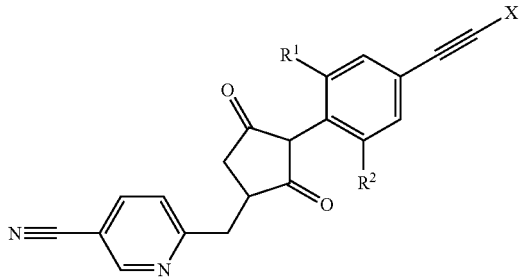

wherein X, R¹ and R² are as defined in Table 1.

Table 24 covers 28 compounds of the following type

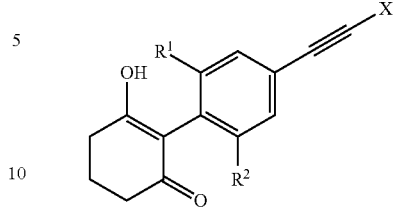

wherein $R_1$, $R_2$ and X are as defined in Table 1.

Table 25 covers 28 compounds of the following type

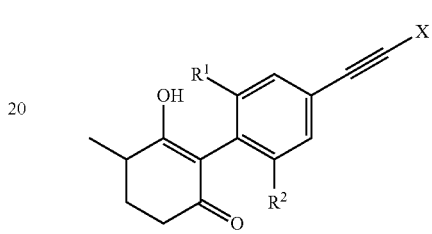

wherein $R_1$, $R_2$ and X are as defined in Table 1.

Table 26 covers 28 compounds of the following type

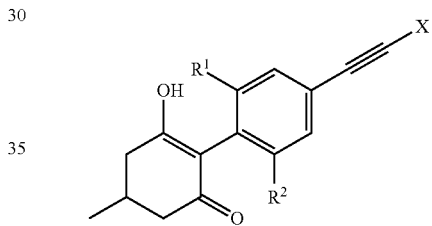

wherein $R_1$, $R_2$ and X are as defined in Table 1.

Table 27 covers 28 compounds of the following type

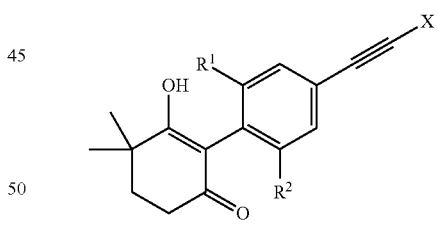

wherein $R_1$, $R_2$ and X are as defined in Table 1.

Table 28 covers 28 compounds of the following type

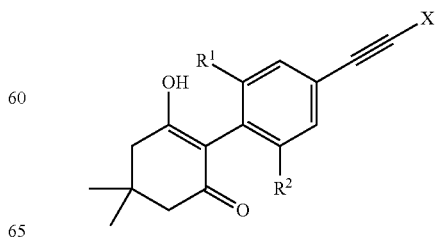

wherein $R_1$, $R_2$ and X are as defined in Table 1.

Table 29 covers 28 compounds of the following type

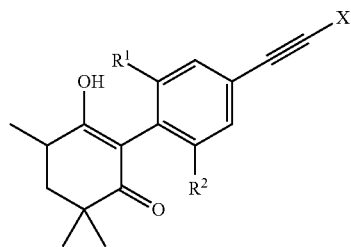

wherein $R_1$, $R_2$ and X are as defined in Table 1.

Table 30 covers 28 compounds of the following type

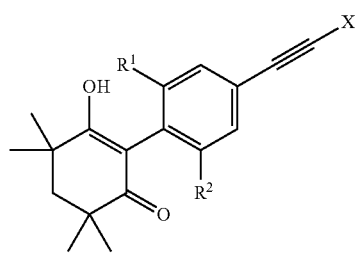

wherein $R_1$, $R_2$ and X are as defined in Table 1.

Table 31 covers 28 compounds of the following type

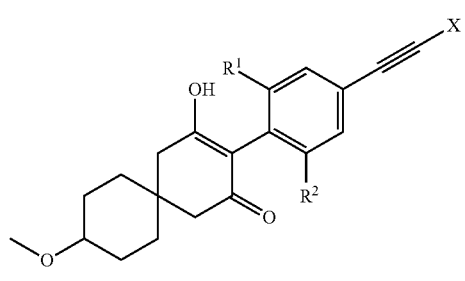

wherein $R_1$, $R_2$ and X are as defined in Table 1.

Table 32 covers 28 compounds of the following type

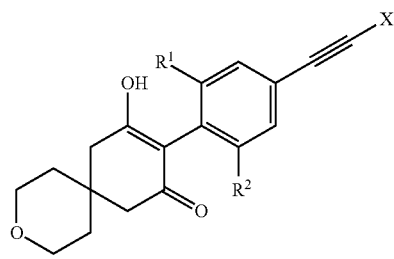

wherein $R_1$, $R_2$ and X are as defined in Table 1.

Table 33 covers 28 compounds of the following type

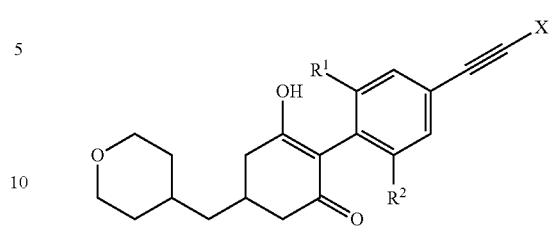

wherein $R_1$, $R_2$ and X are as defined in Table 1.

Table 34 covers 28 compounds of the following type

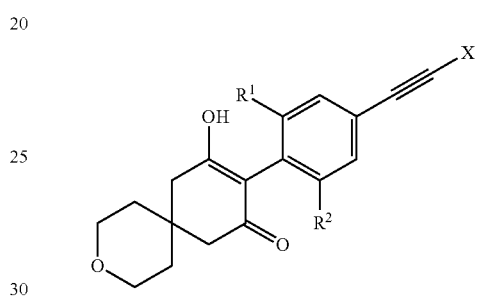

wherein $R_1$, $R_2$ and X are as defined in Table 1.

Table 35 covers 28 compounds of the following type

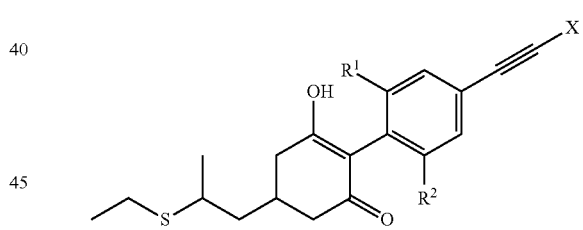

wherein $R_1$, $R_2$ and X are as defined in Table 1.

Table 36 covers 28 compounds of the following type

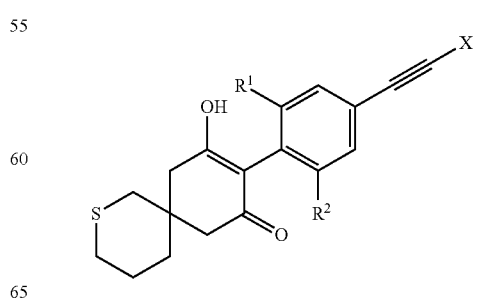

wherein $R_1$, $R_2$ and X are as defined in Table 1.

Table 37 covers 28 compounds of the following type

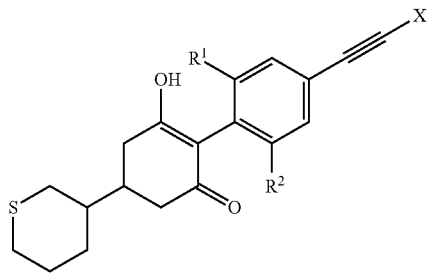

wherein $R_1$, $R_2$ and X are as defined in Table 1.

Table 38 covers 28 compounds of the following type

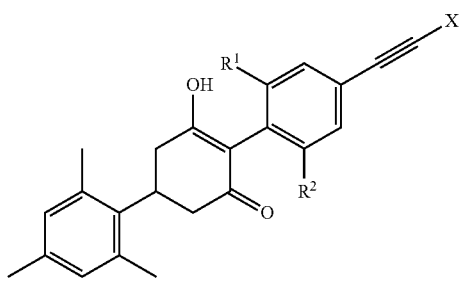

wherein $R_1$, $R_2$ and X are as defined in Table 1.

Table 39 covers 28 compounds of the following type

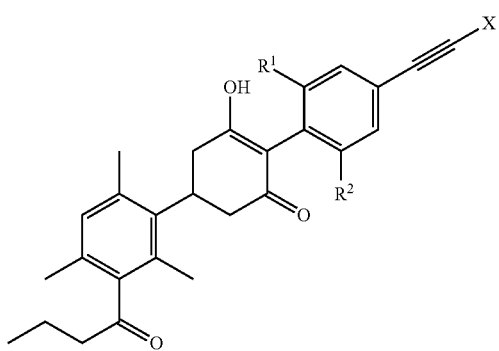

wherein $R_1$, $R_2$ and X are as defined in Table 1.

Table 40 covers 28 compounds of the following type

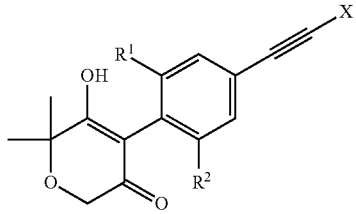

wherein $R_1$, $R_2$ and X are as defined in Table 1.

Table 41 covers 28 compounds of the following type

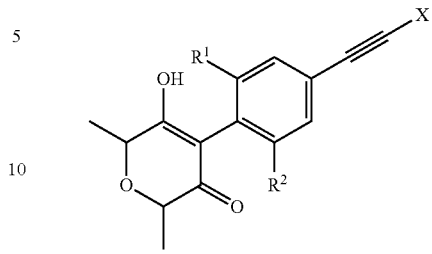

wherein $R_1$, $R_2$ and X are as defined in Table 1.

Table 42 covers 28 compounds of the following type

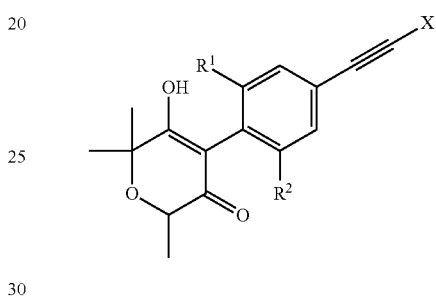

wherein $R_1$, $R_2$ and X are as defined in Table 1.

Table 43 covers 28 compounds of the following type

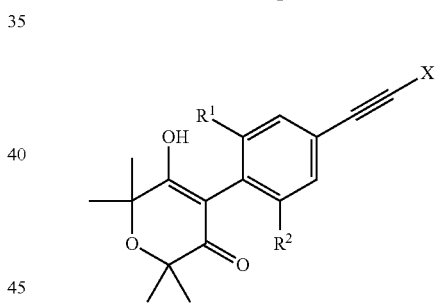

wherein $R_1$, $R_2$ and X are as defined in Table 1.

Table 44 covers 28 compounds of the following type

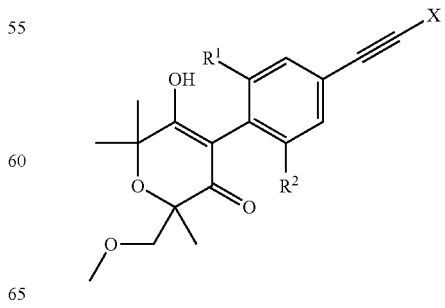

wherein $R_1$, $R_2$ and X are as defined in Table 1.

Table 45 covers 28 compounds of the following type

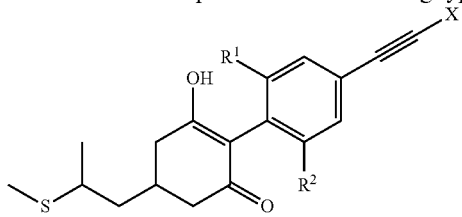

wherein R$_1$, R$_2$ and X are as defined in Table 1.

Table 46 covers 28 compounds of the following type

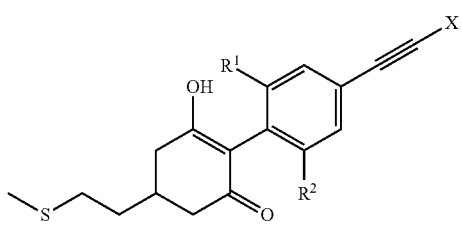

wherein R$_1$, R$_2$ and X are as defined in Table 1.

BIOLOGICAL EXAMPLES

Biological Example 1

Glasshouse Assay for Herbicidal Activity

Seeds of a variety of test plant species were sown in standard soil ** in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient (the test herbicide) in acetone/water (50:50) solution containing 0.5% Tween 20 (polyoxyethylene sorbitan monolaurate, CAS Reg. No. 9005-64-5). The test plants were then grown on under controlled conditions in a glasshouse (at 24/16° C., day/night; 14 hours light; 65% humidity) and watered twice daily. 13 Days after application of the test herbicide, for pre- and post-emergence, the test was evaluated visually for percentage phytotoxicity to each plant (where 100%=total damage to plant; 0%=no damage to plant). Generally, each test herbicide is only tested on 1 plant per plant species for each application rate tested and for each application timing.

** The "standard soil" in Biological Example 1 is usually a "sand" or "sandy loam" type of soil.

Biological Example 1A

Post-Emergence Application—Herbicidal Activity Results (Percentage Phytotoxicity)

Test Weeds:

Dicotyledonous weeds: ABUTH=*Abutilon theophrasti*; AMARE=*Amaranthus retroflexus*. Grassy monocotyledonous weeds: SETFA=*Setaria faberi*; ALOMY=*Alopecurus myosuroides*; ECHCG=*Echinochloa crus-galli*; ZEAMX=*Zea mays* (corn, maize, e.g. volunteer corn). For Compound A16, the grassy monocotyledonous weed LOLPE (*Lolium perenne*) was used in the test insterad of ALOMY.

The results are shown in the table below.

| Compound No. | Application Rate (g/ha) | ABUTH | AMARE | SETFA | ALOMY | ECHCG | ZEAMX | LOLPE |
|---|---|---|---|---|---|---|---|---|
| A8 | 250 | 70 | 0 | 100 | 90 | 100 | 100 | — |
| A8 | 30 | 0 | 0 | 80 | 70 | 100 | 100 | — |
| A9 | 250 | 30 | 20 | 80 | 20 | 70 | 90 | — |
| A9 | 30 | 0 | 0 | 70 | 0 | 60 | 70 | — |
| A10 | 250 | 0 | 0 | 90 | 80 | 80 | 90 | — |
| A10 | 30 | 0 | 0 | 70 | 40 | 50 | 40 | — |
| A11 | 250 | 10 | 50 | 60 | 10 | 10 | 20 | — |
| A11 | 30 | 0 | 30 | 30 | 0 | 0 | 20 | — |
| A12 | 250 | 0 | 0 | 0 | 0 | 20 | 30 | — |
| A14 | 250 | 0 | 10 | 70 | 40 | 20 | 80 | — |
| A16 | 250 | 70 | 10 | 90 | — | 100 | 100 | 90 |
| A16 | 30 | 0 | 0 | 70 | — | 90 | 90 | 70 |
| B2 | 250 | 0 | 0 | 60 | 10 | 30 | 40 | — |

Note:
A [—] in the table above indicates that that compound was not tested on that plant.

The above results from Biological Example 1A appear to show that Compound A14, within the present formula (I), having a 2-fluoro-6-methoxy-4-(prop-1-ynyl)-phenyl moiety attached to the 2-position of a oxygen-containing-spirocyclic cyclohexane-1,3-dione (A14 is

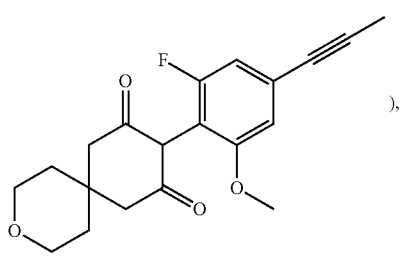 [SMILES: CC#Cc1cc(F)c(C2C(=O)CC3(CCOCC3)CC2=O)c(OC)c1]

is a more potent herbicide against the grassy monocotyledonous weeds ALOMY (*Alopecurus myosuroides*) and ZEAMX (*Zea mays*, corn e.g. volunteer corn), and perhaps also SETFA (*Setaria faberi*), than compound B2 which has a 2-fluoro-6-methoxy-4-ethynyl-phenyl moiety attached to the 2-position of the same oxygen-containing-spirocyclic cyclohexane-1,3-dione (B2 is

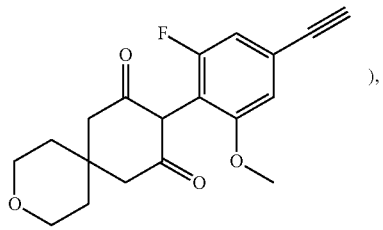 [SMILES: C#Cc1cc(F)c(C2C(=O)CC3(CCOCC3)CC2=O)c(OC)c1]

), when applied post-emergence at 250 g/ha under the conditions stated in Biological Example 1A.

Biological Example 1B

Pre-Emergence Application—Herbicidal Activity Results (Percentage Phytotoxicity)

Test Weeds:
Dicotyledonous weeds: ABUTH=*Abutilon theophrasti*; AMARE=*Amaranthus retroflexus*. Grassy monocotyledonous weeds: SETFA=*Setaria faberi*; ALOMY=*Alopecurus myosuroides*; ECHCG=*Echinochloa crus-galli*; ZEAMX=*Zea mays* (corn, maize, e.g. volunteer corn). For Compound A16, the grassy monocotyledonous weed LOLPE (*Lolium perenne*) was used in the test insterad of ALOMY.

polyoxyethylene glycols and free fatty acids in isopropanol, CAS Registry number 11097-66-8), as the aqueous diluent, to form an aqueous spray solution which contains a predetermined concentration of the active ingredient (which varies depending on the application rate of the active ingredient to the plants) and 0.2% v/v of the adjuvant X-77. This aqueous spray solution is then sprayed onto the plants, after one day's cultivation (for pre-emergence) or after about 12 days' cultivation (for post-emergence).

TABLE

Composition of the mixture of organic solvents and emulsifier to be used as a base for the instant formulation (IF50).

| Component | Supplier | Chemical description | CAS Registry number | Amount/ % w/w |
|---|---|---|---|---|
| Emulsogen EL360 ™ | Clariant | castor oil ethoxylate (as emulsifier) | 61791-12-6 | 11.12 |
| N-methyl-pyrrolidone | widely available | 1-methyl-2-pyrrolidone | 872-50-4 | 44.44 |
| Dowanol DPM ™ glycol ether | Dow | dipropylene glycol monomethyl ether | 34590-94-8 | 44.44 |

The test plants are then grown on, in a glasshouse (greenhouse) under controlled conditions (at either 24/18° C. or 20/16° C. (day/night) as mentioned above; 16 hours light; 65% humidity) and are watered twice daily. Either 14 or 15 days after application of the herbicide (14 or 15 DAA) (for post-emergence), or 20 days after application of the herbicide (20 DAA) (for pre-emergence), the test plants are

| Compound No. | Application Rate (g/ha) | ABUTH | AMARE | SETFA | ALOMY | ECHCG | ZEAMX | LOLPE |
|---|---|---|---|---|---|---|---|---|
| A8 | 250 | 0 | 0 | 90 | 90 | 100 | 100 | — |
| A9 | 250 | 0 | 20 | 80 | 30 | 80 | 80 | — |
| A10 | 250 | 0 | 0 | 70 | 50 | 90 | 50 | — |
| A14 | 250 | 0 | 20 | 20 | 40 | 70 | 30 | — |
| A16 | 250 | 0 | 30 | 70 | — | 90 | 90 | 90 |
| B2 | 250 | 0 | 40 | 30 | 50 | 40 | 50 | — |

Note:
A [—] in the table above indicates that that compound was not tested on that plant.

Biological Example 2

Glasshouse Assay for Herbicidal Activity

Seeds of a variety of monocotyledonous and dicotyledonous test plants are sown in standard soil in pots. The plants are cultivated for one day (for pre-emergence) or for about 12 days (range=10-13 days) (for post-emergence) under controlled conditions in a glasshouse (warm climate species at 24/18° C., cool climate species at 20/16° C., both at day/night; 16 hours light; 65% humidity).
An "instant formulation", known as the "IF50", containing 50 g/litre (i.e. 5% w/v) of the "technical" (i.e. unformulated) active ingredient is prepared by dissolving the active ingredient in a mixture of organic solvents and emulsifier, details of which are provided in the Table below. This IF50 is then mixed with a small, variable amount of acetone to aid dissolution, before addition of a 0.2% v/v aqueous solution of the adjuvant X-77 (which is a mixture of alkyl aryl evaluated visually, and an assessed percentage phytotoxicity score is given for each herbicidal application on each plant species (where 100%=total damage to plant; 0%=no damage to plant).

Some of the typical test plants are as follows:

Cool climate crop plants: *Triticum aestivum* (TRZAW, winter wheat), *Brassica napus* (BRSNN, rape, also called oilseed rape or rapeseed), *Beta vulgaris* (BEAVA, sugarbeet). Warm climate crop plants: *Glycine max* (GLXMA, soybean).

Cool climate ("cool season") grassy monocotyledonous weeds: *Alopecurus myosuroides* (ALOMY), *Avena fatua* (AVEFA), *Lolium perenne* (LOLPE), *Poa annua* (POAAN), *Bromus tectorum* (BROTE).

Warm climate ("warm season") grassy monocotyledonous weeds: *Setaria faberi* (SETFA), SORVU (*Sorghum bicolor* (L.) Moench ssp. Bicolor, or *Sorghum vulgare* Pers.), *Digitaria sanguinalis* (DIGSA), *Echinochloa crus-galli*

(ECHCG), *Brachiaria plantaginea* (BRAPL), *Zea mays* (ZEAMX, corn, maize, e.g. volunteer corn), *Panicum miliaceum* (PANMI).

Biological Example 2

Post-Emergence Herbicidal Activity Results

| Compound Number | Appl. Rate (g/ha) | TRZAW | ZEAMX | GLXMA | BRSNN | BEAVA | ALOMY |
|---|---|---|---|---|---|---|---|
| A8 | 250 g/ha | 70 | 100 | 30 | 60 | 10 | 70 |
| A8 | 125 g/ha | 50 | 100 | 10 | 40 | 10 | 50 |

| Compound Number | AVEFA | LOLPE | SETFA | SORVU | DIGSA | ECHCG | BRAPL |
|---|---|---|---|---|---|---|---|
| A8 | 70 | 80 | 100 | 100 | 100 | 100 | 100 |
| A8 | 30 | 30 | 90 | 100 | 100 | 100 | 100 |

Note:
Extra data from Biological Example 2 is as follows: Compound A8 of the present invention showed phytotoxicity versus *Poa annua* (POAAN) of 80%, when applied post-emergence at 250 g/ha. Compound A8 of the present invention showed phytotoxicity versus *Bromus tectorum* (BROTE) of 70%, when applied post-emergence at 250 g/ha. Compound A8 of the present invention showed phytotoxicity versus *Panicum miliaceum* (PANMI) of 100% and 100%, when applied post-emergence at 250 and 125 g/ha.

Biological Example 3

Assay for Biological Example 3

Glasshouse Assay for Herbicidal Activity, Using Various Adjuvant Systems

Materials and Methods
Herbicide Application:
Post-emergence foliar spray application, 200 L/ha, usually one or two replicates for the weeds (depending on application rate), and two replicates for soybean.
Climate:
Standard warm conditions (tropical), in glasshouse. Specifically, the glasshouse bay conditions are 24° C./18° C. day/night; 16/8 hours light/dark; 65% humidity.
Plants:
The herbicidal application takes place at the following growth stages for plants which include inter alia one or more of the following plants (usually the herbicidal application takes place on at least the following plants: DIGSA, ELEIN, SETFA, ZEAMX, GLXMA Nikko, and GLXMA TMG133, and often also either BRADC or BRAPP):
*Brachiaria decumbens* (BRADC)—growth stage (GS) 12 or 13 (or GS 12)—or, if BRADC is not used, then usually
*Brachiaria platyphylla* (BRAPP)—growth stage 12 or 13
*Digitaria sanguinalis* (DIGSA)—growth stage 12 or 13
*Eleusine indica* (ELEIN)—growth stage 12 or 13
*Setaria faberi* (SETFA)—growth stage 12 or 13
*Echinochloa crus-galli* (ECHCG)—growth stage 12 or 13
*Sorghum halepense* (annual) (SORHA)—growth stage 12 or 13
*Panicum dichotomiflorum* (PANDI)—growth stage 12 or 13
*Zea mays* (ZEAMX, maize/corn, e.g. can occur as volunteer corn) cultivar "Garland"—growth stage 12 or 13
*Glycine max* (GLXMA, soybean) cultivar "Nikko"—growth stage: 1st trifoliate
*Glycine max* (GLXMA, soybean) cultivar "TMG133"—which is Roundup Ready™ glyphosate-tolerant soybean cultivar TMG133 (typically available from Monsanto in Brazil)—growth stage: 1st trifoliate.

Herbicidal Compositions Tested:
Each test compound is applied with one of the following adjuvant systems (all percentages are final concentrations in the aqueous spray mixture):
Adjuvant system 1: 0.5% v/v Adigor™ *, 1.0% v/v AMS (ammonium sulphate) and 12.5% v/v IPA (isopropyl alcohol).
Adjuvant system 1A: 0.5% v/v Adigor™ * and 12.5% v/v IPA (isopropyl alcohol).
Adjuvant system 2: 0.5% v/v Hexamoll™ DINCH **, 1.0% v/v AMS (ammonium sulphate) and 12.5% v/v IPA (isopropyl alcohol).
Adjuvant system 3: 0.5% v/v tris-(2-ethylhexyl) phosphate ("TEHP"), 1.0% v/v AMS (ammonium sulphate) and 12.5% v/v IPA (isopropyl alcohol).
* Adigor™ (currently available in many countries from Syngenta) is an emulsifiable concentrate which consists of:
(i) ethoxylated alcohols, which typically includes ethoxylated higher alcohols (e.g. ethoxylates of alcohols wherein the alcohols are within the range of $C_{12}$-$C_{22}$); and
(ii) a mixture of heavy aromatic hydrocarbons, which typically includes (e.g. includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and
(iii) about 47% w/w and/or about 45% w/v (with respect to the emulsifiable concentrate) of methylated rapeseed oil (rapeseed oil methyl ester) (e.g. Agnique ME 18 RD-F™), as an adjuvant.
** Hexamoll™ DINCH™ is 1,2-cyclohexane dicarboxylic acid di-isononyl ester

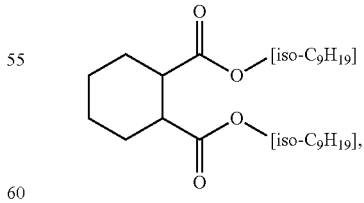

CAS Registry no. 166412-78-8), and is usually available from BASF. "Isononyl" in this context is thought to mean a mixture of two or more branched isomers of $C_9H_{19}$.
Method:
Seeds of the weed (including volunteer) plants, typically including inter alia *Digitaria sanguinalis* (DIGSA), *Eleusine* indica (ELEIN), *Setaria faberi* (SETFA), *Zea mays* (ZEAMX, corn), and sometimes also [either *Brachiaria decumbens* (BRADC) or *Brachiaria platyphylla* (BRAPP)], are sown in seed trays (troughs) containing clay loam soil (pH 7.0, 2.2% organic matter, "Trough Mix A"); and soybean seed is sown in pots containing the same soil with 3 soybean seedlings per pot. The plants are sprayed with the test herbicide when they reach the growth stages mentioned above.

The test herbicidal solutions are prepared by mixing the appropriate aliquots of the test substance(s) and one of the adjuvant systems indicated above *** in deionised water to give the desired treatment concentration.

The herbicidal application is made as a foliar spray, using a tracksprayer. Following the herbicidal application, the plants are watered twice per day for the duration of the test. A visual assessment of the % herbicidal damage is made 7 and 14 Days After herbicide Application (DAA) (or, in a minority of cases, 7 and 15 DAA), and the results are recorded as % visual herbicidal damage where 0%=no damage to plants and 100%=plant totally killed.

*** Adjuvant system=either Adigor™ or Hexamoll DINCH™ or tris-(2-ethylhexyl) phosphate each at 0.5% v/v, and 12.5% v/v IPA (isopropyl alcohol), and 1.0% v/v AMS (ammonium sulphate); or 0.5% v/v Adigor™ and 12.5% v/v IPA (isopropyl alcohol); all percentages are final concentrations in the aqueous spray mixture.

Biological Example 3

Post-Emergence Activity—Results at 14 or 15 Days after Herbicide Application

Compounds A8, A11 and A17, which are compounds of formula (I) according to the present invention, were tested in a test method substantially as described above.

Compound A8 was tested using the 0.5% v/v Adigor™+12.5% v/v IPA adjuvant system. Compounds A11 and A17 were tested using the 0.5% v/v Adigor™+1.0% v/v AMS+12.5% v/v IPA adjuvant system.

The percentages of herbicidal damage/plant control, at 14 Days After herbicide Application (DAA) (or, in a minority of cases, at 15 DAA), for the Compounds tested and for some of the plants tested, were in the following percentage ranges. At least for Compounds A8 and A17, the phytotoxicity results shown herein are the average of 2 repetitions (for the grassy weeds, corn and soybean).

Control of *Brachiaria decumbens* (BRADC), a Warm-Climate (Warm-Season) Grassy Weed At 14 DAA (or at 14 or 15 DAA for A11), Compounds A8, A11 and A17 showed percentage control of (phytotoxicity on) *Brachiaria decumbens* (BRADC) of 0%, when applied post-emergence at an application rate of 8 g/ha.

Control of *Digitaria sanguinalis* (DIGSA), a Warm-Climate (Warm-Season) Grassy Weed At 14 DAA, Compound A8 showed a percentage control of (phytotoxicity on) *Digitaria sanguinalis* (DIGSA) of 65%, when applied post-emergence at an application rate of 8 g/ha.

At 14 or 15 DAA, Compound A11 showed a percentage control of *Digitaria sanguinalis* (DIGSA) of 0%, when applied post-emergence at an application rate of 8 g/ha.

At 14 DAA, Compound A17 showed a percentage control of *Digitaria sanguinalis* (DIGSA) of 0%, when applied post-emergence at an application rate of 8 g/ha.

Control of *Eleusine indica* (ELEIN), a Warm-Climate (Warm-Season) Grassy Weed

At 14 DAA, Compound A8 showed a percentage control of (phytotoxicity on) *Eleusine indica* (ELEIN) of 40%, when applied post-emergence at an application rate of 8 g/ha.

At 14 or 15 DAA, Compound A11 showed a percentage control of *Eleusine indica* (ELEIN) of 0%, when applied post-emergence at an application rate of 8 g/ha.

At 14 DAA, Compound A17 showed a percentage control of *Eleusine indica* (ELEIN) of 0%, when applied post-emergence at an application rate of 8 g/ha.

Control of *Setaria faberi* (SETFA), a Warm-Climate (Warm-Season) Grassy Weed

At 14 DAA, Compound A8 showed a percentage control of (phytotoxicity on) *Setaria faberi* (SETFA) of 75%, when applied post-emergence at an application rate of 8 g/ha.

At 14 or 15 DAA, Compound A11 showed a percentage control of *Setaria faberi* (SETFA) of 0%, when applied post-emergence at an application rate of 8 g/ha.

At 14 DAA, Compound A17 showed a percentage control of *Setaria faberi* (SETFA) of 0%, when applied post-emergence at an application rate of 8 g/ha.

Control of *Zea mays* (ZEAMX, Corn), a Warm-Climate (Warm-Season) Grassy Plant

*Zea mays* (ZEAMX, maize, corn) is often present as a "volunteer" weed ("volunteer" corn) in fields where it was planted as a crop in preceding growing season(s) and where the present field crop is not corn.

At 14 DAA, Compound A8 showed a percentage control of (phytotoxicity on) *Zea mays* (ZEAMX, maize, corn) of 65%, when applied post-emergence at an application rate of 8 g/ha.

At 14 or 15 DAA, Compound A11 showed a percentage control of *Zea mays* (ZEAMX, maize, corn) of 0%, when applied post-emergence at an application rate of 8 g/ha.

At 14 DAA, Compound A17 showed a percentage control of *Zea mays* (ZEAMX, maize, corn) of 0%, when applied post-emergence at an application rate of 8 g/ha.

Phytotoxicity on *Glycine max* (GLXMA, Soybean) Cultivar "Nikko"

At 14 DAA, Compound A8 showed a percentage phytotoxicity on *Glycine max* (GLXMA, soybean) cultivar "Nikko" of 30%, when applied post-emergence at an application rate of 120 g/ha.

At 14 or 15 DAA, Compound A11 showed a percentage phytotoxicity on *Glycine max* (GLXMA, soybean) cultivar "Nikko" of 5% and 5%, when applied post-emergence at an application rate of 120 and 240 g/ha respectively.

At 14 DAA, Compound A17 showed a percentage phytotoxicity on *Glycine max* (GLXMA, soybean) cultivar "Nikko" of 5% and 7.5%, when applied post-emergence at an application rate of 120 and 240 g/ha respectively.

Phytotoxicity on *Glycine max* (GLXMA, Soybean) Cultivar "TMG133"

*Glycine max* (GLXMA, soybean) cultivar "TMG133" is Roundup Ready™ glyphosate-tolerant soybean cultivar TMG133, and is typically available from Monsanto in Brazil.

At 14 DAA, Compound A8 showed a percentage phytotoxicity on *Glycine max* (GLXMA, soybean) cultivar "TMG133" of 17.5%, when applied post-emergence at an application rate of 120 g/ha.

At 14 or 15 DAA, Compound A11 showed a percentage phytotoxicity on *Glycine max* (GLXMA, soybean) cultivar "TMG133" of 5% and 5%, when applied post-emergence at an application rate of 120 and 240 g/ha respectively.

At 14 DAA, Compound A17 showed a percentage phytotoxicity on *Glycine max* (GLXMA, soybean) cultivar "TMG133" of 5% and 7.5%, when applied post-emergence at an application rate of 120 and 240 g/ha respectively.

The invention claimed is:

1. A compound of formula (I):

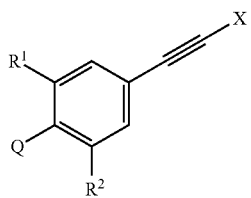

wherein:
X is methyl or chlorine;
$R^1$ is fluorine or bromine;
$R^2$ is ethynyl, $C_1$-$C_3$alkoxy-, $C_1$-$C_3$haloalkoxy-, or $C_1$-$C_3$alkoxy-$C_1$-$C_3$alkoxy-; and
Q is a group of either formula Q1 or Q2:

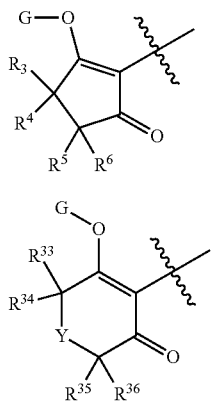

wherein:
$R^3$, $R^4$ and $R^5$, independently of each other, are hydrogen, $C_1$-$C_5$alkyl, $C_2$-$C_4$alkenyl, $C_2$-$C_4$alkynyl, $C_1$-$C_2$fluoroalkyl or $C_1$-$C_3$alkoxy$C_1$-$C_3$alkyl;
$R^6$ is hydrogen, $C_1$-$C_5$alkyl, $C_2$-$C_4$alkenyl, $C_2$-$C_4$alkynyl, $R^{6AA}$—C≡C—$CH_2$—, $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkyl-sulfonyl$C_1$-$C_3$alkyl, $C_3$-$C_4$cycloalkyl, or an unsubstituted 4-, 5- or 6-membered monocyclic heterocyclyl having one ring heteroatom independently selected from oxygen, sulfur and nitrogen, and attached at a ring carbon atom within the heterocyclyl,
or $R^6$ is T-$(CH_2)_m$—CH($R^7$)—, wherein m is 0 or 1 and either $R^7$ is hydrogen or $R^7$ and $R^5$ together are a bond, and T is an optionally substituted heterocyclyl as defined below;
or $R^6$ is Het-CH($R^8$)—, wherein either $R^8$ is hydrogen or $R^8$ and $R^5$ together are a bond, and Het is an optionally substituted heteroaryl as defined below;
or $R^6$ is $C_3$-$C_6$cycloalkyl$C_1$-$C_2$alkyl-; or is $C_4$-$C_6$cycloalkyl$C_1$-$C_2$alkyl-, substituted at a cycloalkyl ring-carbon atom which is not the ring-carbon atom attached to the —$C_1$-$C_2$alkyl- moiety and which is not bonded directly to the ring-carbon atom attached to the —$C_1$-$C_2$alkyl- moiety, by one or two ring substituents which independently are: =N—O—$R^{10}$, oxo (=O), $C_1$-$C_4$alkoxy, $C_1$-$C_2$haloalkoxy, 2-($C_1$-$C_3$alkoxy)-ethoxy, $C_3$-$C_5$cycloalkyloxy, ($C_3$-$C_5$cycloalkyl)methoxy, $C_2$-$C_3$alkenyl-$CH_2$-oxy, $C_1$-$C_3$alkyl or $C_1$-$C_2$fluoroalkyl; or benzyloxy in which the phenyl ring is optionally substituted by one or two substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, $S(O)R^{6E}$, —$S(O)_2$—$R^{6E}$, —N($R^{6F}$)($R^{6G}$), hydroxy, $C_2$-$C_3$alkenyl, —C($R^{6BB}$)=($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro;
or $R^6$ is benzyl optionally substituted on its phenyl ring by one or two substituents which independently are: $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, $S(O)R^{6E}$, $S(O)_2R^{6E}$, —$S(O)_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro; or $R^3$ and $R^4$ taken together are —$(CH_2)_{n1}$— or —$(CH_2)_{n2}$—$X^1$—$(CH_2)_{n3}$— and $R^5$ and $R^6$ are as defined above,
or $R^5$ and $R^6$ taken together are —$(CH_2)_{n1}$— or —$(CH_2)_{n2}$—$X^1$—$(CH_2)_{n3}$— and $R^3$ and $R^4$ are as defined above
or $R^4$ and $R^6$ taken together are
—C($R^{11}$)($R^{12}$)—C($R^{13}$)($R^{14}$)—C($R^{15}$)($R^{16}$)—C($R^{17}$)($R^{18}$)—, —C($R^{11}$)($R^{12}$)—C($R^{13}$)=C($R^{15}$)—C($R^{17}$)($R^{18}$)—, or —CH($R^{19}$)—C($R^{20}$)($R^{21}$)—CH($R^{22}$)—; and
T is a 4 to 7 membered monocyclic- or an 8 to 11 membered fused bicyclic- heterocyclyl, having one or two ring heteroatoms independently selected from oxygen, sulfur and nitrogen; and wherein T is optionally substituted by 1 or 2 ring-carbon substituents independently being $C_1$-$C_3$alkyl, $C_1$-$C_2$fluoroalkyl, —$SC_1$-$C_3$alkyl, —$S(O)C_1$-$C_3$alkyl, —$S(O)_2C_1$-$C_3$alkyl, or oxo (=O), and/or is optionally substituted by one $C_1$-$C_4$alkyl, $C_1$-$C_2$fluoroalkyl, $C_1$-$C_4$alkoxy, $C_1$-$C_2$fluoroalkoxy; or a $R^9$—C(O)—, or a $C_1$-$C_2$alkyl-$S(O)_2$— substituent on a ring nitrogen if present, and/or is optionally substituted by one or two oxo (=O) substituents on a ring sulfur if present;
Het is a heteroaryl, attached at a ring-carbon, which is optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, $S(O)R^{6E}$, $S(O)_2R^{6E}$, —$S(O)_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;
wherein:
$R^{6AA}$ is $C_1$fluoroalkyl, fluorine, chlorine or bromine;
$R^{6B}$, $R^{6C}$ and $R^{6CC}$ independently are hydrogen, methyl, $C_1$fluoroalkyl, fluorine or chlorine;
provided that $R^{6B}$, $R^{6C}$ and $R^{6CC}$ in total contain no more than one carbon atom, and $R^{6B}$, $R^{6C}$ and $R^{6CC}$ in total comprise no more than one chlorine;
$R^{6BB}$, $R^{6C1}$ and $R^{6C2}$ independently are hydrogen, methyl, $C_1$fluoroalkyl, fluorine or chlorine;
provided that $R^{6BB}$, $R^{6C1}$ and $R^{6C2}$ in total contain no more than one carbon atom, and $R^{6BB}$, $R^{6C1}$ and $R^{6C2}$ in total comprise no more than one chlorine; and provided that —C($R^{6BB}$)=C($R^{6C1}$)($R^{6C2}$) is not $C_2$-$C_3$alkenyl;
$R^{6D}$ and $R^{6E}$ independently are $C_1$-$C_3$alkyl, $C_1$fluoroalkyl, or —N($R^{6H}$)($R^{6J}$);
$R^{6F}$ is $C_1$-$C_2$alkyl, —C(O)—$C_1$fluoroalkyl, —S(O)$_2$—$C_1$-$C_2$alkyl, —S(O)$_2$-$C_1$fluoroalkyl, $C_1$-$C_2$alkyl, or $C_1$fluoroalkyl;
$R^{6G}$ and $R^{6J}$ independently are hydrogen, methyl or $C_1$fluoroalkyl; and
$R^{6H}$ is hydrogen, $C_1$-$C_2$alkyl, or $C_1$fluoroalkyl; and
$R^9$ is $C_1$-$C_4$alkyl, $C_2$-$C_4$alkenyl attached at a carbon atom partaking in the C=C double bond, $C_1$-$C_2$fluoroalkyl, $C_1$-$C_2$alkoxymethyl-, $C_1$-$C_3$alkoxy, cyclopropyl, furanyl, morpholin-4-yl, isoxazol-3-yl, 5-methyl-isoxazol-3-yl, pyrazol-5-yl, 3-methylpyrazol-5-yl, 1-methyl-pyrazol-5-yl, 1,3-dimethylpyrazol-5-yl; or phenyl or phenyl substituted by 1 or 2 substituents independently being methyl, ethyl, $C_1$fluoroalkyl, methoxy, $C_1$fluoroalkoxy, fluorine, chlorine, S$C_1$-$C_3$alkyl, S(O)$C_1$-$C_3$alkyl, or S(O)$_2$$C_1$-$C_3$alkyl;
$R^{10}$ is hydrogen, $C_1$-$C_4$alkyl, $C_1$-$C_2$fluoroalkyl, 2-($C_1$-$C_3$alkoxy)-ethyl, $C_3$-$C_5$cycloalkyl or ($C_3$-$C_5$cycloalkyl)methyl;
$X^1$ is O, S, S(O), S(O)$_2$, NH, N($C_1$-$C_3$alkyl), N($C_1$-$C_3$alkoxy), C(H)($C_1$-$C_2$alkyl), C($C_1$-$C_2$alkyl)$_2$, C(H)($C_1$-$C_3$alkoxy) or C(Me)($C_1$-$C_2$alkoxy);
n1 is 2, 3, 4 or 5; and n2 and n3 are independently 1, 2 or 3 provided that n2+n3 is 2, 3 or 4;
$R^{11}$ and $R^{18}$ are both hydrogen, or $R^{11}$ and $R^{18}$ are taken together and form an —O— or —$C_1$-$C_2$alkylene-bridge; and
$R^{12}$ and $R^{17}$ are independently hydrogen, $C_1$-$C_3$alkyl or $C_1$-$C_2$alkoxy$C_1$-$C_2$alkyl;
$R^{13}$, $R^{14}$ and $R^{15}$ are independently hydrogen, $C_1$-$C_3$alkyl or $C_1$-$C_2$alkoxy$C_1$-$C_2$alkyl, provided that one, two or all of $R^{13}$, $R^{14}$ and $R^{15}$ are hydrogen;
$R^{16}$ is hydrogen; $C_1$-$C_3$alkyl; $C_1$-$C_2$alkoxy$C_1$-$C_2$alkyl; phenyl optionally substituted by 1, 2 or 3 of, independently, $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), S$R^{6E}$, S(O)$R^{6E}$, S(O)$_2$$R^{6E}$, —S(O)$_2$—$R^{6E}$, —N($R^{6F}$)($R^{6G}$) hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, CH$_2$=CH—CH$_2$—O—, HC≡C—CH$_2$—O—, halogen, cyano or nitro; or a 5-membered or 6-membered heteroaryl, attached at a ring-carbon and optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), S$R^{6E}$, S(O)$R^{6E}$, S(O)$_2$$R^{6E}$, —S(O)$_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, CH$_2$=CH—CH$_2$—O—, HC≡C—CH$_2$—O—, halogen, cyano or nitro;
$R^{19}$ and $R^{22}$ are independently hydrogen, $C_1$-$C_3$alkyl or $C_1$-$C_2$alkoxy$C_1$-$C_2$alkyl;
and $R^{20}$ and $R^{21}$ are independently hydrogen, $C_1$-$C_3$alkyl or $C_1$-$C_2$alkoxy$C_1$-$C_2$alkyl;
or $R^{20}$ and $R^{21}$ taken together are oxo (=O), =N—O—$R^{10}$, or =CH$_2$;
or $R^{20}$ and $R^{21}$, together with the carbon atom to which they are attached, form a 5, 6 or 7 membered saturated heterocyclyl, wherein the heterocyclyl has two ring heteroatoms independently being oxygen or sulfur and which are not directly bonded to each other, and wherein the heterocyclyl is optionally substituted by 1, 2 or 3 ring-carbon substituents independently being $C_1$-$C_2$alkyl;
and wherein in Q2:
$R^{33}$, $R^{34}$, $R^{35}$ and $R^{36}$, independently of each other, are hydrogen, $C_1$-$C_5$alkyl, $C_2$-$C_4$alkenyl, $C_2$-$C_4$alkynyl, $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl, $C_3$-$C_4$cycloalkyl, or an unsubstituted 4, 5 or 6 membered monocyclic heterocyclyl having one ring heteroatom independently selected from oxygen, sulfur and nitrogen, said heterocyclyl being attached at a ring carbon atom within the heterocyclyl;
provided that no more than one of $R^{33}$, $R^{34}$, $R^{35}$ and $R^{36}$ is alkenyl, alkynyl, alkoxyalkyl, alkylthioalkyl, alkylsulfinylalkyl, alkylsulfonylalkyl, cycloalkyl or heterocyclyl;
or $R^{33}$ and $R^{34}$ taken together are —(CH$_2$)$_{n31}$— or —(CH$_2$)$_{n32}$—$X^{31}$—(CH$_2$)$_{n33}$— and $R^{35}$ and $R^{36}$ are as defined above, or $R^{35}$ and $R^{36}$ taken together are —(CH$_2$)$_{n31}$— or —(CH$_2$)$_{n32}$—$X^1$—(CH$_2$)$_{n33}$— and $R^{33}$ and $R^{34}$ are as defined above;
$X^{31}$ is O, S, S(O), S(O)$_2$, NH, N($C_1$-$C_2$alkyl), N($C_1$-$C_2$alkoxy), C(H)($C_1$-$C_2$alkyl), C($C_1$-$C_2$alkyl)$_2$ or C(H)($C_1$-$C_2$alkoxy);
n31 is 2, 3, 4 or 5;
n32 and n33 are independently 1, 2 or 3 provided that n32+n33 is 2, 3 or 4;
Y is O, S, S(O), S(O)$_2$, N($C_1$-$C_2$alkyl), N($C_1$-$C_2$alkoxy), C(O), C$R^{38}$$R^{39}$ or —C$R^{310}$$R^{311}$C$R^{312}$$R^{313}$—; and
$R^{38}$ and $R^{39}$ are, independently of each other: hydrogen, $C_1$-$C_6$alkyl, $C_2$-$C_4$alkenyl, $C_2$-$C_4$alkynyl, $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl; $C_3$-$C_6$cycloalkyl or $C_3$-$C_6$cycloalkyl substituted by one or two substituents which independently are $C_1$-$C_3$alkyl or $C_1$-$C_2$fluoroalkyl, and in which one ring CH$_2$ moiety of a $C_4$-$C_6$cycloalkyl is optionally replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; $C_3$-$C_6$cycloalkyl substituted by one substituent being $C_1$-$C_3$alkoxy and optionally further substituted by one substituent being $C_1$-$C_2$alkyl; $C_5$-$C_6$cycloalkenyl or $C_5$-$C_6$cycloalkenyl substituted by one or two $C_1$-$C_3$alkyl substituents; $C_3$-$C_6$cycloalkyl$C_1$-$C_2$alkyl- or $C_3$-$C_6$cycloalkyl$C_1$-$C_2$alkyl- substituted by one or two ring substituents which independently are $C_1$-$C_3$alkyl or $C_1$-$C_2$fluoroalkyl, and in which one ring $CH_2$ moiety of a $C_4$-$C_6$cycloalkyl$C_1$-$C_2$alkyl- is optionally replaced by an oxygen or sulfur atom or by a S(O), $S(O)_2$, NH, $N(C_1$-$C_2$alkyl), $N(C_1$-$C_2$fluoroalkyl), $N[C(O)C_1$-$C_3$alkyl], $N[C(O)C_1$-$C_2$fluoroalkyl] or $N(C_1$-$C_2$alkoxy) moiety; $C_3$-$C_6$cycloalkyl$C_1$-$C_2$alkyl- substituted by one ring substituent being $C_1$-$C_3$alkoxy and optionally further substituted by one ring substituent being $C_1$-$C_2$alkyl; or HetA or HetA-$CH_2$—;

wherein HetA is a heteroaryl, attached at a ring-carbon, which is optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—$N(R^{6H})(R^{6J})$, $SR^{6E}$, $S(O)R^{6E}$, —$S(O)_2$—$R^{6E}$, —$N(R^{6F})(R^{6G})$, hydroxy, $C_2$-$C_3$alkenyl, —$C(R^{6BB})$=$C(R^{6C1})(R^{6C2})$, $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-$S(O)_2$— substituent;

provided that no more than one of $R^{38}$ and $R^{39}$ is an optionally substituted cycloalkyl, an optionally substituted cycloalkyl in which one ring $CH_2$ moiety has been replaced by an oxygen or sulfur atom or by a S(O), $S(O)_2$, NH, $N(C_1$-$C_3$alkyl), $N(C_1$-$C_2$fluoroalkyl), $N[C(O)C_1$-$C_3$alkyl]$, $N[C(O)C_1$-$C_2$fluoroalkyl] or $N(C_1$-$C_2$alkoxy) moiety; an optionally substituted cycloalkenyl, an optionally substituted cycloalkyl-alkyl-, an optionally substituted cycloalkyl-alkyl- in which one ring $CH_2$ moiety has been replaced by an oxygen or sulfur atom or by a S(O), $S(O)_2$, NH, $N(C_1$-$C_3$alkyl), $N(C_1$-$C_2$fluoroalkyl), $N[C(O)C_1$-$C_3$alkyl], $N[C(O)C_1$-$C_2$fluoroalkyl] or $N(C_1$-$C_2$alkoxy) moiety, or HetA or HetA-$CH_2$—;

or $R^{38}$ is hydrogen or $C_1$-$C_2$alkyl, and $R^{39}$ is $C_1$-$C_2$alkoxy; or $R^{38}$ and $R^{39}$ taken together are —$(CH_2)_{n37}$— or —$(CH_2)_{n38}$—$X^{32}$—$(CH_2)_{n39}$—;

wherein $X^{32}$ is O, S, S(O), $S(O)_2$, NH, $N(C_1$-$C_3$alkyl), $N(C_1$-$C_2$fluoroalkyl), $N[C(O)C_1$-$C_3$alkyl], $N[C(O)C_1$-$C_2$fluoroalkyl], $N(C_1$-$C_2$alkoxy), C(H)($C_1$-$C_3$alkyl), $C(C_1$-$C_2$alkyl)_2$ or C(H)($C_1$-$C_3$alkoxy);

n37 is 2, 3, 4, 5 or 6; and n38 and n39 are independently 0, 1, 2 or 3 provided that n38+n39 is 2, 3, 4 or 5; and $R^{310}$, $R^{311}$, $R^{312}$ and $R^{313}$ are independently of each other hydrogen or $C_1$-$C_4$alkyl provided that no more than one of $R^{310}$, $R^{311}$, $R^{312}$ and $R^{313}$ is $C_3$-$C_4$alkyl;

and wherein $R^{6AA}$, $R^{6BB}$, $R^{6C1}$, $R^{6C2}$, $R^{6E}$, $R^{6F}$, $R^{6G}$, $R^{6H}$ and $R^{6J}$ are as defined hereinabove for when Q is Q1; and and wherein:

G is hydrogen, an agriculturally acceptable metal, or an agriculturally acceptable sulfonium or ammonium group; or G is —$C(X^a)$—$R^a$, —$C(X^b)$—$X^c$—$R^b$, —$C(X^d)$—N$(R^c)$—$R^d$, —$SO_2$—$R^e$, —$P(X^e)(R^f)$—$R^g$, —$CH_2$—$X^f$—$R^h$; or phenyl-$CH_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—$CH_2$—, $C_1$-$C_6$alkoxy-C(O)—CH=CH—, $C_2$-$C_7$alken-1-yl-$CH_2$—, $C_2$-$C_7$alken-1-yl-CH($C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-CH($C_1$-$C_2$alkyl)-;

$X^a$, $X^b$, $X^c$, $X^d$, $X^e$ and $X^f$ are independently of each other oxygen or sulfur;

$R^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$—$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, form an unsubstituted 4, 5, 6 or 7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)

alkylcarbonyl-N—(C$_2$-C$_5$)alkylaminoalkyl, C$_3$-C$_6$trialkylsilyl(C$_1$-C$_5$)alkyl, phenyl(C$_1$-C$_5$)alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano, or nitro), heteroaryl(C$_1$-C$_5$)alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano, or nitro), C$_2$-C$_5$fluoroalkenyl, C$_3$-C$_8$cycloalkyl; phenyl or phenyl substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; heteroaryl or heteroaryl substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; heteroarylamino or heteroarylamino substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; diheteroarylamino or diheteroarylamino substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; phenylamino or phenylamino substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; diphenylamino or diphenylamino substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; or C$_3$-C$_7$cycloalkylamino, di(C$_3$-C$_7$cycloalkyl)amino, C$_3$-C$_7$cycloalkoxy, C$_1$-C$_{10}$fluoroalkoxy, C$_1$-C$_5$alkylamino or di(C$_1$-C$_4$alkyl)amino; or benzyloxy or phenoxy, wherein the benzyl and phenyl groups are in turn optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; and R$^h$ is C$_1$-C$_{10}$alkyl, C$_3$-C$_{10}$alkenyl, C$_3$-C$_{10}$alkynyl, C$_1$-C$_{10}$fluoroalkyl, C$_1$-C$_{10}$cyanoalkyl, C$_1$-C$_{10}$nitroalkyl, C$_2$-C$_{10}$aminoalkyl, C$_1$-C$_5$alkylamino (C$_1$-C$_5$)alkyl, C$_2$-C$_8$dialkylamino(C$_1$-C$_5$)alkyl, C$_3$-C$_7$cycloalkyl(C$_1$-C$_5$)alkyl, C$_1$-C$_5$alkoxy(C$_1$-C$_5$)alkyl, C$_3$-C$_5$alkenyloxy(C$_1$-C$_5$)alkyl, C$_3$-C$_5$alkynyloxy (C$_1$-C$_5$)alkyl, C$_1$-C$_5$alkylthio(C$_1$-C$_5$)alkyl, C$_1$-C$_5$alkylsulfinyl(C$_1$-C$_5$)alkyl, C$_1$-C$_5$alkylsulfonyl (C$_1$-C$_5$)alkyl, C$_2$-C$_8$alkylideneaminoxy(C$_1$-C$_5$)alkyl, C$_1$-C$_5$alkylcarbonyl(C$_1$-C$_5$)alkyl, C$_1$-C$_5$alkoxycarbonyl(C$_1$-C$_5$)alkyl, aminocarbonyl(C$_1$-C$_5$)alkyl, C$_1$-C$_5$alkylaminocarbonyl(C$_1$-C$_5$)alkyl, C$_2$-C$_8$dialkylaminocarbonyl(C$_1$-C$_5$)alkyl, C$_1$-C$_5$alkylcarbonylamino(C$_1$-C$_5$)alkyl, N—(C$_1$-C$_5$)alkylcarbonyl-N—(C$_1$-C$_5$)alkylamino(C$_1$-C$_5$)alkyl, C$_3$-C$_6$trialkylsilyl(C$_1$-C$_5$)alkyl, phenyl(C$_1$-C$_5$)alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano or nitro), heteroaryl(C$_1$-C$_5$)alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano or nitro), phenoxy(C$_1$-C$_5$)alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano or nitro), heteroaryloxy(C$_1$-C$_5$)alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano or nitro), C$_3$-C$_5$fluoroalkenyl, C$_3$-C$_8$cycloalkyl; phenyl or phenyl substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; heteroaryl or heteroaryl substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; C$_1$-C$_6$alkyl-C(O)—; or phenyl-C(O)— wherein the phenyl is optionally substituted by 1 or 2 of, independently, C$_1$-C$_2$alkyl, C$_1$fluoroalkyl, C$_1$-C$_2$alkoxy, C$_1$fluoroalkoxy, fluorine, chlorine, bromine, cyano or nitro;

and wherein "heteroaryl" means an aromatic ring system containing at least one ring heteroatom and consisting either of a single ring or of two fused rings;

and wherein the compound of formula (I) is optionally present as an agrochemically acceptable salt thereof or a tautomer thereof.

2. The compound of claim 1, wherein X is methyl.

3. The compound of claim 1, wherein R$^1$ is fluorine.

4. The compound of claim 1, wherein R$^2$ is —O—R$^{2A}$, and wherein R$^{2A}$ is methyl, ethyl, trifluoromethyl or difluoromethyl.

5. The compound of claim 1, wherein R$^2$ is —O—R$^{2A}$, and wherein R$^{2A}$ is methyl.

6. The compound of claim 1, wherein G is hydrogen; an agriculturally acceptable metal, or an agriculturally acceptable sulfonium or ammonium group; or G is —C(X$^a$)—R$^a$ or —C(X$^b$)—X$^c$—R$^b$.

7. The compound of claim 1, wherein R$^3$, R$^4$ and R$^5$ are hydrogen; or, R$^3$ and R$^5$ are hydrogen, and R$^4$ and R$^6$ taken together are —C(R$^{11}$)(R$^{12}$)—C(R$^{13}$)(R$^{14}$)—C(R$^{15}$)(R$^{16}$)—C(R$^{17}$)(R$^{18}$)— or —C(R$^{11}$)(R$^{12}$)—C(R$^{13}$)—C(R$^{15}$)c(R$^{17}$)(R$^{18}$)—.

8. The compound of claim 1, wherein

R$^6$ is: hydrogen, C$_1$-C$_4$alkyl, C$_2$-C$_3$alkynyl-CH$_2$—, C$_1$-C$_2$alkoxyC$_1$-C$_2$alkyl; T-CH(R$^7$)— wherein R$^7$ is hydrogen; or Het-CH(R$^8$)— wherein R$^8$ is hydrogen;

or R$^4$ and R$^6$ taken together are —C(R$^{11}$)(R$^{12}$)—C(R$^{13}$)(R$^{14}$)—C(R$^{15}$)(R$^{16}$)—C(R$^{17}$)(R$^{18}$)— or —C(R$^{11}$)(R$^{12}$)—C(R$^{13}$)═C(R$^{15}$)—C(R$^{17}$)(R$^{18}$)—;

and wherein:

and R$^{18}$ are taken together and form an —O— or —C$_1$-C$_2$alkylene- bridge;

R$^{12}$ and R$^{17}$ are independently hydrogen, C$_1$-C$_3$alkyl or C$_1$-C$_2$alkoxyC$_1$-C$_2$alkyl;

R$^{13}$, R$^{14}$ and R$^{15}$ are independently hydrogen or C$_1$-C$_3$alkyl, provided that two or all of R$^{13}$, R$^{14}$ and R$^{15}$ are hydrogen; and R$^{16}$ is hydrogen; C$_1$-C$_3$alkyl; or C$_1$-C$_2$alkoxyC$_1$-C$_2$alkyl.

9. The compound of claim 1, wherein:

R$^6$ is hydrogen, C$_1$-C$_4$alkyl or C$_2$-C$_3$alkynyl-CH$_2$—.

10. The compound of claim 1, wherein:

T is a 4, 5 or 6 membered monocyclic heterocyclyl, having one ring heteroatom independently selected from oxygen, sulfur and nitrogen;

and wherein the heterocyclyl T is optionally substituted by one R$^9$—C(O)— or C$_1$-C$_2$alkyl-S(O)$_2$— substituent on a ring nitrogen if present, or is optionally substituted by one or two oxo (=O) substituents on a ring sulfur if present;

and wherein T is attached at a ring carbon atom to the —(CH$_2$)$_m$—CH(R$^7$)— or —CH(R$^7$)— moiety; and in T, the one ring heteroatom is not directly bonded to the ring atom which is the position of attachment to the —(CH$_2$)$_m$—CH(R$^7$)— or —CH(R$^7$)— moiety; and R$^9$ is C$_1$-C$_3$alkyl, C$_1$-C$_2$fluoroalkyl, methoxymethyl-, or cyclopropyl.

11. The compound of claim 1, wherein:

Het is a heteroaryl, attached at a ring-carbon, which is optionally substituted by 1 or 2 ring-carbon substituents independently being C$_1$-C$_2$alkyl, C$_1$-C$_2$alkoxy, C$_1$fluoroalkyl, C$_1$-C$_2$fluoroalkoxy, C$_1$-C$_2$alkyl-C(O)—, C$_1$fluoroalkyl-C(O)—, SC$_1$-C$_2$alkyl, ethynyl, prop-1-ynyl, fluorine, chlorine or cyano;

and/or, in the case of a 5-membered heteroaryl ring containing a ring-nitrogen atom not partaking in a C=N ring double bond, the heteroaryl is optionally substituted on the ring-nitrogen atom not partaking in the C=N ring double bond by one C$_1$-C$_2$alkyl, C$_1$fluoroalkyl, methyl-C(O)— or C$_1$fluoroalkyl-C(O)— substituent.

12. The compound of claim 1, wherein Het is an optionally substituted monocyclic heteroaryl, attached at a ring-carbon, selected from: pyridinyl, pyrazolyl, imidazolyl, pyrazinyl, pyrimidinyl, and pyridazinyl;

optionally present as an agrochemically acceptable salt thereof; and wherein, in Het, any ring-carbon atom, which is directly bonded to the ring atom which is the point of attachment to the —CH(R$^8$)— moiety, is unsubstituted.

13. The compound of claim 1, wherein, when R$^4$ and R$^6$ taken together are —C(R$^{11}$)(R$^{12}$)—C(R$^{13}$)(R$^{14}$)—C(R$^{15}$)(R$^{16}$)—C(R$^{17}$)(R$^{18}$)—, —C(R$^{11}$)(R$^{12}$)—C(R$^{13}$)=C(R$^{15}$)—C(R$^{17}$)(R$^{18}$)—, or —CH(R$^{19}$)—C(R$^{20}$)(R$^{21}$)—CH(R$^{22}$)—, then R$^4$ and R$^6$ taken together are:

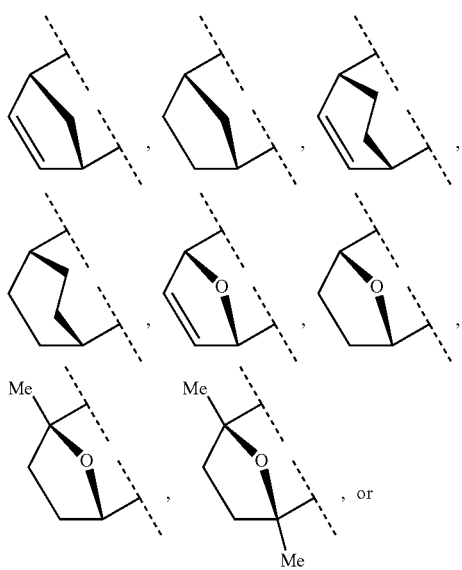

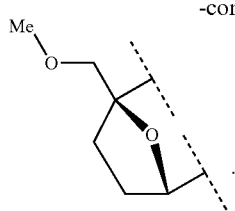

14. The compound of claim 1, wherein R$^{33}$, R$^{34}$, R$^{35}$ and R$^{36}$, independently of each other, are hydrogen, C$_1$-C$_3$alkyl or C$_1$-C$_2$alkoxyC$_1$-C$_2$alkyl; provided that no more than one of R$^{33}$, R$^{34}$, R$^{35}$ and R$^{36}$ is alkoxyalkyl.

15. The compound of claim 1, wherein:

R$^{38}$ and R$^{39}$, independently of each other, are hydrogen or C$_1$-C$_3$alkyl; or R$^{38}$ is hydrogen or C$_1$-C$_2$alkyl; and R$^{39}$ is:

C$_1$-C$_2$alkoxy;

C$_2$-C$_3$alkynyl-CH$_2$—;

C$_1$-C$_3$alkoxyC$_1$-C$_3$alkyl;

C$_1$-C$_3$alkylthioC$_1$-C$_3$alkyl;

C$_1$-C$_3$alkylsulfinylC$_1$-C$_3$alkyl;

C$_1$-C$_3$alkylsulfonylC$_1$-C$_3$alkyl;

C$_3$-C$_6$cycloalkyl or C$_3$-C$_6$cycloalkyl substituted by one or two substituents which independently are C$_1$-C$_3$alkyl or C$_1$-C$_2$fluoroalkyl; and in which one ring CH$_2$ moiety of a C$_4$-C$_6$cycloalkyl is optionally replaced by an oxygen or sulfur atom or by a S(O), S(O)$_2$, NH, N(C$_1$-C$_3$alkyl), N(C$_1$-C$_2$fluoroalkyl), N[C(O)C$_1$-C$_3$alkyl], N[C(O)C$_1$-C$_2$fluoroalkyl] or N(C$_1$-C$_2$alkoxy) moiety;

C$_3$-C$_6$cycloalkyl substituted by one substituent being C$_1$-C$_3$alkoxy and optionally further substituted by one substituent being C$_1$-C$_2$alkyl;

C$_3$-C$_6$cycloalkylmethyl- or C$_3$-C$_6$cycloalkylmethyl- substituted by one or two ring substituents which independently are C$_1$-C$_3$alkyl or C$_1$-C$_2$fluoroalkyl; and in which one ring CH$_2$ moiety of a C$_4$-C$_6$cycloalkylmethyl- is optionally replaced by an oxygen or sulfur atom or by a S(O), S(O)$_2$, NH, N(C$_1$-C$_2$alkyl), N(C$_1$-C$_2$fluoroalkyl), N[C(O)C$_1$-C$_3$alkyl], N[C(O)C$_1$-C$_2$fluoroalkyl] or N(C$_1$-C$_2$alkoxy) moiety;

C$_3$-C$_6$cycloalkylmethyl- substituted by one ring substituent being C$_1$-C$_3$alkoxy and optionally further substituted by one ring substituent being C$_1$-C$_2$alkyl; or HetA or HetA-CH$_2$—, wherein HetA is a heteroaryl, attached at a ring-carbon, which is optionally substituted by 1, 2 or 3 ring-carbon substituents independently being C$_1$-C$_3$alkyl, C$_1$-C$_2$fluoroalkyl, C$_1$-C$_3$alkyl-C(O)—, C$_1$-C$_2$fluoroalkyl-C(O)—, hydroxy (including any oxo tautomer), C$_2$-C$_3$alkenyl, C$_2$-C$_3$alkynyl, C$_1$-C$_3$alkoxy, C$_1$-C$_2$fluoroalkoxy, halogen, cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one C$_1$-C$_3$alkyl, C$_1$-C$_2$fluoroalkyl, C$_1$-C$_3$alkyl-C(O)—, C$_1$-C$_2$fluoroalkyl-C(O)— or C$_1$-C$_2$alkyl-S(O)$_2$— substituent.

16. The compound of claim 1, wherein Y is O or $CR^{38}R^{39}$.

17. The compound of claim 1, wherein:

$R^1$ is fluorine,

X is methyl, $R^2$ is $OR^{24}$, wherein $R^{24}$ is selected from methyl, ethyl and difluoromethyl, and either Q is Q1, wherein $R^3$, $R^4$, and $R^5$ are hydrogen, and $R^6$ is hydrogen or propargyl, and G is hydrogen, and or Q is Q2, wherein Y is $CR^{38}R^{39}$, and $R^{38}$ and $R^{39}$ are each independently hydrogen or methyl.

18. The compound of claim 1, wherein:

Q is a group of formula Q1, or

Q is a group of formula Q2 and Y is O.

19. The compound of claim 1, which is compound A8, A9, A10, A14 or A16:

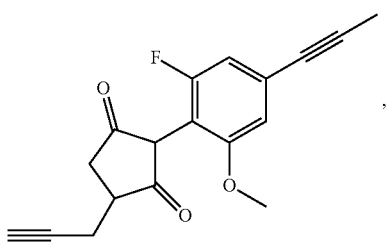

,

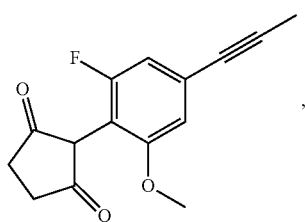

,

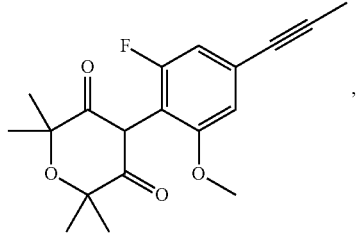

,

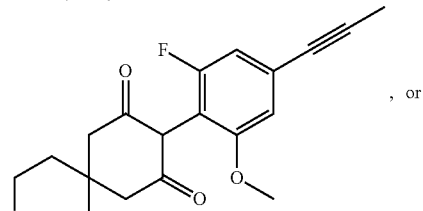

, or

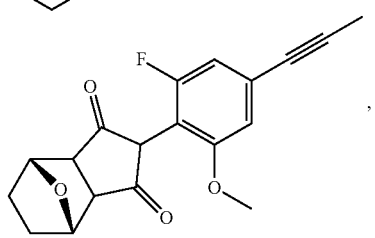

, in each case optionally present as an agrochemically acceptable salt thereof.

20. The compound of claim 1, wherein the tautomer thereof is present only on Q1 or Q2.

21. A herbicidal composition which comprises:

(i) a compound of formula (I), as defined in claim 1, and (ii) an agrochemically acceptable carrier, diluent and/or solvent; and (iii) optionally one or more further herbicides and/or optionally a safener.

22. A method of controlling grassy monocotyledonous weeds in crops of useful plants, comprising applying a compound of formula (I), as defined in claim 1, to the weeds and/or to the plants and/or to the locus thereof.

* * * * *